US007834163B2

(12) United States Patent
Einstein et al.

(10) Patent No.: US 7,834,163 B2

(45) Date of Patent: Nov. 16, 2010

(54) PROSTATE SPECIFIC GENES AND THE USE THEREOF AS TARGETS FOR PROSTATE CANCER THERAPY

(75) Inventors: Richard Einstein, Gaithersburg, MD (US); Kevin M. McGowan, N. Potomac, MD (US); Matthew P. Pando, Arlington, VA (US)

(73) Assignee: Exonhit Therapeutics S.A., Paris (FR)

( * ) Notice: Subject to any disclaimer, the term of this patent is extended or adjusted under 35 U.S.C. 154(b) by 0 days.

(21) Appl. No.: 10/560,723

(22) PCT Filed: Jun. 25, 2004

(86) PCT No.: PCT/IB2004/002394

§ 371 (c)(1), (2), (4) Date: Dec. 15, 2005

(87) PCT Pub. No.: WO2004/113571

PCT Pub. Date: Dec. 29, 2004

(65) Prior Publication Data

US 2006/0115821 A1 Jun. 1, 2006

Related U.S. Application Data

(60) Provisional application No. 60/482,595, filed on Jun. 26, 2003.

(51) Int. Cl.
*C07H 21/02* (2006.01)

(52) U.S. Cl. .................................................... 536/23.1

(58) Field of Classification Search ....................... None
See application file for complete search history.

(56) References Cited

U.S. PATENT DOCUMENTS 6,812,339 B1 * 11/2004 Venter et al. ............. 536/24.31
2007/0014801 A1 * 1/2007 Gish et al. ............... 424/155.1

FOREIGN PATENT DOCUMENTS

| | | |
|---|---|---|
| WO | WO 98/40403 | 9/1998 |
| WO | 99/37811 | 7/1999 |
| WO | 99/43710 | 9/1999 |
| WO | 99/46403 | 9/1999 |
| WO | 00/77258 | 12/2000 |
| WO | 01/34802 | 5/2001 |
| WO | WO 01/60860 A2 * | 8/2001 |
| WO | WO 01/64835 | 9/2001 |
| WO | WO 01/75067 | 10/2001 |
| WO | WO 01/79449 | 10/2001 |
| WO | WO 02/14753 | 2/2002 |

OTHER PUBLICATIONS

Sequence comparison.*

International Search Report of PCT/IB2004/002394, mailed Mar. 1, 2005.

Su et al., “Alternatively spliced variants of prostate-specific membrane antigen RNA: Ratio of expression as a Potential Measurement of Progression”, Cancer Research, vol. 55, No. 7, 1995, pp. 1441-1443, XP002137210.

Database EMBL 'Online! May 31, 2001, “Sequence 461 from Patent WO0134802”, XP002308123, retrieved from EBI accession No. EM_PRO:AZ140971, Database accession No. AX140971.

Corominola et al., “Identification of novel genes differentially expressed in omental fat of obese subjects and obese type 2 diabetic patients”, Diabetes, vol. 50, No. 12, Dec. 2001, pp. 2822-2830, XP002293068.

GenBank Accession No. BX497404, Entry Created Jun. 19, 2003, last updated Sep. 4, 2003, 3 pages.

* cited by examiner

*Primary Examiner*—Sean E Aeder
(74) *Attorney, Agent, or Firm*—Nixon & Vanderhye P.C.

(57) ABSTRACT

Genes that are upregulated in human prostate tumor tissues and the corresponding proteins are identified. These genes and the corresponding antigens are suitable targets for the treatment, diagnosis or prophylaxis of prostate cancer.

5 Claims, 2 Drawing Sheets

Figure 1:
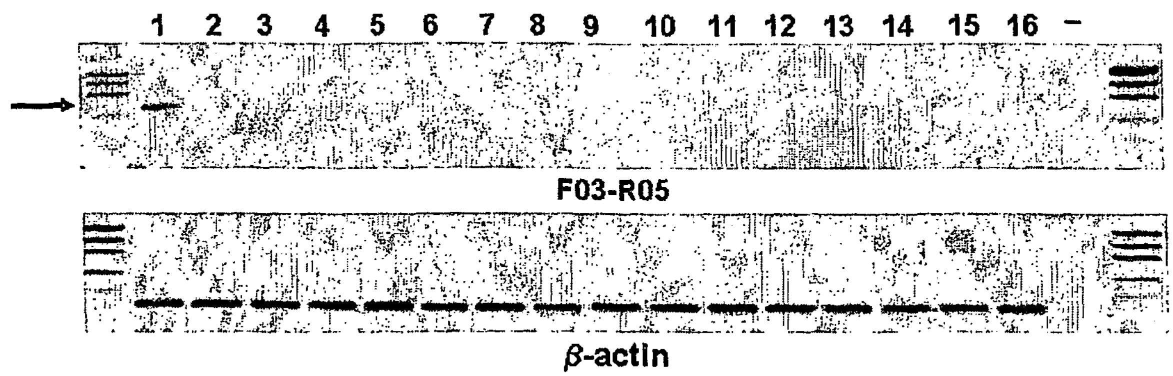

SEQUENCE LISTING

```
<160> NUMBER OF SEQ ID NOS: 185

<210> SEQ ID NO 1
<211> LENGTH: 151
<212> TYPE: DNA
<213> ORGANISM: Homo sapiens

<400> SEQUENCE: 1

ccggcccagg catgcacaca ctcttctgga gcacacgcga ccctccctag accgcctgct     60

tctcggctcc cctgcacatt agagcttctc aagacacggc ctgcacttgc cacctctgca    120

tttcccactc tcgctttgct gcctcccggc c                                   151


<210> SEQ ID NO 2
<211> LENGTH: 138
<212> TYPE: DNA
<213> ORGANISM: Homo sapiens

<400> SEQUENCE: 2

ggaggggaag ttcggctcca gccacatagg tgtgtgtcct ccttatcctc tgaccaaagc     60

ttgtccttcc tacatatgct cctttgctag cactcccacc tgaatgcatc cctatgatcc    120

ttccaccttc cctgctcc                                                  138


<210> SEQ ID NO 3
<211> LENGTH: 459
<212> TYPE: DNA
<213> ORGANISM: Homo sapiens

<400> SEQUENCE: 3

ggaaccctac gaagaaccac agggagaaca ccagcattgc caccaccacc accaccacca     60

cagagtctgt ggaagaggtg gttcgagttc ctacaacagc agccagtacc cctgatgccg    120

ttgacaagta tctcgagaca cctggggatg agaatgaaca tgcccatttc cagaaagcca    180

aagagaggct tgaggccaag caccgagaga gaatgtccca ggtcatgaga gaatgggaag    240

aggcagaacg tcaagcaaag aacttgccta aagctgataa gaaggcagtt atccagcatt    300

tccaggagaa agtggaatct ttggaacagg aagcagccaa cgagagacag cagctggtgg    360

agacacacat ggccagagtg gaagccatgc tcaatgaccg ccgccgcctg gccctggaga    420

actacatcac cgctctgcag gctgttcctc ctcccggcc                           459


<210> SEQ ID NO 4
<211> LENGTH: 562
<212> TYPE: DNA
<213> ORGANISM: Homo sapiens
```

<400> SEQUENCE: 4
tggggggagg gcaggaaaat gaactcaatg agataaccag ggacaagatg atatgatgcc 60
tttcttctag cactcaggga tttcggaatc aaatctgaga gaggcaagaa attgtgagaa 120
gattgtaagc agagatgaaa cagaaaagat acctgaaact ctgatcttgg agcttttctt 180
ccgtgatata agatctaaca gggtccactg catagagctg ttgtgaggat gacaagagat 240
cactaacact gtaaactctc aatccacagc cttcacataa ctgggtctca agacatgccc 300
tctcccttct cctctgcact tcttcatgtg tttaagggag aatgtgggga ggggcttatg 360
taaaataggg gactacaggt atcagactga accaatccta cttgttgaac tttatctact 420
ggatggccaa ggttataagg aacaccacca ccttctcatg ccctggggtg ccctagagaa 480
aggtaagcag accaagggtc tcagactccc tgtggaagaa agaccactgc acccaagctt 540
tacaaacgca tccctcggcc gt 562

<210> SEQ ID NO 5
<211> LENGTH: 328
<212> TYPE: DNA
<213> ORGANISM: Homo sapiens

<400> SEQUENCE: 5
gggcacccta gctgcaaggg aggttagaaa aaatgaggga caggattatc atggtcagca 60
tattacttgg gggccagata tatcacttcc cacacaaaag caggcctctg tcagtgagga 120
agaagtggag aatggatttg ggtgggcat ctgacagcat ttgccacact gccctcccca 180
atcctaatgc aggccagtca acgcaccacc cccactcccc acccacactc caaccccac 240 agtcctaggg tctctcaggg agaccatcgg tggaatccat aacattctaa gaccctgcag 300
tttgtaggca aaatcaggct tcctttgg 328

<210> SEQ ID NO 6
<211> LENGTH: 168
<212> TYPE: DNA
<213> ORGANISM: Homo sapiens

<400> SEQUENCE: 6
gacctcgaat tacaggcatg agccaccgtg cctggccttt tcttttcttt taagctactt 60
tttaatatat agtaatgact gttaatatag tatatactat gctattcatc aatgctgtaa 120
ctttcttagt ttcattttct cactcaattg aagtccaggt acccaggt 168

<210> SEQ ID NO 7
<211> LENGTH: 317
<212> TYPE: DNA
<213> ORGANISM: Homo sapiens

<400> SEQUENCE: 7
agaaccctgg agcacttgag ggaccagaga cccggcatgg tccagacgaa ggtactgtca 60
gtctctcctc cgggacgcag acccattcaa ggtgcctctc tgcggccgtg ttcctgagag 120
gagcacgggg agggcctggt ttaatgtgag ccgcacaccg attgctctgc tctgaccgac 180
ctcgtccatg ccggccttgc atgggcgggg tcacttctgg gcccccaaag gtccactggc 240
gtttcctgca acacctccag atgcagccac atctcaagtc ctaggaactc gatccactgg 300
ctctttccat tcactag 317

<210> SEQ ID NO 8
<211> LENGTH: 277

-continued

<212> TYPE: DNA
<213> ORGANISM: Homo sapiens

<400> SEQUENCE: 8

```
gggtgcgagg attcttgggc ctcatcctac agcacagctt tagtaagctg ggttgacaga     60

gtcctggcgt cagtatattt ggaaacaata agtctgatga acatccccct cgttaagaat    120

ccctgagacc aactttcatt ttacagatga aaaaactgag accggtaggg gtaaaatgcc    180

acagtcatga tcatgccgct agtaggtggc agagtgccat ctacaattca tttgtcatct    240

gagcttgact ggggctcctc ttaccacttc ctcctcg                             277
```

<210> SEQ ID NO 9
<211> LENGTH: 441
<212> TYPE: DNA
<213> ORGANISM: Homo sapiens

<400> SEQUENCE: 9

```
gggggcagga gatagccaga tgtggtggca cacccctgta gtcccagcta ctggggaggc     60

tgagatagga ggatcacttg agcccaggag tttgagacta gaatgagcca tgattgtgcc    120

actgcactcc agcctggtga aagagtgata ccctgttttc ataagaaaaa aataacaaaa    180

acaaaaacaa gaaaggagag agttggctaa gctttatcac ctttgtgggt ttggaaccct    240

tacttgatcc ttcactaaag tacttcttgg gcatccagtg aggttcagtg tgtattgaga    300

ggatggtgag gatggcagcc aggcgtggga tctgtattca agaagaagct gccccactcg    360

ctggccatct atggatttcc agccaacaag catttccaac cacctatgga tttccaacaa    420

ctgagaactc atgagactgg c                                              441
```

<210> SEQ ID NO 10
<211> LENGTH: 508
<212> TYPE: DNA
<213> ORGANISM: Homo sapiens

<400> SEQUENCE: 10

```
aggctatgag ttgaaaattg gctctccttg gacagtcctc aagcactaca ttttttttcag     60

tgactctcac cagacccaca gatgaattta ccttctctgc gtatgccttt tgactggttc    120

tgtttcaggg aaccgcaagc tcaataagct ccactgttct accaagctgg acaaacagcc    180

acgtctctgt tctcttggcc agaccctgag gcctggagtt ctgccttcag gaattccaga    240

attctagaaa gttagagcta gacaagacct cagccttcat ctagtcttgc tccaaccact    300

gtgcggatgg ggaaacaagg catgggctgg ggatgactta aggggtataa aatgttgggc    360

tttcttttgt caagcccagc atgtgcctcc tataggcacc agtggtctct gcaagtcctg    420

gcctgctggc ctcgcagcca cagagagctc ggactctctc aggcagctca cttcattgct    480

ggaacaatag caatgttctt cctaatgc                                       508
```

<210> SEQ ID NO 11
<211> LENGTH: 135
<212> TYPE: DNA
<213> ORGANISM: Homo sapiens

<400> SEQUENCE: 11

```
agaagcgtta tacgggggag gctggagtgg taaaaggctc agaaaaatcc tgcgaagaaa     60

aaaacttctg aggtaataaa taggattatc ccgtatcgaa ggccttttttg gacaggtggt    120

gtgtggtggc ctgcg                                                     135
```

<210> SEQ ID NO 12
<211> LENGTH: 248
<212> TYPE: DNA
<213> ORGANISM: Homo sapiens

<400> SEQUENCE: 12
gaggatgagg tggaggagga gagtgacaag gccgcgctcc tgcaggagca gcagcagcag 60
cagcagccgg gattctggac cttcagctac tatcagagct tctttgacgt ggacacctca 120
caggtcctgg accggatcaa aggctcactg ctgccccggc ctggccacaa ctttgtgcgg 180
caccatctgc ggaatcggcc ggatctgtat ggccccttct ggatctgtgc cacgttggcc 240
tttgtcct 248

<210> SEQ ID NO 13
<211> LENGTH: 183
<212> TYPE: DNA
<213> ORGANISM: Homo sapiens

<400> SEQUENCE: 13
cccgccgacc tggcagggac atgcttagga aaagatggtg tcaacagacc cacaacacag 60
aaccacactg tggggtgggg aagcagagag gcgggaccag ccacttccag caggaagttt 120
ccaacctgga ctgggttggg acggtgaggg gatagtcatc tgccatcagt ttacataggt 180
ggt 183

<210> SEQ ID NO 14
<211> LENGTH: 124
<212> TYPE: DNA
<213> ORGANISM: Homo sapiens

<400> SEQUENCE: 14
cggcaggcat cacacaagag ggtgtcccta agatgcatca cgtccgtgga gaaaacaaag 60
caggacacac gtgtgagtcg tcacaccctt ggtcacccgg cttggccgtc acacatgcct 120
ccct 124

<210> SEQ ID NO 15
<211> LENGTH: 132
<212> TYPE: DNA
<213> ORGANISM: Homo sapiens

<400> SEQUENCE: 15
gtaggggagg gaaccagcta ctagatggtt cgattagtct ttcgccccta tacccaggtc 60
ggacgaccga tttgcacgtc aggaccgcta cggacctcca ccagagtttc ctctggcttc 120
gccctggggc cg 132

<210> SEQ ID NO 16
<211> LENGTH: 124
<212> TYPE: DNA
<213> ORGANISM: Homo sapiens

<400> SEQUENCE: 16
cacaccttgg ggacaggcat gaggaacaga ttaatgtgag atattctaga ggtacatgca 60
tcaggccatg gtgaccaatt gtctgtggag ggtgaggcag aaggaattgt tgaggatgac 120
tgag 124

<210> SEQ ID NO 17
<211> LENGTH: 489

<212> TYPE: DNA
<213> ORGANISM: Homo sapiens

<400> SEQUENCE: 17
gggaggcaat cattgagaga taatagctga gagtttttca gaaaggaaaa gaggtatgag 60
tttcagggag aaagggcggg ccaaggacta agccaaataa ataaaataag tctataccta 120
gacactttgt gggaaattca cagaccatca aagataaggg aaaaacctca tgggctacag 180
cagaaaagag acccattcta cacaaagaac aagttcacaa tatgagacag agccacgcac 240
agaggatgac tgctatgacc tgacgacggg gaagtgtctt gttctctggt aagccgcctc 300
taaagatggc caaagacatg gtttttccta ggtttgaggt gcactacttc agggttcctg 360
cttacctcct gctcgttctc tggccctcat tgtgaccatg cttcactctc ccatcctgtg 420
ctgggacaac catttttctt tccttattgc tgctactgca gagtgaggta gggctgtggc 480
ctcgcaccg 489

<210> SEQ ID NO 18
<211> LENGTH: 244
<212> TYPE: DNA
<213> ORGANISM: Homo sapiens

<400> SEQUENCE: 18
cggtgggagg cggccccgca ctaaggtagg gacccagatg gaaatgggac gctctctgca 60
ccatgggagg caaaaataca aattccatca ccaagagggc acgccatgcg gtgttgttcc 120
ataagggtga gcaaagctgc caggcccaca ggagagagag cccacaggag ccctggatcc 180
tgtgggactt tggatcctac acagtgagtg atctcagaac tttgcaaggc tgaggcaggg 240
agac 244

<210> SEQ ID NO 19
<211> LENGTH: 195
<212> TYPE: DNA
<213> ORGANISM: Homo sapiens

<400> SEQUENCE: 19
gggcgggacc agtgagagaa aggatagagc gtgtgagatg aaagggctgg tcttattaag 60
ccctacaata ctctggggtc caagcaatcc tgctgtggga ccctgctaag tgaacataat 120
gccgaggaag aacagctctc ctctttttgc caaagcctgc caaggtgtca aggcttgaga 180
aagagtggtg gccta 195

<210> SEQ ID NO 20
<211> LENGTH: 346
<212> TYPE: DNA
<213> ORGANISM: Homo sapiens

<400> SEQUENCE: 20
ccggtgcagg cattgtgata atagttggaa tgcagaggtg aattaaagag tatgggcttg 60
tctatataaa taaataaata tatatgtata tggtgtgtat aaccctatta tatatattat 120
gtattaggtg gtgttgtata tatatgttta tatatgtgtg tgtttatgta taagtatata 180
tgtgataaga gtttataatc ctatatagag acagatgtat taaaatggat tttttttttt 240
tgagacagag tcttactctg tcatcaaagc tggagtgcag tggtgcaatc taggctcaca 300
gtgacctaca cctcccatgt tcaaacgatt ctcctgcctc ggccgg 346

<210> SEQ ID NO 21

-continued

<211> LENGTH: 168
<212> TYPE: DNA
<213> ORGANISM: Homo sapiens

<400> SEQUENCE: 21
cgctgggagg ctgtgcgtgt ttgcttttgt tgatctgttt aactgcagcc cgatttatgt 60
ttctggatcc tggaattgag ttgacactat cggtagtatg aaagtgacag acaccaggat 120
gaagtcactc ttgtcagacc cagaggaaac agggtcagga ggcctggg 168

<210> SEQ ID NO 22
<211> LENGTH: 435
<212> TYPE: DNA
<213> ORGANISM: Homo sapiens

<400> SEQUENCE: 22
agccggcagg actgtatcat caacgcaagt ctcttgagat gccttgttga tcggtagatc 60
aagttatagc ctcggtttct gattttgctg tggtgatact ggatgtagca ttcaaggagt 120
aaatggagaa tccacaaaat aactttccca aggattataa ccgtctgaac tttcaatggg 180
tttgtgtaat ttcctgggca cttgtcctca tttggattag gataagaaca aagcacacct 240
gttaaaaatg ctaaaacaac aaacacgaga tgaataaacc acagaagatt cactatgatg 300
actgtaggaa gaggatggaa tcggggtcta aagtgagctt gtaatgagtg gtgtgggaga 360
agctgggcat ccagaagtgg gtcgtcttca atactctggg tgatatccaa ggaaccgtcc 420
tccatcctgc cgcgg 435

<210> SEQ ID NO 23
<211> LENGTH: 199
<212> TYPE: DNA
<213> ORGANISM: Homo sapiens

<400> SEQUENCE: 23
cggggaaagg acaggcctgc tgctttattc acagatttag atgtcgttcc atctgctctc 60
gaagtttgaa tttctggatc tttcctgaaa tggtgagggg gtagtttgtg acaaacacga 120
tgtacttcgg aatcttgaag tgagagatct tccctttgca gaaagctttt atctcctcca 180
ccgtggtctc ctctcggcg 199

<210> SEQ ID NO 24
<211> LENGTH: 258
<212> TYPE: DNA
<213> ORGANISM: Homo sapiens

<400> SEQUENCE: 24
gggcgcaggc tatggaggag accgtggtgg tggcagtggc tacggtggag accgaagtgg 60
aggctatgga ggagacagga gtggtggcgg ctatggagga gaccgaggtg ggggctacgg 120
aggagaccga ggtggctatg gaggcaaaat gggaggaaga aacgactaca gaaatgatca 180
gcgcaaccga ccatactgat gactgttttg aatgttcctt tgtctctgac atgatccata 240
gtgaaattgc cagagttt 258

<210> SEQ ID NO 25
<211> LENGTH: 171
<212> TYPE: DNA
<213> ORGANISM: Homo sapiens

<400> SEQUENCE: 25
ggttcaggca ggtcagcaag gaacacaaag gcatctgcca cctgagcaag tatcgaacac 60

```
catcacctgc atccttcaag ggttccaggt agatctccag cctcttgtag gagagaacca    120

agttgaaaag gtcaaacgct ggggacttgg taggaaaagg tggagactcc a             171


<210> SEQ ID NO 26
<211> LENGTH: 223
<212> TYPE: DNA
<213> ORGANISM: Homo sapiens

<400> SEQUENCE: 26

cagtgcgagg agccgtcact ctgctaagcc tgtatctgct gttcggctac ggagcgtctc     60

tgctgtgcaa tctcatcgga tttgtgtacc ccgcatatgc ctcaatcaaa gctatcgaga    120

gcccaagcaa ggacgacgac actgtgtggc tcacctactg ggtggtgtac gccctgtttg    180

ggctggccga gttcttcagc gatctactcc tgtcctgccc ccc                      223


<210> SEQ ID NO 27
<211> LENGTH: 249
<212> TYPE: DNA
<213> ORGANISM: Homo sapiens

<400> SEQUENCE: 27

tggggagagg tgagcagctt tgaacttttt cttagggagt gtcagaacga ggccagtctg     60

cctttatgcc atgtggcctc aggcacctac agtgaagtct taaaaccagt ggatgctctc    120

tacagtgcct tctagctgtg gtagtctgtg tctccaagga ccaacccttc catttctgag    180

gcttcagaat aaattctggc agttatttct tctctcagac tctatttcag aaaagtgtac    240

ctgcccccca                                                           249


<210> SEQ ID NO 28
<211> LENGTH: 334
<212> TYPE: DNA
<213> ORGANISM: Homo sapiens

<400> SEQUENCE: 28

caggctggag tgtggtagca tgagcatggc tcactgcaat ctccacctcc caggctcaag     60

cgatcctccc acctcaccct ccccggtagt gggaccacag gtgcacacca ccacacctgg    120

ctatatgctt cttttgagat tgcttttttc actcacataa tttgcttgaa atttatccac    180

cagcattttt taaaaattaa ctgtgcatca tcttcagtga gatgtgtgca tttcgtcttt    240

gttcatgcct tttccactgc ctagaatgcc ctctaccaac cctgtctacc gatctgtatt    300

catttccttc agtgtgtctc actgctgtgt gcct                                334


<210> SEQ ID NO 29
<211> LENGTH: 226
<212> TYPE: DNA
<213> ORGANISM: Homo sapiens

<400> SEQUENCE: 29

aggtccaaag tggaaagatg gaaaagctca gatgatacag gcctacagac tagatttttt     60

gtttatttgt ttctgtacac tactactaca aaggatagca aatagagctg aaggaaaagg    120

atggagatac tcaaagtcct aaaaatggaa aggagaaaag ggaatgtcaa cctcaaggac    180

aactgagatg ttcacagaac ttctgcagat tcttgtcccc cacctc                   226


<210> SEQ ID NO 30
<211> LENGTH: 372
<212> TYPE: DNA
```

<213> ORGANISM: Homo sapiens

<400> SEQUENCE: 30

```
gggatagggg agagaagaag aagctgggga gctgggaaca tcatctcagg ctggaggaca     60
agcctgcgac aggaccggtt ccacagagga gtcaaaagag ttaaagccca gaaggcagct    120
ggaagagaag gcaaagctgg aaaaggaagt aaaagcagca gctgttctga ttttgaagga    180
gagtaaatgg gcttatttgc tttatggtct aaggagcaga gaaaactcat tctcctctgg    240
ttataaattc ccgagttgca gaaggaagtc tcctaactac tgatcggttc ctcttggggt    300
gggaaaatct ctgagctaca gtgagtcatt cccaggatgc caacaatggc ctccacttct    360
ccctctgccc ct                                                        372
```

<210> SEQ ID NO 31
<211> LENGTH: 207
<212> TYPE: DNA
<213> ORGANISM: Homo sapiens

<400> SEQUENCE: 31

```
cctctgttct tccagcttgg cttggagaag aactggcaga tgaacacgtc ctgcatggtg     60
gaatgccctg tgaactgtca gctttctgat tggtctcctt ggtcagaatg ttctcaaaca    120
tgtggcctca caggtttgtt tgtaccataa cttatattag gctcctggtc aaggaatatg    180
aaataaaata tccctcttgc tttaacc                                        207
```

<210> SEQ ID NO 32
<211> LENGTH: 179
<212> TYPE: DNA
<213> ORGANISM: Homo sapiens

<400> SEQUENCE: 32

```
tggtgggagg tcactgcttg aaggagtcac atagacgtgg tgtgtgacac ttgtgcccat     60
ttcctgtgcc tgatgtgtag caaagaaagg ttgcatgctc ccttgctccc tgttctcttc    120
cagaccgtct atgaccagta tttcatcacc ctgtataaca tcgtgtacac ctaacgccc     179
```

<210> SEQ ID NO 33
<211> LENGTH: 484
<212> TYPE: DNA
<213> ORGANISM: Homo sapiens

<400> SEQUENCE: 33

```
tgaggaggtg aaggaccgga tcctggagaa catctcgctg tcggtgaaga agttgcagag     60
ctattttgct gcatgtgagg atgagacccc tgccatccgg aaccatgaca aggtcctaca    120
gcgtctgtgt gagcacctgg accacgccct gctgtacgga ctgcaagacc tctcctctgg    180
ctactgggtg ctcgtggtgc attttactcg gagagaggcc atcaagcaga tcgaggtgct    240
gcagcacgtg gccaccaacc tggggcgcag ccgtgcctgg ctgtacctgg ccctcaacga    300
gaactccttg gagagctacc tgcggttgtt ccaggagaac ctgggcctgc tgcataagta    360
ctacgtcaag aatgccctgg tctgcagcca cgatcacctg acgctcttcc tgaccttggt    420
gtccgggcta gagttcattc gtttcgagct ggatctggat gccccttacc tagacctccc    480
cacg                                                                 484
```

<210> SEQ ID NO 34
<211> LENGTH: 443
<212> TYPE: DNA
<213> ORGANISM: Homo sapiens

<400> SEQUENCE: 34

```
ggggaggtga ttccatccag agtcatatct gttgtcaccc caataagtcg atcagcaagg     60

ctgacaggct gtgaggaaac cccggccttg tagcctgtca cctctggggg gatgatgact    120

gcctggcaga cgtaggctgt gatagatttg gagaaccctg actcaccctc aggaatccgg    180

aggtcagtga cattgtcggt gcacacagac attttcctac cctggtttcc acagagactg    240

agggtaaagt gatggaagta tttcaaccct ttggaagtga agcttggccc tccagcaaga    300

gtgacggtgt ttgccaaagc ggagaagttg tagttgaaag tcctggttgg agtgttgcgt    360

gagaaggtgc aatcattgta gcacagagag tggatcttgt tgttcttggt ccctggacca    420

cagggcacac agacctcgcc gca                                            443
```

<210> SEQ ID NO 35
<211> LENGTH: 272
<212> TYPE: DNA
<213> ORGANISM: Homo sapiens

<400> SEQUENCE: 35

```
ggacaggggt ctctccacca tttgaggaag ggatagagga agaccaccat ggggaaagat     60

atcatgcact ggttgaaaag aactgtgcgg atagactggc gcagtttcac aggatccaca    120

ggttcattct tgccgacctg aattcggtag cgagagatga agttaggttt tcctgttgtg    180

tcaaccacca atagaagccc attgaagctc cagaagaaga gacaaggcac ttggatggca    240

cctataaaga agaggatcca ctccttccct ac                                  272
```

<210> SEQ ID NO 36
<211> LENGTH: 224
<212> TYPE: DNA
<213> ORGANISM: Homo sapiens

<400> SEQUENCE: 36

```
gatggaaagg ctgtagtggg gctggtggtg cttccaactg cgggacagga agtggccgta     60

gcggcttgtt ggataagtgg aagatagatg ataagcctgt aaaaattgac aagtgggatg    120

gatcagctgt gaaaaactct ttggatgatt ctgccaaaaa ggtacttctg gaaaaataca    180

aatatgtgga gaattttggt ctaattgatg gtcgccttgt aacc                     224
```

<210> SEQ ID NO 37
<211> LENGTH: 342
<212> TYPE: DNA
<213> ORGANISM: Homo sapiens

<400> SEQUENCE: 37

```
tgtcttgagg cactgtagta tcaatcagac caggaatatc cttctctcct ttttttacaa     60

tagccaagtt gcaatgcaac cgcgaactga ttttctcttt ctttctccag gtctccttgg    120

tcttcctaaa caatcaacag caacccccac ctccactgct ttctgtttgg tttggtttga    180

gtttgggatt ttgggctagc tctttttttct ttgtctgctt tctggtttcc cttcctccct    240

tccctatgta cgctcagagc ctcagacaga ccgtctgggc gcctcattcg cgtgagaagg    300

gccaggggga aggccaccag gccaggatgt aggcgaaacc gt                       342
```

<210> SEQ ID NO 38
<211> LENGTH: 315
<212> TYPE: DNA
<213> ORGANISM: Homo sapiens

<400> SEQUENCE: 38
tcgggggagg tgggacctga gcatgctgtg ttccagaaaa ggctggagca cagactcaga 60
gagagagaga gtggggtgga cgaggctgga gagattggca aagcccagat tatgagggtt 120
ttgtgggtca cagtgaggag cttgaacttc atccttctag tagattctag gctacccctt 180
cagacactcc ttaggaccag ggacacattc cccgagctgc caggagtgtt agcagctgac 240
agatcctggc tgggtatttc tctccaacaa agggagctgc ctccttcaca tctaatgact 300
gtaatgacct accac 315

<210> SEQ ID NO 39
<211> LENGTH: 127
<212> TYPE: DNA
<213> ORGANISM: Homo sapiens

<400> SEQUENCE: 39
tgcttttgag gctggagtgg taaaaggctc agaaaaatcc tgcgaagaaa aaaacttctg 60
aggtaataaa taggattatc ccgtatcgaa ggcctttttg gacaggtggt gtgtggtggc 120
ctggccc 127

<210> SEQ ID NO 40
<211> LENGTH: 408
<212> TYPE: DNA
<213> ORGANISM: Homo sapiens

<400> SEQUENCE: 40
gggggaggca cattctcact gaagataaag aactccgcat gccatcaccc cttcctcacc 60
acaaccccgc gaaacaaaag ctataaacac acacaagtca gaggatctat aaaccagtgg 120
gagaaaaaaa attagatgaa ggttaaccat taaaaagctg cagttgggaa aacacacact 180
cgattgttac atcagaaagt gccgtgggga gaagagccgt gtgctggtaa acatgtccgc 240
gctcagaact tgacatgcag aaaagagaga gcgccaagtc ccacctgaga ttagagagga 300
ctggttttta gtgtaacaca ctttgtttta aaatatcact gtcctcttct tgccccaatt 360
gctcctagaa cgtccctctg tcactcccct cccgggccag cctctccg 408

<210> SEQ ID NO 41
<211> LENGTH: 314
<212> TYPE: DNA
<213> ORGANISM: Homo sapiens

<400> SEQUENCE: 41
ggcgtggagg tacaagcagt cagttctcgg caggggccga ccgggcaact tccccccttg 60
tgtccctcta ccctgctttg gagtgccggg ccctcattca gcagatgtcc ccctctgcct 120
ttggtctgaa tgactgggat gatgatgaga tcctagcttc ggtgctggca gtgtcccaac 180
aggaatacct agacagtatg aagaaaaaca aagtgcacag agacccgccc ccagacaaga 240
gttgatggag acccagggat tggacaccat ctcccaaccc cagtactcct gctctccggt 300
gccacctcac cgcc 314

<210> SEQ ID NO 42
<211> LENGTH: 352
<212> TYPE: DNA
<213> ORGANISM: Homo sapiens

<400> SEQUENCE: 42
tctggggagg tggtccccat gtctgtcgta ggacagcaac aggttgtaca tctggcaggc 60

```
aaaggttttg ttgggctgga ggatgaggat gtgtaacact gtgtttccca gggagtcctg    120

ggcccggatg tcagctccat gctcaatgag cagccgcacg atctcctcac tgttcacaca    180

ggcagcaaag gacaaagggt gctccccaaa gtagatgagg ttgcagggac tacggcggaa    240

ggcagtgcct gtggctctgg cagagacact ggccctgcgg gcaagcaggg ctcgcaccag    300

gttcatgttc tggttcacaa cagcgatgtg cagtgcagtc tgacctccat cc            352


<210> SEQ ID NO 43
<211> LENGTH: 292
<212> TYPE: DNA
<213> ORGANISM: Homo sapiens

<400> SEQUENCE: 43

ggctgggggt aaggaccctg acagggcctc aggtggggac ttgcgcttca ggccgggatc     60

aggtgctgtg aagctgcctg tggagctggc cttggctttc cggaactcct ccagcttctg    120

tcggtagtac ttgtaccctt ggctattggg ctcatacaga aagctgaatg cctggttctc    180

acggttgttc tggagggcaa tggtttccac ctcgggaccc ccgtccgcta tgaacctggc    240

caacttttct gcaaggttct tgacctcttc gtcctctggg ggtgaaactt tc            292


<210> SEQ ID NO 44
<211> LENGTH: 372
<212> TYPE: DNA
<213> ORGANISM: Homo sapiens

<400> SEQUENCE: 44

ttcttagttt aagtgccagt gatcctgctt tgtacctctt caactatgat tcagttttta     60

caagtgaggt tcaattaagc tgagatgtag ttgaaatatt tgagcaccag aatcaccttc    120

tgaactccca atcatctggg gcttaggtgt agttacctcc caggaacaga tctcccagcc    180

caaggtccca cattgtacct tgatgtttct ttactgccta tcaaaatgag ccccaggtac    240

ctacgttatt actgggtttt gctctccaat ttccttattt tcccttgctc ccaaccacat    300

caacagaaca acaacaaaaa gaatccttta tcttcatgca acactacagt agtacagagc    360

aaagaactgg tg                                                        372


<210> SEQ ID NO 45
<211> LENGTH: 158
<212> TYPE: DNA
<213> ORGANISM: Homo sapiens

<400> SEQUENCE: 45

aggcctgaga gggaagtttc tggagttcag atactctctg ttgggaacag gacatctcaa     60

cagtctcagg ttcgatcagt gggtcttttg gcactttgaa ccttgaccac agggaccaag    120

aagtggcaat gaggacacct gcaggagggg ctagcctt                            158


<210> SEQ ID NO 46
<211> LENGTH: 157
<212> TYPE: DNA
<213> ORGANISM: Homo sapiens

<400> SEQUENCE: 46

gagggcttaa gaaagtaccc agctctgggt ccaataaaga ctcttgttat ctgtcagcac     60

tgcatgtggt agcatgggca aaaggcatta agaaagtaaa tatacgtccc tgtgttcccc    120

ttgctctccc tccatgcctg ctcttttctt caccctg                             157
```

<210> SEQ ID NO 47
<211> LENGTH: 310
<212> TYPE: DNA
<213> ORGANISM: Homo sapiens

<400> SEQUENCE: 47
aggacagcac tgacagcgag tggccctgga tcgtgagcat ccagaagaat gggacccacc 60
actgcgcagg ttctctgctc accagccgct gggtgatcac tgctgcccac tgtttcaagg 120
agtatgtaca gccggcctgg ggcacttgat cttctaaggc cctgggcttt gtgccccagg 180
ccctgggctc cctttacagg ctctgcttcc gggcctctgt tcaatcttgg tgcccctcga 240
ttctacctag aagcctctcc tgccttcagg ggccttcaca cccatgctgt tcccccaggt 300
acctcctccc 310

<210> SEQ ID NO 48
<211> LENGTH: 124
<212> TYPE: DNA
<213> ORGANISM: Homo sapiens

<400> SEQUENCE: 48
cccggcacct ggggaagggg gagtagagct aagagataga aaaactctag actcaccgat 60
caccaagctc atttggtcgg tagggcccgc ccaccggact tgagaacaca cacattctct 120
aagg 124

<210> SEQ ID NO 49
<211> LENGTH: 191
<212> TYPE: DNA
<213> ORGANISM: Homo sapiens

<400> SEQUENCE: 49
aatctcctaa tattaatggc aggtattata gtaaaattat catttcccct gaagagaatg 60
ttacattaac ttgcacagca gaaaaccaac tggagagaac agtaaactcc ttgaatgtct 120
ctgctaatga aaacagagaa aaggtgaatg accaggcaaa actaattgtg ggaatcgttg 180
ttggtctcct c 191

<210> SEQ ID NO 50
<211> LENGTH: 305
<212> TYPE: DNA
<213> ORGANISM: Homo sapiens

<400> SEQUENCE: 50
ccgaagtttt tctgtcacct gtgttaggct ccgtcccctt tccgcgtttt atccccgtac 60
cagaaaagga tacatttagt gcctcccacc cagctccact aaacgggttg gatatctcat 120
tctttgagtt ggtgttcctt ccccggcgcc cccatgtagc tgggaagtgg gacctggggg 180
tggttggacc cctgggatcc taaaggaggg gcagggaggg cgcagaactc cgcttctgct 240
ccttgctacc aggacgcgcg gcctcctcag cctctttcct cccgctgcca tgcaccctac 300
gctcg 305

<210> SEQ ID NO 51
<211> LENGTH: 108
<212> TYPE: DNA
<213> ORGANISM: Homo sapiens

<400> SEQUENCE: 51
ggctgacagg gtgggattct cgctccttca tttcaggtta ctcgttcttc agcaagttgg 60

```
caaaacagac atcatgctgg tgagtgccac gttactcccc tggggtgc              108


<210> SEQ ID NO 52
<211> LENGTH: 439
<212> TYPE: DNA
<213> ORGANISM: Homo sapiens

<400> SEQUENCE: 52

cgcggcgagg ggagaggtct ccttgagtcc cacctgagct gcctcagtgc cccccagctg     60

ctgcaggtga gggcctgtca ccatcaagcc atcagtggga caaaaaactt gggccctcaa    120

cccaccagca ctgctctgca ttctctgaag ccctggagat aagctgggga ccatggcccc    180

cacactctca gacacagatg acacaagtgg gaccattctg agcctaagag attttaccaa    240

aaatacctca atatggtttg gctacgtccc cacccaaatc ttatcttgaa ttgtaatcgc    300

cgtaatcccc acgtgttgag ggagggatcc agtggaaggt gattaggtca tggaggtggt    360

tttccccatg ctgttctcat gatagtgagg gagttttcac aagatctgat ggttttataa    420

gccagtttcc cctccggcc                                                 439


<210> SEQ ID NO 53
<211> LENGTH: 234
<212> TYPE: DNA
<213> ORGANISM: Homo sapiens

<400> SEQUENCE: 53

ccgagacagg accaactcac acacctgcca gaaagcctca ctctccagcc tcaggaccaa     60

cttacacacc tgccagaaag cctcactctc cagcctcagg accaacttac acacctgcca    120

gaaagcctca ctctccagcc tcaggaccaa cttacacacc tgctagaaag cctcactctc    180

cagcctcagg accaacttac acacctgcca gaaagcctca ctctcctccc cggg          234


<210> SEQ ID NO 54
<211> LENGTH: 92
<212> TYPE: DNA
<213> ORGANISM: Homo sapiens

<400> SEQUENCE: 54

gcctgcgagg agctttattc ttccagctta atatggttgc tgcgggaaca ctgcaggatg     60

aaactgactt tttttgtggt gatgtttctc ct                                   92


<210> SEQ ID NO 55
<211> LENGTH: 164
<212> TYPE: DNA
<213> ORGANISM: Homo sapiens

<400> SEQUENCE: 55

cgggggtacc tgtaccgtgg aacatggaag ggaagaggag gcaagtacag cagtcctggg     60

tctacattca caaatcagca tactgatagc ttgctggata ttatatcaag acataaaaat    120

tgacacacac ggtctctctt tctctctctc atggaggttc ctgc                     164


<210> SEQ ID NO 56
<211> LENGTH: 202
<212> TYPE: DNA
<213> ORGANISM: Homo sapiens

<400> SEQUENCE: 56

tggggtggac caggagaaac tgaaaactga attaaggaag acttcagatg ccctttctaa     60
```

-continued

```
ggcacaaaat gatgtgatgg aaatgaagat gcagtcagag agattttcga aagaatatga    120

tcaactcctg aaagaacact ctgaacttca ggtttttgtc tattctactt aactacctcc    180

ttatgaggaa gtggtctctc ca                                              202
```

<210> SEQ ID NO 57
<211> LENGTH: 314
<212> TYPE: DNA
<213> ORGANISM: Homo sapiens

<400> SEQUENCE: 57

```
caggggggagg agttcagagc ttacggtgag ccgccatcac gctattgcac tccaacttgg     60

gtgacagacc gagatcctag cttaaaaaaa aaaagaagtt ggtggggaaa atgggaaaat    120

agggtgccat gaaaaagaaa aagaaaaaca caccataatg gcattgtaag ttgggcttac    180

aactgttgtt tactttctta aagttttctg aggatgtaag aggaaaaaaa tattgtaaac    240

cttcaagatc tacttgtaat taaaattccc tgctgcttaa aaaagagtga aatctttgga    300

aggtcctccc ccca                                                       314
```

<210> SEQ ID NO 58
<211> LENGTH: 92
<212> TYPE: DNA
<213> ORGANISM: Homo sapiens

<400> SEQUENCE: 58

```
ggacgggacc acagttctaa acgaataaac gaatgagacg caaatttttt atgttcagtc     60

ctttcatctc tatgaaaacc ctatatggtc gt                                    92
```

<210> SEQ ID NO 59
<211> LENGTH: 179
<212> TYPE: DNA
<213> ORGANISM: Homo sapiens

<400> SEQUENCE: 59

```
cggggccagg atcccagagc cacagccaac atcaagaacg atcttgtcct tgaagtcggt     60

gtggttttgc aggatggcgc gctggtaggt gcctgtccgt ttttagtcct gcatcatgtt    120

ctgctgctgg gacaggtagc cataaaactg gaagtacttc tttgcagaag actcctctt     179
```

<210> SEQ ID NO 60
<211> LENGTH: 89
<212> TYPE: DNA
<213> ORGANISM: Homo sapiens

<400> SEQUENCE: 60

```
tcgcggggag gcgtgaatat tgtggggctg aatcctcagg gccgtggggg gctgcatggc     60

tgatgaccat gaggactggc ctcccgccc                                        89
```

<210> SEQ ID NO 61
<211> LENGTH: 169
<212> TYPE: DNA
<213> ORGANISM: Homo sapiens

<400> SEQUENCE: 61

```
tgggggttcc aggtatagga gggcaggctg agcatgcttg aagatgtgca tgatgaagat     60

ggtaaggccc aggccgaaga tgtaggctgc aaagctggtg tagaagtagg tgtgggtatt    120

cttcttcaag ctgatgtcaa agcgcagcag caaggcaatg aagatccat                 169
```

```
<210> SEQ ID NO 62
<211> LENGTH: 171
<212> TYPE: DNA
<213> ORGANISM: Homo sapiens

<400> SEQUENCE: 62

cagcggtacc atagttcact aggaaaggca ctcatccacc aagttcagag aggtggccat     60

ccgcattgct aaacagaata aaacaaaaat tcactttgtc attttcctga cattggcctt    120

gctataagat agcctcataa actgcctgaa aggccttatt tttttcaaag g             171


<210> SEQ ID NO 63
<211> LENGTH: 140
<212> TYPE: DNA
<213> ORGANISM: Homo sapiens

<400> SEQUENCE: 63

aaggcaattc ttaggtactc tcgtgattga acctctgcac caaagaggga aaagtataag     60

ttagaaagga atttataagc accatacaca aaaatagcca tgactcaggc ctccacatct    120

catttgtgct gtcacttccc                                                140


<210> SEQ ID NO 64
<211> LENGTH: 195
<212> TYPE: DNA
<213> ORGANISM: Homo sapiens

<400> SEQUENCE: 64

tatttggagg ggggtatggg agggaaagag cttaggaaac ggctctccct gcaaagtcca     60

accaaacttt aacgttaacc aaaccattaa tgttgccatg aatttgaagt gaaccagagg    120

gaggtggcag aagaagctta atggggaata gttccggtag agaaatgagg cttaagatga    180

actacccttc tccca                                                     195


<210> SEQ ID NO 65
<211> LENGTH: 397
<212> TYPE: DNA
<213> ORGANISM: Homo sapiens
<220> FEATURE:
<221> NAME/KEY: misc_feature
<222> LOCATION: (364)..(364)
<223> OTHER INFORMATION: n = a t c or g

<400> SEQUENCE: 65

tgccagctga ataaactcag tcacctggtt tcccatctct aagcccctta acctgcagct     60

tcgtttaatg tagctcttgc atgggagttt ctaggatgaa acactcctcc atgggatttg    120

aacatatgaa agttatttgt aggggaagag tcctgagggg caacacacaa gaaccaggtc    180

ccctcagccc acagcactgt ctttttgctg atccaccccc ctcttacctt ttatcaggat    240

gtggcctgtt ggtccttctg ttgccatcac agagacacag gcatttaaat atttaactta    300

tttatttaac aaagtagaag ggaatccatt gctagctttt ctgtgttggt gtctaatatt    360

tggngtaggg tgggggatcc ccaacaatca ggtcccc                             397


<210> SEQ ID NO 66
<211> LENGTH: 2799
<212> TYPE: DNA
<213> ORGANISM: Homo sapiens

<400> SEQUENCE: 66

ctcacacacc ctgaagacac agtgagttag caccaccacc aggaattggc cttttagctc     60
```

-continued

```
tgtgcctgtc tccagtcagg ctggaataag tctcctcata tttgcaagct cggccctccc    120

ctggaatcta aagcctcctc agccttctga gtcagcctga aaggaacagg ccgaactgct    180

gtatgggctc tactgccagt gtgacctcac cctctccagt caccccctcct cagttccagc   240

tatgagttcc tgcaacttca cacatgccac ctttgtgctt attggtatcc caggattaga    300

gaaagcccat ttctgggttg gcttcccccct cctttccatg tatgtagtgg caatgtttgg   360

aaactgcatc gtggtcttca tcgtaaggac ggaacgcagc ctgcacgctc cgatgtacct    420

ctttctctgc atgcttgcag ccattgacct ggccttatcc acatccacca tgcctaagat    480

ccttgccctt ttctggtttg attcccgaga gattagcttt gaggcctgtc ttacccagat    540

gttctttatt catgccctct cagccattga atccaccatc ctgctggcca tggcctttga    600

ccgttatgtg gccatctgcc acccactgcg ccatgctgca gtgctcaaca atacagtaac    660

agcccagatt ggcatcgtgg ctgtggtccg cggatccctc tttttttcc cactgcctct     720

gctgatcaag cggctggcct tctgccactc caatgtcctc tcgcactcct attgtgtcca    780

ccaggatgta atgaagttgg cctatgcaga cactttgccc aatgtggtat atggtcttac    840

tgccattctg ctggtcatgg gcgtggacgt aatgttcatc tccttgtcct attttctgat    900

aatacgaacg gttctgcaac tgccttccaa gtcagagcgg gccaaggcct ttggaacctg    960

tgtgtcacac attggtgtgg tactcgcctt ctatgtgcca cttattggcc tctcagttgt   1020

acaccgcttt ggaaacagcc ttcatcccat tgtgcgtgtt gtcatgggtg acatctacct   1080

gctgctgcct cctgtcatca atcccatcat ctatggtgcc aaaaccaaac agatcagaac   1140

acgggtgctg gctatgttca agatcagctg tgacaaggac ttgcaggctg tgggaggcaa   1200

gtgaccctta acactacact tctccttatc tttattggct tgataaacat aattatttct   1260

aacactagct tatttccagt tgcccataag cacatcagta cttttctctg gctggaatag   1320

taaactaaag tatggtacat ctacctaaag gactattatg tggaataata catactaatg   1380

aagtattaca tgatttaaag actacaataa aaccaaacat gcttataaca ttaagaaaaa   1440

caataaagat acatgattga aaccaagttg aaaaatagca tatgccttgg aggaaatgtg   1500

ctcaaattac taatgattta gtgttgtccc tactttctct ctctttttc tttctttttt    1560

ttttattatg gttagctgtc acatacaact tttttttttt tgagatgggg tctcgctctg   1620

tcaccaggct ggagtgcagt ggcgcgatct cggctcactg caacctccac atcccatgtt   1680

gaagtaattc ttctgcctca gcctcccgag tagctgggac tagaggaacg tgccaccatg   1740

actggctaat ttctgtattt ttttagtaga gacagagttt caccatgttg gccaggatgg   1800

tctcgatctc ctgaccttgt gatccacccg cctcagcctc ccaaagtgtt gggattacag   1860

gtgtgaacca ctgtgcccgg cctgtgtaca actttttaaa tagggaatat gatagcttcg   1920

catggtggtg tgcacctata gcccccactg cctggaaagc tgaggtggga gaatcgcttg   1980

agtccaggag tttgaggtta cagtgatcca cgatcgtacc actacactcc agcctgggca   2040

acggagcaag accctgtctc aaagcataaa atggaataac atatcaaatg aaacagggaa   2100

aatgaagctg acaatttatg gaagccaggg cttgtcacag tctctactgt tattatgcat   2160

tacctgggaa tttatataag cccttaataa taatgccaat gaacatctca tgtgtgctca   2220

caatgttctg gcactattat aagtgcttca caggttttat gtgttcttcg taactttatg   2280

gagtaggtac catttgtgtc tctttattat aagtgagaga aatgaagttt atattatcaa   2340

ggggactaaa gtcacacggc ttgtgggcac tgtgccaaga tttaaaatta aatttgatgg   2400

ttgaatacag ttacttaatg accatgttat attgcttcct gtgtaacatc tgccatttat   2460
```

```
ttcctcagct gtacaaatcc tctgttttct ctctgttaca cactaacatc aatggctttg   2520

tacttgtgat gagagataac cttgccctag ttgtgggcaa cacatgcaga ataatcctgt   2580

tttacagctg cctttcgtga tcttattgct tgctttttc cagattcagg gagaatgttg   2640

ttgtctattt gtctcttaca tctccttgat catgtcttca ttttttaatg tgctctgtac   2700

ctgtcaaaaa ttttgaatgt acaccacatg ctattgtctg aacctgagta taagataaaa   2760

taaaatttta ttttaaattt taaaaaaaaa aaaaaaaaa                          2799
```

<210> SEQ ID NO 67
<211> LENGTH: 1982
<212> TYPE: DNA
<213> ORGANISM: Homo sapiens

<400> SEQUENCE: 67

```
tactcaaagt cctaaaaatg gaaaggagaa aagggaatgt caacctcaag gacaactgag     60

atgttcacag aacttctgca gattctcgtc ccccacctca cctcacaaat gctaacctgt    120

ggacagtcct cctgtccaac agtcctggca gcttataagc ttccatctat aggaaattgg    180

taatgtagac accgagactg ggtgggttgc agaacaaatg tcatgctctg accaagatgg    240

ataagctcac aatgagttgg ggactttcct aaaagccagg gcactagtag tcacatggcc    300

actgttgtag ctacgtgaac atggtagtgg tggtgaagat ggaaataaga ggaaacatgc    360

aaaagatttt tagaaggaaa aatagacaag atcggttgaa taattggatg tgaaggatga    420

ggaaatgcta tgtatcttaa gttcctgtct cacatgacta aattcataag cacttccact    480

tcgtcctcct caaattcacc ctcccaacag cttctggaat agcaatctga aacacatgtc    540

tagttgtgat gtccctgctt aaaaccattt attcacctcc caattcctac aggatgaagt    600

ccttgagttc acagcatatc atcagttcac atccattgac ctctccagtt tctctttcct    660

ttttggttga ctctatgctt cagccaagct acaactcttc gtaattcttc tatagaaaat    720

tctgtttctt tcatgatttt ctgcctgctg aaataccctc tttttggacc cacccaatga    780

ctaaataaat acccttctca agttcctata aaaatctgtg gcattcactg ctctttcata    840

ccatttcagg tttgtttggg taggtgtgta tgaccaccct gaaggcaagg actttgtctt    900

attcacctct ggcaccctaa actcagcaca gtgcctgcac aaaactagcc ttgagaatgt    960

gcttattaca caatgaatga attaattaac tccattgcca gatatagatg accaataaat   1020

acttaatggc tgatggaagt acttctgttt ctgtgttcaa agattacagt gacaatgaca   1080

aagcaagact catgtgtgag gcatacttag aaaggatggc agatagaaca ggttagtgtt   1140

aaatattaat aaagtatgaa ggtaaccctg ctgggtatga cgtaggggac acgtcactgg   1200

aagacagcca tcaagcatca tgaggtactg aggatacctc aatatcctgg agaaggtagt   1260

tggggtgagt ttttttatc tattttgctt ataacattgt aagcctttga caaacatttg   1320

tttaatgtga ataaacagtc ggaatacctg gttctccaac caatattatc actaattaac   1380

tatatgacct aggacaaaaa gctgtcatat catctgggct ttatctgtaa tctaggagca   1440

atgaagagca gctttgatac attaagggct gttttgttaa ccagaagaaa ggttagggaa   1500

agatatggag aattgcatgc ccctattttg aattatggaa ctatactttt gtatttttag   1560

agaggatgca aactcctaaa gcccaaggac catgcctagt cacatatgat gtctgctggt   1620

catgggcgtg gacgtaatgt tcatctcctt gtcctatttt ctgataatac gaacggttct   1680

gcaactgcct tccaatcaga gcgggccaag gcctttggaa cctgtgtgtc acacattggt   1740
```

-continued

```
gtggtactcg ccttctatgt gccacttatt ggcctctcag tggtacaccg ctttggaaac   1800

agccttcatc ccattgtgcg tgttgtcatg ggtgacatct acctgctgct gcctcctgtc   1860

atcaatccca tcatctatgg tgccaaaacc aaacagatca gaacacgggt gctggctatg   1920

ttcaagatca gctgtgacaa ggacttgcag gctgtgggag gcaagtgacc cttaacacta   1980

ca                                                                  1982
```

<210> SEQ ID NO 68
<211> LENGTH: 2306
<212> TYPE: DNA
<213> ORGANISM: Homo sapiens

<400> SEQUENCE: 68

```
gagatactca aagtcctaaa aatggaaagg agaaaaggga atgtcaacct caaggacaac     60

tgagatgttc acagaacttc tgcagattct cgtcccccac ctcacctcac aaatgctaac    120

ctgggacagt cctcctgtcc aacagtcctg gcagcttata agcttccatc tataggaaat    180

tggtaatgta gacaccgaga ctgggtgggt tgcagaacaa atgtcatgct ctgaccaaga    240

tggataagct cacaatgagt tggggacttt cctaaaagcc agagcactag tagtcacatg    300

gccactgttg tagctacgtg aacatggtag tggtggtgaa gatggaaata agaggaaaca    360

tgcaaaagat ttttagaagg aaaaatagac aagatcggtt gaataattgg atgtgaagga    420

tgaggaaatg ctatgtatct taagttcctg tctcacatga ctaaattcat aagcacttcc    480

acttcgtcct cctcaaattc accctcccaa cagcttctgg aatagcaatc tgaaacacat    540

gtctagttgt gatgtccctg cttaaaacca tttattcacc tcccaattcc tacaggatga    600

agtccttgag ttcacagcat atcatcagtt cacatccatt gacctctcca gtttctcttt    660

ccttttggt tgactctatg cttcagccaa gctacaactc ttcgtaattc ttctatagaa    720

aattctgttt ctttcatgat tttctgcctg ctgaaatacc ctcttttgg acccacccaa    780

tgactaaata aataccttc tcaagttcct ataaaaatct gtggcattca ctgctctttc    840

ataccatttc aggtttgttt gggtaggtgt gtatgaccac cctgaaggca aggactttgt    900

cttattcacc tctggcaccc taaactcagc acagtgcctg cacaaaagta gccttgagaa    960

tgtgcttatt acacaatgaa tgaattaatt aactccattg ccagatatag atgaccaata   1020

aatacttaat ggctgatgga agtacttctg tttctgtgtt caaagattac agtgacaatg   1080

acaaagcaag actcatgtgt gaggcatact tagaaaggat ggcagataga acaggttagt   1140

gttaaatatt aataaagtat gaaggtaacc ctgctgggta tgacgtaggg gacacgtcac   1200

tggaagacag ccatcaagca tcatgaggta ctgaggatac atcaatatcc tggagaaggt   1260

agttgggact gccagtgtga cctcaccctc tccagtcacc cctcctcagt tccagctatg   1320

agttcctgca acttcacaca tgccaccttt gtgcttattg gtatcccagg attagagaaa   1380

gcccatttct gggttagctt ccccctcctt tccatgtatg tagtggcaat gtttggaaac   1440

tgcatcgtgg tcttcatcgt aaggacggaa cgcagcctgc acgctccgat gtacctcttt   1500

ctctgcatgc ttgcagccat tgacctggcc ttatccacat ccaccatgcc taagatcctt   1560

gcccttttct ggtttgattc ccgagagatt agctttgagg cctgtcttac ccagatgttc   1620

tttattcatg ccctctcagc cattgaatcc accatcctgc tggccatggc ctttgaccgt   1680

tatgtggcca tctgccaccc actgcgccat gctgcagtgc tcaacaatac agtaacagcc   1740

cagattggca tcgtggctgt ggtccgcgga tccctctttt ttttcccact gcctctgctg   1800

atcaagcggc tggccttctg ccactccaat gtcctctcgc actcctattg tgtccaccag   1860
```

-continued

```
gatgtaatga agttggccta tgcagacact ttgcccaatg tggtatatgg tcttactgcc   1920

attctgctgg tcatgggcgt ggacgtaatg ttcatctcct tgtcctattt tctgataata   1980

cgaacggttc tgcaactgcc ttccaagtca gagcgggcca aggcctttgg aacctgtgtg   2040

tcacacattg gtgtggtact cgccttctat gtgccactta ttggcctctc agttgtacac   2100

cgctttggaa acagccttca tcccattgtg cgtgttgtca tgggtgacat ctacctgctg   2160

ctgcctcctg tcatcaatcc catcatctat ggtgccaaaa ccaaacagat cagaacacgg   2220

gtgctggcta tgttcaagat cagctgtgac aaggacttgc aggctgtggg aggcaagtga   2280

cccttaacac tacacttctc cttatc                                        2306
```

```
<210> SEQ ID NO 69
<211> LENGTH: 2767
<212> TYPE: DNA
<213> ORGANISM: Homo sapiens

<400> SEQUENCE: 69
```

```
gagatactca aagtcctaaa aatggaaagg agaaaaggga atgtcaacct caaggacaac     60

tgagatgttc acagaacttc tgcagattct cgtcccccac ctcacctcac aaatgctaac    120

ctgtggacag tcctcctgtc caacagtcct ggcagcttat aagcttccat ctataggaaa    180

ttggtaatgt agacaccgag actgggtggg ttgcagaaca aatgtcatgc tctgaccaag    240

atggataagc tcacaatgag ttggggactt tcctaaaagc cagagcacta gtagtcacat    300

ggccactgtt gtagctacgt gaacatggta gtggtggtga agatggaaat aagaggaaac    360

atgcaaaaga tttttagaag gaaaaataga caagatcggt tgaataattg gatgtgaagg    420

atgaggaaat gctatgtatc ttaagttcct gtctcacatg actaaattca taagcacttc    480

cacttcgtcc tcctcaaatt caccctccca acagcttctg gaatagcaat ctgaaacaca    540

tgtctagttg tgatgtccct gcttaaagcc atttattcac ctcccaattc ctacaggatg    600

aagtccttga gttcacagca tatcatcagt tcacatccat tgacctctcc agtttctctt    660

tcctttttgg ttgactctat gcttcagcca agctacaact cttcgtaatt cttctataga    720

aaattctgtt tctttcatga ttttctgcct gctgaaatac cctctttttg gacccaccca    780

atgactaaat aaataccctt ctcaagttcc tataaaaatc tgtggcattc actgctcttt    840

cataccattt caggtttgtt tgggtaggtg tgtatgacca ccctgaaggc aaggactttg    900

tcttattcac ctctggcacc ctaaactcag cacagtgcct gcacaaaagt agccttgaga    960

atgtgcttat tacacaatga atgaattaat taactccatt gccagatata gatgaccaat   1020

aaatgcttaa tggctgatgg aagtacttct gtttctgtgt tcaaagatta cagtgacaat   1080

gacgaagcaa gactcatgtg tgaggcatac ttagaaagga tggcagatag aacaggttag   1140

tgttaaatat taataaagta tgaaggtaac cctgctgggt atgacgtagg ggacacgtca   1200

ctggaagaca gccatcaagc atcatgaggt actgaggata catcaatatc ctggagaagg   1260

tagttggggt gagttttttt tatctatttt gcttataaca ttgtaagcct ttgacaaaca   1320

tttgtttaat gtgaataaac agtcggaata cctggttctc caaccaatat tatcactaat   1380

tagctatatg acctaggaca aaaagctgtc atatcatctg ggctttatct gtaatctagg   1440

agcaatgaag agcagctttg atacattaag ggctgttttg ttaaccagaa gaaaggttag   1500

ggaaagatat ggagaattgc atgcccctat tttgaattat ggaactatac ttttgtattt   1560

ttagagagga tgcaaactcc taaagcccaa ggaccatgcc tagtcacata tgatgtctgc   1620
```

-continued

```
tgcgtctagc agagtggcac atgaagaaac acactaatcc tgtggctgac tgtgtgtgct   1680
tggtttagct tggagaagtg ggagcagatt gtcgagagcc ctgtatatac tgccagtgtg   1740
acctcaccct ctccagtcac ccctcctcag ttccagctat gagttcctgc aacttcacac   1800
atgccacctt tgtgcttatt ggtatcccag gattagagaa agcccatttc tgggttggct   1860
tccccctcct ttccatgtat gtagtggcaa tgtttggaaa ctgcatcgtg gtcttcatcg   1920
taaggacgga acgcagcctg cacgctccga tgtacctctt tctctgcatg cttgcagcca   1980
ttgacctggc cttatccaca tccaccatgc ctaagatcct tgcccttttc tggtttgatt   2040
cccgagagat tagctttgag gcctgtctta cccagatgtt ctttattcat gccctctcag   2100
ccattgaatc caccatcctg ctggccatgg cctttgaccg ttatgtggcc atctgccacc   2160
cactgcgcca tgctgcagtg ctcaacaata cagtaacagc ccagattggc atcgtggctg   2220
tggtccgcgg atccctcttt tttttcccac tgcctctgct gatcaagcgg ctggccttct   2280
gccactccaa tgtcctctcg cactcctatt gtgtccacca ggatgtaatg aagttggcct   2340
atgcagacac tttgcccaat gtggtatatg gtcttactgc cattctgctg gtcatgggcg   2400
tggacgtaat gttcatctcc ttgtcctatt ttctgataat acgaacggtt ctgcaactgc   2460
cttccaagtc agagcgggcc aaggcctttg gaacctgtgt gtcacacatt ggtgtggtac   2520
tcgccttcta tgtgccactt attggcctct cagtggtaca ccgctttgga aacagccttc   2580
atcccattgt gcgtgttgtc atgggtgaca tctacctgct gctgcctcct gtcatcaatc   2640
ccatcatcta tggtgccaaa accaaacaga tcagaacacg ggtgctggct atgttcaaga   2700
tcagctgtga caaggacttg caggctgtgg gaggcaagtg acccttaaca ctacacttct   2760
ccttatc                                                             2767
```

<210> SEQ ID NO 70
<211> LENGTH: 322
<212> TYPE: DNA
<213> ORGANISM: Homo sapiens

<400> SEQUENCE: 70

```
tgtgaacatc tcagttgtcc ttgaggttga cattcccttt tctcctttcc atttttagga     60
ctttgagtat ctccgtgtgg gtgagaaagt ccaattcatc tagagtcaag cattttcact    120
gaacaaaaca gttttactta cagagcccat acagcagttc ggcctgttcc tttcaggctg    180
actcagaagg ctgaggaggc tttagattcc aggggagggc cgagcttgca aatatgagga    240
gacttattcc agcctgactg gagacaggca cagagctgaa aggccaattc ctggtggtgg    300
tgctaactca ctgtgtcttc ag                                             322
```

<210> SEQ ID NO 71
<211> LENGTH: 206
<212> TYPE: DNA
<213> ORGANISM: Homo sapiens

<400> SEQUENCE: 71

```
gaatctaaag cctcctcagc ccaccatacc aacatctaat ctaattctgc acattgtgag     60
gaaattactc cctgtgggtg agaaagtcca attcatctag agtcaagcat tttcattgaa    120
caaaacagtt ttacttacag agcccataca gcagttcggc ctgttccttt caggctgact    180
cagaaggctg aggaggcttt agattc                                         206
```

<210> SEQ ID NO 72
<211> LENGTH: 4344

<212> TYPE: DNA
<213> ORGANISM: Homo sapiens

<400> SEQUENCE: 72

```
ctgggtccca tttctctgga acacagtggt ctagtgatct gacctctctt cagggaaggt     60
tccttagttc tgtcccatat atttcagtat gatttgttta aagttctata tccccttccc    120
caagctatga cggatacaga aatggatgga tggatgcaag atgcaaacta tcttgtatct    180
cactaaagga tgcaatcatc tgcttctgaa aagggctttt catgttctga tagcaactgg    240
gagccaaata tgggatttaa tatttgtcaa ggagcttagc tgttttgtct gcacaagttc    300
tgaaggtgga gaagagaaaa tacaggcaga agtatgggtt ttgtaacctt caaaccccaa    360
atctgtcctt ctttgcttat ccaagatggg gagaatccag ttcaaatctc tttgtactaa    420
ttttatcata ttgtacttta agatcactgg tatctaaccc ctctacatta aggccaaact    480
gaagggcatc tcccagctgc agtaagaact cagatgatga gtgaagaatt ctggggttgg    540
gggagtgcaa tataagcaag ctaacctgtt tcaatgaaac agatgatcaa tgaagacact    600
gcatcatttg tttccaaaag ttaggccttg cagccaaggc tttggctttt tagagaaaat    660
tagctctaaa gaccagggca cctaggcaac ctagcagaga agaagtttca tgaagtcaga    720
gcccaggtgt ttgggtgagg gtagggagtt ggggcaaagc aacactgggc ttctaaaaaa    780
gaaatgtctc ccctgagatg aatgacttgt tggcacaagt ttcaggaaag acaaagctct    840
aaaaatatca ttgtaaaatt aataatactt ctccaaagta aggactcaac tcaaactatc    900
cttggatgca attaaaatgg ccttggaaga agctttcagg tgcggaggta ctcaccagtg    960
tcctgccagc accttcatct ctgaagaagt catcggaggg agccactacc ttgattttat   1020
gaccacagat gagtttcctt taatccgaaa gagattgact tttggcattt ttttcttagt   1080
ttttgtttat ttatattctt ttaagcttta aaaaaaagtg tcattgctgt gcttcttatt   1140
cctctggctg actttagaat tgaggactgg gaatcctgaa aatttgcaaa gttatctcct   1200
atcctcactg ccttggaaca cccattattc cactctgtct aatttctact catgtttcaa   1260
gtctaaacag gaagattcct ctgtgatcat gcctctccct ttctcatgaa ttaaatgcat   1320
atattatgct agtaatgctt ctggaatgaa tgaataatag aaagaaagaa agtgggggga   1380
gggaagcagg gaaagtaaaa tgagaaaggc agccttatct ggaaggagct cccaaaagtg   1440
tatctcttaa cacctatcag aaaaaaaagg gccaacaaat atccaggcaa cgaaggtatg   1500
gaccagtagg aagaatctga gggaattaca ttttggaaaa agcattgctc tcccaagatt   1560
ccctttttaaa aatttaaata aaccttgaga gtagtgatgc ataaatgaat ttgatctgtc   1620
acagtcccgc ctttggaaga gggcctcaga gcttatgaaa gaccctaagt gggggtggga   1680
gaagacaaaa ggggtgggat gtcagtttca agtttccagg gcattctctg attgtgctct   1740
atgtccctgc agactgccag tgtgacctca ccctctccag tcacccctcc tcagttccag   1800
ctatgagttc ctgcaacttc acacatgcca cctttgtgct tattggtatc ccaggattag   1860
agaaagccca tttctgggtt ggcttccccc tcctttccat gtatgtagtg gcaatgtttg   1920
gaaactgcat cgtggtcttc atcgtaagga cggaacgcag cctgcacgct ccgatgtacc   1980
tctttctctg catgcttgca gccattgacc tggccttatc cacatccacc atgcctaaga   2040
tccttgccct tttctggttt gattcccgag agattagctt tgaggcctgt cttacccaga   2100
tgttctttat tcatgccctc tcagccattg aatccaccat cctgctggcc atggcctttg   2160
accgttatgt ggccatctgc cacccactgc gccatgctgc agtgctcaac aatacagtaa   2220
```

-continued

```
cagcccagat tggcatcgtg gctgtggtcc gcggatccct cttttttttc ccactgcctc   2280
tgctgatcaa gcggctggcc ttctgccact ccaatgtcct ctcgcactcc tattgtgtcc   2340
accaggatgt aatgaagttg gcctatgcag acactttgcc caatgtggta tatggtctta   2400
ctgccattct gctggtcatg ggcgtggacg taatgttcat ctccttgtcc tattttctga   2460
taatacgaac ggttctgcaa ctgccttcca agtcagagcg ggccaaggcc tttggaacct   2520
gtgtgtcaca cattggtgtg gtactcgcct tctatgtgcc acttattggc ctctcagtgg   2580
tacaccgctt tggaaacagc cttcatccca ttgtgcgtgt tgtcatgggt gacatctacc   2640
tgctgctgcc tcctgtcatc aatcccatca tctatggtgc caaaaccaaa cagatcagaa   2700
cacgggtgct ggctatgttc aagatcagct gtgacaagga cttgcaggct gtgggaggca   2760
agtgaccctt aacactacac ttctccttat ctttattggc ttgataaaca taattatttc   2820
taacactagc ttatttccag ttgcccataa gcacatcagt acttttctct ggctggaata   2880
gtaaactaaa gtatggtaca tctacctaaa ggactattat gtggaataat acatactaat   2940
gaagtattac atgatttaaa gactacaata aaaccaaaca tgcttataac attaagaaaa   3000
acaataaaga tacatgattg aaaccaagtt gaaaaatagc atatgccttg gaggaaatgt   3060
gctcaaatta ctaatgattt agtgttgtcc ctactttctc tctctttttt ctttcttttt   3120
tttttattat ggttagctgt cacatacaac tttttttttt tttgagatgg ggtctcgctc   3180
tgtcaccagg ctggagtgca gtggcgcgat ctcggctcac tgcaacctcc acatcccatg   3240
ttgaagtaat tcttctgcct cagcctcccg agtagctggg actagaggaa cgtgccacca   3300
tgactggcta attttctgta ttttttagta gagacagagt ttcaccatgt tggccaggat   3360
ggtctcgatc tcctgacctt gtgatccacc cgcctcagcc tcccaaagtg ttgggattac   3420
aggtgtgaac cactgtgccc ggcctgtgta caactttttta aatagggaat atgatagctt   3480
cgcatggtgg tgtgcaccta tagcccccac tgcctggaaa gctgaggtgg gagaatcgct   3540
tgagtccagg agtttgaggt tacagtgatc cacgatcgta ccactacact ccagcctggg   3600
caacagagca agaccctgtc tcaaagcata aaatggaata acatatcaaa tgaaacaggg   3660
aaaatgaagc tgacaattta tggaagccag ggcttgtcac agtctctact gttattatgc   3720
attacctggg aatttatata agcccttaat aataatgcca atgaacatct catgtgtgct   3780
cacaatgttc tggcactatt ataagtgctt cacaggtttt atgtgttctt cgtaacttta   3840
tggagtaggt accatttgtg tctctttatt ataagtgaga gaaatgaagt ttatattatc   3900
aaggggacta aagtcacacg gcttgtgggc actgtgccaa gatttaaaat taaatttgat   3960
ggttgaatac agttacttaa tgaccatgtt atattgcttc ctgtgtaaca tctgccattt   4020
atttcctcag ctgtacaaat cctctgtttt ctctctgtta cacactaaca tcaatggctt   4080
tgtacttgtg atgagagata accttgccct agttgtgggc aacacatgca gaataatcct   4140
gttttacagc tgcctttcgt gatcttattg cttgcttttt tccagattca gggagaatgt   4200
tgttgtctat ttgtctctta catctccttg atcatgtctt catttttttaa tgtgctctgt   4260
acctgtcaaa aattttgaat gtacaccaca tgctattgtc tgaacttgag tataagataa   4320
aataaaattt tattttaaat tttg                                          4344
```

<210> SEQ ID NO 73
<211> LENGTH: 2969
<212> TYPE: DNA
<213> ORGANISM: Homo sapiens

<400> SEQUENCE: 73

```
agcaacgacg ccgggcagcg ggagcggcgg ccgcgccatg tggctgctgg ggccgctgtg      60
cctgctgctg agcagcgccg cggagagcca gctgctcccc gggaacaact tcaccaatga     120
gtgcaacata ccaggcaact tcatgtgcag caatggacgg tgcatcccgg gcgcctggca     180
gtgtgacggg ctgcctgact gcttcgacaa gagtgatgag aaggagtgcc ccaaggctaa     240
gtcgaaatgt ggcccaacct tcttcccctg tgccagcggc atccattgca tcattggtcg     300
cttccggtgc aatgggtttg aggactgtcc cgatggcagc gatgaagaga actgcacagc     360
aaaccctctg ctttgctcca ccgcccgcta ccactgcaag aacggcctct gtattgacaa     420
gagcttcatc tgcgatggac agaataactg tcaagacaac agtgatgagg aaagctgtga     480
aagttctcaa gaacccggca gtgggcaggt gtttgtgact tcagagaacc aacttgtgta     540
ttaccccagc atcacctatg ccatcatcgg cagctccgtc atttttgtgc tggtggtggc     600
cctgctggca ctggtcttgc accaccagcg gaagcggaac aacctcatga cgctgcccgt     660
gcaccggctg cagcaccctg tgctgctgtc ccgcctggtg gtcctggacc acccccacca     720
ctgcaacgtc acctacaacg tcaataatgg catccagtat gtggccagcc aggcggagca     780
gaatgcgtcg gaagtaggct ccccaccctc ctactccgag gccttgctgg accagaggcc     840
tgcgtggtat gaccttcctc caccgcccta ctcttctgac acggaatctc tgaaccaagc     900
cgacctgccc ccctaccgct cccggtccgg gagtgccaac agtgccagct cccaggcagc     960
cagcagcctc ctgagcgtgg aagacaccag ccacagcccg gggcagcctg gcccccagga    1020
gggcactgct gagcccaggg actctgagcc cagccagggc actgaagaag tataagtccc    1080
agttattcca aagtccatat gggttaatct gctctgactt gttgccattc taacaatttg    1140
tgctcatggg aagctcttta agcacctgta aggatgtctc aagttacagt ttgggatatt    1200
aactatctct gcattcccct cctcccccag acttcagaga tgtttttctg gcgtctcagt    1260
tgacatgatc tgttgtgcgt cttttctgtc aggtcactct tcccttggga cccgagatca    1320
caccctcatt tttcacatta ttctgtttct gttggagaga cagcatataa aacagtattg    1380
aaataggctg ggagagagca atgtttctgt gctatattgg atgctcagaa gtgcaggaga    1440
cgctggaccc aattctctct gctgggtagt taccttatag catttgggga tttgggttag    1500
atgatctaac caggaggcca tcactggatg gtcacccccc caaaaaaatt ccatttgagc    1560
atcaaaacct gctttgcaca atcctatttg atgcccccag ttcagcagag tcagtggcca    1620
aagaaaactt tggacgtgag taacaccctt cagcagtcgc aacgttattt tggttttgtg    1680
aaggactctg aaaccatcta ccctgtataa attctggctt tagaaatttg cccaagaatg    1740
ctcattctga gagctttcct cagcagcata tatcatcagc ctcatcctaa aataggcagg    1800
gagcccctcc catgagttta tccaagttct cagctcctaa aatgcaggct gccaagaccc    1860
tacacctgcc ctggctctac agccacttac ctggtttctg gactgtcacc ctcccagctg    1920
acctgcccgt agccaaggaa tgaggaccta acttgagttg gcccaaagtc tgacctggct    1980
gtatgtccct gtggcccaca cccagcctgt cttgctcatt catgcagcct caacactggc    2040
ctccaaagtt cccttaacac ttgcaaagtc ctttttacct gtgcatttgg acttgaggac    2100
actggtttct atcacaggtg agagccatgt tcaatacctc cagcaagctc tcctggctcc    2160
ctgcactgtg cacgctcctc ttcccaaggt cccaatacca gcacctctag ttagagttag    2220
ggtcagggtc aggcctctcc caacatccca gtagtttctc ctctgagaca catgggcaag    2280
agacaatttg gagtcaagat tttccatttg gatctatttt aaatctttta gaaatgcatt    2340
```

-continued

```
tgaaacagtg tgtttgtttt ttcccttcta gttaagggac tatttatatg tgtataggaa   2400

agctgtctct ttttttgttt ttcctttaac aaggtccaaa gaaagatgca aaaggagatc   2460

acacccttgc cccgctgagc cccgtgataa caagtcactc cagactaacc tgtgtgccag   2520

acatttgtgc attgttgcac tttgaggtta ttatttatca agttcttgaa ggaagcagaa   2580

agagggactc ctctctccct ccgtgtatag tctctatgtt tgtgctagtt tttctttttt   2640

ttctctgtgt ccagtcagcc acagggcccg cctccctgca ggaataaggg gtaaaacgtt   2700

aggtgttgtt tggcaagaaa ccacactgac tgatgagggg taaaatggaa ccaggtagag   2760

ccactccggg cagctgtcac ccattcagaa cttctttccg cagctgaaga aatgttcagt   2820

aacctgtttg acgctaatta aaacagagcc tgcaggaagt ggggctaaag tggcattcag   2880

tgatcctgtt ctgtagactt ttctttcttt ttttaaccaa atccaaagga tgttacagaa   2940

aagctagcca ctggtatttt gttttgttt                                     2969
```

<210> SEQ ID NO 74
<211> LENGTH: 350
<212> TYPE: DNA
<213> ORGANISM: Homo sapiens

<400> SEQUENCE: 74

```
gccagtcatc acagtgtaac taatttaatg ctaaaataaa acacggatct catttgagaa     60

aaaaagagat gagactattt tctggttggc gtagatttag gcaatgtata aaaaagcttc    120

ctggttggaa tgagttaaaa aatattgctg gacactaatg tgccatcttg agttggaaaa    180

caaacccccct cccccaaaa aaaaccctgc cgctttggtg tcctatttat atatttttaa    240

aaacattcat taaaaaaatc aaatctataa taaaaatgtc cctgtttgtt ttaaaaaagc    300

attagtaggc atcccttatc tactaaaacc atttgttttt cctaagatgc               350
```

<210> SEQ ID NO 75
<211> LENGTH: 2006
<212> TYPE: DNA
<213> ORGANISM: Homo sapiens

<400> SEQUENCE: 75

```
agcaacgacg ccgggcagcg ggagcggcgg ccgcgccatg tggctgctgg ggccgctgtg     60

cctgctgctg agcagcgccg cggccaaggc taagtcgaaa tgtggcccaa ccttcttccc    120

ctgtgccagc ggcatccatt gcatcattgg tcgcttccgg tgcaatgggt ttgaggactg    180

tcccgatggc agcgatgaag agaactgcac agcaaaccct ctgctttgct ccaccgcccg    240

ctaccactgc aagaacggcc tctgtattga caagagcttc atctgcgatg gacagaataa    300

ctgtcaagac aacagtgatg aggaaagctg tgaaagttct caagaacccg gcagtgggca    360

ggtgtttgtg acttcagaga accaacttgt gtattacccc agcatcacct atgccatcat    420

cggcagctcc gtcatttttg tgctggtggt ggccctgctg gcactggtct tgcaccacca    480

gcggaagcgg aacaacctca tgacgctgcc cgtgcaccgg ctgcagcacc ctgtgctgct    540

gtcccgcctg gtggtcctgg accaccccca ccactgcaac gtcacctaca acgtcaataa    600

tggcatccag tatgtggcca gccaggcgga gcagaatgcg tcggaagtag gctccccacc    660

ctcctactcc gaggccttgc tggaccagag gcctgcgtgg tatgaccttc ctccaccgcc    720

ctactcttct gacacggaat ctctgaacca agccgacctg ccccccctacc gctcccggtc    780

cgggagtgcc aacagtgcca gctcccaggc agccagcagc ctcctgagcg tggaagacac    840

cagccacagc ccggggcagc ctggccccca ggagggcact gctgagccca gggactctga    900
```

-continued

```
gcccagccag ggcactgaag aagtataagt cccagttatt ccaaagtcca tatgggttaa    960

tctgctctga cttgttgcca ttctaacaat ttgtgctcat gggaagctct ttaagcacct   1020

gtaaggatgt ctcaagttac agtttgggat attaactatc tctgcattcc cctcctcccc   1080

cagacttcag agatgttttt ctggcgtctc agttgacatg atctgttgtg cgtcttttct   1140

gtcaggtcac tcttcccttg ggacccgaga tcacaccctc atttttcaca ttattctgtt   1200

tctgttggag agacagcata taaaacagta ttgaaatagg ctgggagaga gcaatgtttc   1260

tgtgctatat tggatgctca gaagtgcagg agacgctgga cccaattctc tctgctgggt   1320

agttacctta tagcatttgg ggatttgggt tagatgatct aaccaggagg ccatcactgg   1380

atggtcaccc ccccaaaaaa attccatttg agcatcaaaa cctgctttgc acaatcctat   1440

ttgatgcccc cagttcagca gagtcagtgg ccaaagaaaa ctttggacgt gagtaacacc   1500

cttcagcagt cgcaacgtta ttttggtttt gtgaaggact ctgaaaccat ctaccctgta   1560

taaattctgg ctttagaaat ttgcccaaga atgctcattc tgagagcttt cctcagcagc   1620

atatatcatc agcctcatcc taaaataggc agggagcccc tcccatgagt ttatccaagt   1680

tctcagctcc taaaatgcag gctgccaaga ccctacacct gccctggctc tacagccact   1740

tacctggttt ctggactgtc accctcccag ctgacctgcc cgtagccaag gaatgaggac   1800

ctaacttgag ttggcccaaa gtctgacctg gctgtatgtc cctgtggccc acacccagcc   1860

tgtcttgctc attcatgcag cctcaacact ggcctccaaa gttcccttaa cacttgcaaa   1920

gtccttttta cctgtgcatt tggacttgag gacactggtt tctatcacag gtgagagcca   1980

tgttcaatac ctccagcaag ctctcc                                        2006
```

<210> SEQ ID NO 76
<211> LENGTH: 3094
<212> TYPE: DNA
<213> ORGANISM: Homo sapiens

<400> SEQUENCE: 76

```
agcaacgacg ccgggcagcg ggagcggcgg ccgcgccatg tggctgctgg ggccgctgtg     60

cctgctgctg agcagcgccg cgggtctgtg actactttgc tccaatacca agatggacag    120

aacagccctt tgattaccca gggagactgt caagtttgca tctggtcaat ctctgtttta    180

tatataagga aactgaggca cagggtggag agccagctgc tccccgggaa caacttcacc    240

aatgagtgca acataccagg caacttcatg tgcagcaatg gacggtgcat cccgggcgcc    300

tggcagtgtg acgggctgcc tgactgcttc gacaagagtg atgagaagga gtgccccaag    360

gctaagtcga aatgtggccc aaccttcttc ccctgtgcca gcggcatcca ttgcatcatt    420

ggtcgcttcc ggtgcaatgg gtttgaggac tgtcccgatg gcagcgatga agagaactgc    480

acagcaaacc ctctgctttg ctccaccgcc cgctaccact gcaagaacgg cctctgtatt    540

gacaagagct tcatctgcga tggacagaat aactgtcaag acaacagtga tgaggaaagc    600

tgtgaaagtt ctcaagaacc cggcagtggg caggtgtttg tgacttcaga gaaccaactt    660

gtgtattacc ccagcatcac ctatgccatc atcggcagct ccgtcatttt tgtgctggtg    720

gtggccctgc tggcactggt cttgcaccac cagcggaagc ggaacaacct catgacgctg    780

cccgtgcacc ggctgcagca ccctgtgctg ctgtcccgcc tggtggtcct ggaccacccc    840

caccactgca acgtcaccta caacgtcaat aatggcatcc agtatgtggc cagccaggcg    900

gagcagaatg cgtcggaagt aggctcccca ccctcctact ccgaggcctt gctggaccag    960
```

-continued

```
aggcctgcgt ggtatgacct tcctccaccg ccctactctt ctgacacgga atctctgaac   1020

caagccgacc tgccccccta ccgctcccgg tccgggagtg ccaacagtgc cagctcccag   1080

gcagccagca gcctcctgag cgtggaagac accagccaca gcccggggca gcctggcccc   1140

caggagggca ctgctgagcc cagggactct gagcccagcc agggcactga agaagtataa   1200

gtcccagtta ttccaaagtc catatgggtt aatctgctct gacttgttgc cattctaaca   1260

atttgtgctc atgggaagct ctttaagcac ctgtaaggat gtctcaagtt acagtttggg   1320

atattaacta tctctgcatt cccctcctcc cccagacttc agagatgttt ttctggcgtc   1380

tcagttgaca tgatctgttg tgcgtctttt ctgtcaggtc actcttccct tgggacccga   1440

gatcacaccc tcatttttca cattattctg tttctgttgg agagacagca tataaaacag   1500

tattgaaata ggctgggaga gagcaatgtt tctgtgctat attggatgct cagaagtgca   1560

ggagacgctg gacccaattc tctctgctgg gtagttacct tatagcattt ggggatttgg   1620

gttagatgat ctaaccagga ggccatcact ggatggtcac ccccccaaaa aaattccatt   1680

tgagcatcaa aacctgcttt gcacaatcct atttgatgcc cccagttcag cagagtcagt   1740

ggccaaagaa aactttggac gtgagtaaca cccttcagca gtcgcaacgt tattttggtt   1800

ttgtgaagga ctctgaaacc atctaccctg tataaattct ggctttagaa atttgcccaa   1860

gaatgctcat tctgagagct ttcctcagca gcatatatca tcagcctcat cctaaaatag   1920

gcagggagcc cctcccatga gtttatccaa gttctcagct cctaaaatgc aggctgccaa   1980

gaccctacac ctgccctggc tctacagcca cttacctggt ttctggactg tcaccctccc   2040

agctgacctg cccgtagcca aggaatgagg acctaacttg agttggccca aagtctgacc   2100

tggctgtatg tccctgtggc ccacacccag cctgtcttgc tcattcatgc agcctcaaca   2160

ctggcctcca aagttccctt aacacttgca aagtcctttt tacctgtgca tttggacttg   2220

aggacactgg tttctatcac aggtgagagc catgttcaat acctccagca agctctcctg   2280

gctccctgca ctgtgcacgc tcctcttccc aaggtcccaa taccagcacc tctagttaga   2340

gttagggtca gggtcaggcc tctcccaaca tcccagtagt ttctcctctg agacacatgg   2400

gcaagagaca atttggagtc aagattttcc atttggatct attttaaatc ttttagaaat   2460

gcatttgaaa cagtgtgttt gttttttccc ttctagttaa gggactattt atatgtgtat   2520

aggaaagctg tctctttttt tgtttttcct ttaacaaggt ccaaagaaag atgcaaaagg   2580

agatcacacc cttgccccgc tgagccccgt gataacaagt cactccagac taacctgtgt   2640

gccagacatt tgtgcattgt tgcactttga ggttattatt tatcaagttc ttgaaggaag   2700

cagaaagagg gactcctctc tccctccgtg tatagtctct atgtttgtgc tagtttttct   2760

tttttttctc tgtgtccagt cagccacagg gcccgcctcc ctgcaggaat aaggggtaaa   2820

acgttaggtg ttgtttggca agaaaccaca ctgactgatg aggggtaaaa tggaaccagg   2880

tagagccact ccgggcagct gtcacccatt cagaacttct ttccgcagct gaagaaatgt   2940

tcagtaacct gtttgacgct aattaaaaca gagcctgcag gaagtggggc taaagtggca   3000

ttcagtgatc ctgttctgta gacttttctt tcttttttta accaaatcca aaggatgtta   3060

cagaaaagct agccactggt attttgtttt gttt                              3094
```

<210> SEQ ID NO 77
<211> LENGTH: 3024
<212> TYPE: DNA
<213> ORGANISM: Homo sapiens

<400> SEQUENCE: 77

-continued

```
ctggggccgc tgtgcctgct gctgagcagc gccgcgggaa agtgcctgga aaaatagatg     60
acagccagaa agagagcttg gagaaaaaaa tgactccaag gagaaggtgg tcatttccta    120
gagtctggct tgtcagttag agccagctgc tccccgggaa caacttcacc aatgagtgca    180
acataccagg caacttcatg tgcagcaatg gacggtgcat cccgggcgcc tggcagtgtg    240
acgggctgcc tgactgcttc gacaagagtg atgagaagga gtgccccaag gctaagtcga    300
aatgtggccc aaccttcttc ccctgtgcca gcggcatcca ttgcatcatt ggtcgcttcc    360
ggtgcaatgg gtttgaggac tgtcccgatg gcagcgatga agagaactgc acagcaaacc    420
ctctgctttg ctccaccgcc cgctaccact gcaagaacgg cctctgtatt gacaagagct    480
tcatctgcga tggacagaat aactgtcaag acaacagtga tgaggaaagc tgtgaaagtt    540
ctcaagaacc cggcagtggg caggtgtttg tgacttcaga gaaccaactt gtgtattacc    600
ccagcatcac ctatgccatc atcggcagct ccgtcatttt tgtgctggtg gtggccctgc    660
tggcactggt cttgcaccac cagcggaagc ggaacaacct catgacgctg cccgtgcacc    720
ggctgcagca ccctgtgctg ctgtcccgcc tggtggtcct ggaccacccc caccactgca    780
acgtcaccta caacgtcaat aatggcatcc agtatgtggc cagccaggcg gagcagaatg    840
cgtcggaagt aggctcccca ccctcctact ccgaggcctt gctggaccag aggcctgcgt    900
ggtatgacct tcctccaccg ccctactctt ctgacacgga atctctgaac caagccgacc    960
tgccccccta ccgctcccgg tccgggagtg ccaacagtgc cagctcccag gcagccagca   1020
gcctcctgag cgtggaagac accagccaca gcccggggca gcctggcccc caggagggca   1080
ctgctgagcc cagggactct gagcccagcc agggcactga agaagtataa gtcccagtta   1140
ttccaaagtc catatgggtt aatctgctct gacttgttgc cattctaaca atttgtgctc   1200
atgggaagct ctttaagcac ctgtaaggat gtctcaagtt acagtttggg atattaacta   1260
tctctgcatt cccctcctcc cccagacttc agagatgttt ttctggcgtc tcagttgaca   1320
tgatctgttg tgcgtctttt ctgtcaggtc actcttccct tgggacccga gatcacaccc   1380
tcatttttca cattattctg tttctgttgg agagacagca tataaaacag tattgaaata   1440
ggctgggaga gagcaatgtt tctgtgctat attggatgct cagaagtgca ggagacgctg   1500
gacccaattc tctctgctgg gtagttacct tatagcattt ggggatttgg gttagatgat   1560
ctaaccagga ggccatcact ggatggtcac ccccccaaaa aaattccatt tgagcatcaa   1620
aacctgcttt gcacaatcct atttgatgcc cccagttcag cagagtcagt ggccaaagaa   1680
aactttggac gtgagtaaca cccttcagca gtcgcaacgt tattttggtt ttgtgaagga   1740
ctctgaaacc atctaccctg tataaattct ggctttagaa atttgcccaa gaatgctcat   1800
tctgagagct ttcctcagca gcatatatca tcagcctcat cctaaaatag gcagggagcc   1860
cctcccatga gtttatccaa gttctcagct cctaaaatgc aggctgccaa gaccctacac   1920
ctgccctggc tctacagcca cttacctggt ttctggactg tcaccctccc agctgacctg   1980
cccgtagcca aggaatgagg acctaacttg agttggccca aagtctgacc tggctgtatg   2040
tccctgtggc ccacacccag cctgtcttgc tcattcatgc agcctcaaca ctggcctcca   2100
aagttccctt aacacttgca aagtcctttt tacctgtgca tttggacttg aggacactgg   2160
tttctatcac aggtgagagc catgttcaat acctccagca agctctcctg gctccctgca   2220
ctgtgcacgc tcctcttccc aaggtcccaa taccagcacc tctagttaga gttagggtca   2280
gggtcaggcc tctcccaaca tcccagtagt ttctcctctg agacacatgg gcaagagaca   2340
```

-continued

```
atttggagtc aagattttcc atttggatct attttaaatc ttttagaaat gcatttgaaa   2400
cagtgtgttt gttttttccc ttctagttaa gggactattt atatgtgtat aggaaagctg   2460
tctctttttt tgtttttcct ttaacaaggt ccaaagaaag atgcaaaagg agatcacacc   2520
cttgccccgc tgagccccgt gataacaagt cactccagac taacctgtgt gccagacatt   2580
tgtgcattgt tgcactttga ggttattatt tatcaagttc ttgaaggaag cagaaagagg   2640
gactcctctc tccctccgtg tatagtctct atgtttgtgc tagtttttct tttttttctc   2700
tgtgtccagt cagccacagg gcccgcctcc ctgcaggaat aaggggtaaa acgttaggtg   2760
ttgtttggca agaaaccaca ctgactgatg aggggtaaaa tggaaccagg tagagccact   2820
ccgggcagct gtcacccatt cagaacttct ttccgcagct gaagaaatgt tcagtaacct   2880
gtttgacgct aattaaaaca gagcctgcag gaagtggggc taaagtggca ttcagtgatc   2940
ctgttctgta gacttttctt tcttttttta accaaatcca aaggatgtta cagaaaagct   3000
agccactggt attttgtttt gttt                                           3024
```

<210> SEQ ID NO 78
<211> LENGTH: 1668
<212> TYPE: DNA
<213> ORGANISM: Homo sapiens

<400> SEQUENCE: 78

```
atgggtcctg gggcgcggct ggcggcgctg ctggcggtgc tggcgctcgg gacaggagac     60
ccagaaaggg ctgcggctcg gggcgacacg ttctcggcgc tgaccagcgt ggcgcgcgcc    120
ctggcgcccg agcgccggct gctggggctg ctgaggcggt acctgcgcgg ggaggaggcg    180
cggctgcggg acctgactag attctacgac aaggtacttt ctttgcatga ggattcaaca    240
acccctgtgg ctaaccctct gcttgcattt actctcatca aacgcctgca gtctgactgg    300
aggaatgtgg tacatagtct ggaggccagt gagaacatcc gagctctgaa ggatggctat    360
gagaaggtgg agcaagacct tccagccttt gaggaccttg agggagcagc aagggccctg    420
atgcggctgc aggacgtgta catgctcaat gtgaaaggcc tggcccgagg tgtctttcag    480
agagtcactg gctctgccat cactgacctg tacagcccca aacggctctt ttctctcaca    540
ggggatgact gcttccaagt tggcaaggtg gcctatgaca tgggggatta ttaccatgcc    600
attccatggc tggaggaggc tgtcagtctc ttccgaggat cttacggaga gtggaagaca    660
gaggatgagg caagtctaga agatgccttg gatcacttgg cctttgctta tttccgggta    720
agggagccag ttaggagatt tgaaagatct agtggagcca agaatgaatt agcttccaat    780
tctctgggga agaataggtt gggtcctttt gcaataggct ttggctttct ggacttctct    840
ttcattgcac ttatcatatt ttgttgccca gataataaga ggatggccag gaatgtcttg    900
aaatatgaaa ggctcttggc agagagcccc aaccacgtgg tagctgaggc tgtcatccag    960
aggcccaata taccccacct gcagaccaga gacacctacg aggggctatg tcagaccctg   1020
ggttcccagc ccactctcta ccagatccct agcctctact gttcctatga gaccaattcc   1080
aacgcctacc tgctgctcca gcccatccgg aaggaggtca tccacctgga gccctacatt   1140
gctctctacc atgacttcgt cagtgactca gaggctcaga aaattagaga acttgcagaa   1200
ccatggctac agaggtcagt ggtggcatca ggggagaagc agttacaagt ggagtaccgc   1260
atcagcaaaa gtgcctggct gaaggacact gttgacccaa aactggtgac cctcaaccac   1320
cgcattgctg ccctcacagg ccttgatgtc cggcctccct atgcagagta tctgcaggtg   1380
gtgaactatg gcatcggagg acactatgag cctcactttg accatgctac gctgagctcg   1440
```

-continued

```
gtggaagctg gaggagccac agccttcatc tatgccaacc tcagcgtgcc tgtggttagg   1500
aatgcagcac tgttttggtg gaacctgcac aggagtggtg aaggggacag tgacacactt   1560
catgctggct gtcctgtcct ggtgggagat aagtgggtgg ccaacaagtg gatacatgag   1620
tatggacagg aattccgcag accctgcagc tccagccctg aagactga                 1668
```

<210> SEQ ID NO 79
<211> LENGTH: 997
<212> TYPE: DNA
<213> ORGANISM: Homo sapiens

<400> SEQUENCE: 79

```
gaaggaaaaa gagcaacaga tccagggagc attcacctgc cctgtctcca aacagccttg     60
tgcctcacct acccccaacc tcccagaggg agcagctatt taaggggagc aggagtgcag    120
aacaaacaag acggcctggg gatacaactc tggagtcctc tgagagagcc accaaggagg    180
agcaggggag cgacggccgg ggcagaagtt gagaccaccc agcagaggag ctaggccagt    240
ccatctgcat ttgtcaccca agaactctta ccatgaagac cctcctactg ttggcagtga    300
tcatgatctt tggcctactg caggcccatg ggaatttggt gaatttccac agaatgatca    360
agttgacgac aggaaaggaa gccgcactca gttatggctt ctacggctgc cactgtggcg    420
tgggtggcag aggatccccc aaggatgcaa cggatcgctg ctgtgtcact catgactgtt    480
gctacaaacg tctggagaaa cgtggatgtg gcaccaaatt tctgagctac aagtttagca    540
actcggggag cagaatcacc tgtgcaaaac aggactcctg cagaagtcaa ctgtgtgagt    600
gtgataaggc tgctgccacc tgttttgcta gaaacaagac gacctacaat aaaaagtacc    660
agtactattc caataaacac tgcagaggga gcacccctcg ttgctgagtc ccctcttccc    720
tggaaacctt ccacccagtg ctgaatttcc ctctctcata ccctccctcc ctaccctaac    780
caagttcctt ggccatgcag aaagcatccc tcacccatcc tagaggccag gcaggagccc    840
ttctataccc acccagaatg agacatccag cagatttcca gccttctact gctctcctcc    900
acctcaactc cgtgcttaac caaagaagct gtactccggg gggtctcttc tgaataaagc    960
aattagcaaa aaaaaaaaaa aaaaaaaaaa aaaaaaa                             997
```

<210> SEQ ID NO 80
<211> LENGTH: 260
<212> TYPE: DNA
<213> ORGANISM: Homo sapiens

<400> SEQUENCE: 80

```
tgagaggtgg gtgtgatcac tcatttgctg tttaaaggcc cagaaaggag acagagaagg     60
gatggacaga gagggagaag gggaactgag cgagaaggtc aaggagtcag taaggaaatg    120
gttagcaagg gccaagtgaa cagggagtcc tccatgaaaa gggccaacaa ggctcccctg    180
gatgttgagg cagaaacgca tgagggactc aggggaagct gtttccatgg agtcgggggg    240
gcaaagccag attagaccag                                                260
```

<210> SEQ ID NO 81
<211> LENGTH: 201
<212> TYPE: DNA
<213> ORGANISM: Homo sapiens

<400> SEQUENCE: 81

```
ttcctttcct gtcgtcaact tgatcattca aagatcatga tcactgccaa cagtaggagg     60
```

-continued

```
gtcttcatgg taagagttct tgggtgacaa atgcagatgg actggcctag ctcctctgct    120

gggtggtctc aacttctgcc ccggccgtcg ctcccctgct cctccttggt ggctctgttt    180

ggagacaggg caggtgaatg a                                              201


<210> SEQ ID NO 82
<211> LENGTH: 272
<212> TYPE: DNA
<213> ORGANISM: Homo sapiens

<400> SEQUENCE: 82

tcattcacct gccctgtctc caacaggttg gatgggagag catgtctgtg tgtctcagag     60

ccaccaagga ggagcagggg agcgacggcc ggggcagaag ttgagaccac ccagcagagg    120

agctaggcca gtccatctgc atttgtcacc caagaactct taccatgaag accctcctac    180

tgttggcagt gatcatgatc tttggcctac tgcaggccca tgggaatttg gtgaatttcc    240

acagaatgat caagttgacg acaggaaagg aa                                  272


<210> SEQ ID NO 83
<211> LENGTH: 258
<212> TYPE: DNA
<213> ORGANISM: Homo sapiens

<400> SEQUENCE: 83

tcattcacct gccctgtctc caaacagagc caccaaggag gagcagggga gcgacggccg     60

gggcagaagt tgagaccacc cagcagagga gctaggccag tccatctgca tttgtcaccc    120

aagaactctt accatgaaga ccctcctact gttggcagtg atcatgatct ttggcctact    180

gcaggcccat gggaatttgg tgaatttcca cagaatgatc aagttgacga caggaaagga    240

agccgcactc agttatga                                                  258


<210> SEQ ID NO 84
<211> LENGTH: 2226
<212> TYPE: DNA
<213> ORGANISM: Homo sapiens

<400> SEQUENCE: 84

ggcagcatgg cgtctttccg gcttctccaa acccttgcga aaaactttat tggcaaagct     60

atcagagaac ggacagtgta cccactgagg cggccaaagc ttaactggat cagggcagga    120

tgacatgacc ttgtggtaga tcccagaact gaggccccag gatgacagaa caggagaccc    180

tggccctact ggaagtgaag aggtctgatt ccccagagaa gagctcaccc caggccttgg    240

ttcccaatgg ccggcagcca gaaggggaag gtggggccga atccccggga gctgagtccc    300

tcagagtggg gtcttcagct ggatctccca cagccataga gggggctgag gatggtctag    360

acagcacagt aagtgaggct gccaccttgc cctgggggac tggccctcag cccagtgctc    420

cgttcccgga tcccccctggc tggcgggaca ttgaaccaga gcccccctgag tcagaaccac    480

ttaccaagct agaggagctg cccgaagacg atgccaacct gctgcctgag aaagcggccc    540

gtgccttcgt gcctattgac ctacagtgca ttgagcggca gccccaagaa gaccttatcg    600

tgcgctgtga ggcaggcgag ggcgagtgcc gaaccttcat gccccccccgg gtcacccacc    660

ccgaccccac tgagcgcaag tgggctgagg cagtggtgag gccgcctggc tgttcctgtg    720

ggggctgcgg gagctgtgga gaccgtgagt ggctaagggc tgtggcctcc gtgggagccg    780

cactcattct cttcccttgc ctactatacg gggcatatgc cttcctgccg tttgatgtcc    840

cacggctgcc caccatgagt tcccgcctga tctacacact gcgctgcggg gtctttgcca    900
```

```
ccttccccat tgtgctgggg atcctggtgt acgggctgag cctgttatgc ttttctgccc    960

ttcggccctt tggggagcca cggcgggagg tggagatcca ccggcgatat gtggcccagt   1020

cggtccagct ctttattctc tacttcttca acctggccgt gctttccact tacctgcccc   1080

aggataccct caaactgctc cctctgctca ctggtctctt tgccgtctcc cggctgatct   1140

actggctgac ctttgccgtg ggccgctcct tccgaggctt cggctacggc ctgacgtttc   1200

tgccactgct gtcgatgctg atgtggaacc tctactacat gttcgtggtg gagccggagc   1260

gcatgctcac tgccaccgag agccgcctgg actacccgga ccacgcccgc tcggcctccg   1320

actacaggcc ccgcccctgg ggctgagcct ctccgccctc gccctcggag tagggggtag   1380

cggcttgggt ctgacacatc tttgaacctt gtggccaggc ctggacttcg cccccaggcc   1440

taggaccgcg gtgggtggaa ccctgctact gccccaacag ggactccaat caatcggagt   1500

tctccccttg ccggagctgc ccttcacctt tggggcccga gacagtcata agggatggac   1560

ttagttttct tgcagggaaa aaggtggaca gccgtgtttc ttaaggatgc tgagggcatg   1620

gggccaggac caggggagag gcacagctcc ttcctgagca gcctctcacc actgccacaa   1680

ggctccctaa tgctggtctc tgctccactc cccggcttcc cgtgaggcag gaggcagagc   1740

cacagccaag gccctgacca cttctgtgcc agttgtctaa gcagagcgcc tcagggacgc   1800

tggaaatgcc ttaaggatag aggctgggca tcacatcaaa tgggactgtg gtgtttggtg   1860

aaaaccttcc tgaggatctg gattcaggac cctccatgac tggcctattt actgtttaca   1920

gctggccagt gcagagctgc tgctctttta cctttttagg cccctgtaac ttcccacctt   1980

taaactgccc agaaggcatg cctctcccac aggaagaggg gagcagacag ggaaatctgc   2040

ctaccaagag ggtgtgtgt gtctttgtgc ccacacgtgg tggctgggga gtgcctggat   2100

ggtgcggtgg ttgatgttaa cctagtgtgt gtgtgtgtgt gtgtgtgtgt gtgtgtaaca   2160

ataaattact accagtcaaa aaaaaaaaaa aaaaaaaaaa aaaaaaaaaa aaaaaaaaaa   2220

aaaaaa                                                              2226
```

<210> SEQ ID NO 85
<211> LENGTH: 328
<212> TYPE: DNA
<213> ORGANISM: Homo sapiens

<400> SEQUENCE: 85

```
tgaggccgcc tggctgttcc tgtgggggct gcgggagctg tggagaccgt gagtggctaa     60

gggctgtggc ctccgtggga gccgcactca ttctcttccc ttgcctacta tacggggcat    120

atgccttcct gccgtttgat gtcccacggc tgcccaccat gagttcccgc ctgatctaca    180

cactgcgctg cggggtcttt gccaccttcc ccattgtgct ggggatcctg gtgtacgggc    240

tgagcctgtt atgcttttct gcccttcggc cctttgggga gccacggcgg gaggtggaga    300

tccaccggcg atatgtggcc cagtcggt                                       328
```

<210> SEQ ID NO 86
<211> LENGTH: 1469
<212> TYPE: DNA
<213> ORGANISM: Homo sapiens

<400> SEQUENCE: 86

```
cagagaacgg acagtgtacc cactgaggcg gccaaagctt aactggatca gggcaggatg     60

acatgacctt gtggtagatc ccagaactga ggccccagga tgacagaaca ggagaccctg    120
```

```
gccctactgg aagtgaagag gtctgattcc ccagagaaga gctcacccca ggccttggtt    180

cccaatggcc ggcagccaga aggggaaggt ggggccgaat ccccgggagc tgagtccctc    240

agagtggggt cttcagctgg atctcccaca gccatagagg gggctgagga tggtctagac    300

agcacagtaa gtgaggctgc caccttgccc tgggggactg gccctcagcc cagtgctccg    360

ttcccggatc cccctggctg gcgggacatt gaaccagagc cccctgagtc agaaccactt    420

accaagctag aggagctgcc cgaagacgat gccaacctgc tgcctgagaa agcggcccgt    480

gccttcgtgc ctattgacct acagtgcatt gagcggcagc cccaagaaga ccttatcgtg    540

cgctgtgagg caggcgaggg cgagtgccga accttcatgc ccccccgggt cacccacccc    600

gaccccactg agcgcaagtg ggctgaggca gtggtgaggc cgcctggctg ttcctgtggg    660

ggctgcggga gctgtggaga ccgtgagtgg ctaagggctg tggcctccgt gggagccgca    720

ctcattctct tcccttgcct actatacggg gcatatgcct tcctgccgtt tgatgtccca    780

cggctgccca ccatgagttc ccgcctgatc tacacactgc gctgcggggt ctttgccacc    840

ttccccattg tgctgggtga gccygtgaga agaaaggggg catcgggaag tggacttgag    900

gagggcaggg cctgcctggt gtggggagca ggaggatttc ccttcacttg acctgggccc    960

ctcagggtct cccaccccct gccagtctgc atgcccatct cctcccagga ccacctccac   1020

cccactgtgt agagcccatg cactgcccac agtgaatctg cccccagctt actgcctctt   1080

gtgcccttcc cctgcctttt ctgaccctac ccygtttccc aactccaccc agggatcctg   1140

gtgtacgggc tgagcctgtt atgcttttct gcccttcggc cctttgggga gccacggcgg   1200

gaggtggaga tccaccggcg atatgtggcc cagtcggtcc agctctttat tctctacttc   1260

ttcaacctgg ccgtgctttc cacttacctg ccccaggata ccctcaaact gctccctctg   1320

ctcactggtc tctttgccgt ctcccggctg atctactggc tgacctttgc cgtgggccgc   1380

tccttccgag gcttcggcta cggcctgacg tttctgccac tgctgtcgat gctgatgtgg   1440

aacctctact acatgttcgt ggtggagcc                                     1469
```

```
<210> SEQ ID NO 87
<211> LENGTH: 180
<212> TYPE: DNA
<213> ORGANISM: Homo sapiens

<400> SEQUENCE: 87

tcagagaacg gacagtgtac ccactgaggc ggccaaagct taactggatc agggcaggct     60

gatctactgg ctgacctttg ccgtgggccg ctccttccga ggcttcggct acggcctgac    120

gtttctgcca ctgctgtcga tgctgatgtg gaacctctac tacatgttcg tggtggagcc    180
```

```
<210> SEQ ID NO 88
<211> LENGTH: 477
<212> TYPE: DNA
<213> ORGANISM: Homo sapiens

<400> SEQUENCE: 88

cagagaacgg acagtgtacc cactgaggcg gccaaagctt aactggatca gggcaggatg     60

acatgacctt gtggtagatc ccagaactga ggcccccagga tgacagaaca ggagaccctg    120

gccctactgg aagtgaagag ggatcctggt gtacgggctg agcctgttat gcttttctgc    180

ccttcggccc tttggggagc cacggcggga ggtggagatc caccggcgat atgtggccca    240

gtcggtccaa ctctttattc tctacttctt caacctggcc gtgctttcca cttacctgcc    300

ccaggatacc ctcaaactgc tccctctgct cactggtctc tttgccgtct cccggctgat    360
```

```
ctactggctg acctttgccg tgggccgctc cttccgaggc ttcggctacg gcctgacgtt    420

tctgccactg ctgtcgatgc tgatgtggaa cctctactac atgttcgtgg tggagcc       477


<210> SEQ ID NO 89
<211> LENGTH: 1013
<212> TYPE: DNA
<213> ORGANISM: Homo sapiens

<400> SEQUENCE: 89

cagagaacgg acagtgtacc cactgaggcg gccaaagctt aactggatca gggcaggatg     60

acatgacctt gtggtagatc ccagaactga ggccccagga tgacagaaca ggagaccctg    120

gccctactgg aagtgaagag gtctgattcc ccagagaaga gctcacccca ggccttggtt    180

cccaatggcc ggcagccaga aggggaaggt ggggccgaat ccccgggagc tgagtccctc    240

agagtggggt cttcagctgg atctcccaca gccatagagg gggctgagga tggtctagac    300

agcacagtaa gtgaggctgc cgccttgccc tgggggactg gccctcagcc cagtgctccg    360

ttcccggatc cccctggctg gcgggacatt gaaccagagc cccctgagtc agaaccactt    420

accaagctag aggagctgcc cgaagacgat gccaacctgc tgcctgagaa agcggcccgt    480

gccttcgtgc ctattgacct acagtgcatt gagcggcagc cccaagaaga ccttatcatg    540

cgctgtgagg caggcgaggg cgagtgccga accttcatgc ccccccgggt cacccacccc    600

gaccccactg agcgcaagtg ggctgaggca gtggtgaggc cgcctggctg ttcctgtggg    660

ggctgcggga gctgtggaga cggatctggt gtacggctga cctgttatgc tttctgcctt    720

cggccctttg gggagccacg gcgggaggtg gagatccacc ggcgatatgt ggcccagtcg    780

gtccagctct ttattctcta cttcttcaac ctggccgtgc tttccactta cctgccccag    840

gataccctca aactgctccc tctgctcact ggtctctttg ccgtctcccg gctgatctac    900

tggctgacct ttgccgtggg ccgctccttc cgaggcttcg gctacggcct gacgtttctg    960

ccactgctgt cgatgctgat gtggaacctc tactacatgt tcgtggtgga gcc          1013


<210> SEQ ID NO 90
<211> LENGTH: 737
<212> TYPE: DNA
<213> ORGANISM: Homo sapiens

<400> SEQUENCE: 90

ccccaggatg acagaacagg agaccctggc cctactggaa gtgaagagtg cattgagcgg     60

cagccccaag aagaccttat cgtgcgctgt gaggcaggcg agggcgagtg ccgaaccttc    120

atgccccccc gggtcaccca ccccgacccc actgagcgca agtgggctga ggcagtggtg    180

aggccgcctg gctgttcctg tgggggctgc gggagctgtg gagaccgtga gtggctaagg    240

gctgtggcct ccgtgggagc cgcactcatt ctcttccctt gcctactata cggggcatat    300

gccttcctgc cgtttgatgt cccacggctg cccaccatga gttcccgcct gatctacaca    360

ctgcgctgcg gggtctttgc caccttcccc attgtgctgg ggatcctggt gtacgggctg    420

agcctgttat gcttttctgc ccttcggccc tttggggagc cacggcggga ggtggagatc    480

caccggcgat atgtggccca gtcggtccag ctctttattc tctacttctt caacctggcc    540

gtgctttcca cttacctgcc ccaggatacc ctcaaactgc tccctctgct cactggtctc    600

tttgccgtct cccggctgat ctactggctg acctttgccg tgggccgctc cttccgaggc    660

ttcggctacg gcctgacgtt tctgccactg ctgtcgatgc tgatgtggaa cctctactac    720
```

-continued

```
atgttcgtgg tggagcc                                                737

<210> SEQ ID NO 91
<211> LENGTH: 2469
<212> TYPE: DNA
<213> ORGANISM: Homo sapiens

<400> SEQUENCE: 91

agcgttcctc gggccctcgg cgccacaagc tgtccgggca cgcagcccct agcggcgcgt     60

cgctgccaag ccggcctccg cgcgcctccc tccttccttc tcccctggct gttcgcgatc    120

cagcttgggt aggcggggaa gcagctggag tgcgaccgcc acggcagcca ccctgcaacc    180

gccagtcgga ggtgcagtcc gtaggccctg gcccccgggt gggcccttgg ggagtcggcg    240

ccgctcccga ggagctgcaa ggctcgcccc tgcccggcgt ggagggcgcg gggggcgcgg    300

aggatattct tggtgatctt ggaagtgtcc gtatcatgga atcaatctct atgatgggaa    360

gccctaagag ccttagtgaa acttgtttac ctaatggcat aaatggtatc aaagatgcaa    420

ggaaggtcac tgtaggtgtg attggaagtg gagattttgc caaatccttg accattcgac    480

ttattagatg cggctatcat gtggtcatag gaagtagaaa tcctaagttt gcttctgaat    540

tttttcctca tgtggtagat gtcactcatc atgaagatgc tctcacaaaa acaaatataa    600

tatttgttgc tatacacaga gaacattata cctccctgtg ggacctgaga catctgcttg    660

tgggtaaaat cctgattgat gtgagcaata acatgaggat aaaccagtac ccagaatcca    720

atgctgaata tttggcttca ttattcccag attctttgat tgtcaaagga tttaatgttg    780

tctcagcttg ggcacttcag ttaggaccta aggatgccag ccggcaggtt tatatatgca    840

gcaacaatat tcaagcgcga caacaggtta ttgaacttgc ccgccagttg aatttcattc    900

ccattgactt gggatcctta tcatcagcca gagagattga aaatttaccc ctacgactct    960

ttactctctg gagagggcca gtggtggtag ctatgagctt ggccacattt tttttccttt   1020

attcctttgt cagagatgtg attcatccat atgctagaaa ccaacagagt gacttttaca   1080

aaattcctat agagattgtg aataaaacct tacctatagt tgccattact ttgctctccc   1140

tagtatacct tgcaggtctt ctggcagctg cttatcaact ttattacggc accaagtata   1200

ggagatttcc accttggttg gaaacctggt tacagtgtag aaaacagctt ggattactaa   1260

gtttttttctt cgctatggtc catgttgcct acagcctctg cttaccgatg agaaggtcag   1320

agagatattt gtttctcaac atggcttatc agcaggttca tgcaaatatt gaaaactctt   1380

ggaatgagga agaagtttgg agaattgaaa tgtatatctc ctttggcata atgagccttg   1440

gcttactttc cctcctggca gtcacttcta tcccttcagt gagcaatgct ttaaactgga   1500

gagaattcag ttttattcag tctacacttg gatatgtcgc tctgctcata agtactttcc   1560

atgttttaat ttatggatgg aaacgagctt ttgaggaaga gtactacaga ttttatacac   1620

caccaaactt tgttcttgct cttgttttgc cctcaattgt aattctggat cttttgcagc   1680

tttgcagata cccagactga gctggaactg gaatttgtct tcctattgac tctacttctt   1740

taaaagcggc tgcccattac attcctcagc tgtccttgca gttaggtgta catgtgactg   1800

agtgttggcc agtgagatga agtctcctca aaggaaggca gcatgtgtcc tttttcatcc   1860

cttcatcttg ctgctgggat tgtggatata acaggagccc tggcagctgt ctccagagga   1920

tcaaagccac acccaaagag taaggcagat tagagaccag aaagaccttg actacttccc   1980

tacttccact gctttttcct gcatttaagc cattgtaaat ctgggtgtgt tacatgaagt   2040

gaaaattaat tctttctgcc cttcagttct ttatcctgat accatttaac actgtctgaa   2100
```

```
ttaactagac tgcaataatt ctttcttttg aaagctttta aaggataatg tgcaattcac   2160

attaaaattg attttccatt gtcaattagt tatactcatt ttcctgcctt gatctttcat   2220

tagatatttt gtatctgctt ggaatatatt atcttctttt taactgtgta attggtaatt   2280

actaaaactc tgtaatctcc aaaatattgc tatcaaatta cacaccatgt tttctatcat   2340

tctcatagat ctgccttata aacatttaaa taaaaagtac tatttaatga tttaacttct   2400

gttttgaaat gttgtataca cgtggatttt tttctcatta aataataatt ctagtaaaaa   2460

aaaaaaaag                                                           2469
```

<210> SEQ ID NO 92
<211> LENGTH: 2562
<212> TYPE: DNA
<213> ORGANISM: Homo sapiens

<400> SEQUENCE: 92

```
agcgttcctc gggccctcgg cgccacaagc tgtccgggca cgcagcccct agcggcgcgt     60

cgctgccaag ccggcctccg cgcgcctccc tccttccttc tcccctggct gttcgcgatc    120

cagcttgggt aggcggggaa gcagctggag tgcgaccgcc acggcagcca ccctgcaacc    180

gccagtcgga ggtgcagtcc gtaggccctg gcccccgggt gggcccttgg ggagtcggcg    240

ccgctcccga ggagctgcaa ggctcgcccc tgcccggcgt ggagggcgcg gggggcgcgg    300

aggatattct tggtgatctt ggaagtgtcc gtatcatgga atcaatctct atgatgggaa    360

gccctaagag ccttagtgaa acttgtttac ctaatggcat aaatggtatc aaagatgcaa    420

ggaaggtcac tgtaggtgtg attggaagtg gagattttgc caaatccttg accattcgac    480

ttattagatg cggctatcat gtggtcatag gaagtagaaa tcctaagttt gcttctgaat    540

tttttcctca tgtggtagat gtcactcatc atgaagatgc tctcacaaaa acaaatataa    600

tatttgttgc tatacacaga gaacattata cctccctgtg ggacctgaga catctgcttg    660

tgggtaaaat cctgattgat gtgagcaata acatgaggat aaaccagtac ccagaatcca    720

atgctgaata tttggcttca ttattcccag attctttgat tgtcaaagga tttaatgttg    780

tctcagcttg ggcacttcag ttaggaccta aggatgccag ccggcaggtt tatatatgca    840

gcaacaatat tcaagcgcga caacaggtta ttgaacttgc ccgccagttg aatttcattc    900

ccattgactt gggatcctta tcatcagcca gagagattga aaatttaccc ctacgactct    960

ttactctctg gagagggcca gtggtggtag ctatgagctt ggccacattt tttttccttt   1020

attcctttgt cagagatgtg attcatccat atgctagaaa ccaacagagt gacttttaca   1080

aaattcctat agagattgtg aataaaacct tacctatagt tgccattact ttgctctccc   1140

tagtatacct tgcaggtctt ctggcagctg cttatcaact ttattacggc accaagtata   1200

ggagatttcc accttggttg gaaacctggt tacagtgtag aaaacagctt ggattactaa   1260

gtttttcttt cgctatggtc catgttgcct acagcctctg cttaccgatg agaaggtcag   1320

agagatattt gtttctcaac atggcttatc agcaggttca tgcaaatatt gaaaactctt   1380

ggaatgagga agaagtttgg agaattgaaa tgtatatctc ctttggcata atgagccttg   1440

gcttactttc cctcctggca gtcacttcta tcccttcagt gagcaatgct ttaaactgga   1500

gagaattcag ttttattcag tctacacttg gatatgtcgc tctgctcata agtactttcc   1560

atgttttaat ttatggatgg aaacgagctt ttgaggaaga gtactacaga ttttatacac   1620

caccaaactt tgttcttgct cttgttttgc cctcaattgt aattctggta gagacggagt   1680
```

-continued

```
ttcaccgtgt tagccaggat ggtctcgatc tcctgacctc gtgatccgcc cgccttggcc   1740

tccaaagtgc tgggattaca gatcttttgc agctttgcag atacccagac tgagctggaa   1800

ctggaatttg tcttcctatt gactctactt ctttaaaagc ggctgcccat tacattcctc   1860

agctgtcctt gcagttaggt gtacatgtga ctgagtgttg gccagtgaga tgaagtctcc   1920

tcaaaggaag gcagcatgtg tcctttttca tcccttcatc ttgctgctgg gattgtggat   1980

ataacaggag ccctggcagc tgtctccaga ggatcaaagc cacacccaaa gagtaaggca   2040

gattagagac cagaaagacc ttgactactt ccctacttcc actgcttttt cctgcattta   2100

agccattgta aatctgggtg tgttacatga agtgaaaatt aattctttct gcccttcagt   2160

tctttatcct gataccattt aacactgtct gaattaacta gactgcaata attctttctt   2220

ttgaaagctt ttaaaggata atgtgcaatt cacattaaaa ttgattttcc attgtcaatt   2280

agttatactc attttcctgc cttgatcttt cattagatat tttgtatctg cttggaatat   2340

attatcttct ttttaactgt gtaattggta attactaaaa ctctgtaatc tccaaaatat   2400

tgctatcaaa ttacacacca tgttttctat cattctcata gatctgcctt ataaacattt   2460

aaataaaaag tactatttaa tgatttaact tctgttttga aatgttgtat acacgtggat   2520

tttttctca ttaaataata attctagtaa aaaaaaaaaa ag                       2562
```

```
<210> SEQ ID NO 93
<211> LENGTH: 2321
<212> TYPE: DNA
<213> ORGANISM: Homo sapiens

<400> SEQUENCE: 93

agcgttcctc gggccctcgg cgccacaagc tgtccgggca cgcagcccct agcggcgcgt     60

cgctgccaag ccggcctccg cgcgcctccc tccttccttc tcccctggct gttcgcgatc    120

cagcttgggt aggcggggaa gcagctggag tgcgaccgcc acggcagcca ccctgcaacc    180

gccagtcgga ggtgcagtcc gtaggccctg gcccccgggt gggcccttgg ggagtcggcg    240

ccgctcccga ggagctgcaa ggctcgcccc tgcccggcgt ggagggcgcg gggggcgcgg    300

aggatattct tggtgatctt ggaagtgtcc gtatcatgga atcaatctct atgatgggaa    360

gccctaagag ccttagtgaa acttgtttac ctaatggcat aaatggtatc aaagatgcaa    420

ggaaggtcac tgtaggtgtg attggaagtg gagattttgc caaatccttg accattcgac    480

ttattagatg cggctatcat gtggtcatag gaagtagaaa tcctaagttt gcttctgaat    540

tttttcctca tgtggtagat gtcactcatc atgaagatgc tctcacaaaa acaaatataa    600

tatttgttgc tatacacaga gaacattata cctccctgtg ggacctgaga catctgcttg    660

tgggtaaaat cctgattgat gtgagcaata acatgaggat aaaccagtac ccagaatcca    720

atgctgaata tttggcttca ttattcccag attctttgat tgtcaaagga tttaatgttg    780

tctcagcttg ggcacttcag ttaggaccta aggatgccag ccggcaggtt tatatatgca    840

gcaacaatat tcaagcgcga caacaggtta ttgaacttgc ccgccagttg aatttcattc    900

ccattgactt gggatcctta tcatcagcca gagagattga aaatttaccc ctacgactct    960

ttactctctg gagagggcca gtggtggtag ctatgagctt ggccacattt tttttccttt   1020

attcctttgt cagagatgtg attcatccat atgctagaaa ccaacagagt gacttttaca   1080

aaattcctat agagattgtg aataaaacct tacctatagt tgccattact ttgctctccc   1140

tagtatacct tgcaggtctt ctggcagctg cttatcaact ttattacggc accaagtata   1200

ggagatttcc accttggttg gaaacctggt tacagtgtag aaaacagctt ggattactaa   1260
```

-continued

```
gtttttcttc cgctatggtc catgttgcct acagcctctg cttaccgatg agaaggtcag   1320
agagatattt gtttctcaac atggcttatc agcaggttca tgcaaatatt gaaaactctt   1380
ggaatgagga agaagtttgg agaattgaaa tgtatatctc ctttggcata atgagccttg   1440
gcttactttc cctcctggca gtcacttcta tcccttcagt gagcaatgct ttaaactgga   1500
gagaattcag ttttattcag atcttttgca gctttgcaga tacccagact gagctggaac   1560
tggaatttgt cttcctattg actctacttc tttaaaagcg gctgcccatt acattcctca   1620
gctgtccttg cagttaggtg tacatgtgac tgagtgttgg ccagtgagat gaagtctcct   1680
caaaggaagg cagcatgtgt ccttttttcat cccttcatct tgctgctggg attgtggata   1740
taacaggagc cctggcagct gtctccagag gatcaaagcc acacccaaag agtaaggcag   1800
attagagacc agaaagacct tgactacttc cctacttcca ctgctttttc ctgcatttaa   1860
gccattgtaa atctgggtgt gttacatgaa gtgaaaatta attctttctg cccttcagtt   1920
ctttatcctg ataccattta acactgtctg aattaactag actgcaataa ttctttcttt   1980
tgaaagcttt taaaggataa tgtgcaattc acattaaaat tgattttcca ttgtcaatta   2040
gttatactca ttttcctgcc ttgatctttc attagatatt ttgtatctgc ttggaatata   2100
ttatcttctt tttaactgtg taattggtaa ttactaaaac tctgtaatct ccaaaatatt   2160
gctatcaaat tacacaccat gttttctatc attctcatag atctgcctta taaacattta   2220
aataaaaagt actatttaat gatttaactt ctgttttgaa atgttgtata cacgtggatt   2280
tttttctcat taaataataa ttctagtaaa aaaaaaaaaa g                        2321
```

<210> SEQ ID NO 94
<211> LENGTH: 3226
<212> TYPE: DNA
<213> ORGANISM: Homo sapiens

<400> SEQUENCE: 94

```
cgcgagctaa gcaggaggcg gaggcggagg cggagggcga ggggcgggga gcgccgcctg     60
gagcgcggca ggtcatattg aacattccag atacctatca ttactcgatg ctgttgataa    120
cagcaagatg gctttgaact cagggtcacc accagctatt ggaccttact atgaaaacca    180
tggataccaa ccggaaaacc cctatcccgc acagcccact gtggtcccca ctgtctacga    240
ggtgcatccg gctcagtact acccgtcccc cgtgccccag tacgccccga gggtcctgac    300
gcaggcttcc aaccccgtcg tctgcacgca gcccaaatcc ccatccggga cagtgtgcac    360
ctcaaagact aagaaagcac tgtgcatcac cttgaccctg gggaccttcc tcgtgggagc    420
tgcgctggcc gctggcctac tctggaagtt catgggcagc aagtgctcca actctgggat    480
agagtgcgac tcctcaggta cctgcatcaa cccctctaac tggtgtgatg gcgtgtcaca    540
ctgccccggc ggggaggacg agaatcggtg tgttcgcctc tacggaccaa acttcatcct    600
tcagatgtac tcatctcaga ggaagtcctg gcaccctgtg tgccaagacg actggaacga    660
gaactacggg cgggcggcct gcagggacat gggctataag aataattttt actctagcca    720
aggaatagtg gatgacagcg gatccaccag ctttatgaaa ctgaacacaa gtgccggcaa    780
tgtcgatatc tataaaaaac tgtaccacag tgatgcctgt tcttcaaaag cagtggtttc    840
tttacgctgt atagcctgcg ggtcaactt gaactcaagc cgccagagca ggatcgtggg    900
cggtgagagc gcgctcccgg gggcctggcc ctggcaggtc agcctgcacg tccagaacgt    960
ccacgtgtgc ggaggctcca tcatcacccc cgagtggatc gtgacagccg cccactgcgt   1020
```

-continued

```
ggaaaaacct cttaacaatc catggcattg gacggcattt gcggggattt tgagacaatc   1080

tttcatgttc tatggagccg gataccaagt agaaaaagtg atttctcatc caaattatga   1140

ctccaagacc aagaacaatg acattgcgct gatgaagctg cagaagcctc tgactttcaa   1200

cgacctagtg aaaccagtgt gtctgcccaa cccaggcatg atgctgcagc cagaacagct   1260

ctgctggatt tccgggtggg gggccaccga ggagaaaggg aagacctcag aagtgctgaa   1320

cgctgccaag gtgcttctca ttgagacaca gagatgcaac agcagatatg tctatgacaa   1380

cctgatcaca ccagccatga tctgtgccgg cttcctgcag gggaacgtcg attcttgcca   1440

gggtgacagt ggagggcctc tggtcacttc gaagaacaat atctggtggc tgatagggga   1500

tacaagctgg ggttctggct gtgccaaagc ttacagacca ggagtgtacg ggaatgtgat   1560

ggtattcacg gactggattt atcgacaaat gagggcagac ggctaatcca catggtcttc   1620

gtccttgacg tcgttttaca agaaaacaat ggggctggtt ttgcttcccc gtgcatgatt   1680

tactcttaga gatgattcag aggtcacttc atttttatta aacagtgaac ttgtctggct   1740

ttggcactct ctgccattct gtgcaggctg cagtggctcc cctgcccagc ctgctctccc   1800

taacccettg tccgcaaggg gtgatggccg gctggttgtg ggcactggcg gtcaagtgtg   1860

gaggagaggg gtggaggctg ccccattgag atcttcctgc tgagtccttt ccaggggcca   1920

attttggatg agcatggagc tgtcacctct cagctgctgg atgacttgag atgaaaaagg   1980

agagacatgg aaagggagac agccaggtgg cacctgcagc ggctgccctc tggggccact   2040

tggtagtgtc cccagcctac ctctccacaa ggggattttg ctgatgggtt cttagagcct   2100

tagcagccct ggatggtggc cagaaataaa gggaccagcc cttcatgggt ggtgacgtgg   2160

tagtcacttg taaggggaac agaaacattt ttgttcttat ggggtgagaa tatagacagt   2220

gcccttggtg cgagggaagc aattgaaaag gaacttgccc tgagcactcc tggtgcaggt   2280

ctccacctgc acattgggtg ggctcctgg gagggagact cagccttcct cctcatcctc   2340

cctgaccctg ctcctagcac cctggagagt gcacatgccc cttggtcctg gcagggcgcc   2400

aagtctggca ccatgttggc ctcttcaggc ctgctagtca ctggaaattg aggtccatgg   2460

gggaaatcaa ggatgctcag tttaaggtac actgtttcca tgttatgttt ctacacattg   2520

ctacctcagt gctcctggaa acttagcttt tgatgtctcc aagtagtcca ccttcattta   2580

actctttgaa actgtatcac ctttgccaag taagagtggt ggcctatttc agctgctttg   2640

acaaaatgac tggctcctga cttaacgttc tataaatgaa tgtgctgaag caaagtgccc   2700

atggtggcgg cgaagaagag aaagatgtgt tttgttttgg actctctgtg gtcccttcca   2760

atgctgtggg tttccaacca ggggaagggt cccttttgca ttgccaagtg ccataaccat   2820

gagcactact ctaccatggt tctgcctcct ggccaagcag gctggtttgc aagaatgaaa   2880

tgaatgattc tacagctagg acttaacctt gaaatggaaa gtcttgcaat cccatttgca   2940

ggatccgtct gtgcacatgc ctctgtagag agcagcattc ccagggacct tggaaacagt   3000

tggcactgta aggtgcttgc tccccaagac acatcctaaa aggtgttgta atggtgaaaa   3060

cgtcttcctt ctttattgcc ccttcttatt tatgtgaaca actgtttgtc ttttttgta    3120

tctttttaa actgtaaagt tcaattgtga aaatgaatat catgcaaata aattatgcga    3180

tttttttttc aaagcaaaaa aaaaaaaaaa aaaaaaaaaa aaaaaa                  3226
```

<210> SEQ ID NO 95
<211> LENGTH: 3106
<212> TYPE: DNA
<213> ORGANISM: Homo sapiens

<400> SEQUENCE: 95

```
cgcgagctaa gcaggaggcg gaggcggagg cggagggcga ggggcgggga gcgccgcctg     60
gagcgcggca ggtcatattg aacattccag atacctatca ttactcgatg ctgttgataa    120
cagcaagatg gctttgaact cagggtcacc accagctatt ggaccttact atgaaaacca    180
tggataccaa ccggaaaacc cctatcccgc acagcccact gtggtcccca ctgtctacga    240
ggtgcatccg gctcagtact acccgtcccc cgtgccccag tacgccccga gggtcctgac    300
gcaggcttcc aaccccgtcg tctgcacgca gcccaaatcc ccatccggga cagtgtgcac    360
ctcaaagact aagaaagcac tgtgcatcac cttgaccctg gggaccttcc tcgtgggagc    420
tgcgctggcc gctggcctac tctggaagtt cattcgcctc tacggaccaa acttcatcct    480
tcagatgtac tcatctcaga ggaagtcctg gcaccctgtg tgccaagacg actggaacga    540
gaactacggg cgggcggcct gcagggacat gggctataag aataattttt actctagcca    600
aggaatagtg gatgacagcg gatccaccag ctttatgaaa ctgaacacaa gtgccggcaa    660
tgtcgatatc tataaaaaac tgtaccacag tgatgcctgt tcttcaaaag cagtggtttc    720
tttacgctgt atagcctgcg ggtcaactt gaactcaagc cgccagagca ggatcgtggg    780
cggtgagagc gcgctcccgg gggcctggcc ctggcaggtc agcctgcacg tccagaacgt    840
ccacgtgtgc ggaggctcca tcatcacccc cgagtggatc gtgacagccg cccactgcgt    900
ggaaaaacct cttaacaatc catggcattg gacggcattt gcggggattt tgagacaatc    960
tttcatgttc tatggagccg gataccaagt agaaaaagtg atttctcatc caaattatga   1020
ctccaagacc aagaacaatg acattgcgct gatgaagctg cagaagcctc tgactttcaa   1080
cgacctagtg aaaccagtgt gtctgcccaa cccaggcatg atgctgcagc cagaacagct   1140
ctgctggatt tccgggtggg gggccaccga ggagaaaggg aagacctcag aagtgctgaa   1200
cgctgccaag gtgcttctca ttgagacaca gagatgcaac agcagatatg tctatgacaa   1260
cctgatcaca ccagccatga tctgtgccgg cttcctgcag gggaacgtcg attcttgcca   1320
gggtgacagt ggagggcctc tggtcacttc gaagaacaat atctggtggc tgatagggga   1380
tacaagctgg ggttctggct gtgccaaagc ttacagacca ggagtgtacg ggaatgtgat   1440
ggtattcacg gactggattt atcgacaaat gagggcagac ggctaatcca catggtcttc   1500
gtccttgacg tcgttttaca agaaaacaat ggggctggtt ttgcttcccc gtgcatgatt   1560
tactcttaga gatgattcag aggtcacttc atttttatta aacagtgaac ttgtctggct   1620
ttggcactct ctgccattct gtgcaggctg cagtggctcc cctgcccagc ctgctctccc   1680
taacccttg tccgcaaggg gtgatggccg gctggttgtg ggcactggcg gtcaagtgtg   1740
gaggagaggg gtggaggctg ccccattgag atcttcctgc tgagtccttt ccaggggcca   1800
attttggatg agcatggagc tgtcacctct cagctgctgg atgacttgag atgaaaaagg   1860
agagacatgg aaagggagac agccaggtgg cacctgcagc ggctgccctc tggggccact   1920
tggtagtgtc cccagcctac ctctccacaa ggggattttg ctgatgggtt cttagagcct   1980
tagcagccct ggatggtggc cagaaataaa gggaccagcc cttcatgggt ggtgacgtgg   2040
tagtcacttg taaggggaac agaaacattt ttgttcttat ggggtgagaa tatagacagt   2100
gcccttggtg cgagggaagc aattgaaaag gaacttgccc tgagcactcc tggtgcaggt   2160
ctccacctgc acattgggtg gggctcctgg gagggagact cagccttcct cctcatcctc   2220
cctgaccctg ctcctagcac cctggagagt gcacatgccc cttggtcctg gcagggcgcc   2280
```

-continued

```
aagtctggca ccatgttggc ctcttcaggc ctgctagtca ctggaaattg aggtccatgg   2340

gggaaatcaa ggatgctcag tttaaggtac actgtttcca tgttatgttt ctacacattg   2400

ctacctcagt gctcctggaa acttagcttt tgatgtctcc aagtagtcca ccttcattta   2460

actctttgaa actgtatcac ctttgccaag taagagtggt ggcctatttc agctgctttg   2520

acaaaatgac tggctcctga cttaacgttc tataaatgaa tgtgctgaag caaagtgccc   2580

atggtggcgg cgaagaagag aaagatgtgt tttgttttgg actctctgtg gtcccttcca   2640

atgctgtggg tttccaacca ggggaagggt cccttttgca ttgccaagtg ccataaccat   2700

gagcactact ctaccatggt tctgcctcct ggccaagcag gctggtttgc aagaatgaaa   2760

tgaatgattc tacagctagg acttaacctt gaaatggaaa gtcttgcaat cccatttgca   2820

ggatccgtct gtgcacatgc ctctgtagag agcagcattc ccagggacct tggaaacagt   2880

tggcactgta aggtgcttgc tccccaagac acatcctaaa aggtgttgta atggtgaaaa   2940

cgtcttcctt ctttattgcc ccttcttatt tatgtgaaca actgtttgtc tttttttgta   3000

tctttttttaa actgtaaagt tcaattgtga aaatgaatat catgcaaata aattatgcga   3060

ttttttttttc aaagcaaaaa aaaaaaaaaa aaaaaaaaaa aaaaaa                 3106
```

```
<210> SEQ ID NO 96
<211> LENGTH: 3003
<212> TYPE: DNA
<213> ORGANISM: Homo sapiens

<400> SEQUENCE: 96

cgcgagctaa gcaggaggcg gaggcggagg cggagggcga ggggcgggga gcgccgcctg     60

gagcgcggca ggtcatattg aacattccag atacctatca ttactcgatg ctgttgataa    120

cagcaagatg gctttgaact caagactaag aaagcactgt gcatcacctt gaccctgggg    180

accttcctcg tgggagctgc gctggccgct ggcctactct ggaagttcat gggcagcaag    240

tgctccaact ctgggataga gtgcgactcc tcaggtacct gcatcaaccc ctctaactgg    300

tgtgatggcg tgtcacactg ccccggcggg gaggacgaga atcggtgtgt tcgcctctac    360

ggaccaaact tcatccttca gatgtactca tctcagagga agtcctggca ccctgtgtgc    420

caagacgact ggaacgagaa ctacgggcgg gcggcctgca gggacatggg ctataagaat    480

aatttttact ctagccaagg aatagtggat gacagcggat ccaccagctt tatgaaactg    540

aacacaagtg ccggcaatgt cgatatctat aaaaaactgt accacagtga tgcctgttct    600

tcaaaagcag tggtttcttt acgctgtata gcctgcgggg tcaacttgaa ctcaagccgc    660

cagagcagga tcgtgggcgg tgagagcgcg ctcccggggg cctggccctg gcaggtcagc    720

ctgcacgtcc agaacgtcca cgtgtgcgga ggctccatca tcacccccga gtggatcgtg    780

acagccgccc actgcgtgga aaaacctctt aacaatccat ggcattggac ggcatttgcg    840

gggattttga gacaatcttt catgttctat ggagccggat accaagtaga aaaagtgatt    900

tctcatccaa attatgactc caagaccaag aacaatgaca ttgcgctgat gaagctgcag    960

aagcctctga ctttcaacga cctagtgaaa ccagtgtgtc tgcccaaccc aggcatgatg   1020

ctgcagccag aacagctctg ctggatttcc gggtgggggg ccaccgagga gaaagggaag   1080

acctcagaag tgctgaacgc tgccaaggtg cttctcattg agacacagag atgcaacagc   1140

agatatgtct atgacaacct gatcacacca gccatgatct gtgccggctt cctgcagggg   1200

aacgtcgatt cttgccaggg tgacagtgga gggcctctgg tcacttcgaa gaacaatatc   1260

tggtggctga taggggatac aagctggggt tctggctgtg ccaaagctta cagaccagga   1320
```

-continued

```
gtgtacggga atgtgatggt attcacggac tggatttatc gacaaatgag ggcagacggc   1380

taatccacat ggtcttcgtc cttgacgtcg ttttacaaga aacaatgggg gctggttttg   1440

cttccccgtg catgatttac tcttagagat gattcagagg tcacttcatt tttattaaac   1500

agtgaacttg tctggctttg gcactctctg ccattctgtg caggctgcag tggctcccct   1560

gcccagcctg ctctccctaa ccccttgtcc gcaaggggtg atggccggct ggttgtgggc   1620

actggcggtc aagtgtggag gagaggggtg gaggctgccc cattgagatc ttcctgctga   1680

gtcctttcca ggggccaatt ttggatgagc atggagctgt cacctctcag ctgctggatg   1740

acttgagatg aaaaaggaga gacatggaaa gggagacagc caggtggcac ctgcagcggc   1800

tgccctctgg ggccacttgg tagtgtcccc agcctacctc tccacaaggg gattttgctg   1860

atgggttctt agagccttag cagccctgga tggtggccag aaataaaggg accagccctt   1920

catgggtggt gacgtggtag tcacttgtaa ggggaacaga aacatttttg ttcttatggg   1980

gtgagaatat agacagtgcc cttggtgcga gggaagcaat tgaaaaggaa cttgccctga   2040

gcactcctgg tgcaggtctc cacctgcaca ttgggtgggg ctcctgggag ggagactcag   2100

ccttcctcct catcctccct gaccctgctc ctagcaccct ggagagtgca catgcccctt   2160

ggtcctggca gggcgccaag tctggcacca tgttggcctc ttcaggcctg ctagtcactg   2220

gaaattgagg tccatggggg aaatcaagga tgctcagttt aaggtacact gtttccatgt   2280

tatgtttcta cacattgcta cctcagtgct cctggaaact tagcttttga tgtctccaag   2340

tagtccacct tcatttaact ctttgaaact gtatcacctt tgccaagtaa gagtggtggc   2400

ctatttcagc tgctttgaca aaatgactgg ctcctgactt aacgttctat aaatgaatgt   2460

gctgaagcaa agtgcccatg gtggcggcga agaagagaaa gatgtgtttt gttttggact   2520

ctctgtggtc ccttccaatg ctgtgggttt ccaaccaggg gaagggtccc ttttgcattg   2580

ccaagtgcca taaccatgag cactactcta ccatggttct gcctcctggc caagcaggct   2640

ggtttgcaag aatgaaatga atgattctac agctaggact taaccttgaa atggaaagtc   2700

ttgcaatccc atttgcagga tccgtctgtg cacatgcctc tgtagagagc agcattccca   2760

gggaccttgg aaacagttgg cactgtaagg tgcttgctcc ccaagacaca tcctaaaagg   2820

tgttgtaatg gtgaaaacgt cttccttctt tattgcccct tcttatttat gtgaacaact   2880

gtttgtcttt ttttgtatct tttttaaact gtaaagttca attgtgaaaa tgaatatcat   2940

gcaaataaat tatgcgattt ttttttcaaa gcaaaaaaaa aaaaaaaaaa aaaaaaaaaa   3000

aaa                                                                 3003
```

<210> SEQ ID NO 97
<211> LENGTH: 3102
<212> TYPE: DNA
<213> ORGANISM: Homo sapiens

<400> SEQUENCE: 97

```
cgcgagctaa gcaggaggcg gaggcggagg cggagggcga ggggcgggga gcgccgcctg     60

gagcgcggca ggtcatattg aacattccag atacctatca ttactcgatg ctgttgataa    120

cagcaagatg gctttgaact cagggtcacc accagctatt ggaccttact atgaaaacca    180

tggataccaa ccggaaaacc cctatcccgc acagcccact gtggtcccca ctgtctacga    240

gagactaaga aagcactgtg catcaccttg accctgggga ccttcctcgt gggagctgcg    300

ctggccgctg gcctactctg gaagttcatg ggcagcaagt gctccaactc tgggatagag    360
```

-continued

```
tgcgactcct caggtacctg catcaacccc tctaactggt gtgatggcgt gtcacactgc    420

cccggcgggg aggacgagaa tcggtgtgtt cgcctctacg gaccaaactt catccttcag    480

atgtactcat ctcagaggaa gtcctggcac cctgtgtgcc aagacgactg gaacgagaac    540

tacgggcggg cggcctgcag ggacatgggc tataagaata atttttactc tagccaagga    600

atagtggatg acagcggatc caccagcttt atgaaactga acacaagtgc cggcaatgtc    660

gatatctata aaaaactgta ccacagtgat gcctgttctt caaaagcagt ggtttcttta    720

cgctgtatag cctgcggggt caacttgaac tcaagccgcc agagcaggat cgtgggcggt    780

gagagcgcgc tcccgggggc ctggccctgg caggtcagcc tgcacgtcca gaacgtccac    840

gtgtgcggag gctccatcat cacccccgag tggatcgtga cagccgccca ctgcgtggaa    900

aaacctctta acaatccatg gcattggacg gcatttgcgg ggattttgag acaatctttc    960

atgttctatg gagccggata ccaagtagaa aaagtgattt ctcatccaaa ttatgactcc   1020

aagaccaaga acaatgacat tgcgctgatg aagctgcaga agcctctgac tttcaacgac   1080

ctagtgaaac cagtgtgtct gcccaaccca ggcatgatgc tgcagccaga acagctctgc   1140

tggatttccg ggtgggggc caccgaggag aaagggaaga cctcagaagt gctgaacgct    1200

gccaaggtgc ttctcattga gacacagaga tgcaacagca gatatgtcta tgacaacctg   1260

atcacaccag ccatgatctg tgccggcttc ctgcagggga acgtcgattc ttgccagggt   1320

gacagtggag ggcctctggt cacttcgaag aacaatatct ggtggctgat aggggataca   1380

agctggggtt ctggctgtgc caaagcttac agaccaggag tgtacgggaa tgtgatggta   1440

ttcacggact ggatttatcg acaaatgagg gcagacggct aatccacatg gtcttcgtcc   1500

ttgacgtcgt tttacaagaa aacaatgggg ctggttttgc ttccccgtgc atgatttact   1560

cttagagatg attcagaggt cacttcattt ttattaaaca gtgaacttgt ctggctttgg   1620

cactctctgc cattctgtgc aggctgcagt ggctcccctg cccagcctgc tctccctaac   1680

cccttgtccg caaggggtga tggccggctg gttgtgggca ctggcggtca agtgtggagg   1740

agaggggtgg aggctgcccc attgagatct tcctgctgag tcctttccag gggccaattt   1800

tggatgagca tggagctgtc acctctcagc tgctggatga cttgagatga aaaaggagag   1860

acatggaaag ggagacagcc aggtggcacc tgcagcggct gccctctggg gccacttggt   1920

agtgtcccca gcctacctct ccacaagggg attttgctga tgggttctta gagccttagc   1980

agccctggat ggtggccaga aataaaggga ccagcccttc atgggtggtg acgtggtagt   2040

cacttgtaag gggaacagaa acatttttgt tcttatgggg tgagaatata gacagtgccc   2100

ttggtgcgag ggaagcaatt gaaaaggaac ttgccctgag cactcctggt gcaggtctcc   2160

acctgcacat tgggtggggc tcctgggagg gagactcagc cttcctcctc atcctccctg   2220

accctgctcc tagcaccctg gagagtgcac atgccccttg gtcctggcag ggcgccaagt   2280

ctggcaccat gttggcctct tcaggcctgc tagtcactgg aaattgaggt ccatgggga    2340

aatcaaggat gctcagttta aggtacactg tttccatgtt atgtttctac acattgctac   2400

ctcagtgctc ctggaaactt agcttttgat gtctccaagt agtccacctt catttaactc   2460

tttgaaactg tatcaccttt gccaagtaag agtggtggcc tatttcagct gctttgacaa   2520

aatgactggc tcctgactta acgttctata aatgaatgtg ctgaagcaaa gtgcccatgg   2580

tggcggcgaa gaagagaaag atgtgttttg ttttggactc tctgtggtcc cttccaatgc   2640

tgtgggtttc caaccagggg aagggtccct tttgcattgc caagtgccat aaccatgagc   2700

actactctac catggttctg cctcctggcc aagcaggctg gtttgcaaga atgaaatgaa   2760
```

```
tgattctaca gctaggactt aaccttgaaa tggaaagtct tgcaatccca tttgcaggat   2820

ccgtctgtgc acatgcctct gtagagagca gcattcccag ggaccttgga aacagttggc   2880

actgtaaggt gcttgctccc caagacacat cctaaaaggt gttgtaatgg tgaaaacgtc   2940

ttccttcttt attgcccctt cttatttatg tgaacaactg tttgtctttt tttgtatctt   3000

ttttaaactg taaagttcaa ttgtgaaaat gaatatcatg caaataaatt atgcgatttt   3060

tttttcaaag caaaaaaaaa aaaaaaaaaa aaaaaaaaaa aa                      3102
```

<210> SEQ ID NO 98
<211> LENGTH: 2916
<212> TYPE: DNA
<213> ORGANISM: Homo sapiens

<400> SEQUENCE: 98

```
cgcgagctaa gcaggaggcg gaggcggagg cggagggcga ggggcgggga gcgccgcctg     60

gagcgcggca ggtcatattg aacattccag atacctatca ttactcgatg ctgttgataa    120

cagcaagatg gctttgaact catgggcagc aagtgctcca actctgggat agagtgcgac    180

tcctcaggta cctgcatcaa cccctctaac tggtgtgatg gcgtgtcaca ctgccccggc    240

ggggaggacg agaatcggtg tgttcgcctc tacggaccaa acttcatcct tcagatgtac    300

tcatctcaga ggaagtcctg gcaccctgtg tgccaagacg actggaacga gaactacggg    360

cgggcggcct gcagggacat gggctataag aataattttt actctagcca aggaatagtg    420

gatgacagcg gatccaccag ctttatgaaa ctgaacacaa gtgccggcaa tgtcgatatc    480

tataaaaaac tgtaccacag tgatgcctgt tcttcaaaag cagtggtttc tttacgctgt    540

atagcctgcg gggtcaactt gaactcaagc cgccagagca ggatcgtggg cggtgagagc    600

gcgctcccgg gggcctggcc ctggcaggtc agcctgcacg tccagaacgt ccacgtgtgc    660

ggaggctcca tcatcacccc cgagtggatc gtgacagccg cccactgcgt ggaaaaacct    720

cttaacaatc catggcattg gacggcattt gcggggattt tgagacaatc tttcatgttc    780

tatggagccg gataccaagt agaaaaagtg atttctcatc caaattatga ctccaagacc    840

aagaacaatg acattgcgct gatgaagctg cagaagcctc tgactttcaa cgacctagtg    900

aaaccagtgt gtctgcccaa cccaggcatg atgctgcagc cagaacagct ctgctggatt    960

tccgggtggg gggccaccga ggagaaaggg aagacctcag aagtgctgaa cgctgccaag   1020

gtgcttctca ttgagacaca gagatgcaac agcagatatg tctatgacaa cctgatcaca   1080

ccagccatga tctgtgccgg cttcctgcag gggaacgtcg attcttgcca gggtgacagt   1140

ggagggcctc tggtcacttc gaagaacaat atctggtggc tgatagggga tacaagctgg   1200

ggttctggct gtgccaaagc ttacagacca ggagtgtacg ggaatgtgat ggtattcacg   1260

gactggattt atcgacaaat gagggcagac ggctaatcca catggtcttc gtccttgacg   1320

tcgttttaca agaaaacaat ggggctggtt ttgcttcccc gtgcatgatt tactcttaga   1380

gatgattcag aggtcacttc atttttatta aacagtgaac ttgtctggct ttggcactct   1440

ctgccattct gtgcaggctg cagtggctcc cctgcccagc ctgctctccc taaccccttg   1500

tccgcaaggg gtgatggccg gctggttgtg ggcactggcg gtcaagtgtg gaggagaggg   1560

gtggaggctg ccccattgag atcttcctgc tgagtccttt ccaggggcca attttggatg   1620

agcatggagc tgtcacctct cagctgctgg atgacttgag atgaaaaagg agagacatgg   1680

aaagggagac agccaggtgg cacctgcagc ggctgccctc tggggccact tggtagtgtc   1740
```

-continued

```
cccagcctac ctctccacaa ggggattttg ctgatgggtt cttagagcct tagcagccct   1800

ggatggtggc cagaaataaa gggaccagcc cttcatgggt ggtgacgtgg tagtcacttg   1860

taaggggaac agaaacattt ttgttcttat ggggtgagaa tatagacagt gcccttggtg   1920

cgagggaagc aattgaaaag gaacttgccc tgagcactcc tggtgcaggt ctccacctgc   1980

acattgggtg gggctcctgg gagggagact cagccttcct cctcatcctc cctgaccctg   2040

ctcctagcac cctggagagt gcacatgccc cttggtcctg gcagggcgcc aagtctggca   2100

ccatgttggc ctcttcaggc ctgctagtca ctggaaattg aggtccatgg gggaaatcaa   2160

ggatgctcag tttaaggtac actgtttcca tgttatgttt ctacacattg ctacctcagt   2220

gctcctggaa acttagcttt tgatgtctcc aagtagtcca ccttcattta actctttgaa   2280

actgtatcac ctttgccaag taagagtggt ggcctatttc agctgctttg acaaaatgac   2340

tggctcctga cttaacgttc tataaatgaa tgtgctgaag caaagtgccc atggtggcgg   2400

cgaagaagag aaagatgtgt tttgttttgg actctctgtg gtcccttcca atgctgtggg   2460

tttccaacca ggggaagggt ccctttttgca ttgccaagtg ccataaccat gagcactact   2520

ctaccatggt tctgcctcct ggccaagcag gctggtttgc aagaatgaaa tgaatgattc   2580

tacagctagg acttaacctt gaaatggaaa gtcttgcaat cccatttgca ggatccgtct   2640

gtgcacatgc ctctgtagag agcagcattc ccagggacct tggaaacagt tggcactgta   2700

aggtgcttgc tccccaagac acatcctaaa aggtgttgta atggtgaaaa cgtcttcctt   2760

ctttattgcc ccttcttatt tatgtgaaca actgtttgtc ttttttgta tcttttttaa   2820

actgtaaagt tcaattgtga aaatgaatat catgcaaata aattatgcga ttttttttc   2880

aaagcaaaaa aaaaaaaaaa aaaaaaaaaa aaaaaa                            2916
```

<210> SEQ ID NO 99
<211> LENGTH: 2653
<212> TYPE: DNA
<213> ORGANISM: Homo sapiens

<400> SEQUENCE: 99

```
ctcaaaaggg gccggatttc cttctcctgg aggcagatgt tgcctctctc tctcgctcgg     60

attggttcag tgcactctag aaacactgct gtggtggaga aactggaccc caggtctgga    120

gcgaattcca gcctgcaggg ctgataagcg aggcattagt gagattgaga gagactttac    180

cccgccgtgg tggttggagg gcgcgcagta gagcagcagc acaggcgcgg gtcccgggag    240

gccggctctg ctcgcgccga gatgtggaat ctccttcacg aaaccgactc ggctgtggcc    300

accgcgcgcc gcccgcgctg gctgtgcgct ggggcgctgg tgctggcggg tggcttcttt    360

ctcctcggct tcctcttcgg gtggtttata aaatcctcca atgaagctac taacattact    420

ccaaagcata atatgaaagc atttttggat gaattgaaag ctgagaacat caagaagttc    480

ttatataatt ttacacagat accacattta gcaggaacag aacaaaactt tcagcttgca    540

aagcaaattc aatcccagtg gaaagaattt ggcctggatt ctgttgagct agcacattat    600

gatgtcctgt tgtcctaccc aaataagact catcccaact acatctcaat aattaatgaa    660

gatggaaatg agattttcaa cacatcatta tttgaaccac ctcctccagg atatgaaaat    720

gtttcggata ttgtaccacc tttcagtgct ttctctcctc aaggaatgcc agagggcgat    780

ctagtgtatg ttaactatgc acgaactgaa gacttcttta aattggaacg ggacatgaaa    840

atcaattgct ctgggaaaat tgtaattgcc agatatggga aagttttcag aggaaataag    900

gttaaaaatg cccagctggc aggggccaaa ggagtcattc tctactccga ccctgctgac    960
```

```
tactttgctc ctggggtgaa gtcctatcca gatggttgga atcttcctgg aggtggtgtc   1020

cagcgtggaa atatcctaaa tctgaatggt gcaggagacc ctctcacacc aggttaccca   1080

gcaaatgaat atgcttatag gcgtggaatt gcagaggctg ttggtcttcc aagtattcct   1140

gttcatccaa ttggatacta tgatgcacag aagctcctag aaaaaatggg tggctcagca   1200

ccaccagata gcagctggag aggaagtctc aaagtgccct acaatgttgg acctggcttt   1260

actggaaact tttctacaca aaaagtcaag atgcacatcc actctaccaa tgaagtgaca   1320

agaatttaca atgtgatagg tactctcaga ggagcagtgg aaccagacag atatgtcatt   1380

ctgggaggtc accgggactc atgggtgttt ggtggtattg accctcagag tggagcagct   1440

gttgttcatg aaattgtgag gagctttgga acactgaaaa aggaagggtg gagacctaga   1500

agaacaattt tgtttgcaag ctgggatgca gaagaatttg gtcttcttgg ttctactgag   1560

tgggcagagg agaattcaag actccttcaa gagcgtggcg tggcttatat taatgctgac   1620

tcatctatag aaggaaacta cactctgaga gttgattgta caccgctgat gtacagcttg   1680

gtacacaacc taacaaaaga gctgaaaagc cctgatgaag gctttgaagg caaatctctt   1740

tatgaaagtt ggactaaaaa aagtccttcc ccagagttca gtggcatgcc caggataagc   1800

aaattgggat ctggaaatga ttttgaggtg ttcttccaac gacttggaat tgcttcaggc   1860

agagcacggt atactaaaaa ttgggaaaca aacaaattca gcggctatcc actgtatcac   1920

agtgtctatg aaacatatga gttggtggaa aagttttatg atccaatgtt taaatatcac   1980

ctcactgtgg cccaggttcg aggagggatg gtgtttgagc tagccaattc catagtgctc   2040

ccttttgatt gtcgagatta tgctgtagtt ttaagaaagt atgctgacaa aatctacagt   2100

atttctatga aacatccaca ggaaatgaag acatacagtg tatcatttga ttcacttttt   2160

tctgcagtaa agaattttac agaaattgct tccaagttca gtgagagact ccaggacttt   2220

gacaaaagca acccaatagt attaagaatg atgaatgatc aactcatgtt tctggaaaga   2280

gcatttattg atccattagg gttaccagac aggccttttt ataggcatgt catctatgct   2340

ccaagcagcc acaacaagta tgcaggggag tcattcccag gaatttatga tgctctgttt   2400

gatattgaaa gcaaagtgga cccttccaag gcctggggag aagtgaagag acagatttat   2460

gttgcagcct tcacagtgca ggcagctgca gagactttga gtgaagtagc ctaagaggat   2520

tctttagaga atccgtattg aatttgtgtg gtatgtcact cagaaagaat cgtaatgggt   2580

atattgataa attttaaaat tggtatattt gaaataaagt tgaatattat atataaaaaa   2640

aaaaaaaaaa aaa                                                      2653
```

<210> SEQ ID NO 100
<211> LENGTH: 2466
<212> TYPE: DNA
<213> ORGANISM: Homo sapiens

<400> SEQUENCE: 100

```
ctcaaaaggg gccggatttc cttctcctgg aggcagatgt tgcctctctc tctcgctcgg     60

attggttcag tgcactctag aaacactgct gtggtggaga aactggaccc caggtctgga    120

gcgaattcca gcctgcaggg ctgataagcg aggcattagt gagattgaga gagactttac    180

cccgccgtgg tggttggagg gcgcgcagta gagcagcagc acaggcgcgg gtcccgggag    240

gccggctctg ctcgcgccga gatgtggaat ctccttcacg aaaccgactc ggctgtggcc    300

accgcgcgcc gcccgcgctg gctgtgcgct ggggcgctgg tgctggcggg tggcttcttt    360
```

-continued

```
ctcctcggct tcctcttcgg gtggtttata aaatcctcca atgaagctac taacattact    420
ccaaagcata atatgaaagc atttttggat gaattgaaag ctgagaacat caagaagttc    480
ttatataatt ttacacagat accacattta gcaggaacag aacaaaactt tcagcttgca    540
aagcaaattc aatcccagtg gaaagaattt ggcctggatt ctgttgagct agcacattat    600
gatgtcctgt tgtcctaccc aaataagact catcccaact acatctcaat aattaatgaa    660
gatggaaatg agattttcaa cacatcatta tttgaaccac ctcctccagg atatgaaaat    720
gtttcggata ttgtaccacc tttcagtgct ttctctcctc aaggaatgcc agagggcgat    780
ctagtgtatg ttaactatgc acgaactgaa gacttcttta aattggaacg ggacatgaaa    840
atcaattgct ctgggaaaat tgtaattgcc agatatggga aagttttcag aggaaataag    900
aatatgctta taggcgtgga attgcagagg ctgttggtct tccaagtatt cctgttcatc    960
caattggata ctatgatgca cagaagctcc tagaaaaaat gggtggctca gcaccaccag   1020
atagcagctg gagaggaagt ctcaaagtgc cctacaatgt tggacctggc tttactggaa   1080
acttttctac acaaaaagtc aagatgcaca tccactctac caatgaagtg acaagaattt   1140
acaatgtgat aggtactctc agaggagcag tggaaccaga cagatatgtc attctgggag   1200
gtcaccggga ctcatgggtg tttggtggta ttgaccctca gagtggagca gctgttgttc   1260
atgaaattgt gaggagcttt ggaacactga aaaaggaagg gtggagacct agaagaacaa   1320
ttttgtttgc aagctgggat gcagaagaat ttggtcttct tggttctact gagtgggcag   1380
aggagaattc aagactcctt caagagcgtg gcgtggctta tattaatgct gactcatcta   1440
tagaaggaaa ctacactctg agagttgatt gtacaccgct gatgtacagc ttggtacaca   1500
acctaacaaa agagctgaaa agccctgatg aaggctttga aggcaaatct ctttatgaaa   1560
gttggactaa aaaaagtcct tccccagagt tcagtggcat gcccaggata agcaaattgg   1620
gatctggaaa tgattttgag gtgttcttcc aacgacttgg aattgcttca ggcagagcac   1680
ggtatactaa aaattgggaa acaaacaaat tcagcggcta tccactgtat cacagtgtct   1740
atgaaacata tgagttggtg gaaaagtttt atgatccaat gtttaaatat cacctcactg   1800
tggcccaggt tcgaggaggg atggtgtttg agctagccaa ttccatagtg ctcccttttg   1860
attgtcgaga ttatgctgta gttttaagaa agtatgctga caaaatctac agtatttcta   1920
tgaaacatcc acaggaaatg aagacataca gtgtatcatt tgattcactt ttttctgcag   1980
taaagaattt tacagaaatt gcttccaagt tcagtgagag actccaggac tttgacaaaa   2040
gcaacccaat agtattaaga atgatgaatg atcaactcat gtttctggaa agagcattta   2100
ttgatccatt agggttacca gacaggcctt tttataggca tgtcatctat gctccaagca   2160
gccacaacaa gtatgcaggg gagtcattcc caggaattta tgatgctctg tttgatattg   2220
aaagcaaagt ggacccttcc aaggcctggg gagaagtgaa gagacagatt tatgttgcag   2280
ccttcacagt gcaggcagct gcagagactt tgagtgaagt agcctaagag gattctttag   2340
agaatccgta ttgaatttgt gtggtatgtc actcagaaag aatcgtaatg ggtatattga   2400
taaattttaa aattggtata tttgaaataa agttgaatat tatatataaa aaaaaaaaaa   2460
aaaaaa                                                              2466
```

<210> SEQ ID NO 101
<211> LENGTH: 2560
<212> TYPE: DNA
<213> ORGANISM: Homo sapiens

<400> SEQUENCE: 101

-continued

```
ctcaaaaggg gccggatttc cttctcctgg aggcagatgt tgcctctctc tctcgctcgg     60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
gccggctctg ctcgcgccga gatgtggaat ctccttcacg aaaccgactc ggctgtggcc    300
accgcgcgcc gcccgcgctg gctgtgcgct ggggcgctgg tgctggcggg tggcttcttt    360
ctcctcggct tcctcttcgg gtggtttata aaatcctcca atgaagctac taacattact    420
ccaaagcata atatgaaagc atttttggat gaattgaaag ctgagaacat caagaagttc    480
ttatataatt ttacacagat accacattta gcaggaacag aacaaaactt tcagcttgca    540
aagcaaattc aatcccagtg gaaagaattt ggcctggatt ctgttgagct agcacattat    600
gatgtcctgt tgtcctaccc aaataagact catcccaact acatctcaat aattaatgaa    660
gatggaaatg agattttcaa cacatcatta tttgaaccac ctcctccagg atatgaaaat    720
gtttcggata ttgtaccacc tttcagtgct ttctctcctc aaggaatgcc agagggcgat    780
ctagtgtatg ttaactatgc acgaactgaa gacttcttta aattggaacg ggacatgaaa    840
atcaattgct ctgggaaaat tgtaattgcc agatatggga aagttttcag aggaaataag    900
gttaaaaatg cccagctggc aggggccaaa ggagtcattc tctactccga ccctgctgac    960
tactttgctc ctggggtgaa gtcctatcca gatggttgga atcttcctgg aggtggtgtc   1020
cagcgtggaa atatcctaaa tctgaatggt gcaggagacc ctctcacacc aggttaccca   1080
gcaaatgaat atgcttatag gcgtggaatt gcagaggctg ttggtcttcc aagtattcct   1140
gttcatccaa ttggatacta tgatgcacag aagctcctag aaaaaatggg tggctcagca   1200
ccaccagata gcagctggag aggaagtctc aaagtgccct acaatgttgg acctggcttt   1260
actggaaact tttctacaca aaaagtcaag atgcacatcc actctaccaa tgaagtgaca   1320
agaatttaca atgtgatagg tactctcaga ggagcagtgg aaccagacag atatgtcatt   1380
ctgggaggtc accgggactc atgggtgttt ggtggtattg accctcagag tggagcagct   1440
gttgttcatg aaattgtgag gagctttgga acactgaaaa aggaagggtg gagacctaga   1500
agaacaattt tgtttgcaag ctgggatgca gaagaatttg gtcttcttgg ttctactgag   1560
tgggcagagg agaattcaag actccttcaa gagcgtggcg tggcttatat taatgctgac   1620
tcatctatag aaggaaacta cactctgaga gttgattgta caccgctgat gtacagcttg   1680
gtacacaacc taacaaaaga gctgaaaagc cctgatgaag gctttgaagg caaatctctt   1740
tatgaaagtt ggactaaaaa aagtccttcc ccagagttca gtggcatgcc caggataagc   1800
aaattgggat ctggaaatga ttttgaggtg ttcttccaac gacttggaat tgcttcaggc   1860
agagcacggt atactaaaaa ttgggaaaca aacaaattca gcggctatcc actgtatcac   1920
agtgtctatg aaacatatga gttggtggaa aagttttatg atccaatgtt taaatatcac   1980
ctcactgtgg cccaggttcg aggagggatg gtgtttgagc tagccaattc catagtgctc   2040
ccttttgatt gtcgagatta tgctgtagtt ttaagaaagt atgctgacaa aatctacagt   2100
atttctatga aacatccaca ggaaatgaag acatacagtg tatcatttga ttcacttttt   2160
tctgcagtaa agaattttac agaaattgct tccaagttca gtgagagact ccaggacttt   2220
gacaaaagca agcatgtcat ctatgctcca agcagccaca acaagtatgc aggggagtca   2280
ttcccaggaa tttatgatgc tctgtttgat attgaaagca aagtggaccc ttccaaggcc   2340
```

```
tggggagaag tgaagagaca gatttatgtt gcagccttca cagtgcaggc agctgcagag   2400

actttgagtg aagtagccta agaggattct ttagagaatc cgtattgaat ttgtgtggta   2460

tgtcactcag aaagaatcgt aatgggtata ttgataaatt ttaaaattgg tatatttgaa   2520

ataaagttga atattatata taaaaaaaaa aaaaaaaaaa                         2560


<210> SEQ ID NO 102
<211> LENGTH: 212
<212> TYPE: DNA
<213> ORGANISM: Homo sapiens

<400> SEQUENCE: 102

ggagtgcacc cgctgtccac atgccgcgat ctggtggcgg tcgtgcatcg tccagcaaac     60

ggaagatgac cctgggaacg ttcaaaccgg gcgtccagca gcggctgact gtagagctcc    120

tatctgatag ctgcgtgttc agggtagatg gtgaagtgtt cgagacgatc cggccttccg    180

acatggcgga tggatatatc tgggtcccca cg                                  212


<210> SEQ ID NO 103
<211> LENGTH: 675
<212> TYPE: DNA
<213> ORGANISM: Homo sapiens

<400> SEQUENCE: 103

ctagactgac tgaatcaaaa tccctggggt tgtgtgcaca tgacggttcg agaaacgcca     60

gcctaaggga ccctctgcag tctgtccagc ttgtcccttc aacctcatgc caaccaacac    120

actccagact caaagtgcct tctctcaacc cccgctattg aagtacctga ccccaagcca    180

gttacaagtt cattcctgtt tcattttctc tggagggctg ccatcaatga gattgttatt    240

tatgttggta tgtcctcacc aaagtgtctg ccaggcctat cacagtcctg gagctcaggg    300

gagacccaag caaaccaaca cacatttgcc aggcacccag gatggaccta agcaagctgt    360

ctgggcccac caggagttcc tggttgggcc aggaggacct gcctgttaca catgaactat    420

gattcaaaac gtagacatat agtcttcaat taataataac atttaaaaaa gacaaaaagt    480

aggtatacat tttgaatgag aatacaaatg agaaatgccc ccattcctcc aagtgcactt    540

tgttgaaaaa tgagaaggaa agggaggtgc ctggtggttt caggggaagg aatgtgtgga    600

acgcaggtct tccatgagca tggggctggc agtaggaaca aagactcgct tgcactgggc    660

ttgcgcctgc gctgg                                                     675


<210> SEQ ID NO 104
<211> LENGTH: 476
<212> TYPE: DNA
<213> ORGANISM: Homo sapiens
<220> FEATURE:
<221> NAME/KEY: misc_feature
<222> LOCATION: (464)..(464)
<223> OTHER INFORMATION: n = a t g or c

<400> SEQUENCE: 104

ctgctccctc acactctcca ttggctcact cagccccttt cctgtgcttc tttttatgtg     60

tttgtcacac tgtccttggt tttgtggagg ccagttcacc atcctaactt ataaattctc    120

aagagcaagg accagggctt gttgtgtgtt gcattttgga ttaccccaag aagcagactg    180

tgggatgaca tttaggtaca ggccatttaa caaaggagct cctttgagga acacacttgt    240

gaaagtggag gtgggagaag aagcataatt agaaagaaga agaagtcaga tgtgatggag    300

acccagggac agcttccata cctgaggaat tctggagcta gctagtggtc gctggcagtt    360
```

```
gtcccaaatt gaaaagagat ggccaggcat tgataaacct gatatttaga gacagatagt    420

ggctctgggc agaaagatca tctgatggtg ttctcagcac cggngaacaa catttc        476


<210> SEQ ID NO 105
<211> LENGTH: 265
<212> TYPE: DNA
<213> ORGANISM: Homo sapiens

<400> SEQUENCE: 105

gaccaggaaa tcgaagggaa gcgtccgcgc acagaacgtg gcccgatcct tgccgtgatc     60

gataccccag ggtcgatgca cggactacca gagcaggtgg ctaaagctat cgtgctggaa    120

gcgcttcgaa cagcgcatga agaaaagcgc cgatgtttcc tttacgccta cagtggacca    180

gggcaagtcc ttgagcacga gcttgatctt tcaccggacg gcatggggcg gcttctagaa    240

tttctcggct tctcttttgg tggcg                                          265


<210> SEQ ID NO 106
<211> LENGTH: 726
<212> TYPE: DNA
<213> ORGANISM: Homo sapiens

<400> SEQUENCE: 106

cgtaattgtg gaaggagtca cgggaagtgg agacaggaaa ggctgtgagg agccaaggga     60

aagaggcgaa gagaaaggcg gacaggagag aggacgagaa tgaaagagaa atcaacaggg    120

ggaaagagaa caacaggcag agggaaaagg aagtaagttt gctgaattct atattaagaa    180

actggtaaat gtcctgtagg tcaataaaac cataaacttt gaggttatct ttgctattag    240

tcagaaaaaa atgagaaccc tttgtcagat ttctgcaagt taaccgctaa ttttacaggg    300

ttgtaaaaca cctgggtctc aatcaattgc tagtgaaaca caattaccct tcccatgagt    360

cagatgacct tcaggtggac atgatattca caggttgtga aaccatgttt tgcccttttt    420

caaatgttag gctacttttt cctgaaaatc ctctgcatga aaaattctac cgcccttagt    480

gtgtctcaca caaggataac ttcaacccaa gctgtgttca acctggcctc caggtccctg    540

tccttagggc gggacccatc ctctgcttcc cgaataacca acactccttt ccattgccca    600

gaaaccatcc ctgctacctc gtgaggaatt aactttaccc aaagaaaggc ctgacctctg    660

tcccaggtcc tgggagaaag tccctgaact cctagaaggt cccaagcgac aggagtgtct    720

gttcac                                                               726


<210> SEQ ID NO 107
<211> LENGTH: 253
<212> TYPE: DNA
<213> ORGANISM: Homo sapiens
<220> FEATURE:
<221> NAME/KEY: misc_feature
<222> LOCATION: (98)..(98)
<223> OTHER INFORMATION: n = a t g or c

<400> SEQUENCE: 107

cggggatgag aacgtatctg ggaggagcac tgcgggcaag ggggtgctgaa ggattccatg    60

tgccggcagg gcattcccaa ccgtgaatcg tctccagnga gtccgccaac gcttcgagat    120

cctggcggcg aatgccatcc ccaaaggctt catggacggg aagcaggcct gcattctcat    180

gatcaaagcc ctggaacttg accccaactt atacaggata gggcagagca aaatcttctt    240

ccgaactggc gtc                                                       253
```

-continued

<210> SEQ ID NO 108
<211> LENGTH: 448
<212> TYPE: DNA
<213> ORGANISM: Homo sapiens

<400> SEQUENCE: 108
ccggcaggct gttggttccc gatctccgag cgcaggctcg atcccgtggc gccgccggaa 60
cgccgcaagc gcgctctctt gccgcgcgag cttgcgagtc aacgcgtcga tctcggcgcg 120
ccgcgtgagg gcaagcgccg ctatattttc gcggaaagcc cgttcgtccg cgcgtgtcca 180
tcttgaggta ccaccgccgg actgccggcg cttggtgcag gacgtgatcg tcatgcgctc 240
ggcgcgagct tcgatctgcc gttcaatgat gccgagatga cggcttgtct cgagaagtgc 300
attttccatg cgcaggagta aggccgattg aggcgtgagc gacatcagaa tgccctccat 360
ggcctgaccc ataacgcttc tcaatcacta gtgcggccgc ctgcaggtcg accatatggg 420
agagctccca acgcgttgga tgcatagc 448

<210> SEQ ID NO 109
<211> LENGTH: 437
<212> TYPE: DNA
<213> ORGANISM: Homo sapiens

<400> SEQUENCE: 109
cagaggttgc agtgagccga gatcatgcca ctgtactgca gtctgggcga cagagcaaga 60
ttccatctca taaaaactgt gaactaggca aagtttgttt ccaggaaata atcacatccc 120
catcttaata atcccatccc tatctaatat taggcacaat tcttagctgg ccccatgatc 180
tccaatcctt ggtgttacat cctgtataat attctttcct tgagtgtggg tgggacctgt 240
gacttgcttc tagttgagat tatctacatt acataaggct ccatcttgga gtaagagatt 300
tctctgctgg ccctgaagta gcagctatgt tgtgaacagc caatggagaa agccatatgg 360
cagagacctg caacagaagg tggacctgaa ggtggcctct ggtcaccagc aacagcccca 420
aggaaatgaa ttctgcc 437

<210> SEQ ID NO 110
<211> LENGTH: 244
<212> TYPE: DNA
<213> ORGANISM: Homo sapiens

<400> SEQUENCE: 110
ctggcaggtc gtagcaggcc ggccctgggt aggcccccat actgtcgggg ccgagcgtca 60
ctatgtcgcc tctcacgcgc gcaacgctgc cacctccgag agcggccgat ctgagaagaa 120
tccaaggtgt cttcagcggt attccaaaga agtttgtctc ctcggaggtt aacggttctc 180
cgttaacgac gatcccgatc ttcgccgtag ttccaccgac atcaagcgag ataacctccc 240
caga 244

<210> SEQ ID NO 111
<211> LENGTH: 272
<212> TYPE: DNA
<213> ORGANISM: Homo sapiens

<400> SEQUENCE: 111
gtgacgagaa gagcagatta aagaagatta gataccactg gtcaatcatg gtagatgcag 60
agaagccaca gaaaaactgg aaccaaaaca ggaggcccac gaacattgtg tttttgtaga 120
agaagtacag caccatgttg gcaagtcggg agtagcacca atgcccgtga agaatcaaga 180

```
gcctctccag gtatcggaat ttcggcactg caaagtcgct ggccatcact gccttcaaag    240

ggagagggat tcctgttact ggtgatgccg ac                                  272


<210> SEQ ID NO 112
<211> LENGTH: 413
<212> TYPE: DNA
<213> ORGANISM: Homo sapiens

<400> SEQUENCE: 112

gtggagccca cagaaaggag agggcatcaa agacacactt cgctggctgc accatttgct     60

cagggttggg cccagctccg gttacagctc cataatccat tgtgttcacc actgtttgct    120

taggtttaac tcggagttag aattctggtt ttgtttctca cttagggaaa aaaaatagct    180

ttgtaaaggg aggttactaa ataaaacttt gagaactcta ttcaccctca caggatgact    240

tttggcttgc aattcaatcc ctggcaggtt actgttcatg tatagaattt ccaggcgact    300

agaaggcatt tgaaaggaat tcttaccgaa cattaacctg ccttggtaac cacagaaggc    360

atttctacct gccaagctca ggctgggagc tttggtgcag tccgacctgc gcc           413


<210> SEQ ID NO 113
<211> LENGTH: 541
<212> TYPE: DNA
<213> ORGANISM: Homo sapiens

<400> SEQUENCE: 113

gtcaggctga cctggttctt ggtcatctcc tcccgggatg ggggcagggt gtacacctgt     60

ggttctcggg gctgtccttt ggttttggag atggttttct cgatgggggc tgggagggct    120

ttgttggaga ccttgcactt gtactccttg ccgttcagcc agtcctggtg caggacggtg    180

aggacgctga ccacacggaa cgtgctgttg gactgctcct cccgcggctt tgtcttggca    240

ttatgcacct accacgccgt ccacgttaca gttaaacttg acctcagggt cttcgtggct    300

cacgtccacc accacgcatg tgacctcagg ggtccgggag atcatgaggg tgtccttggg    360

ttttgggggg aagaggaaga actgacggtc cccccaggag ttcaggtgct gggcacggtg    420

ggcatgtgtg agttttgtca caagatttgg gctcaactct cttgtccacc atggtgttgc    480

tgggcttgtg attcactttg cagatgtaag tctcatgaat acggttttct aattcccgcg    540

g                                                                    541


<210> SEQ ID NO 114
<211> LENGTH: 226
<212> TYPE: DNA
<213> ORGANISM: Homo sapiens

<400> SEQUENCE: 114

gtggtgaggc cagggcttcc agcctcgtgc tgtctcggga ctcctgaccg tggtgtgcgt     60

gtgtgcccat ctgtgacttt ctactcacca aggttgaaga aaggaaacgg ggaaaatcaa    120

aaggggttca aaccccacct cagtaggtgg aggggagcgc ctgccattgg ttgtattttt    180

gttctgagtt ttcggtgccg tgttcctaac tactccatcc catgac                   226


<210> SEQ ID NO 115
<211> LENGTH: 439
<212> TYPE: DNA
<213> ORGANISM: Homo sapiens

<400> SEQUENCE: 115
```

-continued

```
tttgagccaa gatacggcgt atatgcaagg gtttgcgagt ttattagaag ggattgtgaa     60

gccggtatag ctagtgcttt tttaaaaagt tgtttaaaaa agagccgtat taaacattaa    120

tatggctctt ttttattgtt gagtttttat tattacaaaa tcaatttaaa caaataaaag    180

ccaattgccg ttgctaataa cgtcagcccc acatgtaacc caatcagtcc taaacccgca    240

agcagtttgc cgttatggat aaaggtaaat acttcagcac taaaggtact aaaagtcgtc    300

agtccgccca aaaaaccagt tatgacaaac aacctgacat tgggagacaa gtcgctgcac    360

ataacgcttc tcaatcacta gtgcggccgc ctgcaggtcg accatatggg agagctccca    420

acgcgttgga tgcatagct                                                 439
```

<210> SEQ ID NO 116
<211> LENGTH: 175
<212> TYPE: DNA
<213> ORGANISM: Homo sapiens

<400> SEQUENCE: 116

```
gggagtgaag atttctcacc tcgggtcttc ctagaccttc aggtcacacg ggaattgttc     60

tgtttataga cggcgctggc cttagtactc actctccctc tattttcctt gcttccttat    120

aactaggttt ccctactcac ttcctcaaaa agagtgatgt aggtccacgt gtacc         175
```

<210> SEQ ID NO 117
<211> LENGTH: 521
<212> TYPE: DNA
<213> ORGANISM: Homo sapiens

<400> SEQUENCE: 117

```
gctacaacca catttgttca caggagtttt tggtgcgggg tgggaaggat ggaaggcctt     60

ggatttatat tgcacttcat agacccctag gctgctgtgc ggtgggactc cacatgcgcc    120

ggaaggagct tcaggtgagc actgctcatg tgtggatgcc cctgcaacag gcttccctgt    180

ctgtagagcc aggggtgcaa gtgccatcca cacttgcagt gaatggcttt tccttttagg    240

tttaagtcct gtctgtctgt aaggcgtaga atctgtccgt ctgtaaggcg tagaatgagg    300

gttgttaatc catcacaagc aaaaggtcag aacagttaaa cactgccttt cctcctcctc    360

ttattttatg ataaaagcaa atgtggcctt ctcagtatca ttcgattgct atttgagact    420

tttaaattaa ggtaaaggct gctggtgttg gtacctgtgg atttttctat actgatgttt    480

tcgttttgcc aatataatga gtattacatt ggcctctcgt a                        521
```

<210> SEQ ID NO 118
<211> LENGTH: 131
<212> TYPE: DNA
<213> ORGANISM: Homo sapiens

<400> SEQUENCE: 118

```
ctgaagatgc ccctatattc tgtcaaaggt tggcgggggg aggtgttggg gtcctttcat     60

ctggctccgt ttctggtgct tctggaagtc tctgctcagc acagggaaga actaacacga    120

ctaacctagg c                                                         131
```

<210> SEQ ID NO 119
<211> LENGTH: 212
<212> TYPE: DNA
<213> ORGANISM: Homo sapiens

<400> SEQUENCE: 119

```
gtggtggaga tggttgaaaa cgacatatct gctttcacct acgagaggac actaatgatg     60
```

-continued

```
gagcagaggt cgcagatgct gaagcagatg cagctgtcca agaacgagca ggagcgagag    120

gcccagctga tccacgacag gaacaccgcg tcccacaccg cggcggcagc caggacccaa    180

gcgccgccta cgccagacaa ggtgcagatg ac                                  212


<210> SEQ ID NO 120
<211> LENGTH: 137
<212> TYPE: DNA
<213> ORGANISM: Homo sapiens

<400> SEQUENCE: 120

accgaagggc tgcatttctt tgtgggctta ttctcgagaa aactgggggc agatccctcc     60

tcaaggaggg gagggccacc ttggtttcca gtcaagtatt gtgaaaatta tccaacactc    120

aggcaatcca cccaacc                                                   137


<210> SEQ ID NO 121
<211> LENGTH: 265
<212> TYPE: DNA
<213> ORGANISM: Homo sapiens

<400> SEQUENCE: 121

gtggcagtga aggaaaaatc ccacaacagc cttggaatac cagagctcct gaccgtgggt     60

tagaatggtc ttttattatg aaggacaacc cattgaattt gagaagtcta cagtgaaagc    120

aaaatgtgtt cttaaaatgc aatactatct cgaggcagtt taaattctaa caataggagc    180

ctacatacca gatggctttg aaatatttac aggtcctctt tgcctgaatt tttagttatc    240

caggaacaac cattataact tatac                                          265


<210> SEQ ID NO 122
<211> LENGTH: 285
<212> TYPE: DNA
<213> ORGANISM: Homo sapiens

<400> SEQUENCE: 122

gtcctcgcat cagcgtcatc gtgtgcaccg gcttgggggg ctggagttcc ggttttcttt     60

gtttttctc tttattcgtc ctttctcaaa gatgggatac tgatcagaat tgctctgtat    120

atgcttggga ctggatggaa agactttgga gcagctgtgg ggggtggggg gacaccgaca    180

accaaacaga cgtgctggct ccagtcctgt ttttactttc aaaaaccaac aagcccgaca    240

gtggagcctg tcccctcccg ggagggtgct catggcccca ctcac                    285


<210> SEQ ID NO 123
<211> LENGTH: 269
<212> TYPE: DNA
<213> ORGANISM: Homo sapiens

<400> SEQUENCE: 123

gggccggatc tacgccatag attgcacatt gatttctata ctcaatagta cgtataggaa     60

tattaaaaac catacgccct tctggtaata acatacctat cgttccacaa taaattgagc    120

gaggagatga ctctaattgt tcaatatatt tcatggtact taatttatgt ggcggggata    180

acgcttctca atcactagtg cggccgcctg caggtcgacc atatgggaga gctcccaacg    240

cgttggatgc atagcttgag tattctata                                      269


<210> SEQ ID NO 124
<211> LENGTH: 203
<212> TYPE: DNA
```

-continued

<213> ORGANISM: Homo sapiens

<400> SEQUENCE: 124
gccgacgatc tcctcggttc tgcctcttca ccacaaacac cctctgtcct gacaccgtca 60
ccagcagtgt gtgttctcca aagaccacag acaggcgctt gaagggcaca ttcatgccgc 120
ggtgcggccg gaaaccgcag gctgtgctga ccagctcaga gatggcactg gctgcctgct 180
catcattctc caggtccacc cga 203

<210> SEQ ID NO 125
<211> LENGTH: 239
<212> TYPE: DNA
<213> ORGANISM: Homo sapiens

<400> SEQUENCE: 125
atacagaaga ggggtttgct ggggatgagg acagcagggc agtcaccatc tcgaagcacc 60
tcagccactc ctttattgtt cttgaagcca ggaacacaga actgcttata gtactcaaag 120
tcccgggagc tgcgagcatt caggtacgtg aggtagcggt cggggcattt ttccacgcag 180
atctggggag cgggacattg gaattccagc agaaccaggg ggctggcaca tttcacaat 239

<210> SEQ ID NO 126
<211> LENGTH: 461
<212> TYPE: DNA
<213> ORGANISM: Homo sapiens

<400> SEQUENCE: 126
gacgtcgcat gctcccggcc gccatggccg cgggattagc gttatcggcg gcaggcgtca 60
gtccgtatac atcaacataa gttttcgcac ggacctgtgt ttttagtaaa cagtcgcttt 120
cccctagcct ctgcgaccac cccacgccca ccaaccgcaa gagtcggcga cccaaggtgg 180
ctccccatct cccaaagtta cggggacaat ttgccgaatt ccttaaccac agttcacccg 240
caagccttag tatactcaac ccaactacca gcgtcggttt cgggtacggg caacaccacc 300
actcgcttag aggcttttct cgacagcaca ggatcaccac catcaccaca aacgtggcta 360
cgcatcacgc ctcctctgca taacgcttct caatcactag tgcggccgcc tgcaggtcga 420
ccatatggga gagctcccaa cgcgttggat gcatagcttg a 461

<210> SEQ ID NO 127
<211> LENGTH: 284
<212> TYPE: DNA
<213> ORGANISM: Homo sapiens

<400> SEQUENCE: 127
tcaccgaatc tactgataaa aggaagagaa gaatacttta agaagagctc aacctccagc 60
tggtatcaga gaagtcagta gaggtcactg agaccggcag tctttcttgc tttttgcatt 120
agtgccctca gctggaactg tttacgggac agaagacgta catgcttcag gaagacatcc 180
aggtcggtac cataacgctt ctaatcacta gtgcggccgc ctgcaggtcg accatatggg 240
agagctccca acgcgttgga tgcatagctt gagtattcta tagt 284

<210> SEQ ID NO 128
<211> LENGTH: 252
<212> TYPE: DNA
<213> ORGANISM: Homo sapiens

<400> SEQUENCE: 128
accatgaaac ctacagcggc atctaataca acaacaccag ggatggtctc aacaaatatg 60

```
acttctacca ccttaaagtc tacacccaaa acaacaagtg tttcacagaa cacatctcag    120

atatcaacat ccacaatgac cgtaacccac aatagttcag tgacatctgc tgcttcatca    180

gtaacaatca caacaactat gcattctgaa gcaaagaaag gatcaaaatt tgatactggg    240

agctttgttg gt                                                        252


<210> SEQ ID NO 129
<211> LENGTH: 382
<212> TYPE: DNA
<213> ORGANISM: Homo sapiens
<220> FEATURE:
<221> NAME/KEY: misc_feature
<222> LOCATION: (380)..(380)
<223> OTHER INFORMATION: n = a t c or g

<400> SEQUENCE: 129

gcaggccagg aattaacctt gactataaat aggccatcaa tgacctttcc agagaatgtt     60

cagagacctc aactttgttt agaggtcttg tgtgggtgga acttcctgtt tgcacacaga    120

gcagcataaa gcccagttgc tttgggaagt gtttgggacc agatggattg ttgggagtag    180

ggtacaatac agtctggtct cctccagctc cttctttctg caacatgggg aagaacaaac    240

tccttcatcc aagtctggtt cttctcctct tggtcctcct cgctataacg cttctcaatc    300

actagtgcgg ccgcctgcag gtcgaccata tgggagagct cccaacgcgt tggatgcata    360

gcttgagtat tctatagtgn tc                                             382


<210> SEQ ID NO 130
<211> LENGTH: 305
<212> TYPE: DNA
<213> ORGANISM: Homo sapiens

<400> SEQUENCE: 130

ggctaatgac gttctcgtgg atttcttcgg tcctgctcag ggtctccagc aggacgttgt     60

actcgtgaac tttctctttg tgatgcagga actcccgcca gagcttgtcc agttcttcgc    120

cggagaattt cccagaggtc ttcgccttgt gccacagctt ttccagcctg gggtcatcca    180

gcccgtcttc ctgggtgcca ctgagagagt tgctggtcac ctgccgagcg tccttctttc    240

cgtccagacc atacttggcc aagatgacat tgaggttgcg tatgagtctc gcttccttct    300

ccccc                                                                305


<210> SEQ ID NO 131
<211> LENGTH: 337
<212> TYPE: DNA
<213> ORGANISM: Homo sapiens

<400> SEQUENCE: 131

atatattatt aggtggggaa acaaaacccc acttttctct ctgatcattt tttcataaga     60

gattctaaga gggagtgaaa aagtaccaac tggactccat tccaggtctt acctctagaa    120

gacagccagc tctcatttaa gaatctcaga acttggaagg aaggaggaaa tccacattaa    180

attctagggc ccaacagaca gagtgtcttc attgccaccc ccagtagtgg ggactacagt    240

gcacctgtag tcccagtaga tgctctgaca tcacagagct tcctgctcta ccagcccacc    300

tcatgcatgt caccaccata actatagcct gcaagtc                             337


<210> SEQ ID NO 132
<211> LENGTH: 174
<212> TYPE: DNA
```

<213> ORGANISM: Homo sapiens

<400> SEQUENCE: 132
ataaaaaggt ggaaactctc atggtaccat caaaaaggca agaagcattg cccctccacc 60
aagagactaa acaagaaagt ggatcaggga agaagaaagc ttcatcaaag aaacaaaaga 120
cagaaaatgt cttcgtagat gaacccctta ttcgtgcaac tacttatatt cctc 174

<210> SEQ ID NO 133
<211> LENGTH: 113
<212> TYPE: DNA
<213> ORGANISM: Homo sapiens

<400> SEQUENCE: 133
cataaagtac tgacatgatc agaggaatca tcagcaactg catatccatt gctaagccag 60
taatcacgat gcaaatccag ttaaagagga gcatgaataa atagtctgct ggc 113

<210> SEQ ID NO 134
<211> LENGTH: 191
<212> TYPE: DNA
<213> ORGANISM: Homo sapiens

<400> SEQUENCE: 134
aaattatgca tctgtgagga gagaagagag ggaaaaaaaa aggaaaaaca aaccaagaaa 60
gtatgccttt ttactttcct attatcctga atagggcata ctccattcac ccttaaggtt 120
ctagaatgaa ccagtcttac tatgtatcta taaccttgcc tttatctcta ttctaatatg 180
gtaatctgtt a 191

<210> SEQ ID NO 135
<211> LENGTH: 1481
<212> TYPE: DNA
<213> ORGANISM: Homo sapiens

<400> SEQUENCE: 135
ggcacgaggg ggacgcctct ctcctcctta ttcggtttac tatttattgt tcggggtgtt 60
ttttaattcc tgtattgctc ggcccgggga gtttcgcccc ctgcccggct ccgcggcgcg 120
gaggatggtg tggaaacggc tgggcgcgct ggtgatgttc cctctacaga tgatctatct 180
ggtggtgaaa gcagccgtcg gactggtgct gcccgccaag ctgcgggacc tgtcgcggga 240
gaacgtcctc atcaccggcg gcgggagagg catcgggcgt cagctcgccc gcgagttcgc 300
ggagcgcggc gccagaaaga ttgttctctg gggccggact gagaaatgcc tgaaggagac 360
gacggaggag atccggcaga tgggcactga gtgccattac ttcatctgtg atgtgggcaa 420
ccgggaggag gtgtaccaga cggccaaggc cgtccgggag aaggtgggtg acatcaccat 480
cctggtgaac aatgccgccg tggtccatgg gaagagccta atggacagtg atgatgatgc 540
cctcctcaag tcccaacaca tcaacaccct gggccagttc tggaccacca aggccttcct 600
gccgcgtatg ctggagctgc agaatggcca catcgtgtgc ctcaactccg tgctggcact 660
gtctgccatc cccggtgcca tcgactactg cacatccaaa gcgtcagcct tcgccttcat 720
ggagagcctg accctggggc tgctggactg tccgggagtc agcgccacca cagtgctgcc 780
cttccacacc agcaccgaga tgttccaggg catgagagtc aggtttccca acctctttcc 840
cccactgaag ccggagacgg tggcccggag gacagtggaa gctgtgcagc tcaaccaggc 900
cctcctcctc ctcccatgga caatgcatgc cctcgttatc ttgaaaagca tacttccaca 960
ggctgcactc gaggagatcc acaaattctc aggaacctac acctgcatga acactttcaa 1020

-continued

```
agggcggaca tagagacagg atgaagacat gcttgaggag ccacggagtt tgggggccac   1080
agcacctggg cacacacccg agcacctgtc cattggcatg cttctgctgg gtgagcagga   1140
cagctcctgt ccccagcgaa gaatccggct gcccctgggc cagtcccagg acctttgcac   1200
aggactgatg ggtataactg acccccacag ggaggcagga aaacagccag aagccacctt   1260
gacacttttg aacatttcca gttctgtaga gtttattgtc aattgcttct caagtctaac   1320
cagcctcagc agtgtgcata gaccatttcc aggagggtct gtccccagat gctctgcctc   1380
ccgttccaaa acccactcat cctcagcttg cacaaactgg ttgaacggca ggaatgaaaa   1440
ataaagagag atggcttttg tgaaaaaaaa aaaaaaaaaa a                        1481
```

<210> SEQ ID NO 136
<211> LENGTH: 344
<212> TYPE: DNA
<213> ORGANISM: Homo sapiens

<400> SEQUENCE: 136

```
gggtgttttt taattcctgt attgctcggc ccggggagtt tcgcccccctg cccggctccg     60
cggcgcggag gatggtgtgg aaacggctgg gcgcgctggt gatgttccct ctacagacga    120
tctatctggt ggtgaaagca gccgtcggac tggtgctgcc cgccaagctg cgggacctgt    180
cgcgggagaa cgtcctcatc accggcggcg ggagaggcat cgggcgtcag ctcgcccgcg    240
agttcgcgga gcgcggcgcc agaatgattg ttctctgggg ccggactgag aaatgcctga    300
aggagacgac ggaggagatc cggcagatgg gcactgagtg ccat                     344
```

<210> SEQ ID NO 137
<211> LENGTH: 1088
<212> TYPE: DNA
<213> ORGANISM: Homo sapiens

<400> SEQUENCE: 137

```
tgatctatct ggtggtgaaa gcagccgtcg gactggtgct gcccgccaag ctgcgggacc     60
tgtcgcggga gaacgtcctc atcaccggcg gcgggagagg catcgggcgt cagctcgccc    120
gcgagttcgc ggagcgcggc gccagaaaga ttgttctctg gggccggact gagaaatgcc    180
tgaaggagac gacagaggag atccggcaga tgggcactga gtgccattac ttcatctgtg    240
atgtgggcaa ccgggaggag gtgtaccaga cggccaaggc cgtccgggag aaggtgggtg    300
acatcaccat cctggtgaac aatgccgccg tggtccatgg gaagagccta atggacagtg    360
atgatgatgc cctcctcaag tcccaacaca tcaacaccct gggccagttc tggaccacca    420
aggccttcct gccgcgtatg ctggagctgc agaatggcca catcgtgtgc ctcaactccg    480
tgctggcact gtctgccatc cccggtgcca tcgactactg cacatccaaa gcgtcagcct    540
tcgccttcat ggagagcctg accctggggc tgctggactg tccgggagtc agcgccacca    600
cagtgctgcc cttccacacc agcaccgaga tgttccaggg catgagagtc aggtttccca    660
acctctttcc cccactgaag ccggagacgg tggcccggag gacagtggaa gctgtgcagc    720
tcaaccaggc cctcctcctc ctcccatgga caatgcatgc cctcgttatc ttgaaaagca    780
tacttccaca ggctgcactc gaggagatcc acaaattctc aggaacctac acctgcatga    840
acactttcaa agggcggaca tagagacagg atgaagacat gcttgaggag ccacggagtt    900
tgggggccac agcacctggg cacacacccg agcacctgtc cattggcatg cttctgctgg    960
gtgagcagga cagctcctgt ccccagcgaa gaatccggct gcccctgggc cagtcccagg   1020
```

-continued

```
acctttgcac aggactgatg ggtataactg acccccacag ggaggcagga aaacagccag   1080

aagccacc                                                            1088


<210> SEQ ID NO 138
<211> LENGTH: 399
<212> TYPE: DNA
<213> ORGANISM: Homo sapiens

<400> SEQUENCE: 138

tgcattgtcc atgggaggag gaggagggcc tggttgagct gcacagcttc cactgtcctc     60

cgggccaccg tctccggctt cagtggggga aagaggttgg gaaaccttct cccggacggc    120

cttggccgtc tggtacacct cctcccggtt gcccacatca cagatgaagt aatggcactc    180

agtgcccatc tgccggatct cctccgtcgt ctccttcagg catttctcag tccggcccca    240

gagaacaatc tttctggcgc cgcgctccgc gaactcgcgg gcgagctgac gcccgatgcc    300

tctcccgccg ccggtgatga ggacgttctc ccgcgacagg tcccgcagct tggcgggcag    360

caccagtccg acggctgctt tcaccaccag atagatcat                           399


<210> SEQ ID NO 139
<211> LENGTH: 745
<212> TYPE: DNA
<213> ORGANISM: Homo sapiens

<400> SEQUENCE: 139

ggtggcttct ggctgttttc ctgcctccct gtgggggtca gttacaccca tcagtcctgt     60

gcaaaggtcc tgggactggc ccaggggcag ccggattctt cgctggggac aggagctgtc    120

ctgctcaccc agcagaagca tgccaatgga caggtgctcg ggtgtgtgcc caggtgctgt    180

ggcccccaaa ctccgtggct cctcaagcat gtcttcatcc tgtctctatg tccgcccttt    240

gaaagtgttc atgcaggtgt aggttcctga gaatttgtgg atctcctcga gtgcagcctg    300

tggaagtatg ctgactctca tgccctggaa catctcggtg ctggtgtgga agggcagcac    360

tgtggtggcg ctgactcccg gacagtccag cagccccagg gtcaggctct ccatgaaggc    420

gaaggctgac gctttggatg tgcagtagtc gacggcaccg gggatggcag acagtgccag    480

cacggagttg aggcacacga tgtggccatt ctgcagctcc agcatacgcg gcaggaaggc    540

cttggtggtc cagaactggc ccagggtgtt gatgtgttgg gacttgagga gggcatcatc    600

atcactgtcc attaggctct tcccatggac cacggcggca ttgttcacca ggatggtgat    660

gtcacccacc ttctcccgga cggccttggc cgtctggtac acctcctccc ggttgcccac    720

atcacagatg aagtaatggc actca                                          745


<210> SEQ ID NO 140
<211> LENGTH: 3875
<212> TYPE: DNA
<213> ORGANISM: Homo sapiens

<400> SEQUENCE: 140

cgggggacgt cagcgctgcc agcgtggaag gagctgcggg gcgcgggagg aggaagtaga     60

gcccgggacc gccaggccac caccggccgc ctcagccatg gacgcgtccc tggagaagat    120

agcagacccc acgttagctg aaatgggaaa aaacttgaag gaggcagtga agatgctgga    180

ggacagtcag agaagaacag aagaggaaaa tggaaagaag ctcatatccg gagatattcc    240

aggcccactc cagggcagtg ggcaagatat ggtgagcatc ctccagttag ttcagaatct    300

catgcatgga gatgaagatg aggagcccca gagccccaga atccaaaata ttggagaaca    360
```

-continued

```
aggtcatatg gctttgttgg gacatagtct gggagcttat atttcaactc tggacaaaga    420
gaagctgaga aaacttacaa ctaggatact ttcagatacc accttatggc tatgcagaat    480
tttcagatat gaaaatgggt gtgcttattt ccacgaagag gaaagagaag gacttgcaaa    540
gatatgtagg cttgccattc attctcgata tgaagacttc gtagtggatg gcttcaatgt    600
gttatataac aagaagcctg tcatatatct tagtgctgct gctagacctg gcctgggcca    660
ataccttgt aatcagctcg gcttgccctt cccctgcttg tgccgtgtac cctgtaacac    720
tgtgtttgga tcccagcatc agatggatgt tgccttcctg gagaaactga ttaaagatga    780
tatagagcga ggaagactgc ccctgttgct tgtcgcaaat gcaggaacgg cagcagtagg    840
acacacagac aagattggga gattgaaaga actctgtgag cagtatggca tatggcttca    900
tgtggagggt gtgaatctgg caacattggc tctgggttat gtctcctcat cagtgctggc    960
tgcagccaaa tgtgatagca tgacgatgac tcctggcccg tggctgggtt tgccagctgt   1020
tcctgcggtg acactgtata aacacgatga ccctgccttg actttagttg ctggtcttac   1080
atcaaataag cccacagaca aactccgtgc cctgcctctg tggttatctt tacaatactt   1140
gggacttgat gggtttgtgg agaggatcaa gcatgcctgt caactgagtc aacggttgca   1200
ggaaagtttg aagaaagtga attacatcaa aatcttggtg gaagatgagc tcagctcccc   1260
agtggtggtg ttcagatttt tccaggaatt accaggctca gatccggtgt ttaaagccgt   1320
cccagtgccc aacatgacac cttcaggagt cggccgggag aggcactcgt gtgacgcgct   1380
gaatcgctgg ctgggagaac agctgaagca gctggtgcct gcaagcggcc tcacagtcat   1440
ggatctggaa gctgagggca cgtgtttgcg gttcagccct ttgatgaccg cagcagtttt   1500
aggaactcgg ggagaggatg tggatcagct cgtagcctgc atagaaagca aactgccagt   1560
gctgtgctgt acgctccagt tgcgtgaaga gttcaagcag gaagtggaag caacagcagg   1620
tctcctatat gttgatgacc ctaactggtc tggaataggg gttgtcaggt atgaacatgc   1680
taatgatgat aagagcagtt tgaaatcaga tcccgaaggg gaaaacatcc atgctggact   1740
cctgaagaag ttaaatgaac tggaatctga cctaaccttt aaaataggcc ctgagtataa   1800
gagcatgaag agctgccttt atgtcggcat ggcgagcgac aacgtcgatg ctgctgagct   1860
cgtggagacc attgcggcca cagcccggga gatagaggag aactcgaggc ttctggaaaa   1920
catgacagaa gtggttcgga aaggcattca ggaagctcaa gtggagctgc agaaggcaag   1980
tgaagaacgg cttctggaag agggggtgtt gcggcagatc cctgtagtgg gctccgtgct   2040
gaattggttt tctccggtcc aggctttaca gaagggaaga acttttaact tgacagcagg   2100
ctctctggag tccacagaac ccatatatgt ctacaaagca caaggtgcag gagtcacgct   2160
gcctccaacg ccctcgggca gtcgcaccaa gcagaggctt ccaggccaga agccttttaa   2220
aaggtccctg cgaggttcag atgctttgag tgagaccagc tcagtcagtc acattgaaga   2280
cttagaaaag gtggagcgcc tatccagtgg gccggagcag atcaccctcg aggccagcag   2340
cactgaggga cacccagggg ctcccagccc tcagcacacc gaccagaccg aggccttcca   2400
gaaaggggtc ccacacccag aagatgacca ctcacaggta gaaggaccgg agagcttaag   2460
atgagactca ttgtgtggtt tgagactgta ctgagtattg tttcagggaa gatgaagttc   2520
tattggaaat gtgaactgtg ccacatacta atataaatta ctgttgtttg tgcttcactg   2580
ggattttggc acaaatatgt gcctgaaagg taggctttct aggaggggag tcagcttgtc   2640
taacttcatg tacatgtaga accacgtttg ctgtcctact acgacttttc cctaagttac   2700
```

-continued

```
cataaacaca ttttattcac aaaaaacact tcgaatttca agtgtctacc agtagcaccc   2760

ttgctctttc taaacataag cctaagtata tgaggttgcc cgtggcaact tttggtaaa   2820

acagcttttc attagcactc tccaggttct ctgcaacact tcacagaggc gagactggct   2880

gtatcctttg ctgtcggtct ttagtacgat caagttgcaa tatacagtgg gactgctaga   2940

cttgaaggag agcagtgatt gtgggattgt aaataagagc atcagaagcc ctccccagct   3000

actgctcttc gtggagactt agtaaggact gtgtctactt gagctgtggc aaggctgctg   3060

tctgggactg tcctctgcca caaggccatt tctcccatta tataccgttt gtaaagagaa   3120

actgtaaagt ctcctcctga ccatatattt ttaaatactg gcaaagcttt taaaattggc   3180

acacaagtac agactgtgct catttctgtt tagtatctga aaacctgata gatgctaccc   3240

ttaagagctt gctcttccgt gtgctacgta gcacccacct ggttaaaatc tgaaaacaag   3300

taccccctttg acctgtctcc cactgaagct tctactgccc tggcagctcg cctgggccca   3360

actcagaaac aggagccagc agagcactct ctcacgctga tccagccggg caccctgctt   3420

aagtcagtag aagctcgctg gcactgcccg ttcctacttt tccgaagtac tgcgtcactt   3480

tgtcgtaagt aatggcccct gtgccttctt aatccagcag tcaagctttt gggagacctg   3540

aaaatgggaa aattcacact gggtttctgg actgtagtat tggaagcctt agttatagta   3600

tattaagcct ataattatac tctgatttga tgggattttt gacatttaca cttgtcaaaa   3660

tgcagggggt tttttttggt gcagatgatt aaacagtctt ccctatttgg tgcaatgaag   3720

tatagcagat aaaatggggg aggggtaaat tatcaccttc aagaaaatta catgttttta   3780

tatatatttg gaattgttaa attggttttg ctgaaacatt tcacccttga gatattattt   3840

gaatgttggt ttcaataaag gttcttgaaa ttgtt                              3875
```

<210> SEQ ID NO 141
<211> LENGTH: 493
<212> TYPE: DNA
<213> ORGANISM: Homo sapiens

<400> SEQUENCE: 141

```
aggcagtgaa gatgctggag gacagtcaga gaagaacaga agaggaaaat ggaaagaagc     60

tcatatccgg agatattcca ggcccactcc agggcagtgg gcaagatatg gtgagcatcc    120

tccagttagt tcacaatcta atgcatggag atgaagatga ggagccccag agccccagaa    180

tgcaaaatat tggagaacaa gggcatatgg ctttgttgag acatagtctg ggagcttata    240

tttcaactct ggacaaagag aagctgagaa aacttacaac taggatactt tcagatacca    300

ccttatggct atgcagaatt ttcagatatg aaaatgggtg tgcttatttc cacgaagagg    360

aaagagaagg acttgcaaag atatgtaggc ttgccattca ttctcgatat gaagacttcg    420

tagtggatgg cttcaatgtg ttatataaca agaagcctgt catatatctt agtgctgctg    480

ctagacctgg cct                                                       493
```

<210> SEQ ID NO 142
<211> LENGTH: 6263
<212> TYPE: DNA
<213> ORGANISM: Homo sapiens

<400> SEQUENCE: 142

```
gtggatttgg tcgtctccct gattccgagc tgcgggcagg gagaggggcc tcgcgccgcc     60

ctcagcagcc ggcggcggcc gaggtagacc gagcggggac ggaaggacag accgacgtcg    120

ccgagctgga atcatgtgag ggccaaccgg ggaaggtgga gcagatgagc acacacagga    180
```

-continued

```
gccgtctcct caccgccgcc cctctcagca tggaacagag gcggccctgg ccccgggccc    240
tggaggtgga cagccgctct gtggtcctgc tctcagtggt ctgggtgctg ctggcccccc    300
cagcagccgg catgcctcag ttcagcacct tccactctga gaatcgtgac tggaccttca    360
accacttgac cgtccaccaa gggacggggg ccgtctatgt gggggccatc aaccgggtct    420
ataagctgac aggcaacctg accatccagg tggctcataa gacagggcca gaagaggaca    480
acaagtcttg ttacccgccc ctcatcgtgc agccctgcag cgaagtgctc accctcacca    540
acaatgtcaa caagctgctc atcattgact actctgagaa ccgcctgctg gcctgtggga    600
gcctctacca gggggtctgc aagctgctgc ggctggatga cctcttcatc ctggtggagc    660
catcccacaa gaaggagcac tacctgtcca gtgtcaacaa gacgggcacc atgtacgggg    720
tgattgtgcg ctctgagggt gaggatggca agctcttcat cggcacggct gtggatggga    780
agcaggatta cttcccgacc ctgtccagcc ggaagctgcc ccgagaccct gagtcctcag    840
ccatgctcga ctatgagcta cacagcgatt ttgtctcctc tctcatcaag atcccttcag    900
acaccctggc cctggtctcc cactttgaca tcttctacat ctacggcttt gctagtgggg    960
gctttgtcta ctttctcact gtccagcccg agacccctga gggtgtggcc atcaactccg   1020
ctggagacct cttctacacc tcacgcatcg tgcggctctg caaggatgac cccaagttcc   1080
actcatacgt gtccctgccc ttcggctgca cccgggccgg ggtggaatac cgcctcctgc   1140
aggctgctta cctggccaag cctggggact cactggccca ggccttcaat atcaccagcc   1200
aggacgatgt actctttgcc atcttctcca aagggcagaa gcagtatcac cacccgcccg   1260
atgactctgc cctgtgtgcc ttccctatcc gggccatcaa cttgcagatc aaggggcgcc   1320
tacagtcctg ctaccagggc gagggcaacc tggagctcaa ctggctgctg gggaaggacg   1380
tccagtgcac caaggcgcct gtccccatcg atgataactt ctgtggactg gacatcaacc   1440
agcccctggg aggctcaact ccagtggagg gcctgaccct gtacaccacc agcagggacc   1500
gcatgacctc tgtggcctcc tacgtttaca acggctacag cgtggttttt gtggggacta   1560
agagtggcaa gctgaaaaag attcgggccg acggtccccc ccatggtggg gtccagtacg   1620
agatggtctc tgtgctcaag gacggaagcc ccatcctccg ggacatggcc ttctccattg   1680
atcagcgcta cctgtacgtc atgtctgaga gacaggtcac cagggtcccc gtggagtcat   1740
gtgagcagta tacgacttgt ggggagtgcc tgagctctgg ggaccctcac tgtggctggt   1800
gtgccctgca caacatgtgc tcccgcaggg acaaatgcca acaggcctgg gaacctaatc   1860
gatttgctgc cagcatcagc cagtgtgtga gccttgcagt gcatcccagc agcatctcag   1920
tatctgagca cagccggttg cttagcctgg tagtgagtga tgctcctgat ctatctgcgg   1980
gtatcgcctg tgcctttggg aacctgacag aggtggaggg gcaggtgtcc gggagccagg   2040
tcatctgcat ctcacctggg cccaaggatg tccctgtcat cccgctggat caagactggt   2100
ttgggctgga gctacagctg aggtccaagg agacagggaa gatatttgtc agcaccgagt   2160
tcaagtttta caactgcagt gcccaccaac tgtgcctgtc ctgtgtcaac agcgccttcc   2220
gctgccattg gtgcaagtac cgcaacctct gcactcatga ccccaccacc tgctccttcc   2280
aggagggccg gatcaatatt tcagaggact gtccccagct ggtgcccaca gaggagatct   2340
tgattccagt cggggaggta aagccaatca cccttaaggc gcgaaatctg ccccagccgc   2400
agtccggcca gcgaggctat gagtgtgtcc tcaacataca aggagccatc caccgggtcc   2460
ccgctctgcg cttcaacagc tccagcgttc agtgtcagaa cagctcgtac cagtatgatg   2520
```

-continued

```
gcatggacat cagcaatctg gccgtggatt tcgctgtggt gtggaacggc aatttcatca   2580

ttgacaaccc tcaggacctg aaagtccatc tctacaagtg tgcagcccag cgggagagct   2640

gcggcctctg cctcaaggcc gaccggaagt ttgagtgtgg ctggtgcagc ggcgagcgca   2700

ggtgcaccct ccaccagcac tgtaccagcc cttccagccc ctggctcgac tggtccagcc   2760

acaatgtcaa gtgctccaac cctcaaatca ccgagatttt gacggtgtct ggaccgccgg   2820

aaggagggac gcgagtgacc atccatggcg tgaacctggg tctggacttc tccgagatcg   2880

cccaccatgt gcaggtggct ggggtgccct gcacgcccct cccaggggaa tacatcatcg   2940

ctgagcagat tgtctgtgag atgggccatg ccctcgtggg aaccacctcc gggccagtac   3000

gcctgtgtat tggcgagtgt aagccagagt tcatgacgaa gtcccatcag cagtacacct   3060

tcgtgaaccc ttctgtgctg tcactcaacc caatccgagg tcccgagtca ggaggcacta   3120

tggtgaccat taccggccat taccttgggg ctgggagcag cgtggcagtc tacctgggca   3180

accagacctg cgagttctac gggaggtcaa tgagtgagat cgtgtgtgtc tcacccccat   3240

catccaatgg ccttggcccg gtccctgttt ctgtgagtgt cgaccgagcc catgtggata   3300

gcaacctgca gtttgagtac atagatgacc ctcgggtcca gcgcatcgag ccagagtgga   3360

gcattgccag tggccacaca cccctgacca tcacaggctt caacctggat gtcattcagg   3420

agccaaggat ccgagtcaaa ttcaatggca aagaatctgt caatgtgtgt aaagttgtga   3480

acacaaccac cctcacctgc ctggcaccct ctctgaccac ggactaccgc cctggcctgg   3540

acactgtgga acgcccagat gagtttggat ttgtctttaa caatgtccaa tccttgctaa   3600

tttacaacga caccaagttt atctactacc ccaacccgac ctttgaactg cttagcccta   3660

ctggagtctt ggatcaaaag ccaggatcgc ccatcattct gaagggcaaa aacctctgcc   3720

ctcctgcctc tggaggggcc aaactcaact acactgtgct catcggagag acccccttgtg  3780

ctgtcaccgt atctgagacc cagcttctct gcgagcctcc caacctcacc gggcagcaca   3840

aggtcatggt tcacgtgggc gggatggtgt tctcgcctgg ctcggtgagt gtcatctcag   3900

acagcttgct gaccctgcca gccatcgtca gcatcgcggc cggcggcagc ctcctcctca   3960

tcatcgtcat catcgtcctc attgcctaca agcgcaagtc tcgagaaaat gacctcactc   4020

tcaagcggct gcaaatgcag atggacaatc tggagtcccg tgtggccttg gagtgcaagg   4080

aagcttttgc tgagctccag acggatatca atgagttgac cagtgacctg gaccgctcag   4140

gaatccctta cctggactat cgtacctacg ctatgcgagt cctgttcccg ggcatcgagg   4200

accaccccgt cctgcgggag ctggaggtac aaggaaacgg gcagcagcac gtggagaagg   4260

ccctgaagct ctttgcccag ctcatcaaca acaaggtgtt cctgctgacc ttcatccgca   4320

ccctggagct gcagcgcagt ttctccatgc gcgaccgggg caacgtggct tcgctcatca   4380

tgaccggcct gcagggccgc ctggaatatg ccactgatgt cctcaagcag ctgctctctg   4440

acctcatcga taagaacctg gagaacaaga accaccccaa gctgctactc cggaggacag   4500

agtctgtggc tgaaaagatg ctgaccaatt ggttcgcctt cctcctgcac aagttcctaa   4560

aggagtgcgc aggggagcca ctcttcatgc tatactgtgc catcaagcag cagatggaga   4620

agggccccat tgatgccatc acgggcgagg cccgctactc cctgagcgag gacaagctca   4680

tccggcagca gatcgagtac aagaccctga tcctgaactg cgtcaaccct gacaacgaga   4740

acagtccaga gatcccagtg aaggtgttaa actgtgacac catcacacag gtcaaggaga   4800

agattcttga tgccgtgtat aagaatgtgc cctattccca gcggccgagg gcagtggaca   4860

tggacttgga gtggcgccaa ggccggatcg cccgggtcgt gctgcaagat gaggacatca   4920
```

-continued

```
ccaccaagat tgagggtgac tggaagcggc tcaacacact gatgcattat caggtgtcag   4980
acaggtcggt ggtggctctg gtccccaaac agacctcctc ctacaacatc cctgcctctg   5040
ccagcatctc ccggacgtcc atcagcagat atgactcctc cttcaggtat acgggcagcc   5100
ccgacagcct gcggtcccgg gccccgatga tcaccccaga cctggaaagt ggggtcaagg   5160
tgtggcatct ggtgaagaac catgaccacg gtgaccagaa ggagggtgac cggggcagca   5220
agatggtgtc cgagatctac ctgacccggc tactggccac caagggcacc ctgcagaagt   5280
ttgtggacga cttgtttgag accttgttca gcactgtgca ccggggcagc gctctccccc   5340
tggccatcaa gtacatgttt gatttcctag atgagcaggc agacaggcac agcatccatg   5400
acacagatgt gcggcacacc tggaaaagca actgcctccc tctgcgcttc tgggtgaacg   5460
tgattaagaa cccccagttc gtgtttgaca tccacaaggg cagcatcacg gacgcctgcc   5520
tctctgtggt ggcccagacc ttcatggact cttgttcaac gtcagagcac cggctgggca   5580
aggactcccc ctccaacaag ctgctctatg ccaaggacat ccccagctac aagagctggg   5640
tggagagata ctacgcagac atcgccaagc tcccagccat cagtgaccag gacatgaatg   5700
cctacctcgc cgagcagtcc cgcctgcacg ccgtggagtt caacatgctg agtgccctca   5760
atgagatcta ctcctatgtc agcaagtata gtgaggagct catcggggcc ctagagcagg   5820
atgagcaggc acggcggcag cggctggctt ataaggtgga gcagctcatt aatgccatgt   5880
ccattgagag ctgagaggag gagcctcgca ttcctgggaa gagggacctg tccaagctgt   5940
cacactggga gtctcagatg gaaggacaag tgatggggat caggccccag agcttgctgt   6000
cccctgagac cccatcctgg ggagagggga ggactcctct ccctacgcca gccaagtttc   6060
gtcatagcca gttccagctg ggagagacag tgggcgtcgt ccatcctcag tgagaacacc   6120
agagaacccg gggccgggag aaggtggttc ttcaagccga gaggcacgag ctggggacag   6180
ttctgcctct gtgactgctg ctttgcatga aaactcattt gatgtatatt ggggaaataa   6240
tgagaacttt atttaatttt ttt                                           6263
```

<210> SEQ ID NO 143
<211> LENGTH: 1725
<212> TYPE: DNA
<213> ORGANISM: Homo sapiens

<400> SEQUENCE: 143

```
tgtgtcaaca gcgccttccg ctgccattgg tgcaagtacc gcaacctctg cactcatgac     60
cccaccacct gctccttcca ggagggccgg atcaatattt cagaggactg tccccagctg    120
gtgcccacag aggagatctt gattccagtc ggggaggtaa agccaatcac ccttaaggcg    180
cgaaatctgc cccagccgca gtccggccag cgaggctatg agtgtgtcct caacatacaa    240
ggagccatcc accgggtccc cgctctgcgc ttcaacagct ccagcgttca gtgtcagaac    300
agctcgtacc agtatgatgg catggacatc agcaatctgg ccgtggattt cgctgtggtg    360
tggaacggca atttcatcat tgacaaccct caggacctga aagtccatct ctacaagtgt    420
gcagcccagc gggagagctg cggcctctgc ctcaaggccg accggaagtt tgagtgtggc    480
tggtgcagcg gcgagcgcag gtgcaccctc caccagcact gtaccagccc ttccagcccc    540
tggctcgact ggtccagcca caatgtcaag tgctccaacc ctcaaatcac cgagattttg    600
acggtgtctg gaccgccgga aggagggacg cgagtgacca tccatggcgt gaacctgggt    660
ctggacttct ccgagatcgc ccaccatgtg caggtggctg ggtgccctg cacgcccctc    720
```

```
ccaggggaat acatcatcgc tgagcagatt gtctgtgaga tgggccatgc cctcgtggga     780

accacctccg ggccagtacg cctgtgtatt ggcgagtgta agccagagtt catgacgaag     840

tcccatcagc agtacacctt cgtgaaccct tctgtgctgt cactcaaccc aatccgaggt     900

cccgagtcag gaggcactat ggtgaccatt accggccatt accttggggc tgggagcagc     960

gtggcagtct acctgggcaa ccagacctgc gagttctacg ggaggtcaat gagtgagatc    1020

gtgtgtgtct cacccccatc atccaatggc cttggcccgg tccctgtttc tgtgagtgtc    1080

gaccgagccc atgtggatag caacctgcag tttgagtaca tagatgaccc tcgggtccag    1140

cgcatcgagc cagagtggag cattgccagt ggccacacac ccctgaccat cacaggcttc    1200

aacctggatg tcattcagga gccaaggatc cgagtcaaat tcaatggcaa agaatctgtc    1260

aatgtgtgta aagttgtgaa cacaaccacc ctcacctgcc tggcaccctc tctgaccacg    1320

gactaccgcc ctggcctgga cactgtggaa cgcccagatg agtttggatt tgtctttaac    1380

aatgtccaat ccttgctaat ttacaacgac accaagttta tctactaccc caacccgacc    1440

tttgaactgc ttagccctac tggagtcttg gatcaaaagc caggatcgcc catcattctg    1500

aagggcaaaa acctctgccc tcctgcctct ggaggggcca aactcaacta cactgtgctc    1560

atcggagaga ccccttgtgc tgtcaccgta tctgagaccc agcttctctg cgagcctccc    1620

aacctcaccg ggcagcacaa ggtcatggtt cacgtgggcg ggatggtgtt ctcgcctggc    1680

tcggtgagtg tcatctcaga cagcttgctg accctgccag ccatc                    1725
```

<210> SEQ ID NO 144
<211> LENGTH: 558
<212> TYPE: DNA
<213> ORGANISM: Homo sapiens
<220> FEATURE:
<221> NAME/KEY: misc_feature
<222> LOCATION: (462)..(462)
<223> OTHER INFORMATION: n = a t c or g

<400> SEQUENCE: 144

```
gggcccttct ccatctgctg cttgatggca cagtatagca tgaagagtgg ctcccctgcg      60

cactccttta ggaacttgtg caggaggaag gcgaaccaat tggtcagcat cttttcagcc     120

acagactctg tcctccggag tagcagcttg ggtggttct tgttctccag gttcttatcg     180

atgaggtcag agagcagctg cttgaggaca tcagtggcat attccaggcg gccctgcagg     240

ccggtcatga tgagcgaagc cacgttgccc cggtcgcgca tggagaaact gcgctgcagc     300

tccagggtgc ggatgaaggt cagcaggaac accttgttgt tgatgagctg ggcaaagagc     360

ttcagggcct tctccacgtg ctgctgcccg tttccttgta cctccagctc ccgcaggacg     420

gggtggtcct cgatgcccgg gaacaggact cgcatagcgt angtacgata gtccaggtaa     480

gggattcctg agcggtccag gtcactggtc aactcattga tatccgtctg gagctcagca     540

aaagcttcct tgcactcc                                                   558
```

<210> SEQ ID NO 145
<211> LENGTH: 5567
<212> TYPE: DNA
<213> ORGANISM: Homo sapiens

<400> SEQUENCE: 145

```
atggtggaac acgctgccca caaacatgga aacgaccgtt ctcagtggga tcaacttcga      60

gtacaagggc atgacaggct gggaggtggc tggtgatcac atttacacag ctgctggagc     120

ctcagacaat gacttcatga ttctcactct ggttgtgcca ggatttagac ctccgcagtc     180
```

-continued

```
ggtgatggca gacacagaga ataaagaggt ggccagaatc acatttgtct ttgagaccct    240
ctgttctgtg aactgtgagc tctacttcat ggtgggtgtg aattctagga ccaacactcc    300
tgtggagacg tggaaaggtt ccaaaggcaa acagtcctat acctacatca ttgaggagaa    360
cactaccacg agcttcacct gggccttcca gaggaccact tttcatgagg caagcaggaa    420
gtacaccaat gacgttgcca agatctactc catcaatgtc accaatgtta tgaatggcgt    480
ggcctcctac tgccgtccct gtgccctaga agcctctgat gtgggctcct cctgcacctc    540
ttgtcctgct ggttactata ttgaccgaga ttcaggaacc tgccactcct gccccccctaa    600
cacaattctg aaagcccacc agccttatgg tgtccaggcc tgtgtgccct gtggtccagg    660
gaccaagaac aacaagatcc actctctgtg ctacaatgat tgcaccttct cacgcaacac    720
tccaaccagg actttcaact acaacttctc cgctttggca aacaccgtca ctcttgctgg    780
agggccaagc ttcacttcca aagggttgaa atacttccat cactttaccc tcagtctctg    840
tggaaaccag ggtaggaaaa tgtctgtgtg caccgacaat gtcactgacc tccggattcc    900
tgagggtgag tcagggttct ccaaatctat cacagcctac gtctgccagg cagtcatcat    960
ccccccagag gtgacaggct acaaggccgg ggtttcctca cagcctgtca gccttgctga   1020
tcgacttatt ggggtgacaa cagatatgac tctggatgga atcacctccc cagctgaact   1080
tttccacctg gagtccttgg gaataccgga cgtgatcttc ttttataggt ccaatgatgt   1140
gacccagtcc tgcagttctg ggagatcaac caccatccgc gtcaggtgca gtccacagaa   1200
aactgtccct ggaagtttgc tgctgccagg aacgtgctca gatgggacct gtgatggctg   1260
caacttccac ttcctgtggg agagcgcggc tgcttgcccg ctctgctcag tggctgacta   1320
ccatgctatc gtcagcagct gtgtggctgg gatccagaag actacttacg tgtggcgaga   1380
acccaagcta tgctctggtg gcatttctct gcctgagcag agagtcacca tctgcaaaac   1440
catagatttc tggctgaaag tgggcatctc tgcaggcacc tgtactgcca tcctgctcac   1500
cgtcttgacc tgctactttt ggaaaaagaa tcaaaaacta gagtacaagt actccaagct   1560
ggtgatgaat gctactctca aggactgtga cctgccagca gctgacagct gcgccatcat   1620
ggaaggcgag gatgtagagg acgacctcat ctttaccagc aagaagtcac tctttgggaa   1680
gatcaaatca tttacctcca agcagccagc tcctgtcacc atctctcttt cagaggactc   1740
ctgatggatt tgactcagtg ccgctgaaga catcctcagg aggcccagac atggacctgt   1800
gagaggcact gcctgcctca cctgcctcct caccttgcat agcacctttg caagcctgcg   1860
gcgatttggg tgccagcatc ctgcaacacc cactgctgga aatctcttca ttgtggcctt   1920
atcagatgtt tgaatttcag atcttttttt atagagtacc caaaccctcc tttctgcttg   1980
cctcaaacct gccaaatata cccacacttt gtttgtaaat tatgcccttg cttgtatctt   2040
gtttcccaaa atggcccatc cgccagagcc atagcttcgt ctgctcataa ttcttatagc   2100
tttggaatga aaatatttct atcttcttaa gtatagaaac tatttcctct gtcctctaac   2160
ttaagggcag aaacagctgg gagttttcct cgcatgccct cagctcatga tctcttcagg   2220
agagaggctg ggtgaggagg gtgtcggggt tccctggtgg ataatcttca tagcagcctg   2280
gatccatttc ccctggataa ccagctcaaa gggagtgaaa atggtagtct gagggcaagg   2340
ggagcaaggc ctgggtaaga aaagccttga aaagcataaa aagaggccgg gcgcggtggc   2400
tcacgcctgt aatcccagca ctttgggagg ccgaggcggg cagatcatga ggtcgggaga   2460
ttgagaccat cctggctaac acggtgaagc cccgtctcta ctggaaatac aaaaaattag   2520
```

-continued

```
ccgggcgtgg tggcgggtgc ctgtggtccc agctactcgg gaggctgagg cgggagaata   2580
gcgtgggcct ggaaggcgga gcttgcagtg agccgagatc gcgccactgc actccatcca   2640
gcctgggtga cagagtgaga ctctgcctca aaaaaaaaaa aaaaaaagaa aagcacaaag   2700
agaggcaaca aggaatgttt ttgtttttga gacaggctct cactctgtca cctaggctgg   2760
agtgcagtgg cgtaatcact gttcagtgca gcctcaagct cttgggctca ggctatcctc   2820
ccatctcagc ctctcaagta gctgggacta cgagtgtgca ccaccaggct cactaatttt   2880
tgtgtttttt gtagacacgg ggtttcaccg tgttgcccag gctggtctcc aactcctggg   2940
ctcaagtgat ctgtccgcct cggcctccca aactgctggg attacaggca taagccactg   3000
cactcagcct tttatttgtt ttttaaacca cgtagctcat tgccttctct taagtaaatg   3060
atagatattc tcactgaagc caaaggaata agttcatcaa gaaaatgccc aaagccctgg   3120
tggatacatc ctccctatct tttttttaaa ccttccacta tcactctatg acactgaaaa   3180
gaaccaggta agccccaaac ccagatgttc cagccttatc ctctattggg tttacccaca   3240
gacatagcaa accctgtcag tgaggaaaat tccccatcct tgagtgcccc cgtcctagaa   3300
gtttgggcca tattatggaa caggggtctc ttatttgaaa agagcacaag gaggccaaga   3360
ttttaatggg gcactttagg ggatacagcc cacaatggca tgggcctgag gtggccgtga   3420
tgtctgcttc taagcttaac gcatctgctc aggcacagaa taaacgtcta ggctggccaa   3480
aaaaggaact gaatcccagg cccatacgcc agcaccagaa tcaaaccagt cttcaaggaa   3540
ggaaggctag gagagtttaa caagattttc actgggccca gcatggtggc tcacacctgt   3600
aatcccaagg cagaatggtg gcttgagctc aggagttcaa gaccagcctg ggcaacacag   3660
tgagaccctg tctctaaaaa atttaaaaat aaacaaggtg ttcaccaagc tgggatactt   3720
ctcactatta agcccctatc tttctctttt tttcattctc aattgctttg tgtgataaaa   3780
aactaaagag acttctggtc caatttctgg caacatccct tctgaaaggt gagtagagtg   3840
ggtgtcttct atgcccattt tccccaattt tacacaaact attatcaatg aacttttaag   3900
tacctagaat gggtaaaacc agagcaagac tttaaattac cttcttcttt cttctactgg   3960
cagttctgcc tccatcacta tcaggctagg gtgaccttcc cttggtcaag ccccaattgc   4020
ccatgatttg tgcctgtgcc ctttctccag tgaccatttg gtgaccagat ggtagatata   4080
gaaaggggat ggcatttgca agtgactagt ctgccacaaa atgctcatct gattagccac   4140
tgctgccctg gcaatggctt tgtaagagtc aatgagaact agagccaggc tgtggtccct   4200
ggccatcaac agtgttggtg acggcaggga gtccctttgg tttaataaat ccagtttttc   4260
tttgggtatc caaattctcc cctccttttg taggagtcag gctctcagaa cctgtgtcca   4320
tgttggaact tcccccagtg tggatgcaga tacgcagctc ctgagctcca gcctaaagtc   4380
ttctgtagcc tcagcaatac ttgggcacct gctgtctcac tgaatagctt tcttttgtga   4440
caaaggccac agacagccct tagactattc cggaaacagt aggaaaaatt acatatgtct   4500
ttgacttctt tattctgact ccactgattt tagccataat actttaagga gctacttttt   4560
actacccctt accgtgctga cttctgcagg tctgccctgt gacctgtcag gaactcctga   4620
gttacgctac tggggtcacc tgttgctccc ctagcaagtt aggcatgtca tatattttta   4680
acagctttat tgagatataa ttcacatatt atacaattca cctttaaaac atacgattca   4740
atggttttca gcaaactcac agagttgtcc gcccacttga gagcaaacac atgttcaatt   4800
ttcttttcct tttttttttt gagacagagt cagctttgtc gcccaggctg gagtgcagtg   4860
ccatgatctt ggctcactgc agcctcccca tcctgggttc aagtgatcct tctgcttcag   4920
```

-continued cctccccagt agctgggatt acaggcatgc gccaccacgc ctagctaatt tttgtgtttt 4980
tagtagagat ggggtttcac cgtgttggcc aggctggtct caaactcctg gactcaagtg 5040
atccacccac ctcggcctcc caaagtgctg ggattgcagg tgtgagccac cgtgcctggc 5100
ctacgtgttc aattttctat gaacaaaggc tttagtcctt gacccagggc taaagtggtc 5160
tgtccaagct gttgttggta gagggagtat gataaaatgt ttaaatctca tttggttacc 5220
ttgagtcctg gaacacgcag taactgtcat gctatagtca tcatctgtat ttggctggga 5280
atacaaatga agattgtggt gtattcaagc agtagggttt ttgcttttgt ttttgtttta 5340
gtgccaacaa aacttttttt tgtctgacta cattaaagat aagactgact atatttatac 5400
aacagaaact ttgtaataga ttttttcagc tttgtgaaat cgaatttttt ttcatcaggg 5460
ctggttggat ttccttttta ccctgtaatc caagcgttaa tagtttgtta gaagatgggt 5520
tattgcatgt cacttttttt tttttgtaaa ataaaaacat accttac 5567

<210> SEQ ID NO 146
<211> LENGTH: 299
<212> TYPE: DNA
<213> ORGANISM: Homo sapiens

<400> SEQUENCE: 146
gtaaaaagga aatccaacca gccctgatga aaaaaaattc gatttcacaa agctgaaaaa 60
atctattaca aagtttctgt tgtataaata tagtcagtct tatctttaat gtagtcagac 120
aaaaaaaagt tttgttggca ctaaaacaaa aacaaaagca aaaaccctac tgcttgaata 180
caccacaatc ttcatttgta ttcccagcca aatacagatg acgactatag catgacagtt 240
actgcgtgtt ccaggactca aggtaaccaa atgagattta aacattttat catactccc 299

<210> SEQ ID NO 147
<211> LENGTH: 1326
<212> TYPE: DNA
<213> ORGANISM: Homo sapiens

<400> SEQUENCE: 147
gactcaggca ctgggctagg tgcttgggat acatccgtga gccacacaaa gttccccacc 60
ccagaggagc tcttacctgg cccagaatct ggatctctgc ccccagcccc tatcctcaag 120
gtagagtccc aaagatgtcc taaatctcac acaggctgag ttgtgcttaa tccatttctg 180
cagacacaac tcatgtacaa atgggccaag ccgaaaatct gtagcgagga ccttgagggg 240
gcagtgaagc tgcctgcctc tggtgtgaag acccactgcc caccctgcaa cccaggcttc 300
ttcaaaacca acaacagcac ctgccagccc tgcccatatg gttcctactc caatggctca 360
gactgtaccc gctgccctgc agggactgaa cctgctgtgg gatttgaata caaatggtgg 420
aacacgctgc ccacaaacat ggaaacgacc gttctcagtg ggatcaactt cgagtacaag 480
ggcatgacag gctgggaggt ggctggtgat cacatttaca cagctgctgg agcctcagac 540
aatgacttca tgattctcac tctggttgtg ccaggattta gacctccgca gtcggtgatg 600
gcagacacag agaataaaga ggtggccaga atcacatttg tctttgagac cctctgttct 660
gtgaactgtg agctctactt catggtgggt gtgaattcta ggaccaacac tcctgtggag 720
acgtggaaag gttccaaagg caaacagtcc tatacctaca tcattgagga gaacactacc 780
acgagcttca cctgggcctt ccagaggacc acttttcatg aggcaagcag gaagtacacc 840
aatgacgttg ccaagatcta ctccatcaat gtcaccaatg ttatgaatgg tgtggcctcc 900

-continued

```
tactgccgtc cctgtgccct agaagcctct gatgtgggct cctcctgcac ctcttgtcct     960

gctggttact atattgaccg agattcagga acctgccact cctgccccac taacacaatt    1020

ctgaaagccc accagcctta tggtgtccag gcctgtgtgc cctgtggtcc agggaccaag    1080

aacaacaaga tccactctct gtgctacaac gattgcacct tctcacgcaa cactccgacc    1140

aggactttca actacaactt ctccgctttg gcaaacactg tcactcttgc tggagggcca    1200

agcttcactt ccaaagggct gaaatacttc catcacttta ccctcagtct ctgtggaaac    1260

cagggtagga aaatgtctgt gtgcaccgac aatgtcactg acctccggat tcctgagggt    1320

gagtca                                                               1326
```

<210> SEQ ID NO 148
<211> LENGTH: 698
<212> TYPE: DNA
<213> ORGANISM: Homo sapiens

<400> SEQUENCE: 148

```
cttccatgat ggcgcagctg tcagctgctg gcaggtcaca gtccttgaga gtagcattca      60

tcaccagctt ggagtacttg tactctagtt tttgattctt tttccaaaag tagcaggtca     120

agacggtgag caggatggca gtacaggtgc ctgcagagat gcccactttc agccagaaat     180

ctatggtttt gcagatggtg actctctgct caggcagaga aatgccacca gagcatagct     240

tgggttctcg ccacacgtaa gtagtcttct ggatcccagc cacacagctg ctgacgatag     300

catggtagtc agccactgag cagagcgggc aagcagccgc gctctcccac aggaagtgga     360

agttgcagcc atcacaggtc ccatctgagc acgttcctgg cagcagcaaa cttccaggga     420

cagttttctg tggactgcac ctgacgcgga tggtggttga tctcccagaa ctgcaggact     480

gggtcacatc attggaccta taaaagaaga tcacgtccgg tattcccaag gactccaggt     540

ggaaaagttc agctggggag gtgattccat ccagagtcat atctgttgtc accccaataa     600

gtcgatcagc aaggctgaca ggctgtgagg aaaccccggc cttgtagcct gtcacctctg     660

gggggatgat gactgcctgg cagacgtagg ctgtgata                             698
```

<210> SEQ ID NO 149
<211> LENGTH: 478
<212> TYPE: DNA
<213> ORGANISM: Homo sapiens

<400> SEQUENCE: 149

```
cttccatgat ggcgcagctg tcagctgctg gcaggtcaca gtccttgaga gtagcattca      60

tcaccagctt ggagtacttg tactctagtt tttgattctt tttccaaaag tagcaggtca     120

agacggtgag caggatggca gtacaggtgc ctgcagagat gcccactttc agccagaaat     180

ctatggtttt gcagatggtg actctctgct caggcagaga aatgccacca gagcatagct     240

tgggttctcg ccacacgtaa gtagtcttct ggccacctct ttattctctg tgtctgccat     300

caccgactgc ggaggtctaa atcctggcac aaccagagtg agaatcatga agtcattgtc     360

tgaggctcca gtagctgtgt aaatgtgatc accagccacc tcccagcctg tcatgccctt     420

gtactcgaag ttgatcccac tgagaacggt cgtttccgtg tttgtgggca gcgtgttc       478
```

<210> SEQ ID NO 150
<211> LENGTH: 315
<212> TYPE: DNA
<213> ORGANISM: Homo sapiens

<400> SEQUENCE: 150

-continued

```
cgtgggtagg gcacggggtc tgttctgaaa tgtaaagggt tcagacgggg tttctggttt     60

tagaaggttg cgtggtcttc gagttgggct aaagtagagt tcgttgtgct gtttctgact    120

cctaatgaga gttccttcca gaccgttacg tgtctcctgg ccaagcccca ggaaggaaat    180

gatgcagctc tggctccttg tctcccaggc tgatccttta ttcagaatac cacaaagaaa    240

ggacattcag ctcaaggctc cctgccgtgt tgaagagttc tgactgcaca aaccagcttc    300

tggtttcttc tggaa                                                     315
```

```
<210> SEQ ID NO 151
<211> LENGTH: 219
<212> TYPE: DNA
<213> ORGANISM: Homo sapiens

<400> SEQUENCE: 151

tttgagggca agtagtgtct tggcacagag aagagcccag agtatagagc ggaagcaaga     60

gagtgagcca cgtattgtta gtagaatttt ccagtgttgt gcttggaatg gtggagtgtt    120

ctggttcagt ctcctcttgt tttatcgagt atttattcct gtgcttcagt cggtaacagc    180

ccgaattatc ggtgacccat cactacatgg agatgtttg                           219
```

```
<210> SEQ ID NO 152
<211> LENGTH: 351
<212> TYPE: DNA
<213> ORGANISM: Homo sapiens

<400> SEQUENCE: 152

gcctttaacc atgtacaact ggctggcggc caggaccgac agggcagcaa ggctccaggg     60

gtgctttcgc cggaagtccc cacaacagct gaggacgatg agagagatga agaacacagc    120

ataggagaca tagtaggtcc aaacattctc ccggacaaag cccttcacct ccgcaacaga    180

agtgaacaca gacaccgtgg acagggtcac cgacagctgc aaggtcagca ctaggaacac    240

cttgcggatg aaggcctgtc ggatgctctt gtcatcccag ttggtggcag ggaagtcctg    300

gttgtcatag taagatgggg gaccctcctc ctggtgaaat tgataacgct t             351
```

```
<210> SEQ ID NO 153
<211> LENGTH: 286
<212> TYPE: DNA
<213> ORGANISM: Homo sapiens

<400> SEQUENCE: 153

tgagctgagg gttagtggtg actttttgat acgaaaaaat gcattttgtg cagctggtga     60

ggtataatcc aaagcaaaag caggggcaaa aatggacttc ctgaagttat ctctgctcct    120

gctggttatc ctccagaatc tgtcatgttg actgagagtg cgtgcttgct ttctcaggcc    180

tcctggctaa tagcacaggt ctgctggaaa tcacccacat ggtttttcat tgcctgtgca    240

gtcaggtgat gcctctatgt tttggaggt ccacccccttt actcaa                   286
```

```
<210> SEQ ID NO 154
<211> LENGTH: 419
<212> TYPE: DNA
<213> ORGANISM: Homo sapiens

<400> SEQUENCE: 154

gttaggtagg ctatggatga ggctgactat tactgtcagg cgtgggacag caacattgct     60

tatgtcttcg gaactgggac caaggtcacc gtcttaggtc agcccaaggc caaccccact    120
```

-continued

```
gtcactctgt tcccgccctc ctctgaggag ctccaagcca acaaggccac actagtgtgt    180

ctgatcagtg acttctaccc gggagctgtg acagaggcct ggaaggcaga tggcagcccc    240

gtcaaggcgg gagtggagac caccaaaccc tccaaacaga gcaacaacaa gtacgcggcc    300

agcagctacc tgagcctgtc cataataacg cttctcaatc actagtgcgg ccgcctgcag    360

gtcgaccata tgggagagct cccaacgcgt tggatgcata gcttgagtat tctatagtg     419
```

```
<210> SEQ ID NO 155
<211> LENGTH: 424
<212> TYPE: DNA
<213> ORGANISM: Homo sapiens

<400> SEQUENCE: 155

tagggggagg tctgggggct cacggcgccg aagtggaaga catggcgctt gttcccgtgg     60

gggttggagg cttcacagga gatgccatcg cggctcaggg cgctggtcac tttcagggtc    120

agagagctgc tcacccaacc ctgccgtccg gggattggct ctgcggggct gccccccaat    180

tggctccagc tgagtttggg gtctggatgg ccgcgggcag agcagatgag tgtgacttcg    240

tctccttccc tccagctgcc atctgccttg ggctctattt ccgctgtctt tagctctggc    300

gagccttgga ccagcagcgt gaagttctgg gtgcggctga ggaccgggac tgtgggcagg    360

gaggcctcac atacgtaggt gccattggaa tcgaaggtga tagaactgag cgacagcatg    420

gggc                                                                 424
```

```
<210> SEQ ID NO 156
<211> LENGTH: 396
<212> TYPE: DNA
<213> ORGANISM: Homo sapiens

<400> SEQUENCE: 156

gcagggaagg tcagaagcca gtcatggatg accagcgcga ccttatctcc aacaatgagc     60

aactgcccat gctgggccgg cgccctgggg ccccggagag caagtgcagc cgcggagccc    120

tgtacacagg cttttccatc ctggtgactc tgctcctcgc tggccaggcc accaccgcct    180

acttcctgta ccagcagcag ggccggctgg acaaactgac agtcacctcc cagaacctgc    240

agctggagaa cctgcgcatg aagcttccca agcctcccaa gcctgtgagc aagatgcgca    300

tggccacccc gctgctgatg caggcgctgc ccatgggagc cctgccccag ggggcccatgc   360

agaatgccac caagtatggc aacatgacag aggacc                              396
```

```
<210> SEQ ID NO 157
<211> LENGTH: 161
<212> TYPE: DNA
<213> ORGANISM: Homo sapiens

<400> SEQUENCE: 157

gcagaggggg ggtggggagg ggtgctctgc tggtcttcaa ttaccaagaa ttctccaaaa     60

caattttctg caggatgatt gtacagaatc attgcttatg acatgatcgc tttctacact    120

gtattacata aataaattaa ataaaataac cccgggtcct a                        161
```

```
<210> SEQ ID NO 158
<211> LENGTH: 382
<212> TYPE: DNA
<213> ORGANISM: Homo sapiens

<400> SEQUENCE: 158

acgtcgcggg gattgttctg gaggttcacc ttttccgtca catcatcata cttccgaatt     60
```

-continued

```
tcgcgcacgg catcgatgac caacagcaca aggatgacaa tgagaaccac aaagaaggtg    120

ttgccatagg acactaacaa ctccaccagc cgggacttga aaatcttctg ccatctttta    180

ggagaaatga agggaatgca gagaagcaac acaacaaaga cctccgcata gaggaaggtg    240

gcaactgcag tccactgcag actcatcctg ttgctagaag gtttcccaca ggaagatgtg    300

agcttgtttc cgagtttccc acagtcaacg tgcaggcccc gccgcagcaa ccgaactctc    360

ccacagcagc cccccattcc ca                                              382
```

<210> SEQ ID NO 159
<211> LENGTH: 292
<212> TYPE: DNA
<213> ORGANISM: Homo sapiens

<400> SEQUENCE: 159

```
gtacaggcag gcttgaagat gggagttttc atggcttgac catgaatgat ctcaagatga     60

tttcataaga ttaaaagcca tcacgaaaat actgaaagca acaggtaata atctggattc    120

agtctgtagt tgctcatgaa ccacgcgttt taataaaagg aacattaagt aaattgtagg    180

tataaaagaa tcagtgcata tctgttaatg tcattgacaa taaaaataca ttatcttctc    240

agctcagctc taaattaaca aaacacctat tttttttcc cactcctagc ca             292
```

<210> SEQ ID NO 160
<211> LENGTH: 447
<212> TYPE: DNA
<213> ORGANISM: Homo sapiens

<400> SEQUENCE: 160

```
gggggggagg tggagtctgg agacgacgtg cagaaatggc acctcgaaag gggaaggaaa     60

agaaggaaga acaggtcatc agcctcggac ctcaggtggc tgaaggagag aatgtatttg    120

gtgtctgcca tatctttgca tccttcaatg acacttttgt ccatgtcact gatctttctg    180

gcaaggaaac catctgccgt gtgactggtg ggatgaaggt aaaggcagac cgagatgaat    240

cctcaccata tgctgctatg ttggctgccc aggatgtggc ccagaggtgc aaggagctgg    300

gtatcaccgc cctacacatc aaactccggg ccacaggagg aaataggacc aagacccctg    360

gacctccacc caataacgct tctcaatcac tagtgcggcc gcctgcaggt cgaccatatg    420

ggagagctcc caacgcgttg gatgcat                                         447
```

<210> SEQ ID NO 161
<211> LENGTH: 239
<212> TYPE: DNA
<213> ORGANISM: Homo sapiens

<400> SEQUENCE: 161

```
ttgggtaagg catcatagat aaacgtaatt gtttggggag ttaaatttaa tgaacttatc     60

taactttgta acccatcttg gctttagtaa ctttatcaag gtggtggctt tagtgaatat    120

aatggtaaac tttagaggac gctaaagcct cactaaaata acgcttctca atcactagtg    180

cggccgcctg caggtcgacc atatgggaga gctcccaacg cgttggatgc atagcttga     239
```

<210> SEQ ID NO 162
<211> LENGTH: 410
<212> TYPE: DNA
<213> ORGANISM: Homo sapiens

<400> SEQUENCE: 162

-continued

```
tgctgggagg tcctcacggt ccaccgggcc ctgaacagtg ataagtccag tgttcctgtc     60

cagtcgaaga agacgcctca caacttcggg cgcctggtgg aatgtgtatt cgatttctgc    120

attggcacct tggtctgagt cattgacctt cacctggatg accgagtggc ctatggggct    180

attctcagat agttcggcct cataggaggg ccgctcaaac ttgggggcgt tgtcattggt    240

gtcaagcacg gtgacacgca gcagggcact gctggcgcgt ggggggctgc cgccatcctg    300

caccttgatg gtgaggtcat aggagtccca gcgctcacgg tccaggttgc ccatcacaat    360

gagctgtggt tgcttctcct cctggtcctc tgccacctcg gccccataac                410
```

<210> SEQ ID NO 163
<211> LENGTH: 327
<212> TYPE: DNA
<213> ORGANISM: Homo sapiens

<400> SEQUENCE: 163

```
tgaggaaggc catgttctgg gtttccttca atcctagccg aagaccattc attgcaccaa     60

acgcagcccc tgtcatgcaa catcctccaa tcgtaaagaa ggccagctca aatctgcccc    120

gggttttatt agctccggta ggtaaaataa actcatctgt atcctgcacg aggtatcgtg    180

gatccacatt taaataagga gacagagggt tcataccagt tagcgggacg ccagccaaat    240

ccgcgtgcga gtaacctgct ccgccggctc cgaaaaagca ggccaatccc cctgtggttt    300

tgttgccgct tcccccgcct cccccca                                         327
```

<210> SEQ ID NO 164
<211> LENGTH: 300
<212> TYPE: DNA
<213> ORGANISM: Homo sapiens
<220> FEATURE:
<221> NAME/KEY: misc_feature
<222> LOCATION: (204)..(204)
<223> OTHER INFORMATION: n = a t c or g

<400> SEQUENCE: 164

```
tagcgggaga aagatgggaa ctccgtttcc acctgcactc tctcgcgccc ctctattctt     60

tcaccacatt gctttatcct tttacccttt tttttatttt aaattaaaga atgaactgaa    120

aagatataac atgacgtaca attaaagaat aattttaaag tgaatactac gtaactccat    180

ccaagtcaag aaattgccag cttncggaag cccactgtgc tcctccccct cataacgctt    240

ctcatcctag tgcgccgcct gcagcgacca tatggagagc tccaacgcgt tggatgcata    300
```

<210> SEQ ID NO 165
<211> LENGTH: 351
<212> TYPE: DNA
<213> ORGANISM: Homo sapiens

<400> SEQUENCE: 165

```
cggagccagg caatacaaaa aatgcaatta tccattgcaa tggaaccacc aaagaatgcc     60

tcgcaaccga atataccatc cccttttttgg gtccggtttt attcgctccc aagcgcctaa    120

tctttgagtt taagccgtcg ttaaaggatt caagtcaggc atttaaggaa cgacactacg    180

agatgggatg aggccgaaga tgatcaattt taaaggcgcc gcccgcaaac gggcctccga    240

caccgcctcc ccgtaataac gcttctcaat cactagtgcg gccgcctgca ggtcgaccat    300

atgggagagc tcccaacgcg ttggatgcat agcttgagta ttctatagtg t              351
```

<210> SEQ ID NO 166
<211> LENGTH: 4839

<212> TYPE: DNA
<213> ORGANISM: Homo sapiens

<400> SEQUENCE: 166

```
ggaaagctag cggcagaggc tcagccccgg cggcagcgcg cgccccgctg ccagcccatt     60
ttccggacgc cacccgcggg cactgccgac gcccccgggg ctgccgaggg gaggccgggg    120
gggcgcagcg gagcgcggtc ccgcgcactg agccccgcgg cgccccggga acttggcggc    180
gacccgagcc cggcgagccg gggcgcgcct cccccgccgc gcgcctcctg catgcggggc    240
cccagctccg ggcgccggcc ggagcccccc ccggccgccc ccgagccccc cgcgccccgc    300
gccgcgccgc cgcgccgtcc atgcaccgct tgatgggggt caacagcacc gccgccgccg    360
ccgccgggca gcccaatgtc tcctgcacgt gcaactgcaa acgctctttg ttccagagca    420
tggagatcac ggagctggag tttgttcaga tcatcatcat cgtggtggtg atgatggtga    480
tggtggtggt gatcacgtgc ctgctgagcc actacaagct gtctgcacgg tccttcatca    540
gccggcacag ccaggggcgg aggagagaag atgccctgtc ctcagaagga tgcctgtggc    600
cctcggagag cacagtgtca ggcaacggaa tcccagagcc gcaggtctac gccccgcctc    660
ggcccaccga ccgcctggcc gtgccgccct tcgcccagcg ggagcgcttc caccgcttcc    720
agcccaccta tccgtacctg cagcacgaga tcgacctgcc acccaccatc tcgctgtcag    780
acggggagga gcccccaccc taccagggcc cctgcaccct ccagcttcgg gaccccgagc    840
agcagctgga actgaaccgg gagtcggtgc gcgcaccccc aaacagaacc atcttcgaca    900
gtgacctgat ggatagtgcc aggctgggcg gcccctgccc ccccagcagt aactcgggca    960
tcagcgccac gtgctacggc agcggcgggc gcatggaggg gccgccgccc acctacagcg   1020
aggtcatcgg ccactacccg ggtcctcct tccagcacca gcagagcagt gggccgccct   1080
ccttgctgga ggggacccgg ctccaccaca cacacatcgc gcccctagag agcgcagcca   1140
tctggagcaa agagaaggat aaacagaaag gacaccctct ctagggtccc caggggggcc   1200
gggctggggc tgcgtaggtg aaaaggcaga acactccgcg cttcttagaa gaggagtgag   1260
aggaaggcgg ggggcgcagc aacgcatcgt gtggccctcc cctcccacct ccctgtgtat   1320
aaatatttac atgtgatgtc tggtctgaat gcacaagcta agagagcttg caaaaaaaaa   1380
aagaaaaaag aaaaaaaaaa accacgtttc tttgttgagc tgtgtcttga aggcaaaaga   1440
aaaaaaattt ctacagtagt ctttcttgtt tctagttgag ctgcgtgcgt gaatgcttat   1500
tttcttttgt ttatgataat ttcacttaac tttaaagaca tatttgcaca aaacctttgt   1560
ttaaagatct gcaatattat atatataaat atatataaga taagagaaac tgtatgtgcg   1620
agggcaggag tatttttgta ttagaagagg cctattaaaa aaaaaagttg ttttctgaac   1680
tagaagagga aaaaaatggc aatttttgag tgccaagtca gaaagtgtgt attaccttgt   1740
aaagaaaaaa attacaaagc aggggtttag agttatttat ataaatgttg agattttgca   1800
ctattttttta atataaatat gtcagtgctt gcttgatgga aacttctctt gtgtctgttg   1860
agactttaag ggagaaatgt cggaatttca gagtcgcctg acggcagagg gtgagccccc   1920
gtggagtctg cagagaggcc ttggccagga gcggcgggct ttcccgaggg gccactgtcc   1980
ctgcagagtg gatgcttctg cctagtgaca ggttatcacc acgttatata ttccctaccg   2040
aaggagacac cttttccccc ctgacccaga acagccttta aatcacaagc aaaataggaa   2100
agttaaccac ggaggcaccg agttccaggt agtggttttg cctttcccaa aaatgaaaat   2160
aaactgttac cgaaggaatt agtttttcct cttctttttt ccaactgtga aggtccccgt   2220
```

-continued

```
ggggtggagc atggtgcccc tcacaagccg cagcggctgg tgcccgggct accagggaca   2280
tgccagaggg ctcgatgact tgtctctgca gggcgctttg gtggttgttc agctggctaa   2340
aggttcaccg gtgaaggcag gtgcggtaac tgccgcactg gaccctagga agccccaggt   2400
attcgcaatc tgacctcctc ctgtctgttt cccttcacgg atcaattctc acttaagagg   2460
ccaataaaca acccaacatg aaaaggtgac aagcctgggt ttctcccagg ataggtgaaa   2520
gggttaaaat gagtaaagca gttgagcaaa caccaacccg agcttcgggc gcagaattct   2580
tcaccttctc ttccccttc catctccttt ccccgcggaa acaacgcttc ccttctggtg   2640
tgtctgttga tctgtgtttt catttacatc tctcttagac tccgctcttg ttctccaggt   2700
tttcaccaga tagatttggg gttggcggga cctgctggtg acgtgcaggt gaaggacagg   2760
aaggggcatg tgagcgtaaa tagaggtgac cagaggagag catgaggggt ggggctttgg   2820
gacccaccgg ggccagtggc tggagcttga cgtctttcct ccccatgggg gtgggagggc   2880
ccccagctgg aagagcagac tcccagctgc taccccctcc cttcccatgg gagtggcttt   2940
ccattttggg cagaatgctg actagtagac taacataaaa gatataaaag gcaataacta   3000
ttgtttgtga gcaacttttt tataacttcc aaaacaaaaa cctgagcaca gttttgaagt   3060
tctagccact cgagctcatg catgtgaaac gtgtgcttta cgaaggtggc agctgacaga   3120
cgtgggctct gcatgccgcc agcctagtag aaagttctcg ttcattggca acagcagaac   3180
ctgcctctcc gtgaagtcgt cagcctaaaa tttgtttctc tcttgaagag gattctttga   3240
aaaggtcctg cagagaaatc agtacaggtt atcccgaaag gtacaaggac gcacttgtaa   3300
agatgattaa aacgtatctt tcctttatgt gacgcgtctc tagtgcctta ctgaagaagc   3360
agtgacactc ccgtcgctcg gtgaggacgt tcccggacag tgcctcactc acctgggact   3420
ggtatcccct cccagggtcc accaagggct cctgcttttc agacacccca tcatcctcgc   3480
gcgtcctcac cctgtctcta ccagggaggt gcctagcttg gtgaggttac tcctgctcct   3540
ccaacctttt tttgccaagg tttgtacacg actcccatct aggctgaaaa cctagaagtg   3600
gaccttgtgt gtgtgcatgg tgtcagccca aagccaggct gagacagtcc tcatatcctc   3660
ttgagccaaa ctgtttgggt ctcgttgctt catggtatgg tctggatttg tgggaatggc   3720
tttgcgtgag aaaggggagg agagtggttg ctgccctcag ccggcttgag gacagagcct   3780
gtccctctca tgacaactca gtgttgaagc ccagtgtcct cagcttcatg tccagtggat   3840
ggcagaagtt catggggtag tggcctctca aaggctgggc gcatcccaag acagccagca   3900
ggttgtctct ggaaacgacc agagttaagc tctcggcttc tctgctgagg gtgcaccctt   3960
tcctctagat ggtagttgtc acgttatctt tgaaaactct tggactgctc ctgaggaggc   4020
cctcttttcc agtaggaagt tagatggggg ttctcagaag tggctgattg gaaggggaca   4080
agcttcgttt caggggtctg ccgttccatc ctggttcaga gaaggccgag cgtggctttc   4140
tctagccttg tcactgtctc cctgcctgtc aatcaccacc tttcctccag aggaggaaaa   4200
ttatctcccc tgcaaagccc ggttctacac agatttcaca aattgtgcta agaaccgtcc   4260
gtgttctcag aaagcccagt gtttttgcaa agaatgaaaa gggaccccat atgtagcaaa   4320
aatcagggct gggggagagc cgggttcatt ccctgtcctc attggtcgtc cctatgaatt   4380
gtacgtttca gagaaatttt ttttcctatg tgcaacacga agcttccaga accataaaat   4440
atcccgtcga taaggaaaga aaatgtcgtt gttgttgttt ttctggaaac tgcttgaaat   4500
cttgctgtac tatagagctc agaaggacac agcccgtcct cccctgcctg cctgattcca   4560
tggctgttgt gctgattcca atgctttcac gttggttcct ggcgtgggaa ctgctctcct   4620
```

```
ttgcagcccc atttcccaag ctctgttcaa gttaaactta tgtaagcttt ccgtggcatg   4680

cggggcgcgc acccacgtcc ccgctgcgta agactctgta tttggatgcc aatccacagg   4740

cctgaagaaa ctgcttgttg tgtatcagta atcattagtg gcaatgatga cattctgaaa   4800

agctgcaata cttatacaat aaattttaca attctttgg                            4839


<210> SEQ ID NO 167
<211> LENGTH: 200
<212> TYPE: DNA
<213> ORGANISM: Homo sapiens

<400> SEQUENCE: 167

cccagcaagg gatgccatca gggacttcag gggttcaccc cactttccag aggagaaact     60

ggggatgaga gaggtggaac atttgccgga ggccacactg cttgtcactg ccggtgtgaa    120

gagcccacag cctattccgt cctccctcaa gtgctgggga gagtgacggt gcctggacat    180

tccagaaggc accagccctg                                                200


<210> SEQ ID NO 168
<211> LENGTH: 355
<212> TYPE: DNA
<213> ORGANISM: Homo sapiens

<400> SEQUENCE: 168

agggggggaaa aggtgtctcc ttcggtaggg aatatataac gtggtgataa cctgtcacta     60

ggcagaagca tccactctgc agggacagtg gcccctcggg aaagcccgcc gctcctggcc    120

aaggcctctc tgcagactcc acgggggctc accctctgcc gtcaggcgac tctgaaattc    180

cgacatttct cccttaaagt ctcaacagac acaagagaag tttccatcaa gcaagcactg    240

acatatttat attaaaaaat agtgcaaaat ctcaacattt atataaataa ctctaaaccc    300

ctgctttgta attttttttct ttacaaggta atacacactt tctgacttgg cactc         355


<210> SEQ ID NO 169
<211> LENGTH: 579
<212> TYPE: DNA
<213> ORGANISM: Homo sapiens

<400> SEQUENCE: 169

ttcccagtat gcaagtcgca tcagcatcag gagtggaaga gtctctgctg gtccttaagg     60

tctccaggag gggccagttc catcactggc tttgggagca tgaaagtgac aaatccagcc    120

atgaatttgc ctgagtgtca gtggttaaga atacaaaaag gggtcccctt ctcctcccaa    180

ctgctccctc cctgggcccc taagaagggt ctgtgaccgt ctgcccgagc ctttgcccag    240

cgacaggagc cagtgcgcag ggctcccttt ctgccagtca gctcacgctg tgcatctgca    300

gaacggctcc aggaggctct gagagcagag agcagggcct tcctcctgcc tgtcccgtta    360

cctccttccg cggagctgga gtttgttcag atcatcatca tcgtggtggt gatgatggtg    420

atggtggtgg tgatcacgtg cctgctgagc cactacaagc tgtctgcacg gtccttcatc    480

agccggcaca gccaggggcg gaggagagaa gatgccctgt cctcagaagg atgcctgtgg    540

ccctcggaga gcacagtgtc aggcaacgga atcccagag                            579


<210> SEQ ID NO 170
<211> LENGTH: 310
<212> TYPE: DNA
<213> ORGANISM: Homo sapiens
```

-continued

<400> SEQUENCE: 170

```
tccttgggtt cgggtgaaag cgcttggggg ttcagtgggc catgatcccc gagctgctgg     60
agaactgaag gcggacagtc tcctgcgaaa ccaggcaatg gcggagctgg agtttgttca    120
gatcatcatc atcgtggtgg tgatgatggt gatggtggtg gtgatcacgt gcctgctgag    180
ccactacaag ctgtctgcac ggtccttcat cagccggcac agccaggggc ggaggagaga    240
agatgccctg tcctcagaag gatgcctgtg gccctcggag agcacagtgt caggcaacgg    300
aatcccagag                                                          310
```

<210> SEQ ID NO 171
<211> LENGTH: 301
<212> TYPE: DNA
<213> ORGANISM: Homo sapiens

<400> SEQUENCE: 171

```
ggacagggca tcttctctcc tccgcccctg gctgtgccgg ctgatgaagg accgtgcaga     60
cagcttgtag tggctcagca ggcacgtgat caccaccacc atcaccatca tcaccaccac    120
gatgatgatg atctgaacaa actccagctc cgctagacca gagcgaattc atcctgaaga    180
actcagagaa agccggtgca ggaagtgggt tcccgctctc cctgcacagg cacagtgatg    240
ctgccagagc tctcccagaa agaccaggag gcttgttctg gagaagtcaa gcccagggat    300
g                                                                   301
```

<210> SEQ ID NO 172
<211> LENGTH: 529
<212> TYPE: DNA
<213> ORGANISM: Homo sapiens

<400> SEQUENCE: 172

```
ctctgggatt ccgttgcctg acactgtgct ctccgagggc cacaggcatc cttctgagga     60
cagggcatct tctctcctcc gcccctggct gtgccggctg atgaaggacc gtgcagacag    120
cttgtagtgg ctcagcaggc acgtgatcac caccaccatc accatcatca ccaccacgat    180
gatgatgatc tgaacaaact ccagctccgc tttttgtatt cttaaccact gacactcagg    240
caaattcatg gctggatttg tcactttcat gctcccaaag ccagtgatgg aactggcccc    300
tcctggagac cttaaggacc agcagagact cttccactcc tgatgctgat gcgacttgca    360
tactgggaat ccatgacaac ctagaccaga gcgaattcat cctgaagaac tcagagaaag    420
ccggtgcagg aagtgggttc ccgttctccc tgcacaggca cagtgatgct gccagagctc    480
tcccagaaag accaggaggc ttgttctgga gaagtcaagc ccagggatg               529
```

<210> SEQ ID NO 173
<211> LENGTH: 1429
<212> TYPE: DNA
<213> ORGANISM: Homo sapiens

<400> SEQUENCE: 173

```
ttggaagtgt ccgtatcatg gaatcaatct ctatgatggg aagccctaag agccttagtg     60
aaacttgttt acctaatggc ataaatggta tcaaagatgc aaggaaggtc actgtaggtg    120
tgattggaag tggagatttt gccaaatcct tgaccattcg acttattaga tgcggctatc    180
atgtggtcat aggaagtaga aatcctaagt ttgcttctga attttttcct catgtggtag    240
atgtcactca tcatgaagat gctctcacaa aaacaaatat aatatttgtt gctatacaca    300
gagaacatta tacctccctg tgggacctga gacatctgct tgtgggtaaa atcctgattg    360
```

```
atgtgagcaa taacatgagg ataaaccagt acccagaatc caatgctgaa tatttggctt    420

cattattccc agattctttg attgtcaaag gatttaatgt tgtctcagct tgggcacttc    480

agttaggacc taaggatgcc agccggcagg tttatatatg cagcaacaat attcaagcgc    540

gacaacaggt tattgaactt gcccgccagt tgaatttcat tcccattgac ttgggatcct    600

tatcatcagc cagagagatt gaaaatttac ccctacgact ctttactctc tggagagggc    660

cagtggtggt agctataagc ttggccacat ttttttcct ttattccttt gtcagagatg    720

tgattcatcc atatgctaga aaccaacaga gtgactttta caaaattcct atagagattg    780

tgaataaaac cttacctata gttgccatta ctttgctctc cctagtatac cttgcaggtc    840

ttctggcagc tgcttatcaa ctttattatg gcaccaagta taggagattt ccaccttggt    900

tggaaacctg gttacagtgt agaaaacagc ttggattact aagtttttc ttcgctatgg    960

tccatgttgc ctacagcctc tgcttaccga tgagaaggtc agagagatat ttgtttctca   1020

acatggctta tcagcaggtt catgcaaata ttgaaaactc ttggaatgag gaagaagttt   1080

ggagaattga aatgtatatc tcctttggca taatgagcct tggcttactt tccctcctgg   1140

cagtcacttc tatcccttca gtgagcaatg ctttaaactg gagagaattc agttttattc   1200

agtctacact tggatatgtc gctctgctca taagtacttt ccatgtttta atttatggat   1260

ggaaacgagc ttttgaggaa gagtactaca gattttatac accaccaaac tttgttcttg   1320

ctcttgtttt gccctcaatt gtaattctgg tagagacgga gtttcaccgt gttagccagg   1380

atggtctcga tctcctgacc tcgtgatccg cccgccttgg cctccaaag               1429
```

```
<210> SEQ ID NO 174
<211> LENGTH: 462
<212> TYPE: PRT
<213> ORGANISM: Homo sapiens

<400> SEQUENCE: 174

Met Glu Ser Ile Ser Met Met Gly Ser Pro Lys Ser Leu Ser Glu Thr
1               5                   10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
```

-continued

```
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
    290                 295                 300

Leu Gly Leu Leu Ser Phe Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
    370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430

Val Leu Ala Leu Val Leu Pro Ser Ile Val Ile Leu Val Glu Thr Glu
        435                 440                 445

Phe His Arg Val Ser Gln Asp Gly Leu Asp Leu Leu Thr Ser
    450                 455                 460
```

<210> SEQ ID NO 175
<211> LENGTH: 1329
<212> TYPE: DNA
<213> ORGANISM: Homo sapiens

<400> SEQUENCE: 175

```
atggaatcaa tctctatgat gggaagccct aagagcctta gtgaaacttt tttacctaat      60

ggcataaatg gtatcaaaga tgcaaggaag gtcactgtag gtgtgattgg aagtggagat     120

tttgccaaat ccttgaccat tcgacttatt agatgcggct atcatgtggt cataggaagt     180

agaaatccta agtttgcttc tgaatttttt cctcatgtgg tagatgtcac tcatcatgaa     240

gatgctctca caaaaacaaa tataatattt gttgctatac acagagaaca ttatacctcc     300

ctgtgggacc tgagacatct gcttgtgggt aaaatcctga ttgatgtgag caataacatg     360

aggataaacc agtacccaga atccaatgct gaatatttgg cttcattatt cccagattct     420

ttgattgtca aaggatttaa tgttgtctca gcttgggcac ttcagttagg acctaaggat     480

gccagccggc aggtttatat atgcagcaac aatattcaag cgcgacaaca ggttattgaa     540
```

-continued

```
cttgcccgcc agttgaattt cattcccatt gacttgggat ccttatcatc agccagagag    600

attgaaaatt taccccctacg actctttact ctctggagag ggccagtggt ggtagctata    660

agcttggcca catttttttt cctttattcc tttgtcagag atgtgattca tccatatgct    720

agaaaccaac agagtgactt ttacaaaatt cctatagaga ttgtgaataa aaccttacct    780

atagttgcca ttactttgct ctccctagta tacctcgcag gtcttctggc agctgcttat    840

caactttatt acggcaccaa gtataggaga tttccacctt ggttggaaac ctggttacag    900

tgtagaaaac agcttggatt actaagtttt ttcttcgcta tggtccatgt tgcctacagc    960

ctctgcttac cgatgagaag gtcagagaga tatttgtttc tcaacatggc ttatcagcag   1020

gttcatgcaa atattgaaaa ctcttggaat gaggaagaag tttggagaat tgaaatgtat   1080

atctcctttg gcataatgag ccttggctta ctttccctcc tggcagtcac ttctatccct   1140

tcagtgagca atgctttaaa ctggagagaa ttcagtttta ttcagatctt ttgcagcttt   1200

gcagataccc agactgagct ggaactggaa tttgtcttcc tattgactct acttctttaa   1260

aagcggctgc ccattacatt cctcagctgt ccttgcagtt aggtgtacat gtgactgagt   1320

gttggccag                                                            1329
```

<210> SEQ ID NO 176
<211> LENGTH: 419
<212> TYPE: PRT
<213> ORGANISM: Homo sapiens

<400> SEQUENCE: 176

```
Met Glu Ser Ile Ser Met Met Gly Ser Pro Lys Ser Leu Ser Glu Thr
1               5                   10                  15

Phe Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Asp Asn Leu Pro Leu Arg Leu
        195                 200                 205

Phe Thr Leu Trp Arg Gly Pro Val Val Val Ala Ile Ser Leu Ala Thr
    210                 215                 220

Phe Phe Phe Leu Tyr Ser Phe Val Arg Asp Val Ile His Pro Tyr Ala
```

-continued

```
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
    290                 295                 300

Leu Gly Leu Leu Ser Phe Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
    370                 375                 380

Ala Leu Asn Trp Arg Glu Phe Ser Phe Ile Gln Ile Phe Cys Ser Phe
385                 390                 395                 400

Ala Asp Thr Gln Thr Glu Leu Glu Leu Glu Phe Val Phe Leu Leu Thr
                405                 410                 415

Leu Leu Leu
```

<210> SEQ ID NO 177
<211> LENGTH: 940
<212> TYPE: DNA
<213> ORGANISM: Homo sapiens

<400> SEQUENCE: 177

```
tggaagtgtc cgtatcatgg aatcaatctc tatgatggga agccctaaga gccttagtga     60

aacttgttta cctaatggca taaatggtat caaagatgca aggaaggtca ctgtaggtgt    120

gattggaagt ggagattttg ccaaatcctt gaccattcga cttattagat gcggctatca    180

tgtggtcata ggaagtagaa atcctaagtt tgcttctgaa ttttttcctc atgtggtaga    240

tgtcactcat catgaagatg ctctcacaaa aacaaatata atatttgttg ctatacacag    300

agaacattat acctccctgt gggacctgag acatctgctt gtgggtaaaa tcctgattga    360

tgtgagcaat aacatgagga taaaccagta cccagaatcc aatgctgaat atttggcttc    420

attattccca gattctttga ttgtcaaagg atttaatgtt gtctcagctt gggcacttca    480

gttaggacct aaggatgcca gccggcaggt ttatatatgc agcaacaata ttcaagcgcg    540

acaacaggtt catgcaaata ttgaaaactc ttggaatgag gaagaagttt ggagaattga    600

aatgtatatc tcctttggca taatgagcct tggcttactt tccctcctgg cagtcacttc    660

tatcccttca gtgagcaatg ctttaaactg gagagaattc agttttattc agtctacact    720

tggatatgtc gctctgctca taagtacttt ccatgtttta atttatggat ggaaacgagc    780

ttttgaggaa gagtactaca gattttatac accaccaaac tttgttcttg ctcttgtttt    840

gccctcaatt gtaattctgg tagagacgga gtttcaccgt gttagccagg atggtctcga    900

tctcctgacc tcgtgatccg cccgccttgg cctccaaagt                          940
```

<210> SEQ ID NO 178

<211> LENGTH: 299
<212> TYPE: PRT
<213> ORGANISM: Homo sapiens

<400> SEQUENCE: 178

```
Met Glu Ser Ile Ser Met Met Gly Ser Pro Lys Ser Leu Ser Glu Thr
1               5                   10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val His Ala Asn Ile Glu Asn Ser Trp Asn Glu Glu Glu Val Trp
            180                 185                 190

Arg Ile Glu Met Tyr Ile Ser Phe Gly Ile Met Ser Leu Gly Leu Leu
        195                 200                 205

Ser Leu Leu Ala Val Thr Ser Ile Pro Ser Val Ser Asn Ala Leu Asn
    210                 215                 220

Trp Arg Glu Phe Ser Phe Ile Gln Ser Thr Leu Gly Tyr Val Ala Leu
225                 230                 235                 240

Leu Ile Ser Thr Phe His Val Leu Ile Tyr Gly Trp Lys Arg Ala Phe
                245                 250                 255

Glu Glu Glu Tyr Tyr Arg Phe Tyr Thr Pro Pro Asn Phe Val Leu Ala
            260                 265                 270

Leu Val Leu Pro Ser Ile Val Ile Leu Val Glu Thr Glu Phe His Arg
        275                 280                 285

Val Ser Gln Asp Gly Leu Asp Leu Leu Thr Ser
    290                 295
```

<210> SEQ ID NO 179
<211> LENGTH: 1388
<212> TYPE: DNA
<213> ORGANISM: Homo sapiens

<400> SEQUENCE: 179

```
tggaagtgtc cgtatcatgg aatcaatctc tatgatggga agccctaaga gccttagtga     60

aacttgttta cctaatggca taaatggtat caaagatgca aggaaggtca ctgtaggtgt    120

gattggaagt ggagattttg ccaaatcctt gaccattcga cttattagat gcggctatca    180

tgtggtcata ggaagtagaa atcctaagtt tgcttctgaa tttttcctc atgtggtaga    240
```

-continued

```
tgtcactcat catgaagatg ctctcacaaa aacaaatata atatttgttg ctatacacag    300

agaacattat acctccctgt gggacctgag acatctgctt gtgggtaaaa tcctgattga    360

tgtgagcaat aacatgagga taaaccagta cccagaatcc aatgctgaat atttggcttc    420

attattccca gattctttga ttgtcaaagg atttaatgtt gtctcagctt gggcacttca    480

gttaggacct aaggatgcca gccggcaggt ttatatatgc agcaacaata ttcaagcgcg    540

acaacaggtt attgaacttg cccgccagtt gaatttcatt cccattgact tgggatcctt    600

atcatcagcc agagagattg aaaatttacc cctacgactc tttactctct ggagagggcc    660

agtggtggta gctataagct tggccacatt tttttccttt attcctttgt cagagatgtg    720

attcatccat atgctagaaa ccaacagagt gacttttaca aaattcctat agagattgtg    780

aataaaacct tacctatagt tgccattact ttgctctccc tagtatacct tgcaggtctt    840

ctggcagctg cttatcaact ttattacggc accaagtata ggagatttcc accttggttg    900

gaaacctggt tacagtgtag aaaacagctt ggattactaa gtttttttctt cgctatggtc    960

catgttgcct acagcctctg cttaccgatg agaaggttca tgcaaatatt gaaaactctt   1020

ggaatgagga agaagtttgg agaattgaaa tgtatatctc ctttggcata atgagccttg   1080

gcttactttc cctcctggca gtcacttcta tcccgtcagt gagcaatgct ttaaactgga   1140

gagaattcag ttttattcag tctacacttg gatatgtcgc tctgctcata agtactttcc   1200

atgttttaat ttatggatgg aaacgagctt ttgaggaaga gtactacaga ttttatacac   1260

caccaaactt tgttcttgct cttgttttgc cctcaattgt aattctggta gagacggagt   1320

ttcaccgtgt tagccaggat ggtctcgatc tcctgacctc gtgatccgcc cgccttggcc   1380

tccaaagt                                                            1388
```

<210> SEQ ID NO 180
<211> LENGTH: 234
<212> TYPE: PRT
<213> ORGANISM: Homo sapiens

<400> SEQUENCE: 180

```
Met Glu Ser Ile Ser Met Met Gly Ser Pro Lys Ser Leu Ser Glu Thr
1               5                   10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
```

-continued

```
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Val Ala Ile Ser Leu Ala Thr
    210                 215                 220

Phe Phe Ser Phe Ile Pro Leu Ser Glu Met
225                 230


<210> SEQ ID NO 181
<211> LENGTH: 1425
<212> TYPE: DNA
<213> ORGANISM: Homo sapiens

<400> SEQUENCE: 181

tggaagtgtc cgtatcatgg aatcaatctc tatgatggga agccctaaga gccttagtga     60

aacttgttta cctaatggca taaatggtat caaagatgca aggaaggtca ctgtaggtgt    120

gattggaagt ggagattttg ccaaatcctt gaccattcga cttattagat gcggctatca    180

tgtggtcata ggaagtagaa atcctaagtt tgcttctgaa ttttttcctc atgtggtaga    240

tgtcactcat catgaagatg ctctcacaaa aacaaatata atatttgttg ctatacacag    300

agaacattat acctccctgt gggacctgag acatctgctt gtgggtaaaa tcctgattga    360

tgtgagcaat aacatgagga taaaccagta cccagaatcc aatgctgaat atttggcttc    420

attattccca gattctttga ttgtcaaagg atttaatgtt gtctcagctt gggcacttca    480

gttaggacct aaggatgcca gccggcaggt ttatatatgc agcaacaata ttcaagcgcg    540

acaacaggtt attgaacttg cccgccagtt gaatttcatt cccattgact tgggatcctt    600

atcatcagcc agagagattg aaaatttacc cctacgactc tttactctct ggagagggcc    660

agtggtggta gctataagct tggccacatt ttttttcctt tattcctttg tcagagatgt    720

gattcatcca tatgctagaa accaacagag tgacttttac aaaattccta tagagattgt    780

gaataaaacc ttacctatag ttgccattac tttgctctcc ctagtatacc ttgcaggtct    840

tctggcagct gcttatcaac tttattatgg caccaagtat aggagatttc caccttggtt    900

ggaaacctgg ttacagtgta gaaaacagct tggattacta agtttttttct tcgctatggt    960

ccatgttgcc tacagcctct gcttaccgat gagaaggtca gagagatatt tgtttctcaa   1020

catggcttat cagcaggttc atgcaaatat tgaaaactct tggaatgagg aagaagtttg   1080

gagaattgaa atgtatatct cctttggcat aatgagcctt ggcttacttt ccctcctggc   1140

agtcacttct atcccttcag tgagcaatgc tttaaactgg agagaattca gttttattca   1200

gtctacactt ggatatgtcg ctctgctcat aagtactttc catgttttaa tttatggatg   1260

gaaacgagct tttgaggaag agtactacag attttataca ccaccaaact ttgttcttgc   1320

tcttgttttg ccctcaattg taattctgga gacggagttt caccgtgtta gccaggatgg   1380

tctcgatctc ctgacctcgt gatccgcccg ccttggcctc caaag                   1425


<210> SEQ ID NO 182
<211> LENGTH: 461
<212> TYPE: PRT
<213> ORGANISM: Homo sapiens

<400> SEQUENCE: 182

Met Glu Ser Ile Ser Met Met Gly Ser Pro Lys Ser Leu Ser Glu Thr
```

-continued

```
1               5                   10                  15

Cys Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
    290                 295                 300

Leu Gly Leu Leu Ser Phe Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350

Glu Val Trp Arg Ile Glu Met Tyr Ile Ser Phe Gly Ile Met Ser Leu
        355                 360                 365

Gly Leu Leu Ser Leu Leu Ala Val Thr Ser Ile Pro Ser Val Ser Asn
    370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Glu Tyr Tyr Arg Phe Tyr Thr Pro Pro Asn Phe
            420                 425                 430
```

-continued

```
Val Leu Ala Leu Val Leu Pro Ser Ile Val Ile Leu Glu Thr Glu Phe
        435                 440                 445

His Arg Val Ser Gln Asp Gly Leu Asp Leu Leu Thr Ser
    450                 455                 460


<210> SEQ ID NO 183
<211> LENGTH: 18
<212> TYPE: PRT
<213> ORGANISM: Homo sapiens

<400> SEQUENCE: 183

Val Glu Thr Glu Phe His Arg Val Ser Gln Asp Gly Leu Asp Leu Leu
1               5                   10                  15

Thr Ser


<210> SEQ ID NO 184
<211> LENGTH: 24
<212> TYPE: PRT
<213> ORGANISM: Homo sapiens

<400> SEQUENCE: 184

Ile Phe Cys Ser Phe Ala Asp Thr Gln Thr Glu Leu Glu Leu Glu Phe
1               5                   10                  15

Val Phe Leu Leu Thr Leu Leu Leu
            20


<210> SEQ ID NO 185
<211> LENGTH: 8
<212> TYPE: PRT
<213> ORGANISM: Homo sapiens

<400> SEQUENCE: 185

Ser Phe Ile Pro Leu Ser Glu Met
1               5
```

PROSTATE SPECIFIC GENES AND THE USE THEREOF AS TARGETS FOR PROSTATE CANCER THERAPY

This application is the US national phase of international application PCT/IB2004/002394, filed 25 Jun. 2004, which designated the U.S. and claims benefit of U.S. Provisional No. 60/482,595, filed 26 Jun. 2003, the entire contents of each of which are hereby incorporated by reference.

FIELD OF THE INVENTION

The present invention relates to the identification of DNA sequences that correspond to alternatively spliced events in genes expressed on the surface of prostate cancer cells. These genes or their corresponding proteins are to be targeted for the treatment, prevention and/or diagnosis of cancers wherein these genes are differentially regulated and/or spliced, particularly in prostate cancer.

BACKGROUND OF THE INVENTION

Genetic detection of human disease states is a rapidly developing field (Taparowsky et al., 1982; Slamon et al., 1989; Sidransky et al., 1992; Miki et al., 1994; Dong et al., 1995; Morahan et al., 1996; Lifton, 1996; Barinaga, 1996). However, some problems exist with this approach. A number of known genetic lesions merely predispose an individual to the development of specific disease states. Individuals carrying the genetic lesion may not develop the disease state, while other individuals may develop the disease state without possessing a particular genetic lesion. In human cancers, genetic defects may potentially occur in a large number of known tumor suppresser genes and proto-oncogenes.

Genetic detection of cancer has a long history. Some of the earliest genetic lesions shown to predispose to cancer were transforming point mutations in the ras oncogenes (Taparowsky et al., 1982). Transforming ras point mutations may be detected in the stool of individuals with benign and malignant colorectal tumors (Sidransky et al., 1992). However, only 50% of such tumors contained a ras mutation (Sidransky et al., 1992). Similar results have been obtained with amplification of HER-2/neu in breast and prostate cancer (Slamon et al., 1989), deletion and mutation of p53 in bladder cancer (Sidransky et al., 1991), deletion of DCC in colorectal cancer (Fearon et al., 1990) and mutation of BRCA1 in breast and prostate cancer (Miki et al., 1994).

None of these genetic lesions are capable of predicting a majority of individuals with cancer and most require direct sampling of a suspected tumor, and make screening difficult. Further, none of the markers described above are capable of distinguishing between metastatic and non-metastatic forms of cancer. In effective management of cancer patients, identification of those individuals whose tumors have already metastasized or are likely to metastasize is critical. Because metastatic cancer kills 560,000 people in the U.S. each year (ACS home page), identification of markers for metastatic prostate cancer would be an important advance.

A particular problem in cancer detection and diagnosis occurs with prostate cancer. Carcinoma of the prostate is the most frequently diagnosed cancer among men in the United States (Veltri et al., 1996). Prostate cancer was diagnosed in approximately 189,500 men in 1998 and about 40,000 men succumbed to the malignancy (Landis et al, 1998). Although relatively few prostate tumors progress to clinical significance during the lifetime of the patient, those which are progressive in nature are likely to have metastasized by the time of detection. Survival rates for individuals with metastatic prostate cancer are quite low. Between these extremes are patients with prostate tumors that will metastasize but have not yet done so, for whom surgical prostate removal is curative. Determination of which group a patient falls within is critical in determining optimal treatment and patient survival.

The FDA approval of the serum prostate specific antigen (PSA) test in 1984 changed the way that prostate disease was managed (Allhoff et al., 1989; Cooner et al., 1990; Jacobson et al, 1995; Orozco et al., 1998). PSA is widely used as a serum biomarker to detect and monitor therapeutic response in prostate cancer patients (Badalament et al., 1996; O'Dowd et al., 1997). Several modifications in PSA assays (Partin and Oesterling, 1994; Babian et al., 1996; Zlotta et al, 1997) have resulted in earlier diagnoses and improved treatment.

Although PSA has been widely used as a clinical marker of prostate cancer since 1988 (Partin and Oesterling, 1994), screening programs utilizing PSA alone or in combination with digital rectal examination (DRE) have not been successful in improving the survival rate for men with prostate cancer (Partin and Oesterling, 1994). Although PSA is specific to prostate tissue, it is produced by normal and benign as well as malignant prostatic epithelium, resulting in a high false-positive rate for prostate cancer detection (Partin and Oesterling, 1994).

While an effective indicator of prostate cancer when serum levels are relatively high, PSA serum levels are more ambiguous indicators of prostate cancer when only modestly elevated, for example when levels are between 2-10 ng/ml. At these modest elevations, serum PSA may have originated from non-cancerous disease states such as BPH (benign prostatic hyperplasia), prostatitis or physical trauma (McCormack et al, 1995). Although application of the lower 2.0 ng/ml cancer detection cutoff concentration of serum PSA has increased the diagnosis of prostate cancer, especially in younger men with nonpalpable early stage tumors (Stage Tlc) (Soh et al., 1997; Carter and Coffey, 1997; Harris et al., 1997; Orozco et al., 1998), the specificity of the PSA assay for prostate cancer detection at low serum PSA levels remains a problem.

Several investigators have sought to improve upon the specificity of serologic detection of prostate cancer by examining a variety of other biomarkers besides serum PSA concentration (Ralph and Veltri, 1997). One of the most heavily investigated of these other biomarkers is the ratio of free versus total PSA (f/t PSA) in a patient's blood. Most PSA in serum is in a molecular form that is bound to other proteins such as alpha1-antichymotrypsin (ACT) or alpha2-macroglobulin (Christensson et al, 1993; Stenman et al., 1991; Lilja et al., 1991). Free PSA is not bound to other proteins. The ratio of free to total PSA (f/tPSA) is usually significantly higher in patients with BPH compared to those with organ confined prostate cancer (Marley et al., 1996; Oesterling et al., 1995; Pettersson et al., 1995). When an appropriate cutoff is determined for the f/tPSA assay, the f/tPSA assay can help distinguish patients with BPH from those with prostate cancer in cases in which serum PSA levels are only modestly elevated (Marley et al., 1996; Partin and Oesterling, 1996). Unfortunately, while f/tPSA may improve on the detection of prostate cancer, information in the f/tPSA ratio is insufficient to improve the sensitivity and specificity of serologic detection of prostate cancer to desirable levels.

Other markers that have been used for prostate cancer detection include prostatic acid phosphatase (PAP) and prostate secreted protein (PSP). PAP is secreted by prostate cells under hormonal control (Brawn et al., 1996). It has less specificity and sensitivity than does PSA. As a result, it is used much less now, although PAP may still have some applications for monitoring metastatic patients that have failed primary treatments. In general, PSP is a more sensitive biomarker than PAP, but is not as sensitive as PSA (Huang et al., 1993). Like PSA, PSP levels are frequently elevated in patients with BPH as well as those with prostate cancer.

Another serum marker associated with prostate disease is prostate specific membrane antigen (PSMA) (Horoszewicz et al., 1987; Carter and Coffey, 1996; Murphy et al., 1996). PSMA is a Type II cell membrane protein and has been identified as Folic Acid Hydrolase (FAH) (Carter and Coffey, 1996). Antibodies against PSMA react with both normal prostate tissue and prostate cancer tissue (Horoszewicz et al., 1987). Murphy et al. (1995) used ELISA to detect serum PSMA in advanced prostate cancer. As a serum test, PSMA levels are a relatively poor indicator of prostate cancer. However, PSMA may have utility in certain circumstances. PSMA is expressed in metastatic prostate tumor capillary beds (Silver et al., 1997) and is reported to be more abundant in the blood of metastatic cancer patients (Murphy et al., 1996). PSMA messenger RNA (mRNA) is down-regulated 8-10 fold in the LNCaP prostate cancer cell line after exposure to 5-alpha-dihydroxytestosterone (DHT) (Israeli et al., 1994).

Two relatively new potential biomarkers for prostate cancer are human kallekrein 2 (HK2) (Piironen et al., 1996) and prostate specific transglutaminase (pTGase) (Dubbink et al., 1996). HK2 is a member of the kallekrein family that is secreted by the prostate gland (Piironen et al., 1996). Prostate specific transglutaminase is a calcium-dependent enzyme expressed in prostate cells that catalyzes post-translational cross-linking of proteins (Dubbink et al., 1996). In theory, serum concentrations of HK2 or pTGase maybe of utility in prostate cancer detection or diagnosis, but the usefulness of these markers is still being evaluated.

Interleukin 8 (IL-8) has also been reported as a marker for prostate cancer. (Veltri et al., 1999). Serum IL-8 concentrations were reported to be correlated with increasing stage of prostate cancer and to be capable of differentiating BPH from malignant prostate tumors. (Id.) The wide-scale applicability of this marker for prostate cancer detection and diagnosis is still under investigation.

In addition to these protein markers for prostate cancer, several genetic changes have been reported to be associated with prostate cancer, including: allelic loss (Bova, et al., 1993; Macoska et al., 1994; Carter et al., 1990); DNA hypermethylation (Isaacs et al., 1994); point mutations or deletions of the retinoblastoma (Rb), p53 and KAI1 genes (Bookstein et al., 1990a; Bookstein et al., 1990b; Isaacs et al., 1991; Dong et al., 1995); and aneuploidy and aneusomy of chromosomes detected by fluorescence in situ hybridization (FISH) (Macoska et al., 1994; Visakorpi et al., 1994; Takahashi et al., 1994; Alcaraz et al., 1994). None of these have been reported to exhibit sufficient sensitivity and specificity to be useful as general screening tools for asymptomatic prostate cancer.

In current clinical practice, the serum PSA assay and digital rectal exam (DRE) is used to indicate which patients should have a prostate biopsy (Lithrup et al., 1994; Orozco et al., 1998). Histological examination of the biopsied tissue is used to make the diagnosis of prostate cancer. Based upon the 189,500 cases of diagnosed prostate cancer in 1998 (Landis, 1998) and a known cancer detection rate of about 35% (Parker et al., 1996), it is estimated that in 1998 over one-half million prostate biopsies were performed in the United States (Orozco et al., 1998; Veltri et al., 1998). Clearly, there would be much benefit derived from a serological test that was sensitive enough to detect small and early stage prostate tumors that also had sufficient specificity to exclude a greater portion of patients with noncancerous or clinically insignificant conditions.

There remain deficiencies in the prior art with respect to the identification of the genes linked with the progression of prostate cancer and the development of diagnostic methods to monitor disease progression. Likewise, the identification of genes, which are differentially expressed in prostate cancer, would be of considerable importance in the development of a rapid, inexpensive method to diagnose cancer. Although a few prostate specific genes have been cloned (PSA, PSMA, HK2, pTGase, etc.), these are typically not upregulated in prostate cancer. The identification of a novel, prostate specific gene that is differentially expressed in prostate cancer, compared to non-malignant prostate tissue, would represent a major, unexpected advance for the diagnosis, prognosis and treatment of prostate cancer.

The use of therapeutic antibodies for treatment of cancers that target surface proteins is known. Examples thereof include RITUXAN® that targets CD20 on B cell lymphoma, Campath® that targets a surface antigen CD52 expressed by chronic lymphocytic leukemia, Herceptin® that targets erbB2 on breast and other cancers and Mybtara that targets CD33 surface antigen expressed on leukemia cells. However, to date, a monoclonal antibody for treatment of prostate cancer has not been approved for therapeutic use.

SUMMARY OF THE INVENTION

The present invention relates to the identification of novel nucleic acid and amino acid sequences that are characteristic of prostate cancer cell or tissue, and which represent targets for therapy or diagnosis of such a condition in a subject.

The invention more specifically discloses 159 specific, isolated nucleic acid molecules that encode novel expression sequences. Of these, 122 are expressed sequence tags that are differentially spliced and correspond to SEQ ID NOS 1-65, 74, 80, 85, 102-134, 136, 141, 146, 150-165, 167, 168. In addition, 42 specific isoforms of known genes have been identified corresponding to SEQ ID NOS. 67-72, 75-77, 81-83, 86-90, 92, 93, 95-98, 100, 101, 137-139, 143, 144, 147-149, 169-173, 175, 177, 179, and 181. These novel sequences were found to be differentially expressed between normal prostate and prostate cancer. The expressed sequence tag represent novel exons that are alternatively spliced in prostate cancer, and as such, directly identify distinct isoforms. These sequences and molecules represent targets and valuable information to develop methods and materials for the detection, diagnosis, and treatment of prostate cancer.

It is an object of the invention to provide methods and materials for treatment and diagnosis of prostate cancer.

It is a more specific object of the invention to identify novel exons (novel splice variants) that are expressed by prostate cancer tissue which are potential gene targets for treatment and diagnosis of prostate cancer.

It is a specific object of the invention to develop novel therapies for treatment of prostate cancer involving the administration or use of anti-sense oligonucleotides corresponding to novel gene targets that are specifically expressed by the prostate cancer.

It is another specific object of the invention to identify exons and the corresponding protein domain encoded by those exons specifically upregulated in prostate cancer cells.

It is another specific object of the invention to produce ligands that bind antigens encoded by the exons, expressed as a protein domain by certain prostate cancers, including, but not limited to, monoclonal antibodies.

It is another specific object of the invention to provide novel therapeutic regimens for the treatment of prostate cancer that involve the administration or use of antigens expressed by certain prostate cancers, alone or in combination with adjuvants that elicit an antigen-specific cytotoxic T-cell lymphocyte response against cancer cells that express such antigen.

It is another object of the invention to provide novel therapeutic regimens for the treatment of prostate cancer that involve the administration or use of ligands, especially monoclonal antibodies that specifically bind novel antigens that are expressed by certain prostate cancers.

It is an other object of this invention to provide pharmaceutical compositions comprising a ligand or antigen as defined above, in combination with a pharmaceutically acceptable carrier or excipient and/or an adjuvant.

It is another object of the invention to provide a novel method for diagnosis of prostate cancer by using ligands, e.g., monoclonal antibodies, which specifically bind to antigens that are specifically expressed by certain prostate cancers, in order to detect whether a subject has or is at increased risk of developing prostate cancer.

It is another object of the invention to provide a novel method of detecting persons having, or at increased risk of developing prostate cancer by use of labeled DNAs that hybridize to novel gene targets expressed by certain prostate cancers.

It is yet another object of the invention to provide diagnostic test kits for the detection of persons having or at increased risk of developing prostate cancer that comprise a ligand, e.g., monoclonal antibody that specifically binds to an antigen expressed by prostate cancer cells, and a detectable label, e.g. indicator enzymes, a radiolabels, fluorophores, or paramagnetic particles.

It is another object of the invention to provide diagnostic kits for detection of persons having or at risk of developing prostate cancer that comprise DNA primers or probes specific for novel gene targets specifically expressed by prostate cancer cells, and a detectable label, e.g. indicator enzymes, a radiolabels, fluorophores, or paramagnetic particles.

It is another object of this invention to provide methods for selecting, identifying, screening, characterizing or optimizing biologically active compounds, comprising a determination of whether a candidate compound binds, preferably selectively, an antigen or a polynucleotide as disclosed in the present application. Such compounds represent drug candidates or leads for treating cancer diseases, particularly prostate cancer.

It is another object of the invention to identify genes that are expressed in altered forms in prostate cancer cells. These forms represent splice variants of the gene, where the DATAS™ fragment either 1) indicates the splice event occurring within the gene, or 2) points to a gene that is actively spliced to produce different gene products. These different splice variants or isoforms can be targets for therapeutic intervention.

LEGEND TO THE FIGURES

FIG. 1: Expression of Sequence ID: No. 92 in normal human tissue. Primers were designed to detect the DATAS clone sequence and RT-PCR analysis was performed for 30 cycles. Lane 1, Prostate; lane 2, Heart; lane 3, Lung; lane 4, Kidney; lane 5, Liver; lane 6, Brain; lane 7, Placenta; lane 8, Sk. Muscle; lane 9, Pancreas; lane 10, Spleen; lane 11, Thymus; lane 12, Testis; lane 13, Ovary; lane 14, Sm. Intestine; lane 15, Colon; lane 16 Leukocyte.

Figure 2:
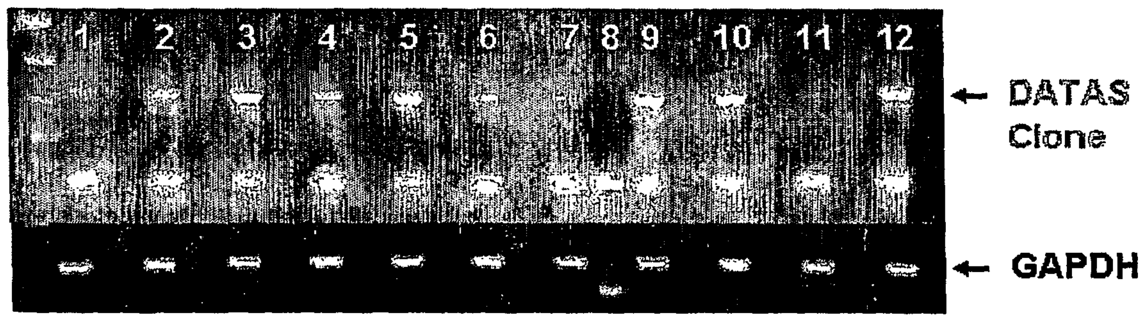

FIG. 2: Expression of clone (SEQ ID NO 92) in normal and tumor prostate samples. Primers were designed to detect the DATAS clone and RT-PCR analysis was performed for 40 cycles. Individual RNA samples (normal and tumor) were tested both as pooled and as individual samples. The pooled RNA samples were used to produce cDNA using either an oligo dT approach (dT) or through a random primer protocol (RP). Individual patient cDNA samples (lanes 9-12) were prepared through the random primed protocol. Lane 1, prostate tumor pool 1 (RP cDNA); lane 2, normal prostate pool 1 (RP cDNA); lane 3, prostate tumor pool 2 (RP cDNA); lane 4, normal prostate pool 2 (RP cDNA); lane 5, prostate tumor pool 1 (dT cDNA); lane 6, normal prostate pool 1 (dT cDNA); lane 7, normal prostate pool 2 (dT cDNA); lane 8, NTC; lane 9, Patient 1 (OHK); lane 10, Patient 2 (T523); lane 11, Patient 3 (82B); lane 12, Patient 4 (4BK).

Figure 3:
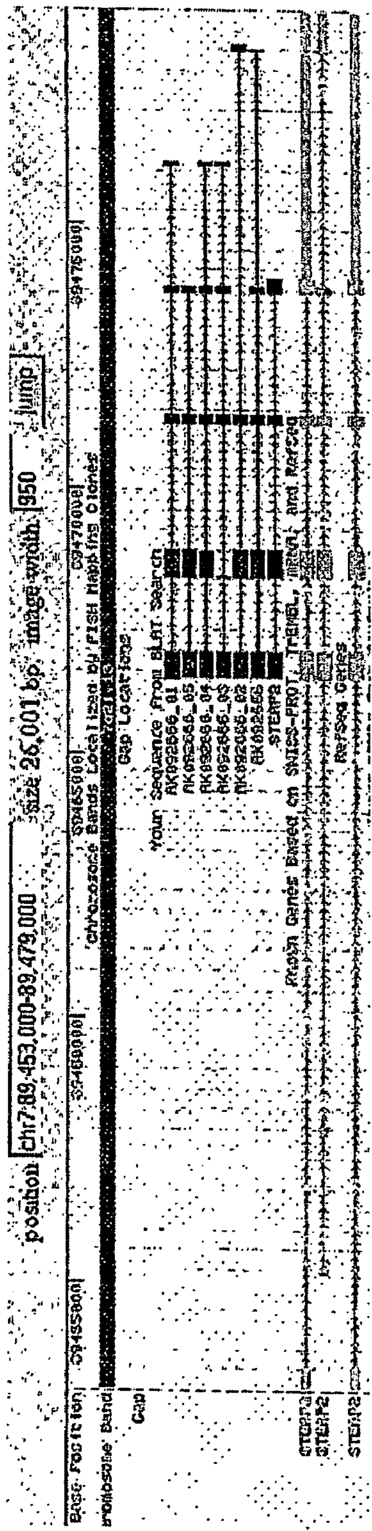

FIG. 3: Alignment of the different isoforms isolated from structural analysis of clone (DATAS clone number). The sequences isolated from the DATAS derived events were mapped using Blat against the Human genome to annotate the gene and determine the each unique splicing event. Five events are mapped with AK092666, an EST that closely resembles the five events.

Figure 4:
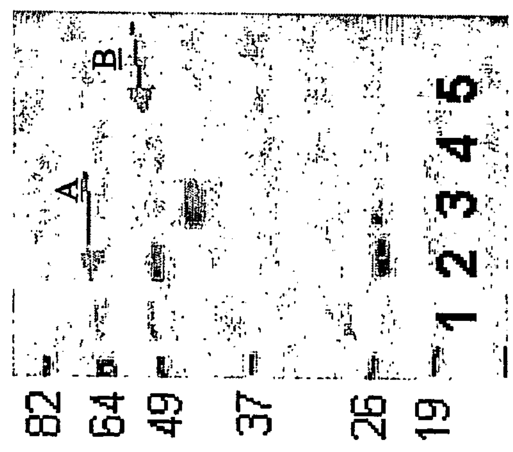

FIG. 4: Western blot analysis for the expression of STEAP2 isoforms. Protein extracts from prostate cancer cell lines were separated on SDS_PAGE gels and transferred to nitrocellulose, and probed with an antibody raised against a peptide sequence present in the N-terminal portion of the wild type STEAP2 protein. Five different cell lines were analyzed: lane 1) LNCaP; 2) 22Rv1 3) MDA-PCa2b; 4) PC3; 5) DU145. The blot was developed using standard chemilumninescence reagents.

DETAILED DESCRIPTION OF THE INVENTION

DATAS (Different Analysis of Transcripts with Alternative Splicing) analyzes structural differences between expressed genes and provides systematic access to alterations in RNA splicing (disclosed in U.S. Pat. No.6,251,590, the disclosure of which is incorporated by reference in its entirety). Having access to these spliced sequences, which are critical for cellular homeostasis, represents a useful advance in functional genomics.

The DATAS Technology generates two libraries when comparing two samples, such as normal vs. tumor tissue. Each library specifically contains clones of sequences that are present and more highly expressed in one sample. For example, library A will contain sequences that are present in genes in the normal samples but absent in the tumor samples. These sequences are identified as being removed or spliced out from the genes in the tumor samples. In contrast, library B will contain sequences that are present only in the tumor samples and not present in the normal samples. These represent exons/introns that are alternatively spliced into genes expressed only in the tumor samples.

The present invention is based in part on the identification of exons that are isolated using DATAS and then determined to be differentially regulated or expressed in prostate tumor samples. Specifically, 122 expressed sequence tags were identified through DATAS and confirmed to be differentially expressed between normal prostate tissue and prostate tumor tissue. These DATAS fragments (DF) are small sections of genes that are selected for inclusion or exclusion in one sample but not the other. These small sections are part of the expressed gene transcript, and can consist of sequences derived from several different regions of the gene, including, but not limited to, portions of single exons, several exons, sequence from introns, and sequences from exons and introns. This alternative usage of exons in different biological samples produces different gene products from the same gene through a process well known in the art as alternative RNA splicing. In particular, 37 alternatively spliced isoforms have been identified from the DATAS fragment sequences, and produce alternate gene products that fit all the descriptions of targets and gene products below.

Alternatively spliced mRNA's produced from the same gene contain different ribonucleotide sequence, and therefore translate into proteins with different amino acid sequences. Nucleic acid sequences that are alternatively spliced into or out of the gene products can be inserted or deleted in frame or out of frame from the original gene sequence. This leads to the translation of different proteins from each variant. Differences can include simple sequence deletions, or novel sequence information inserted into the gene product. Sequences inserted out of frame can lead to the production of an early stop codon and produce a truncated form of the protein. Alternatively, in-frame insertions of nucleic acid may cause an additional protein domain to be expressed from the mRNA. The end stage target is a novel protein containing either a novel epitope or function. Many variations of known genes have been identified and produce protein variants that can be agonistic or antagonistic with the original biological activity of the protein.

DATAS fragments thus identify genes and proteins which are subject to differential regulation and alternative splicing(s) in prostate cancer cells. DATAS fragments thus allow the definition of target molecules suitable for diagnosis or therapy of prostate cancers, which target molecules comprise all or a portion of genes or RNAs comprising the sequence of a DATAS fragment, or of genes or RNA from which the sequence of a DATAS fragment derives, as well as corresponding polypeptides or proteins, and variants thereof.

A first type of target molecule is a target nucleic acid molecule comprising the sequence of a full gene or RNA molecule comprising the sequence of a DATAS fragment as disclosed in the present application. Indeed, since DATAS identifies genetic deregulations associated with prostate tumor, the whole gene or RNA sequence from which said DATAS fragment derives can be used as a target of therapeutic intervention or diagnosis.

Similarly, another type of target molecule is a target polypeptide molecule comprising the sequence of a full-length protein comprising the amino acid sequence encoded by a DATAS fragment as disclosed in the present application.

A further type of target molecule is a target nucleic acid molecule comprising a fragment of a gene or RNA as disclosed above. Indeed, since DATAS identifies genes and RNAs that are altered in prostate tumor cells, portions of such genes or RNAs, including portions that do not comprise the sequence of a DATAS fragment, can be used as a target for therapeutic intervention or diagnosis. Examples of such portions include DATAS fragments, portions thereof, alternative exons or introns of said gene or RNA, exon-exon, exon-intron or intron-intron junction sequences generated by splicing(s) in said RNA, etc. Particular portions comprise a sequence encoding a extra-cellular domain of a polypeptide.

Similarly, another type of target molecule is a fragment of a protein comprising the amino acid sequence encoded by a DATAS fragment as disclosed in the present application. Such fragments may comprise or not the DATAS sequence, and may comprise newly generated amino acid sequence resulting, for instance, from a frame shift, a novel exon-exon or exon-intron junction, the creation of new stop codon, etc.

These target molecules (including genes, fragments, proteins and their variants) can serve as diagnostic agents and as targets for the development of therapeutics. For example, these therapeutics may modulate biological processes associated with prostate tumor viability. Agents may also be identified that are associated with the induction of apoptosis (cell death) in prostate tumor cells. Other agents can also be developed, such as monoclonal antibodies, that bind to the protein or its variant and alter the biological processes important for cell growth. Alternatively, antibodies can deliver a toxin which can inhibit cell growth and lead to cell death.

Specifically, the invention provides sequences that are expressed in a variant protein and are prostate tumor specific or prostate specific. These sequences are portions of genes identified to be in the plasma membrane of the cell through bioinformatic analysis, and the specific sequences of the invention are expressed on the extracellular region of the protein, so that the sequences may be useful in the preparation of prostate tumor vaccines, including prophylatic and therapeutic vaccines.

Based thereon, it is anticipated that the disclosed genes that are associated with the differentially expressed sequences and the corresponding variant proteins should be suitable targets for prostate cancer therapy, prevention or diagnosis, e.g. for the development of antibodies, small molecular inhibitors, anti-sense therapeutics, and ribozymes. The potential therapies are described in greater detail below.

Such therapies will include the synthesis of oligonucleotides having sequences in the antisense orientation relative to the subject nucleic acids which appear to be up-regulated in prostate cancer. Suitable therapeutic antisense oligonucleotides will typically vary in length from two to several hundred nucleotides in length, more typically about 50-70 nucleotides in length or shorter. These antisense oligonucleotides may be administered as naked nucleic acids or in protected forms, e.g., encapsulated in liposomes. The use of liposomal or other protected forms may be advantageous as it may enhance in vivo stability and thus facilitate delivery to target sites, i.e., prostate tumor cells.

Also, the subject novel genes may be used to design novel ribozymes that target the cleavage of the corresponding mRNAs in prostate tumor cells. Similarly, these ribozymes may be administered in free (naked) form or by the use of delivery systems that enhance stability and/or targeting, e.g., liposomes.

Also, the present invention embraces the administration of use of nucleic acids that hybridize to the novel nucleic acid targets identified infra, attached to therapeutic effector moieties, e.g., radiolabels, (e.g., $^{90}Y$, $^{131}I$) cytotoxins, cytotoxic enzymes, and the like in order to selectively target and kill cells that express these nucleic acids, i.e., prostate tumor cells.

Also, the present invention embraces the treatment and/or diagnosis of prostate cancer by targeting altered genes or the corresponding altered protein particularly splice variants that are expressed in altered form in prostate tumor cells. These methods will provide for the selective detection of cells and/or eradication of cells that express such altered forms thereby minimizing adverse effects to normal cells.

Still further, the present invention encompasses non-nucleic acid based therapies. For example, the invention encompasses the use of a DNA containing one of the novel cDNAs corresponding to novel antigen identified herein. It is anticipated that the antigens so encoded may be used as therapeutic or prophylactic anti-tumor vaccines. For example, a particular contemplated application of these antigens involves their administration with adjuvants that induce a cytotoxic T lymphocyte response.

Administration of the subject novel antigens in combination with an adjuvant may result in a humoral immune response against such antigens, thereby delaying or preventing the development of prostate cancer.

These embodiments of the invention will comprise administration of one or more of the subject novel prostate cancer antigens, ideally in combination with an adjuvant, e.g., PROVAX™ (as disclosed U.S. Pat. Nos. 5,709,860, 5,695,770, and 5,585,103, which comprises a microfluidized adjuvant containing Squalene, Tween and Pluronic), ISCOM'S®, DETOX®, SAF, Freund's adjuvant, Alum®, Saponin®, among others. This composition will be administered in an amount sufficient to be therapeutically or prophylactically effective, e.g. on the order of 50 to 20,000 mg/kg body weight, 100 to 5000 mg/kg body weight.

Yet another embodiment of the invention will comprise the preparation of monoclonal antibodies against the antigens encoded by the novel genes containing the nucleic acid sequences disclosed infra. Such monoclonal antibodies may be produced by conventional methods and include human monoclonal antibodies, humanized monoclonal antibodies, chimeric monoclonal antibodies, single chain antibodies, e.g., scFv's and antigen-binding antibody fragments such as Fab and Fab' fragments. Methods for the preparation of monoclonal antibodies are known in the art. In general, preparation of monoclonal antibodies will comprise immunization of an appropriate (non-homologous) host with the subject prostate cancer antigens, isolation of immune cells therefrom, use of such immune cells to isolate monoclonal antibodies and screening for monoclonal antibodies that specifically bind to either of such antigens. Antibody fragments maybe prepared by known methods, e.g., enzymatic change of monoclonal antibodies.

These monoclonal antibodies and fragments will be useful for passive anti-tumor immunotherapy, or may be attached to therapeutic effector moieties, e.g., radiolabels, cytotoxins, therapeutic enzymes, agents that induce apoptosis, and the like in order to provide for targeted cytotoxicity, i.e., killing of human prostate tumor cells. Given the fact that the subject genes are apparently not significantly expressed by many normal tissues this should not result in significant adverse side effects (toxicity to non-target tissues).

In one embodiment, of the present invention such antibodies or fragments will be administered in labeled or unlabeled form, alone or in conjunction with other therapeutics, e.g., chemotherapeutics such as cisplatin, methotrexate, adriamycin, and the like suitable for prostate cancer therapy. The administered composition will also typically include a pharmaceutically acceptable carrier, and optionally adjuvants, stabilizers, etc., used in antibody compositions for therapeutic use.

Preferably, the subject monoclonal antibodies will bind the target antigens with high affinity, e.g., possess a binding affinity (Kd) on the order of $10^{-6}$ to $10^{-12}$ M.

As noted, the present invention also embraces diagnostic applications that provide for detection of the expression of prostate specific splice variants disclosed herein. This will comprise detecting the expression of one or more of these genes at the RNA level and/or at the protein level.

For nucleic acids, expression of the subject genes will be detected by known nucleic acid detection methods, e.g., Northern blot hybridization, strand displacement amplification (SDA), catalytic hybridization amplification (CHA), and other known nucleic acid detection methods. Preferably, a cDNA library will be made from prostate cells obtained from a subject to be tested for prostate cancer by PCR using primers corresponding to the novel isoforms disclosed in this application.

The presence or absence of prostate cancer can be determined based on whether PCR products are obtained, and the level of expression. The levels of expression of such PCR product may be quantified in order to determine the prognosis of a particular prostate cancer patient (as the levels of expression of the PCR product often will increase or decrease significantly as the disease progresses.) This may provide a method for monitoring the status of a prostate cancer patient.

Alternatively, the status of a subject to be tested for prostate cancer may be evaluated by testing biological fluids, e.g., blood, urine, lymph, and the like with an antibody or antibodies or fragment that specifically binds to the novel prostate tumor antigens disclosed herein.

Methods for using antibodies to detect antigen expression are well known and include ELISA, competitive binding assays, and the like. In general, such assays use an antibody or antibody fragment that specifically binds the target antigen directly or indirectly bound to a label that provides for detection, e.g. indicator enzymes, a radiolabels, fluorophores, or paramagnetic particles.

Patients which test positive for the enhanced presence of the antigen on prostate cells will be diagnosed as having or being at increased risk of developing prostate cancer. Additionally, the levels of antigen expression may be useful in determining patient status, i.e., how far disease has advanced (stage of prostate cancer).

As noted, the present invention provides novel splice variants that encode antigens that correlate to human prostate cancer. The present invention also embraces variants thereof. As used herein "variants" means sequences that are at least about 75% identical thereto, more preferably at least about 85% identical, and most preferably at least 90% identical and still more preferably at least about 95-99% identified when these DNA sequences are compared to a nucleic acid sequence encoding the subject DNAs or a fragment thereof having a size of at least about 50 nucleotides. This includes allelic and splice variants of the subject genes. The present invention also encompasses nucleic acid sequences that hybridize to the subject splice variants under high, moderate or low stringency conditions e.g., as described infra.

Also, the present invention provides for primer pairs that result in the amplification of DNAs encoding the subject novel genes or a portion thereof in an mRNA library obtained from a desired cell source, typically human prostate cell or tissue sample. Typically, such primers will be on the order of 12 to 50 nucleotides in length, and will be constructed such that they provide for amplification of the entire or most of the target gene.

Also, the invention embraces the antigens encoded by the subject DNAs or fragments thereof that bind to or elicits antibodies specific to the full-length antigens. Typically, such fragments will be at least 10 amino acids in length, more typically at least 25 amino acids in length.

As noted, the subject DNA fragments are expressed in a majority of prostate tumor samples tested. The invention further contemplates the identification of other cancers that express such genes and the use thereof to detect and treat such cancers. For example, the subject DNA fragments or variants thereof may be expressed on other cancers, e.g., breast, ovary, pancreas, lung or prostate cancers. Essentially, the present invention embraces the detection of any cancer wherein the expression of the subject novel genes or variants thereof correlate to a cancer or an increased likelihood of cancer. To facilitate under-study of the invention, the following definitions are provided.

"Isolated tumor antigen or tumor protein" refers to any protein that is not in its normal cellular environment. This includes by way of example compositions comprising recombinant proteins encoded by the genes disclosed infra, pharmaceutical compositions comprising such purified proteins, diagnostic compositions comprising such purified proteins, and isolated protein compositions comprising such proteins. In preferred embodiments, an isolated prostate tumor protein according to the invention will comprise a substantially pure protein, in that it is substantially free of other proteins, preferably that is at least 90% pure, that comprises the amino acid sequence contained herein or natural homologues or mutants having essentially the same sequence. A naturally occurring mutant might be found, for instance, in tumor cells expressing a gene encoding a mutated protein according to the invention.

"Native tumor antigen or tumor protein" refers to a protein that is a non-human primate homologue of the protein having the amino acid sequence contained infra.

"Isolated prostate tumor gene or nucleic acid sequence" refers to a nucleic acid molecule that encodes a tumor antigen according to the invention which is not in its normal human cellular environment, e.g., is not comprised in the human or non-human primate chromosomal DNA. This includes by way of example vectors that comprise a gene according to the invention, a probe that comprises a gene according to the invention, and a nucleic acid sequence directly or indirectly attached to a detectable moiety, e.g. a fluorescent or radioactive label, or a DNA fusion that comprises a nucleic acid molecule encoding a gene according to the invention fused at its 5' or 3' end to a different DNA, e.g. a promoter or a DNA encoding a detectable marker or effector moiety. Also included are natural homologues or mutants having substantially the same sequence. Naturally occurring homologies that are degenerate would encode the same protein including nucleotide differences that do not change the corresponding amino acid sequence. Naturally occurring mutants might be found in tumor cells, wherein such nucleotide differences may result in a mutant tumor antigen. Naturally occurring homologues containing conservative substitutions are also encompassed.

"Variant of prostate tumor antigen or tumor protein" refers to a protein possessing an amino acid sequence that possess at least 90% sequence identity, more preferably at least 91% sequence identity, even more preferably at least 92% sequence identity, still more preferably at least 93% sequence identity, still more preferably at least 94% sequence identity, even more preferably at least 95% sequence identity, still more preferably at least 96% sequence identity, even more preferably at least 97% sequence identity, still more preferably at least 98% sequence identity, and most preferably at least 99% sequence identity, to the corresponding native tumor antigen wherein sequence identity is as defined infra. Preferably, this variant will possess at least one biological property in common with the native protein.

"Variant of prostate tumor gene or nucleic acid molecule or sequence" refers to a nucleic acid sequence that possesses at least 90% sequence identity, more preferably at least 91%, more preferably at least 92%, even more preferably at least 93%, still more preferably at least 94%, even more preferably at least 95%, still more preferably at least 96%, even more preferably at least 97%, even more preferably at least 98% sequence identity, and most preferably at least 99% sequence identity, to the corresponding native human nucleic acid sequence, wherein "sequence identity" is as defined infra.

"Fragment of prostate antigen encoding nucleic acid molecule or sequence" refers to a nucleic acid sequence corresponding to a portion of the native human gene wherein said portion is at least about 50 nucleotides in length, or 100, more preferably at least 150 nucleotides in length.

"Antigenic fragments of prostate tumor antigen" refer to polypeptides corresponding to a fragment of a prostate protein or a variant or homologue thereof that when used itself or attached to an immunogenic carrier elicits antibodies that specifically bind the protein. Typically such antigenic fragments will be at least 8-15 amino acids in length, and may be much longer.

Sequence identity or percent identity is intended to mean the percentage of the same residues shared between two sequences, referenced to human protein A or protein B or gene A or gene B, when the two sequences are aligned using the Clustal method [Higgins et al, Cabios 8:189-191 (1992)] of multiple sequence alignment in the Lasergene biocomputing software (DNASTAR, INC, Madison, Wis.), or alignment programs available from the Genetics Computer Group (GCG Wisconsin package, Accelrys, San Diego, Calif.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM25O [Dayhoffet al., in Atlas of Protein Sequence and Structure, Dayhoff, Ed., NDRF, Washington, Vol. 5, suppl. 3, p. 345, (1978)].

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to human Gene A or gene B when determining percent conservation with non-human Gene A or gene B, e.g. mgene A or gene B, when determining percent conservation. Conservative amino acid changes satisfying this requirement include: R-K; E-D, Y-F, L-M; V-I, Q-H.

Polypeptide Fragments

The invention provides polypeptide fragments of the disclosed proteins. Polypeptide fragments of the invention can comprise at least 8, more preferably at least 25, still more preferably at least 50 amino acid residues of the protein or an analogue thereof. More particularly such fragment will comprise at least 75, 100, 125, 150, 175, 200, 225, 250, 275 residues of the polypeptide encoded by the corresponding gene. Even more preferably, the protein fragment will comprise the majority of the native protein, e.g. about 100 contiguous residues of the native protein.

Biologically Active Variants

The invention also encompasses mutants of the novel prostate proteins disclosed infra which comprise an amino acid sequence that is at least 80%, more preferably 90%, still more preferably 95-99% similar to the native protein.

Guidance in determining which amino acid residues can be substituted, inserted, or deleted without abolishing biological or immunological activity can be found using computer programs well known in the art, such as DNASTAR or software from the Genectics Computer Group (GCG). Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

A subset of mutants, called muteins, is a group of polypeptides in which neutral amino acids, such as serines, are substituted for cysteine residues which do not participate in disulfide bonds. These mutants may be stable over a broader temperature range than native secreted proteins. See Mark et al., U.S. Pat. No. 4,959,314.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant.

Protein variants include glycosylated forms, aggregative conjugates with other molecules, and covalent conjugates with unrelated chemical moieties. Also, protein variants also include allelic variants, species variants, and muteins. Truncations or deletions of regions which do not affect the differential expression of the gene are also variants. Covalent variants can be prepared by linking functionalities to groups which are found in the amino acid chain or at the N— or C-terminal residue, as is known in the art.

It will be recognized in the art that some amino acid sequence of the prostate proteins of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the polypeptides of the present invention may include one or more amino acid substitutions, deletions or additions, either from natural mutations or human manipulation.

The invention further includes variations of the prostate proteins disclosed infra which show comparable expression patterns or which include antigenic regions. Such mutants include deletions, insertions, inversions, repeats, and site substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be imnmunogenic. (Pinckard et al., *Clin. Exp. Immunol.* 2:331-340 (1967); Robbins et al., *Diabetes* 36:838-845 (1987); Cleland et al., *Crit. Rev. Therapeutic Drug Carrier Systems* 10:307-377 (1993)).

Amino acids in the polypeptides of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J Mol. Biol.* 224:899-904(1992) and de Vos et al. *Science* 255:306-312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

Fusion Proteins

Fusion proteins comprising proteins or polypeptide fragments of the subject prostate tumor antigen can also be constructed. Fusion proteins are useful for generating antibodies against amino acid sequences and for use in various assay systems. For example, fusion proteins can be used to identify proteins which interact with a protein of the invention or which interfere with its biological function. Physical methods, such as protein afinnity chromatography, or library-based assays for protein-protein interactions, such as the yeast two-hybrid or phage display systems, can also be used for this purpose. Such methods are well known in the art and can also be used as drug screens. Fusion proteins comprising a signal sequence and/or a transmembrane domain of a protein according to the invention or a fragment thereof can be used to target other protein domains to cellular locations in which the domains are not normally found, such as bound to a cellular membrane or secreted extracellularly.

A fusion protein comprises two protein segments fused together by means of a peptide bond. As noted, these fragments may range in size from about 8 amino acids up to the full length of the protein.

The second protein segment can be a full-length protein or a polypeptide fragment.

Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GALA DNA binding domain fusions, and herpes simplex virus (HSV) BP 16 protein fusions.

These fusions can be made, for example, by covalently linking two protein segments or by standard procedures in the art of molecular biology. Recombinant DNA methods can be used to prepare fusion proteins, for example, by making a DNA construct which comprises a coding sequence encoding a possible antigen according to the invention or a fragment thereof in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Proteins, fusion proteins, or polypeptides of the invention can be produced by recombinant DNA methods. For production of recombinant proteins, fusion proteins, or polypeptides, a sequence encoding the protein can be expressed in prokaryotic or eukaryotic host cells using expression systems known in the art. These expression systems include bacterial, yeast, insect, and mammalian cells.

The resulting expressed protein can then be purified from the culture medium or from extracts of the cultured cells using purification procedures known in the art. For example, for proteins fully secreted into the culture medium, cell-free medium can be diluted with sodium acetate and contacted with a cation exchange resin, followed by hydrophobic interaction chromatography. Using this method, the desired protein or polypeptide is typically greater than 95% pure. Further purification can be undertaken, using, for example, any of the techniques listed above.

It may be necessary to modify a protein produced in yeast or bacteria, for example by phosphorylation or glycosylation of the appropriate sites, in order to obtain a functional protein. Such covalent attachments can be made using known chemical or enzymatic methods.

A protein or polypeptide of the invention can also be expressed in cultured host cells in a form which will facilitate purification. For example, a protein or polypeptide can be expressed as a fusion protein comprising, for example, maltose binding protein, glutathione-S-transferase, or thioredoxin, and purified using a commercially available kit. Kits for expression and purification of such fusion proteins are available from companies such as New England BioLabs, Pharmacia, and Invitrogen. Proteins, fusion proteins, or polypeptides can also be tagged with an epitope, such as a "Flag" epitope (Kodak), and purified using an antibody which specifically binds to that epitope.

The coding sequence of the protein variants identified through the sequences disclosed herein can also be used to construct transgenic animals, such as mice, rats, guinea pigs, cows, goats, pigs, or sheep. Female transgenic animals can then produce proteins, polypeptides, or fusion proteins of the invention in their milk. Methods for constructing such animals are known and widely used in the art.

Alternatively, synthetic chemical methods, such as solid phase peptide synthesis, can be used to synthesize a secreted protein or polypeptide. General means for the production of peptides, analogs or derivatives are outlined in Chemistry and Biochemistry of Amino Acids, Peptides, and Proteins—A Survey of Recent Developments, B. Weinstein, ed. (1983). Substitution of D-amino acids for the normal L-stereoisomer can be carried out to increase the half-life of the molecule.

Typically, homologous polynucleotide sequences can be confirmed by hybridization under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each, homologous sequences can be identified which contain at most about 25-30% basepair mismatches. More preferably, homologous nucleic acid strands contain 15-25% basepair mismatches, even more preferably 5-15% basepair mismatches.

The invention also provides polynucleotide probes which can be used to detect complementary nucleotide sequences, for example, in hybridization protocols such as Northern or Southern blotting or in situ hybridizations. Polynucleotide probes of the invention comprise at least 12, 13, 14, 15, 16, 17, 18, 19, 20, 30, or 40 or more contiguous nucleotides of the nucleic acid sequences provided herein. Polynucleotide probes of the invention can comprise a detectable label, such as a radioisotopic, fluorescent, enzymatic, or chemiluminescent label.

Isolated genes corresponding to the cDNA sequences disclosed herein are also provided. Standard molecular biology methods can be used to isolate the corresponding genes using the cDNA sequences provided herein. These methods include preparation of probes or primers from the nucleotide sequence disclosed herein for use in identifying or amplifying the genes from mammalian, including human, genomic libraries or other sources of human genomic DNA.

Polynucleotide molecules of the invention can also be used as primers to obtain additional copies of the polynucleotides, using polynucleotide amplification methods. Polynucleotide molecules can be propagated in vectors and cell lines using techniques well known in the art. Polynucleotide molecules can be on linear or circular molecules. They can be on autonomously replicating molecules or on molecules without replication sequences. They can be regulated by their own or by other regulatory sequences, as is known in the art.

Polynucleotide Constructs

Polynucleotide molecules comprising the coding sequences of the gene variants identified through the sequences disclosed herein can be used in a polynucleotide construct, such as a DNA or RNA construct. Polynucleotide molecules of the invention can be used, for example, in an expression construct to express all or a portion of a protein, variant, fusion protein, or single-chain antibody in a host cell. An expression construct comprises a promoter which is functional in a chosen host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes all or a portion of the desired protein. The polynucleotide segment is located downstream from the promoter. Transcription of the polynucleotide segment initiates at the promoter. The expression construct can be linear or circular and can contain sequences, if desired, for autonomous replication.

Also included are polynucleotide molecules comprising the promoter and UTR sequences of the subject novel genes, operably linked to the associated protein coding sequence and/or other sequences encoding a detectable or selectable marker. Such promoter and/or UTR-based constructs are useful for studying the transcriptional and translational regulation of protein expression, and for identifying activating and/or inhibitory regulatory proteins.

Host Cells

An expression construct can be introduced into a host cell. The host cell comprising the expression construct can be any suitable prokaryotic or eukaryotic cell. Expression systems in bacteria include those described in Chang et al., *Nature* 275: 615 (1978); Goeddel et al., *Nature* 281: 544 (1979); Goeddel et al., *Nucleic Acids Res.* 8:4057 (1980); EP 36,776; U.S. Pat. No. 4,551,433; deBoer et al., *Proc. Natl. Acad Sci. USA* 80: 21-25 (1983); and Siebenlist et al., *Cell* 20: 269 (1980).

Expression systems in yeast include those described in Hinnnen et al., *Proc. Natl. Acad. Sci. USA* 75: 1929 (1978); Ito et al., *J Bacteriol* 153: 163 (1983); Kurtz et al., *Mol. Cell. Biol.* 6: 142 (1986); Kunze et al., *J Basic Microbiol.* 25: 141 (1985); Gleeson et al., *J. Gen. Microbiol.* 132: 3459 (1986), Roggenkamp et al., *Mol. Gen. Genet.* 202: 302 (1986)); Das et al., J Bacteriol. 158: 1165 (1984); De Louvencourt et al., *J Bacteriol.* 154:737 (1983), Van den Berg et al., *Bio/Technology* 8: 135 (1990); Kunze et al., *J. Basic Microbiol.* 25: 141 (1985); Cregg et al., *Mol. Cell. Biol.* 5: 3376 (1985); U.S. Pat. No. 4,837,148; U.S. Pat. No. 4,929,555; Beach and Nurse, *Nature* 300: 706 (1981); Davidow et al., *Curr. Genet.* 10: 380(1985); Gaillardin et al., Curr. *Genet.* 10: 49 (1985); Ballance et al., *Biochem. Biophys. Res. Commun.* 112: 284-289 (1983); Tilburn et al., *Gene* 26: 205-22 (1983); Yelton et al., *Proc. Natl. Acad, Sci. USA* 81: 1470-1474 (1984); Kelly and Hynes, *EMBO J.* 4: 475479 (1985); EP 244,234; and WO 91/00357.

Expression of heterologous genes in insects can be accomplished as described in U.S. Pat. No. 4,745,051; Friesen et al. (1986) "The Regulation of Baculovirus Gene Expression" in: THE MOLECULAR BIOLOGY OF BACULOVIRUSES (W. Doerfler, ed.); EP 127,839; EP 155,476; Vlak et al., *J. Gen. Virol.* 69: 765-776 (1988); Miller et al., *Ann. Rev. Microbiol.* 42: 177 (1988); Carbonell et al., *Gene* 73: 409 (1988); Maeda et al., *Nature* 315: 592-594 (1985); Lebacq-Verheyden et al., *Mol. Cell Biol.* 8: 3129 (1988); Smith et al., *Proc. Natl. Acad. Sci. USA* 82: 8404 (1985); Miyajima et al., *Gene* 58: 273 (1987); and Martin et al., *DNA* 7:99 (1988). Numerous baculoviral strains and variants and corresponding permissive insect host cells from hosts are described in Luckow et al., *Bio/Technology* (1988) 6: 47-55, Miller et al., in GENETIC ENGINEERING (Setlow, J. K. et al. eds.), Vol. 8, pp. 277-279 (Plenum Publishing, 1986); and Maeda et al., *Nature,* 315: 592-594 (1985).

Mammalian expression can be accomplished as described in Dijkema et al., *EMBO J.* 4: 761(1985); Gormanetal., *Proc. Natl. Acad. Sci. USA* 79: 6777 (1982b); Boshart et al., *Cell* 41: 521 (1985); and U.S. Pat. No. 4,399,216. Other features of mammalian expression can be facilitated as described in Ham and Wallace, *Meth Enz.* 58: 44 (1979);

Expression constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and calcium phosphate-mediated transfection.

The invention can also include hybrid and modified forms thereof including fusion proteins, fragments and hybrid and modified forms in which certain amino acids have been deleted or replaced, modifications such as where one or more amino acids have been changed to a modified amino acid or unusual amino acid.

Also included within the meaning of substantially homologous is any human or non-human primate protein which may be isolated by virtue of cross-reactivity with antibodies to proteins encoded by a gene described herein or whose encoding nucleotide sequences including genomic DNA, mRNA or cDNA may be isolated through hybridization with the complementary sequence of genomic or subgenomic nucleotide sequences or cDNA of a gene herein or fragments thereof It will also be appreciated by one skilled in the art that degenerate DNA sequences can encode a tumor protein according to the invention and these are also intended to be included within the present invention as are allelic variants of the subject genes.

Preferred is a prostate protein according to the invention prepared by recombinant DNA technology. By "pure form" or "purified form" or "substantially purified form" it is meant that a protein composition is substantially free of other proteins which are not the desired protein.

The present invention also includes therapeutic or pharmaceutical compositions comprising a protein according to the invention in an effective amount for treating patients with disease, and a method comprising administering a therapeutically effective amount of the protein. These compositions and methods are useful for treating cancers associated with the subject proteins, e.g. prostate cancer. One skilled in the art can readily use a variety of assays known in the art to determine whether the protein would be useful in promoting survival or functioning in a particular cell type.

Anti-Prostate Antigen Antibodies

As noted, the invention includes the preparation and use of anti-prostate antigen antibodies and fragments for use as diagnostics and therapeutics. These antibodies may be polyclonal or monoclonal. Polyclonal antibodies can be prepared by immunizing rabbits or other animals by injecting antigen followed by subsequent boosts at appropriate intervals. The animals are bled and sera assayed against purified protein usually by ELISA or by bioassay based upon the ability to block the action of the corresponding gene. When using avian species, e.g., chicken, turkey and the like, the antibody can be isolated from the yolk of the egg. Monoclonal antibodies can be prepared after the method of Milstein and Kohler by fusing splenocytes from immunized mice with continuously replicating tumor cells such as myeloma or lymphoma cells. [Milstein and Kohler, *Nature* 256:495-497 (1975); Gulfre and Milstein, *Methods in Enzymology: Immunochemical Techniques* 73:1-46, Langone and Banatis eds., Academic Press, (1981) which are incorporated by reference]. The hybridoma cells so formed are then cloned by limiting dilution methods and supernates assayed for antibody production by ELISA, RIA or bioassay.

The unique ability of antibodies to recognize and specifically bind to target proteins provides an approach for treating an overexpression of the protein. Thus, another aspect of the present invention provides for a method for preventing or treating diseases involving overexpression of the protein by treatment of a patient with specific antibodies to the protein.

Specific antibodies, either polyclonal or monoclonal, to the protein can be produced by any suitable method known in the art as discussed above. For example, by recombinant methods, preferably in eukaryotic cells murine or human monoclonal antibodies can be produced by hybridoma technology or, alternatively, the protein, or an immunologically active fragment thereof, or an anti-idiotypic antibody, or fragment thereof can be administered to an animal to elicit the production of antibodies capable of recognizing and binding to the protein. Such antibodies can be from any class of antibodies including, but not limited to IgG, IgA, 1 gM, IgD, and IgE or in the case of avian species, IgY and from any subclass of antibodies.

The availability of isolated protein allows for the identification of small molecules and low molecular weight compounds that inhibit the binding of protein to binding partners, through routine application of high-throughput screening methods (HTS). HTS methods generally refer to technologies that permit the rapid assaying of lead compounds for therapeutic potential. HTS techniques employ robotic handling of test materials, detection of positive signals, and interpretation of data. Lead compounds may be identified via the incorporation of radioactivity or through optical assays that rely on absorbance, fluorescence or luminescence as read-outs. [Gonzalez, J. E. et al., *Curr. Opin. Biotech.* 9:624-63 1 (1998)].

Model systems are available that can be adapted for use in high throughput screening for compounds that inhibit the interaction of protein with its ligand, for example by competing with protein for ligand binding. Sarubbi et al., *Anal. Biochem.* 237:70-75(1996) describe cell-free, non-isotopic assays for discovering molecules that compete with natural ligands for binding to the active site of IL-1 receptor. Martens, C. et al., *Anal. Biochem.* 273:20-31 (1999) describe a generic particle-based nonradioactive method in which a labeled ligand binds to its receptor immobilized on a particle; label on the particle decreases in the presence of a molecule that competes with the labeled ligand for receptor binding.

Antibody Preparation (i) Starting Materials and Methods

Immunoglobulins (Ig) and certain variants thereof are known and many have been prepared in recombinant cell culture. For example, see U.S. Pat. No. 4,745,055; EP 256,654; EP 120,694; EP 125,023; EP 255,694; EP 266,663; WO 88/03559; Faulkneret al., Nature, 298: 286 (1982); Morrison, J. Immun., 123: 793 (1979); Koehler et al., Proc. Natl. Acad. Sci. USA, 77: 2197 (1980); Raso et al., Cancer Res., 41: 2073 (1981); Morrison et al., Ann. Rev. Immunol., 2: 239 (1984); Morrison, Science, 229: 1202 (1985); and Morrison et al., Proc. Natl. Acad. Sci. USA, 81: 6851 (1984). Reassorted immunoglobulin chains are also known. See, for example, U.S. Pat. No. 4,444,878; WO 88/03565; and EP 68,763 and references cited therein. The immunoglobulin moiety in the chimeras of the present invention may be obtained from IgG-1, IgG-2, IgG-3, or IgG-4 subtypes, IgA, IgE, IgD, or IgM, but preferably from IgG-1 or IgG-3.

(ii) Polyclonal Antibodies

Polyclonal antibodies to the subject prostate antigens are generally raised in animals by multiple subcutaneous (sc) or intraperitoneal (ip) injections of the antigen and an adjuvant. It maybe useful to conjugate the antigen or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde or succinic anhydride.

Animals are immunized against the polypeptide or fragment, immunogenic conjugates, or derivatives by combining about 1 mg or 1 μg of the peptide or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer to the antigen or a fragment thereof. Animals are boosted until the titer plateaus. Preferably, the animal is boosted with the conjugate of the same polypeptide or fragment thereof, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, monoclonal antibodies using for practicing this invention may be made using the hybridoma method first described by Kohler and Milstein, Nature, 256: 495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the antigen or fragment thereof used for immunization. Alternatively, lymphocytes maybe immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against the prostate antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, Anal. Biochem., 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells maybe grown in vivo as ascites tumors in an animal.

The monoclonal antibodies secreted by the subdlones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA maybe placed into expression vectors, which are then transfected into host cells such as *E. Coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5: 256-262 (1993) and Pluckthun, Immunol. Revs., 130: 151-188 (1992).

The DNA also may be modified, for example, by substituting the coding sequence for human heavy- and light-chain constant domains in place of the homologous murine sequences (Morrison, et al., Proc. Natl. Acad. Sci. USA, 81: 6851 [1984]), or by covalently joining to the immunoglobulin coding sequence all or part of the coding sequence for a non-immunoglobulin polypeptide. In that manner, "chimeric" or "hybrid" antibodies are prepared that have the binding specificity of an anti-prostate antigen monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for prostate antigen according to the invention and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(iv) Humanized Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321, 522-525 [1986]; Riechmann et al., Nature 332,323-327 [1988]; Verhoeyen et al., Science 239,1534-1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151: 2296 [1993]; Chothia and Lesk, J. Mol. Biol., 196: 901 [1987]). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89: 4285 [1992]; Presta et al., J. Immnol., 151: 2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

(v) Human Antibodies

Human monoclonal antibodies can be made by the hybridoma method. Human myeloma and mouse-human heteromyeloma cell lines for the production of human monoclonal antibodies have been described, for example, by Kozbor, J. Immunol. 133, 3001 (1984); Brodeur, et al., Monoclonal Antibody Production Techniques and Applications, pp. 51-63 (Marcel Dekker, Inc., New York, 1987); and Boerner et al., J. Immunol., 147: 86-95 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255-258 (1993); Bruggermann et al., Year in Immuno., 7: 33 (1993).

Alternatively, the phage display technology (McCafferty et al., Nature, 348: 552-553 [1990]) can be used to produce human antibodies and antibody fragments in vitro, from immunoglobulin variable (V) domain gene repertoires from non-immunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson and Chiswell, Curr. Op. Struct. Biol., 3: 564-571 (1993). Several sources of V-gene segments can be used for phage display. Clackson et al., Nature, 352: 624-628 (1991) isolated a diverse array of anti-oxazolone antibodies from a small random combinatorial library of V genes derived from the spleens of immunized mice. A repertoire of V genes from non-immunized human donors can be constructed and antibodies to a diverse array of antigens (including self-antigens) can be isolated essentially following the techniques described by Marks et al., J. Mol. Biol., 222: 581-597 (1991), or Griffith et al., EMBO J., 12: 725-734 (1993).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technology, 10: 779-783 [1992]). In this method, the affinity of "primary" human antibodies obtained by phage display can be improved by sequentially replacing the heavy and light chain V region genes with repertoires of naturally occurring variants (repertoires) of V domain genes obtained from non-immunized donors. This technique allows the production of antibodies and antibody fragments with affinities in the nM range. A strategy for making very large phage antibody repertoires has been described by Waterhouse et al., Nucl. Acids Res., 21: 2265-2266 (1993).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e., the epitope governs (imprints) the choice of partner. When the process is repeated in order to replace the remaining rodent V domain, a human antibody is obtained (see PCT WO 93/06213, published Apr. 1, 1993). Unlike traditional humanization of rodent antibodies by CDR grafting, this technique provides completely human antibodies, which have no framework or CDR residues of rodent origin.

(vi) Bispecific Antibodies

Bispecific antibodies are monoclonal, preferably human or humanized, antibodies that have binding specificities for at least two different antigens. In the present case, one of the binding specificities will be to a prostate antigen according to the invention. Methods for making bispecific antibodies are known in the art.

Traditionally, the recombinant production of bispecific antibodies is based on the co-expression of two immunoglobulin heavy chain-light chain pairs, where the two heavy chains have different specificities (Milstein and Cuello, Nature, 305: 537-539 [1983]). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655-3659 (1991).

According to a different and more preferred approach, antibody-variable domains with the desired binding specificities (antibody-antigencombining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

For further details of generating bispecific antibodies, see, for example, Suresh et al., Methods in Enzymology, 121: 210 (1986).

(vii) Heteroconjuqate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/00373; and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

The polynucleotides and polypeptides of the present invention maybe utilized in gene delivery vehicles. The gene delivery vehicle may be of viral or non-viral origin (see generally, Jolly, *Cancer Gene Therapy* 1:51-64 (1994); Kimura, *Human Gene Therapy* 5:845-852 (1994); Connelly, *Human Gene Therapy* 1:185-193 (1995); and Kaplitt, *Nature Genetics* 6:148-153 (1994)). Gene therapy vehicles for delivery of constructs including a coding sequence of a therapeutic according to the invention can be administered either locally or systemically. These constructs can utilize viral or non-viral vector approaches. Expression of such coding sequences can be induced using endogenous mammalian or heterologous promoters. Expression of the coding sequence can be either constitutive or regulated. Preferred vehicles for gene therapy include retroviral and adeno-viral vectors.

Representative examples of adenoviral vectors include those described by Berkner, *Biotechniques* 6:616-627 (Biotechniques); Rosenfeld et al., *Science* 252:431-434 (1991); WO 93/19191; Kolls et al., *P.N.A.S.* 215-219(1994); Kass-Bisleret al., P.N.A.S. 90:11498-11502 (1993); Guzman et al., *Circulation* 88: 2838-2848 (1993); Guzman et al., *Cir. Res.* 73:1202-1207 (1993); Zabner et al., *Cell* 75: 207-216 (1993); Li et al., *Hum. Gene Other.* 4: 403-409 (1993); Cailaud et al., *Eur. J. Neurosci.* 5: 1287-1291 (1993); Vincent et al., *Nat. Genet.* 5: 130-134 (1993); Jaffe et al., *Nat. Genet.* 1: 372-378 (1992); and Levrero et al., *Gene* 101: 195-202 (1992). Exemplary adenoviral gene therapy vectors employable in this invention also include those described in WO 94/12649, WO 93/03769; WO 93/19191; WO 94/28938; WO 95/11984 and WO 95/00655. Administration of DNA linked to kill adenovirus as described in Curiel, *Hum. Gene Other.* 3: 147-154 (1992) maybe employed.

Other gene delivery vehicles and methods may be employed; including polycationic condensed DNA linked or unlinked to kill adenovirus alone, for example Curiel, *Hum. Gene Other.* 3: 147-154 (1992); ligand-linked DNA, for example see Wu, *J. Biol. Chem.* 264:16985-16987 (1989); eukaryotic cell delivery vehicles cells, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Biol.* 14:2411-2418 (1994), and in Woffendin, *Proc. Natl. Acad. Sci.* 91:1581-1585 (1994).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Patent Publication Nos. WO 95/13796, WO 94/23697, and WO 91/14445, and EP No. 0 524 968.

Further non-viral delivery suitable for use includes mechanical delivery systems such as the approach described in Woffendin et al., *Proc. Natl. Acad. Sci. USA* 91(24): 11581-11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033.

The subject antibodies or antibody fragments maybe conjugated directly or indirectly to effective moieties, e.g., radionuclides, toxins, chemotherapeutic agents, prodrugs, cytoslatic agents, enzymes and the like. In a preferred embodiment the antibody or fragment will be attached to a therapeutic or diagnostic radiolabel directly or by use of a chelating agent. Examples of suitable radiolabels are well known and include $^{90}$Y, $^{125}$I, $^{131}$I, $^{111}$I, $^{105}$Rh, $^{153}$Sm, $^{67}$Cu, $^{67}$Ga, $^{166}$Ho, $^{177}$Lu, $^{186}$Re and $^{188}$Re.

Examples of suitable drugs that my be coupled to antibodies include methotrexate, adriamycine and lymphokines such as interferons, interleukins and the like. Suitable toxins which may be coupled include ricin, cholera and diptheria toxin.

In a preferred embodiment, the subject antibodies will be attached to a therapeutic radiolabel and used for radioimmunotherapy.

Anti-Sense Oligonucleotides

In certain circumstances, it maybe desirable to modulate or decrease the amount of the protein expressed by a prostate cell. Thus, in another aspect of the present invention, anti-sense oligonucleotides can be made and a method utilized for diminishing the level of expression a prostate antigen according to the invention by a cell comprising administering one or more anti-sense oligonucleotides. By anti-sense oligonucleotides reference is made to oligonucleotides that have a nucleotide sequence that interacts through base pairing with a specific complementary nucleic acid sequence involved in the expression of the target such that the expression of the gene is reduced. Preferably, the specific nucleic acid sequence involved in the expression of the gene is a genomic DNA molecule or mRNA molecule that encodes the gene. This genomic DNA molecule can comprise regulatory regions of the gene, or the coding sequence for the mature gene.

The term complementary to a nucleotide sequence in the context of antisense oligonucleotides and methods therefor means sufficiently complementary to such a sequence as to allow hybridization to that sequence in a cell, i.e., under physiological conditions. Antisense oligonucleotides preferably comprise a sequence containing from about 8 to about 100 nucleotides and more preferably the antisense oligonucleotides comprise from about 15 to about 30 nucleotides. Antisense oligonucleotides can also contain a variety of modifications that confer resistance to nucleolytic degradation such as, for example, modified internucleoside linages [Uhlmann and Peyman, *Chemical Reviews* 90:543-548 (1990); Schneider and Banner, *Tetrahedron Lett.* 31:335, (1990) which are incorporated by reference], modified nucleic acid bases as disclosed in U.S. Pat. No. 5,958,773 and patents disclosed therein, and/or sugars and the like.

Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

Chimeric antisense oligonucleotides are also within the scope of the invention, and can be prepared from the present inventive oligonucleotides using the methods described in, for example, U.S. Pat. Nos. 5,013,830, 5,149,797, 5,403,711, 5,491,133, 5,565,350, 5,652,355, 5,700,922 and 5,958,773.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. mRNA levels in the cell can be measured routinely in treated and control cells by reverse transcription of the mRNA and assaying the cDNA levels. The biological effect can be determined routinely by measuring cell growth or viability as is known in the art.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. [Branch, A. D., *T.I.B.S.* 23:45-50 (1998)].

The therapeutic or pharmaceutical compositions of the present invention can be administered by any suitable route known in the art including for example intravenous, subcutaneous, intramuscular, transdermal, intrathecal or intracerebral. Administration can be either rapid as by injection or over a period of time as by slow infusion or administration of slow release formulation.

Additionally, the subject prostate tumor proteins can also be linked or conjugated with agents that provide desirable pharmaceutical or pharmacodynamic properties. For example, the protein can be coupled to any substance known in the art to promote penetration or transport across the blood-brain barrier such as an antibody to the transferrin receptor, and administered by intravenous injection (see, for example, Friden et al., *Science* 259:373-377 (1993) which is incorporated by reference). Furthermore, the subject protein A or protein B can be stably linked to a polymer such as polyethylene glycol to obtain desirable properties of solubility, stability, half-life and other pharmaceutically advantageous properties. [See, for example, Davis et al.,*Enzyme Eng.* 4:169-73 (1978); Buruham,*Am. J. Hosp. Pharm.* 51:210-218 (1994) which are incorporated by reference].

The compositions are usually employed in the form of pharmaceutical preparations. Such preparations are made in a manner well known in the pharmaceutical art. See, e.g. Remington Pharmaceutical Science, 18th Ed., Merck Publishing Co. Eastern Pa., (1990). One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. The subject prostate tumor antigens, fragments or variants thereof can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parental administration in either unit dosage or multi-dose form or for direct infusion into the cerebrospinal fluid by continuous or periodic infusion.

Dose administration can be repeated depending upon the pharmacokinetic parameters of the dosage formulation and the route of administration used.

It is also contemplated that certain formulations containing the subject antibody or nucleic acid antagonists are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In one embodiment of this invention, the protein may be therapeutically administered by implanting into patients vectors or cells capable of producing a biologically-active form of the protein or a precursor of protein, i.e., a molecule that can be readily converted to a biological-active form of the protein by the body. In one approach, cells that secrete the protein may be encapsulated into semipermeable membranes for implantation into a patient. The cells can be cells that normally express the protein or a precursor thereof or the cells can be transformed to express the protein or a precursor thereof It is preferred that the cell be of human origin and that the protein be a human protein when the patient is human. However, it is anticipated that non-human primate homologues of the protein discussed infra may also be effective.

Detection of Subject Prostate Proteins or Nucleic Acids

In a number of circumstances it would be desirable to determine the levels of protein or corresponding mRNA in a patient. Evidence disclosed infra suggests the subject prostate proteins may be expressed at different levels during some diseases, e.g., cancers, provides the basis for the conclusion that the presence of these proteins serves a normal physiological function related to cell growth and survival. Endogenously produced protein according to the invention may also play a role in certain disease conditions.

The term "detection" as used herein in the context of detecting the presence of protein in a patient is intended to include the determining of the amount of protein or the ability to express an amount of protein in a patient, the estimation of prognosis in terms of probable outcome of a disease and prospect for recovery, the monitoring of the protein levels over a period of time as a measure of status of the condition, and the monitoring of protein levels for determining a preferred therapeutic regimen for the patient, e.g. one with prostate cancer.

To detect the presence of a prostate protein according to the invention in a patient, a sample is obtained from the patient. The sample can be a tissue biopsy sample or a sample of blood, plasma, serum, CSF, urine or the like. It has been found that the subject proteins are expressed at high levels in some cancers. Samples for detecting protein can be taken from prostate tissues. When assessing peripheral levels of protein, it is preferred that the sample be a sample of blood, plasma or serum. When assessing the levels of protein in the central nervous system a preferred sample is a sample obtained from cerebrospinal fluid or neural tissue. The sample may be obtained by non-invasive methods, such as from tissue collection(s) or cultute(s), or using directly available tissue material (urine, saliva, stools, hair, etc.).

In some instances, it is desirable to determine whether the gene is intact in the patient or in a tissue or cell line within the patient. By an intact gene, it is meant that there are no alterations in the gene such as point mutations, deletions, insertions, chromosomal breakage, chromosomal rearrangements and the like wherein such alteration might alter production of the corresponding protein or alter its biological activity, stability or the like to lead to disease processes. Thus, in one embodiment of the present invention a method is provided for detecting and characterizing any alterations in the gene. The method comprises providing an oligonucleotide that contains the gene, genomic DNA or a fragment thereof or a derivative thereof. By a derivative of an oligonucleotide, it is meant that the derived oligonucleotide is substantially the same as the sequence from which it is derived in that the derived sequence has sufficient sequence complementarily to the sequence from which it is derived to hybridize specifically to the gene. The derived nucleotide sequence is not necessarily physically derived from the nucleotide sequence, but may be generated in any manner including for example, chemical synthesis or DNA replication or reverse transcription or transcription.

Typically, patient genomic DNA is isolated from a cell sample from the patient and digested with one or more restriction endonucleases such as, for example, TaqI and AluI. Using the Southern blot protocol, which is well known in the art, this assay determines whether a patient or a particular tissue in a patient has an intact prostate gene according to the invention or a gene abnormality.

Hybridization to a gene would involve denaturing the chromosomal DNA to obtain a single-stranded DNA; contacting the single-stranded DNA with a gene probe associated with the gene sequence; and identifying the hybridized DNA-probe to detect chromosomal DNA containing at least a portion of a gene.

The term "probe" as used herein refers to a structure comprised of a polynucleotide that forms a hybrid structure with a target sequence, due to complementarily of probe sequence with a sequence in the target region. Oligomers suitable for use as probes may contain a minimum of about 8-12 contiguous nucleotides which are complementary to the targeted sequence and preferably a minimum of about 20.

A gene according to the present invention can be DNA or RNA oligonucleotides and can be made by any method known in the art such as, for example, excision, transcription or chemical synthesis. Probes maybe labeled with any detectable label known in the art such as, for example, radioactive or fluorescent labels or enzymatic marker. Labeling of the probe can be accomplished by any method known in the art such as by PCR, random priming, end labeling, nick translation or the like. One skilled in the art will also recognize that other methods not employing a labeled probe can be used to determine the hybridization. Examples of methods that can be used for detecting hybridization include Southern blotting, fluorescence in situ hybridization, and single-strand conformation polymorphism with PCR amplification.

Hybridization is typically carried out at 25°-45° C., more preferably at 32°-40° C. and more preferably at 37°-38° C. The time required for hybridization is from about 0.25 to about 96 hours, more preferably from about one to about 72 hours, and most preferably from about 4 to about 24 hours.

Gene abnormalities can also be detected by using the PCR method and primers that flank or lie within the gene. The PCR method is well known in the art. Briefly, this method is performed using two oligonucleotide primers which are capable of hybridizing to the nucleic acid sequences flanking a target sequence that lies within a gene and amplifying the target sequence. The terms "oligonucleotide primer" as used herein refers to a short strand of DNA or RNA ranging in length from about 8 to about 30 bases. The upstream and downstream primers are typically from about 20 to about 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, a method of physical denaturation is used involving heating the nucleic acid, typically to temperatures from about 80° C. to 105° C. for times ranging from about 1 to about 10 minutes. The process is repeated for the desired number of cycles.

The primers are selected to be substantially complementary to the strand of DNA being amplified. Therefore, the primers need not reflect the exact sequence of the template, but must be sufficiently complementary to selectively hybridize with the strand being amplified.

After PCR amplification, the DNA sequence comprising the gene or a fragment thereof is then directly sequenced and analyzed by comparison of the sequence with the sequences disclosed herein to identify alterations which might change activity or expression levels or the like.

In another embodiment, a method for detecting a tumor protein according to the invention is provided based upon an analysis of tissue expressing the gene. Certain tissues such as prostate tissues have been found to overexpress the subject gene. The method comprises hybridizing a polynucleotide to mRNA from a sample of tissue that normally expresses the gene. The sample is obtained from a patient suspected of having an abnormality in the gene.

To detect the presence of mRNA encoding the protein, a sample is obtained from a patient. The sample can be from blood or from a tissue biopsy sample. The sample may be treated to extract the nucleic acids contained therein. The resulting nucleic acid from the sample is subjected to gel electrophoresis or other size separation techniques.

The mRNA of the sample is contacted with a DNA sequence serving as a probe to form hybrid duplexes. The use of a labeled probes as discussed above allows detection of the resulting duplex.

When using the cDNA encoding the protein or a derivative of the cDNA as a probe, high stringency conditions can be used in order to prevent false positives, that is the hybridization and apparent detection of the gene nucleotide sequence when in fact an intact and functioning gene is not present. When using sequences derived from the gene cDNA, less stringent conditions could be used, however, this would be a less preferred approach because of the likelihood of false positives. The stringency of hybridization is determined by a number of factors during hybridization and during the washing procedure, including temperature, ionic strength, length of time and concentration of formamide. These factors are outlined in, for example, Sambrook et al. [Sambrook et al. (1989), supra].

In order to increase the sensitivity of the detection in a sample of mRNA encoding the protein A or protein B, the technique of reverse transcription/polymerization chain reaction (RT/PCR) can be used to amplify cDNA transcribed from mRNA encoding the prostate tumor antigen. The method of RT/PCR is well known in the art, and can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and gene A or gene B specific primers. [Belyavsky et al., *Nucl. Acid Res.* 17:2919-2932 (1989); Krug and Berger, *Methods in Enzymology,* 152:316-325, Academic Press, NY (1987) which are incorporated by reference].

The polymerase chain reaction method is performed as described above using two oligonucleotide primers that are substantially complementary to the two flanking regions of the DNA segment to be amplified. Following amplification, the PCR product is then electrophoresed and detected by ethidium bromide staining or by phosphoimaging.

The present invention further provides for methods to detect the presence of the protein in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. [*Basic and Clinical Immunology,* 217-262, Sites and Terr, eds., Appleton & Lange, Norwalk, Conn., (1991),which is incorporated by reference]. Preferred are binder-ligand immunoassay methods including reacting antibodies with an epitope or epitopes of the prostate tumor antigen protein and competitively displacing a labeled prostate antigen according to the invention or derivative thereof.

As used herein, a derivative of the subject prostate tumor antigen is intended to include a polypeptide in which certain amino acids have been deleted or replaced or changed to modified or unusual amino acids wherein the derivative is biologically equivalent to gene and wherein the polypeptide derivative cross-reacts with antibodies raised against the protein. By cross-reaction it is meant that an antibody reacts with an antigen other than the one that induced its formation.

Numerous competitive and non-competitive protein binding immunoassays are well known in the art. Antibodies employed in such assays maybe unlabeled, for example as used in agglutination tests, or labeled for use in a wide variety of assay methods. Labels that can be used include radionuclides, enzymes, fluorescers, chemiluminescers, enzyme substrates or co-factors, enzyme inhibitors, particles, dyes and the like for use in radioinununoassay (RIA), enzyme immnunoassays, e.g., enzyme-linked immunosorbent assay (ELISA), fluorescent immunoassays and the like.

A further aspect of this invention relates to a method for selecting, identifying, screening, characterizing or optimizing biologically active compounds, comprising a determination of whether a candidate compound binds, preferably selectively, a target molecule as disclosed above. Such target molecules include nucleic acid sequences, polypeptides and fragments thereof, typically prostate-specific antigens, even more preferably extracellular portions thereof. Binding may be assessed in vitro or in vivo, typically in vitro, in cell based or accellular systems. Typically, the target molecule is contacted with the candidate compound in any appropriate device, and the formation of a complex is determined. The target molecule and/or the candidate compound maybe immobilized on a support. The compounds identified or selected represent drug candidates or leads for treating cancer diseases, particularly prostate cancer.

While the invention has been described supra, including preferred embodiments, the following examples are provided to further illustrate the invention.

EXAMPLE

Tissue Sources:

Appropriate patient samples were procured for evaluation of research protocol. Samples were provided with relevant clinical parameters, and patient consent. Histological assessment was performed on all samples and diagnosis by pathology confirmed the presence and/or absence of malignancy within each sample. Clinical data generally included patent history, physiopathology, and parameters relating to prostate cancer physiology. Ten normal and ten malignant samples were procured along with available clinical information. In addition, ten samples from organs other than normal prostate and prostate cancer were procured to determine the tissue specific expression profile of epitopes. RNA derived from normal tissue samples was obtained from known commercial sources.

Generation of the DATAS Library

Samples were pooled based on their pathological diagnosis (normal vs. tumor). Samples were pooled based on equivalent amounts of total RNA to produce total pooled RNA samples of 100 ug. DATAS libraries were constructed as previously disclosed in U.S. Pat. No. 6,251,590, the disclosure of which is incorporated by reference in its entirety. Briefly, total RNA was isolated from the normal and tumor pooled samples and mRNA was subsequently purified from the total RNA for each pooled sample. Synthesis of cDNA was performed using a biotinylated oligo (dT) primer. The biotinylated cDNA was hybridized with the mRNA of the opposite sample to form heteroduplexes between the cDNA and the mRNA. For example, the biotinylated cDNA of the pooled normal prostate sample was hybridized with prostate tumor mRNA. Similarly, prostate tumor biotinylated cDNA was hybridized with prostate normal RNA to generate the second DATAS library. Streptavidin coated beads were used to purify the complexes by binding the biotin present on the cDNA. The heteroduplexes were digested with RNAse H to degrade the RNA that was complementary to the cDNA. All mRNA sequences that were different from the cDNA remained intact. These single stranded RNA fragments or "loops" were subsequently amplified with degenerate primers and cloned into either pGEM-Tor pCR II TOPO vector (Company source) to produce the DATAS library.

Clone sequencing and Bioinformatics Analysis:

The DATAS library was used to transform *E. Coli* so that individual clones could be isolated using standard molecular biology techniques. From these libraries, 10,665 individual clones were isolated and sequenced using an automated Applied Biosystems 3100 sequencer. The nucleotide sequences that were obtained were submitted to the bioinformatics pipeline for analysis. As the DATAS library is prepared with PCR amplified DNA, many copies of the same sequence are present in the clones isolated from the libraries. Therefore it is important to reduce the redundancy of the clones to identify the number of unique, nonrepeating sequences that are isolated. From this large set of DATAS fragments, 1699 unique, nonredundant sequences were identified and each DATAS fragment was annotated with a candidate gene. The annotation was performed by aligning the DATAS fragment to the human genome sequence by two methods; 1) a publicly available alignment and genome viewer tool, Blat (Kent et al., 2002); and 2) a commercially available genomic alignment andviewer tool, Prophecy (Doubletwist). Each DATAS fragment sequence was annotated with a corresponding gene that overlapped the genomic sequence containing the DATAS fragment. Genes were annotated with either the RefSeq accession number, or a hypothetical gene prediction from different algorithms, for example, Genscan, Twinscan, or Fgenesh++. Identified genes were either matched to the sequence of the DATAS fragment (in case of exon to fragment match), or overlapped with the DATAS fragment (in case of intron to fragment match), and the full length sequence of the gene was identified. These sequences were further analyzed to detect all potential membrane spanning proteins. Membrane proteins were predicted through the use of different algorithms publicly available. For example, TMHMM (CBS) was used to identify membrane-spanning domains present within the amino acid sequence of the candidate gene. DATAS fragments were located within the sequence in an attempt to determine whether the spliced event affected intracellular or extraceullar domains. Genes associated with the sequence were ranked in order to maximize the identification of successful therapeutic targets. The highest priority genes had characteristics where the gene was a known membrane protein, the function of the gene was known, and the DATAS fragment mapped to an intron on the extracellular domain of the protein, indicating that the DATAS fragment would be presented outside the cell, and available for therapeutic intervention by monoclonal antibodies.

Based on the bioinformatic analysis, clones were prioritized in three groups:

A) Known transmembrane genes with DATAS fragments located in introns on the extracellular domain.

B) Known and predicted transmembrane genes with DATAS fragments located in exons in either the extracellular or intracellular domain.

C) DATAS fragments that did not match the genome

Expression Monitoring:

A valid epitope target for prostate cancer requires that the expression of the epitope be limited to prostate tissue, or preferably to prostate tumors. Assessment of the expression profile for each prioritized sequence was performed by RT-PCR, a procedure well known in the art. A protocol known as touchdown PCR was used, described in the user's manual for the GeneAmp PCR system 9700, Applied Biosystems. Briefly, PCR primers were designed to the DATAS fragment and used for end point RT-PCR analysis. Each RT reaction contained 5 μg of total RNA and was performed in a 100 μl volume using Archive RT Kit (Applied Biosystems). The RT reactions were diluted 1:50 with water and 4 μl of the diluted stock was used in a 50 μl PCR reaction consisting of one cycle at 94° C. for 3 min, 5 cycles at 94° C. for 30 seconds, 60° C. for 30 seconds and 72° C. for 45 seconds, with each cycle reducing the annealing temperature by 0.5 degree. This was followed by 30 cycles at 94° C. for 30 seconds, 55° C. for 30 seconds, and 72° C. for 45 seconds. 15 μl was removed from each reaction for analysis and the reactions were allowed to proceed for an additional 10 cycles. This produced reactions for analysis at 30 and 40 cycles, and allowed the detection of differences in expression where the 40 cycle reactions had saturated. The level of expression profile of the DATAS fragment was determined in normal and tumor prostate total RNA, as well as total RNA from normal samples of brain, heart, liver, lung, kidney, colon, bone marrow, muscle, spleen, and testis. Expression profiles were prioritized accordingly for specific expression in prostate tumor and low expression found in normal tissues, including normal prostate.

Verification of RNA Structure:

DATAS identifies sequences that are altered between the experimental samples. However, the exact sequence of the junctions or borders that the DATAS fragment represents can not be determined directly from the isolated DATAS fragment sequence. The DATAS fragment was used, however, to design experiments that elucidate the sequence of each transcript present in each sample. Primers were designed to amplify a region of the gene larger than the proposed DATAS fragment sequence. These amplicons were subsequently cloned and sequenced for the identification of the exact junctions of all exons and introns. This required partial cloning of the isoforms from an identified sample to verify the primary structure (sequence) of the isoforms. All twenty samples (10 normal and 10 tumor samples) initially used to generate the DATAS libraries were used for the verification of the mRNA structure of the prioritized genes.

Isolation of Full-Length Clones of Isoforms:

Isolation of the full-length clones containing both isoforms was accomplished utilizing the information and DNA fragments generated during the structure validation process. Several methods are applicable to isolation of the full length clone. Where full sequence information regarding the coding sequence is available, gene specific primers were designed from the sequence and used to amplify the coding sequence directly from the total RNA of the tissue samples. An RT-PCR reaction was set up using these gene specific primers. The RT reaction was performed as described infra, using oligo dT to prime for cDNA. Second strand was produced by standard methods to produce double stranded cDNA. PCR amplification of the gene was accomplished using gene specific primers. PCR consisted of 30 cycles at 94° C. for 30 seconds, 55° C. for 30 seconds, and 72° C. for 45 seconds. The reaction products were analyzed on 1% agarose gels and the amplicons were ligated into prepared vectors with A overhangs for amplicon cloning. 1 μl of the ligation mixture was used to transform *E. Coli* for cloning and isolation of the amplicon. Once purified, the plasmid containing the amplicon was sequenced on an ABI 3100 automated sequencer.

Where limited sequence information was available, the oligo pulling method was utilized. Briefly, a gene-specific oligonucleotide was designed based on the DATAS fragment. The oligonucleotide was labeled with biotin and used to hybridize with a single stranded plasmid DNA library prepared from either normal prostate tissue or prostate tumor tissue following the procedures of Sambrook et al (1989). The hybridized cDNA was separated by streptavidin conjugated beads and eluted by heating. The eluted cDNA was converted to double strand plasmid DNA and used to transform *E. Coli* cells and the longest cDNA clone was subjected to DNA sequencing.

RESULTS

Using methods described above, 1699 DNA fragments have been identified that putatively correspond to exons (novel splice variants) expressed exclusively or at an increased level in prostate tumor tissue when compared to matched normal prostate tissue.

These sequences were used to search public databases containing human genomic sequences to identify related genes. This search identified 122 fragments that correspond to exons of either known or potential cell surface proteins.

Additionally, thirty seven distinct alternatively spliced isoforms were identified from the initial sequence tags that appear to contain novel sequence information of cell surface proteins.

These DNA sequences are disclosed in the Sequence Listing as well as in Table 1, and correspond to the nucleic acid sequences having SEQ ID NOS: 1-173, 175, 177, 179, and 181. Oligonucleotide primers were designed to each DATAS fragment to determine the specific expression of the mRNA in a panel of normal human tissue. An example is shown in FIG. 1, where the clone corresponding to Sequence ID: No.92 displays specific expression in prostate with very low levels detected in kidney (lane 4) and pancreas (lane 9). All clones that were found to be either specifically expressed in prostate or highly expressed in prostate compared to other tissues were analyzed for expression in tumor samples.

FIG. 2 illustrates the expression profile of one DATAS clone in normal and tumor prostate tissue. Expression of this clone is upregulated in two of the three tumor pooled samples and is highly expressed in three of the four individual tumor samples. The high expression of this splice event in tumor samples as compared to normal prostate, and the low expression in other normal human tissues is an example of one candidate that has utility for development as a novel epitope for prostate cancer.

The splice events for DATAS clones that displayed a specific expression profile for prostate and a high differential expression profile for prostate tumors were isolated and the sequences for each event was determined. An example is shown in FIG. 3, where the sequence of the isolated event was mapped to the genome in Blat, and genomic viewer developed by the bioinformatics department at UCSC (Kent et al., 2002). Five distinct clones were isolated that mapped to the gene locus for STEAP2. One expressed sequence tag (EST), AK092666, contained many similar domains as the splice events that were isolated using DATAS. The sequences and predicted protein translations for all five clones are described in SEQ NOS. 173-182 and are graphically illustrated in FIG. 3. The length of the open reading frame and the predicted protein size for each isoform is described in Table 2. The EST, AK092666 contains a large deletion in exon 5, the terminal 3' exon of STEAP2, with two novel exons in the 5' region of the transcript. The nomenclature for the DATAS derived events was based on AK092666 because of higher similarity when compared to the RefSeq sequence for STEAP2. The first isoform identified, AK092666__01 (SEQ ID NO 173), contains a novel C-terminal exon when compared to AK092666, and therefore generates a novel junction, and a novel sequence for translation and generates a unique amino acid sequence (SEQ ID NO 183). The same novel sequence was generated by isoform AK092666__03 (SEQ ID NO 177), which contains the same novel exon with an additional splicing event of an in frame truncation of exon 4, and by isoform AK092666__05 (SEQ ID NO 181), which contains a single codon deletion from AK092666__01. AK092666__02 (SEQ ID NO 175) skipped exon 6 of AK092666 and generated the novel amino acid sequence in SEQ ID NO 184. AK092666__04 (SEQ ID NO 179) contains a short out of frame truncation of exon 4, which results in the creation of 8 novel amino acids before encountering a premature stop codon (SEQ ID NO 185).

TABLE 2

Length of the open reading frame and the predicted protein size for each novel isoform.

| Clone Name | ORF length (bp) | Protein size (KD) |
|---|---|---|
| STEAP2 | 1473 | 56 |
| AK092666 | 1365 | 51.7 |
| AK092666_01 | 1389 | 52.7 |
| AK092666_02 | 1260 | 47.8 |
| AK092666_03 | 900 | 34.1 |
| AK092666_04 | 705 | 26.7 |
| AK092666_05 | 1386 | 52.5 |

The novel amino acids found in SEQ ID NOS 183 and 184 represent novel epitopes that are specifically expressed in prostate cancer in a membrane protein. These epitopes are targets for monoclonal antibody immunotherapy for the treatment of prostate cancer. To illustrate the different isoforms present, an antibody was generated from the invariant sequence present in the 5' region (or the amino terminal portion of the protein) that recognizes all the different isoforms.

An antibody was generated against an amino acid sequence that was common to all five isoforms, as well as present in STEAP2 and AK092666. Prostate cancer cell lines were analyzed by western blot to determine what different isoforms would be expressed at the protein level. FIG. 4 illustrates two bands that were specifically detected by the antibody. Band A potentially represents the glycosylated, wild type STEAP2 and band B indicates isoforms AK092666, AK092666__01, or AK092666__05, which is unresolvable in the gel analysis. In addition, multiple bands of the proper size were detected suggesting that isoforms of the STEAP2 locus are expressed and represent targets for the immunotherapy in prostate cancer.

TABLE 1

Sequence information of the DATAS fragments and the alternatively spliced isoforms.

Sequence ID: No. 1
Accession #: NM_005656
Genomic sequence: chr21: 39407238-39450894
Sequence definition: transmembrane protease serine 2
Sequence ID: No. 2
Accession #: NM_001423
Genomic sequence: chr12: 13265134-13265266
Sequence definition: *Homo sapiens* epithelial membrane protein 1 EMP1
Sequence ID: No. 3
Accession #: NM_000484
Genomic sequence: chr21: 23832850-24123073
Sequence definition: beta amyloid A4

TABLE 1-continued

Sequence information of the DATAS fragments and the alternatively spliced isoforms.

Sequence ID: No. 4
Accession #: NM_002841
Genomic sequence: chr3: 62548596-63240788_1
Sequence definition: protein tyrosine phosphatase G-type
Sequence ID: No. 5
Accession #: NM_022124
Genomic sequence: chr10: 74968313-75112962
Sequence definition: cadherin related 23 isoform 1 precursor
Sequence ID: No. 6
Accession #: NM_033056
Genomic sequence: chr10: 55940286-56920530_02
Sequence definition: protocadherin 15 precursor
Sequence ID: No. 7
Accession #: NM_002847
Genomic sequence: chr7: 158586667-159621018_01
Sequence definition: protein tyrosine phosphatase receptor type N
Sequence ID: No. 8
Accession #: NM_002222
Genomic sequence: chr3: 5000696-5354641_1
Sequence definition: ITPR inositol 145-triphosphate receptor type 1
Sequence ID: No. 9
Accession #: AC078864.20
Genomic sequence: chr12: 52201280-52201714
Sequence definition: Genscan prediction
Sequence ID: No. 10
Accession #: NM_014554; NM_001844; NT_009785.3
Genomic sequence: chr12: 45785273-45856561
Sequence definition: chr12_498 potential fusion of SENP1 and Collagen 2A; also overlaps GS perdiction
Sequence ID: No. 11
Accession #: AB064665
Genomic sequence: chrM: 9411-9524
Sequence definition: *Homo sapiens* mRNA for OK/SW-CL.16
Sequence ID: No. 12
Accession #: NM_024029
Genomic sequence: chr19: 10880041-10883719
Sequence definition: hypothetical protein MGC3262
Sequence ID: No. 13
Accession #: NT_008748.79
Genomic sequence: chr10: 80881918-80882092
Sequence definition: Genscan prediction
Sequence ID: No. 14
Accession #: AB002360
Genomic sequence: chr13: 112761227-112761344
Sequence definition: KIAA0362
Sequence ID: No. 15
Accession #: AK057572
Genomic sequence: chr16: 14547315-14547422
Sequence definition: FLJ33010
Sequence ID: No. 16
Accession #: NT_034410.56/NM_033102.1
Genomic sequence: chr1: 203503646-203554883/chr1: 192169879-192474008
Sequence definition: Genscan - Elk4/LOC85414 - *Homo sapiens* prostein protein LOC85414
Sequence ID: No. 17
Accession #: NT_019696.29
Genomic sequence: chrx: 64173951-64275396
Sequence definition: Genscan prediction
Sequence ID: No. 18
Accession #: NT_007834.17
Genomic sequence: chr7: 71656530-71727938
Sequence definition: Genscan prediction
Sequence ID: No. 19
Accession #: NT_005403.1000
Genomic sequence: chr2: 208067141-208067324
Sequence definition: Genscan prediction
Sequence ID: No. 20
Accession #: NT_009654.19
Genomic sequence: chr12: 116716120-116840364
Sequence definition: Genscan prediction
Sequence ID: No. 21
Accession #: AC126564.7
Genomic sequence: chr12: 131440407-131440735
Sequence definition: genomic match TABLE 1-continued Sequence information of the DATAS fragments and the alternatively spliced isoforms.

Sequence ID: No. 22
Accession #: NT_006171.64
Genomic sequence: chr4: 172269202-172299375
Sequence definition: Genscan prediction
Sequence ID: No. 23
Accession #: NM_025149.1
Genomic sequence: chr17: 61361324-61409903
Sequence definition: FLJ20920
Sequence ID: No. 24
Accession #: NT_026437.145
Genomic sequence: chr14: 72272372-72462407
Sequence definition: Genscan prediction
Sequence ID: No. 25
Accession #: NT_030059.13
Genomic sequence: chr10: 103933731-103955924
Sequence definition: Genscan prediction
Sequence ID: No. 26
Accession #: AK058112
Genomic sequence: chr19: 1815692-1822319
Sequence definition: FLJ25383
Sequence ID: No. 27
Accession #: NM_002205.1
Genomic sequence: chr12: 55541534-55565494
Sequence definition: *Homo sapiens* integrin alpha 5 fibronectin receptor alpha polypeptide
Sequence ID: No. 28
Accession #: NM_004716.1
Genomic sequence: chr11: 117114115-117114448
Sequence definition: *Homo sapiens* proprotein convertase subtilisin/kexin type 7 PCSK7 mRNA
Sequence ID: No. 29
Accession #: NM_030774
Genomic sequence: chr11: 5003431-5021099
Sequence definition: prostate specific G-protein coupled receptor [*Homo sapiens*]
Sequence ID: No. 30
Accession #: AB007932
Genomic sequence: chr1: 204846394-204846755
Sequence definition: *Homo sapiens* plexin A2 PLXNA2 mRNA
Sequence ID: No. 31
Accession #: AB023177
Genomic sequence: chr7: 11157196-11157402
Sequence definition: *Homo sapiens* mRNA for KIAA0960 protein
Sequence ID: No. 32
Accession #: NT_004858.23
Genomic sequence: chr1: 147688399-147725025
Sequence definition: Genscan prediction
Sequence ID: No. 33
Accession #: NT_004873.61
Genomic sequence: chr1: 14678698-14732191
Sequence definition: Genscan prediction
Sequence ID: No. 34
Accession #: NT_029860.99
Genomic sequence: chr1: 110751286-110854188
Sequence definition: Genscan prediction
Sequence ID: No. 35
Accession #: NM_032385.1
Genomic sequence: chr5: 170086201-170251515
Sequence definition: *Homo sapiens* chromosome 5 open reading frame 4 C5orf4
Sequence ID: No. 36
Accession #: NM_014752.1
Genomic sequence: chr11: 73182947-73211393
Sequence definition: KIAA0102
Sequence ID: No. 37
Accession #: NP_000295
Genomic sequence: chr17: 15500091-15500332
Sequence definition: *Homo sapiens* peripheral myelin protein 22
Sequence ID: No. 38
Accession #: NM_020433
Genomic sequence: chr20: 42528457-42528759
Sequence definition: *Homo sapiens* junctophilin 2
Sequence ID: No. 39
Accession #: NT_999999.2
Genomic sequence: chrM: 9411-9524
Sequence definition: Genscan Gene Predictions TABLE 1-continued Sequence information of the DATAS fragments and the alternatively spliced isoforms.

Sequence ID: No. 40
Accession #: NT_004754.1
Genomic sequence: chr1: 117988850-117989247
Sequence definition: Genscan Gene Predictions
Sequence ID: No. 41
Accession #: NT_011568.108
Genomic sequence: chrX: 47583156-47583796
Sequence definition: Acembly Gene Predictions/Genscan Gene Predictions
Sequence ID: No. 42
Accession #: NP_061116
Genomic sequence: chr7: 140900079-140900876
Sequence definition: transient receptor potential cation channel
Sequence ID: No. 43
Accession #: NT_011295.163
Genomic sequence: chr19: 19799239-19804450
Sequence definition: Genscan prediction
Sequence ID: No. 44
Accession #: NP_056051
Genomic sequence: chr4: 62284401-62284770
Sequence definition: lectomedin-3
Sequence ID: No. 45
Accession #: NT_033927.57
Genomic sequence: chr11: 75518014-75562375
Sequence definition: Genscan prediction
Sequence ID: No. 46
Accession #: NM_030774
Genomic sequence: chr11: 5003431-5021099
Sequence definition: prostate specific G-protein coupled receptor *Homo sapiens*
Sequence ID: No. 47
Accession #: NM_022119
Genomic sequence: chr16: 2939532-2939842
Sequence definition: protease serine 22
Sequence ID: No. 48
Accession #: NP_000155
Genomic sequence: chr19: 46824678-46824801
Sequence definition: *Homo sapiens* gastric inhibitory polypeptide receptor
Sequence ID: No. 49
Accession #: NM_001627
Genomic sequence: chr3: 104784804-104787209
Sequence definition: activated leukocyte cell adhesion molecule
Sequence ID: No. 50
Accession #: NP_056343
Genomic sequence: chr17: 5263335-5263632
Sequence definition: *Homo sapiens* DKFZP566H073 protein
Sequence ID: No. 51
Accession #: NT_033275.9
Genomic sequence: chr15: 19767754-19767842
Sequence definition: Acembly Gene Predictions/Genscan Gene Predictions
Sequence ID: No. 52
Accession #: NT_004511.105
Genomic sequence: chr1: 37657082-37657508
Sequence definition: Genscan Gene Predictions
Sequence ID: No. 53
Accession #: NT_007819.76
Genomic sequence: chr7: 2293638-2293859
Sequence definition: Acembly Gene Predictions/Genscan Gene Predictions
Sequence ID: No. 54
Accession #: NT_008046.179
Genomic sequence: chr8: 101509107-101509191
Sequence definition: Acembly Gene Predictions/Genscan Gene Predictions
Sequence ID: No. 55
Accession #: NP_001668
Genomic sequence: chr1: 166712801-166712951
Sequence definition: ATPase Na+/K+ transporting beta 1 polypeptide
Sequence ID: No. 56
Accession #: NP_061332
Genomic sequence: chr7: 105724807-105753208
Sequence definition: B-cell receptor-associated protein BAP29
Sequence ID: No. 57
Accession #: NT_008251.42
Genomic sequence: chr8: 36531104-36531405
Sequence definition: Acembly Gene Predictions/Genscan Gene Predictions
Sequence ID: No. 58
Accession #: NT_008984.116
Genomic sequence: chr11: 97792879-97792961

TABLE 1-continued

Sequence information of the DATAS fragments and the alternatively spliced isoforms.

Sequence definition: Genscan Gene Predictions
Sequence ID: No. 59
Accession #: NT_011176.84
Genomic sequence: chr19: 11151260-11154382
Sequence definition: Acembly Gene Predictions/Genscan Gene Predictions
Sequence ID: No. 60
Accession #: ENST00000255124
Genomic sequence: chr20: 46047371-46047445
Sequence definition: Acembly Gene Predictions/Genscan Gene Predictions
Sequence ID: No. 61
Accession #: ENST00000262657
Genomic sequence: chr20: 29935469-29937596
Sequence definition: Acembly Gene Predictions/Genscan Gene Predictions
Sequence ID: No. 62
Accession #: NT_033903.44
Genomic sequence: chr11: 58671001-58671164
Sequence definition: Genscan Gene Predictions
Sequence ID: No. 63
Accession #: NP_000360
Genomic sequence: chr14: 78989775-78989913
Sequence definition: *Homo sapiens* thyroid stimulating hormone receptor
Sequence ID: No. 64
Accession #: NP_005219
Genomic sequence: chr7: 54724858-54725037
Sequence definition: *Homo sapiens* epidermal growth factor receptor erythroblastic leukemia viral v-erb-b oncogene homolog avian
Sequence ID: No. 65
Accession #: NP_149093
Genomic sequence: chr1: 203548697-203549088
Sequence definition: *Homo sapiens* prostein protein
Sequence ID: No. 66
Accession #: NM_030774
Genomic sequence: chr11: 5003431-5021099
Sequence definition: prostate specific G-protein coupled receptor *Homo sapiens*
Sequence ID: No. 67
Accession #: NM_030774
Genomic sequence: chr11: 5004995-5010301
Sequence definition: prostate specific G-protein coupled receptor *Homo sapiens*
Sequence ID: No. 68
Accession #: NM_030774
Genomic sequence: chr11: 5004983-5010305
Sequence definition: prostate specific G-protein coupled receptor *Homo sapiens*
Sequence ID: No. 69
Accession #: NM_030774
Genomic sequence: chr11: 5004983-5010305
Sequence definition: prostate specific G-protein coupled receptor *Homo sapiens*
Sequence ID: No. 70
Accession #: NM_030774
Genomic sequence: chr11: 4667240-4678100
Sequence definition: prostate specific G-protein coupled receptor *Homo sapiens*
Sequence ID: No. 71
Accession #: NM_030774
Genomic sequence: chr11: 4677792-4677987
Sequence definition: prostate specific G-protein coupled receptor *Homo sapiens*
Sequence ID: No. 72
Accession #: NM_030774
Genomic sequence: chr11: 5003430-5007773
Sequence definition: prostate specific G-protein coupled receptor *Homo sapiens*
Sequence ID: No. 73
Accession #: AK075546
Genomic sequence: chr11: 36643617-36930167
Sequence definition: predicted protein
Sequence ID: No. 74
Accession #: AK075546
Genomic sequence: chr11: 36643626-36931023
Sequence definition: predicted protein
Sequence ID: No. 75
Accession #: AK075546
Genomic sequence: chr11: 36643617-36929351

TABLE 1-continued

| Sequence information of the DATAS fragments and the alternatively spliced isoforms. |
|---|
| Sequence definition: predicted protein |
| Sequence ID: No. 76 |
| Accession #: AK075546 |
| Genomic sequence: chr11: 36643617-36929351 |
| Sequence definition: predicted protein |
| Sequence ID: No. 77 |
| Accession #: AK075546 |
| Genomic sequence: chr11: 36643617-36929351 |
| Sequence definition: predicted protein |
| Sequence ID: No. 78 |
| Accession #: NT_033927.57 |
| Genomic sequence: chr11: 75518014-75562375 |
| Sequence definition: Genscan prediction |
| Sequence ID: No. 79 |
| Accession #: NM_000300 |
| Genomic sequence: chr1: 19337078-19342056 |
| Sequence definition: phospholipase A2 group IIA platelets synovial |
| Sequence ID: No. 80 |
| Accession #: NM_000300 |
| Genomic sequence: chr1: 19337078-19342056 |
| Sequence definition: phospholipase A2 group IIA platelets synovial |
| Sequence ID: No. 81 |
| Accession #: NM_000300 |
| Genomic sequence: chr1: 19337078-19342056 |
| Sequence definition: phospholipase A2 group IIA platelets synovial |
| Sequence ID: No. 82 |
| Accession #: NM_000300 |
| Genomic sequence: chr1: 19337078-19342056 |
| Sequence definition: phospholipase A2 group IIA platelets synovial |
| Sequence ID: No. 83 |
| Accession #: NM_000300 |
| Genomic sequence: chr1: 19337078-19342056 |
| Sequence definition: phospholipase A2 group IIA platelets synovial |
| Sequence ID: No. 84 |
| Accession #: NM_032323 |
| Genomic sequence: chr1: 152017962-152027457 |
| Sequence definition: hypothetical protein MGC13102 - refseq |
| Sequence ID: No. 85 |
| Accession #: NM_032323 |
| Genomic sequence: chr1: 152017962-152027457 |
| Sequence definition: hypothetical protein MGC13102 |
| Sequence ID: No. 86 |
| Accession #: NM_032323 |
| Genomic sequence: chr1: 152017962-152027457 |
| Sequence definition: hypothetical protein MGC13102 |
| Sequence ID: No. 87 |
| Accession #: NM_032323 |
| Genomic sequence: chr1: 152017962-152027457 |
| Sequence definition: hypothetical protein MGC13102 |
| Sequence ID: No. 88 |
| Accession #: NM_032323 |
| Genomic sequence: chr1: 152017962-152027457 |
| Sequence definition: hypothetical protein MGC13102 |
| Sequence ID: No. 89 |
| Accession #: NM_032323 |
| Genomic sequence: chr1: 152017962-152027457 |
| Sequence definition: hypothetical protein MGC13102 |
| Sequence ID: No. 90 |
| Accession #: NM_032323 |
| Genomic sequence: chr1: 152017962-152027457 |
| Sequence definition: hypothetical protein MGC13102 |
| Sequence ID: No. 91 |
| Accession #: AK092666 |
| Genomic sequence: chr7: 88376306-88402240 |
| Sequence definition: STEAP2/AK092666 |
| Sequence ID: No. 92 |
| Accession #: AK092666 |
| Genomic sequence: chr7: 88376306-88402240 |
| Sequence definition: STEAP2/AK092666 |
| Sequence ID: No. 93 |
| Accession #: AK092666 |
| Genomic sequence: chr7: 88376306-88402240 |
| Sequence definition: STEAP2/AK092666 |
| Sequence ID: No. 94 |
| Accession #: NM_005656 |
| Genomic sequence: chr21: 39493446-39537043 |

TABLE 1-continued

| Sequence information of the DATAS fragments and the alternatively spliced isoforms. |
|---|
| Sequence definition: TMPRSS2 |
| Sequence ID: No. 95 |
| Accession #: NM_005656 |
| Genomic sequence: chr21: 39493446-39537043 |
| Sequence definition: TMPRSS2 |
| Sequence ID: No. 96 |
| Accession #: NM_005656 |
| Genomic sequence: chr21: 39493446-39537043 |
| Sequence definition: TMPRSS2 |
| Sequence ID: No. 97 |
| Accession #: NM_005656 |
| Genomic sequence: chr21: 39493446-39537043 |
| Sequence definition: TMPRSS2 |
| Sequence ID: No. 98 |
| Accession #: NM_005656 |
| Genomic sequence: chr21: 39493446-39537043 |
| Sequence definition: TMPRSS2 |
| Sequence ID: No. 99 |
| Accession #: NM_004476 |
| Genomic sequence: chr11: 50361918-50423952 |
| Sequence definition: PSMA/FOLH1 |
| Sequence ID: No. 100 |
| Accession #: NM_004476 |
| Genomic sequence: chr11: 50361918-50423952 |
| Sequence definition: PSMA/FOLH1 |
| Sequence ID: No. 101 |
| Accession #: NM_004476 |
| Genomic sequence: chr11: 50361918-50423952 |
| Sequence definition: PSMA/FOLH1 |
| Sequence ID: No. 102 |
| Accession #: no match to index |
| Genomic sequence: No match BLAT |
| Sequence definition: No match BLAT |
| Sequence ID: No. 103 |
| Accession #: AC105101.8 |
| Genomic sequence: chr18: 45441503-45442177 |
| Sequence definition: genomic match |
| Sequence ID: No. 104 |
| Accession #: BC043509 |
| Genomic sequence: chr2: 7566735-7567210 |
| Sequence definition: genomic match |
| Sequence ID: No. 105 |
| Accession #: no match to index |
| Genomic sequence: No match BLAT |
| Sequence definition: No match BLAT |
| Sequence ID: No. 106 |
| Accession #: NT_007914.345 |
| Genomic sequence: chr7: 150965224-150965948 |
| Sequence definition: Genscan prediction |
| Sequence ID: No. 107 |
| Accession #: NM_002474 |
| Genomic sequence: chr16: 15123743-15124024 |
| Sequence definition: smooth muscle myosin heavy chain 11 isoform |
| Sequence ID: No. 108 |
| Accession #: no match to index |
| Genomic sequence: No match BLAT |
| Sequence definition: No match BLAT |
| Sequence ID: No. 109 |
| Accession #: AL450472.14 |
| Genomic sequence: chrX: 132596913-132597349 |
| Sequence definition: genomic match |
| Sequence ID: No. 110 |
| Accession #: no match to index |
| Genomic sequence: No match BLAT |
| Sequence definition: No match BLAT |
| Sequence ID: No. 111 |
| Accession #: NM_024490 |
| Genomic sequence: chr15: 18676827-18681314 |
| Sequence definition: ATPase Class V type 10A |
| Sequence ID: No. 112 |
| Accession #: NT_007741.24 |
| Genomic sequence: chr7: 154483727-154484200 |
| Sequence definition: Genscan prediction |
| Sequence ID: No. 113 |
| Accession #: NT_010168.1 |
| Genomic sequence: chr14: 100136759-100137109 |

TABLE 1-continued

Sequence information of the DATAS fragments and the alternatively spliced isoforms.

Sequence definition: Genscan prediction
Sequence ID: No. 114
Accession #: AK074158
Genomic sequence: chr7: 2347770-2347996
Sequence definition: *Homo sapiens* mRNA for FLJ00231 protein
Sequence ID: No. 115
Accession #: no match to index
Genomic sequence: No match BLAT
Sequence definition: No match BLAT
Sequence ID: No. 116
Accession #: AL549429
Genomic sequence: chr11: 9027915-9028089
Sequence definition: genomic match
Sequence ID: No. 117
Accession #: NM_015541
Genomic sequence: chr3: 65899978-65900329
Sequence definition: leucine-rich repeats and immunoglobulin-like
Sequence ID: No. 118
Accession #: NM_024897
Genomic sequence: chr1: 151978744-151978881
Sequence definition: hypothetical protein FLJ22672
Sequence ID: No. 119
Accession #: NM_006598
Genomic sequence: chr5: 1165896-1168793
Sequence definition: solute carrier family 12 potassium/chloride
Sequence ID: No. 120
Accession #: NM_021569
Genomic sequence: chr9: 131740238-131740388
Sequence definition: NMDA receptor 1 isoform NR1-2 precursor
Sequence ID: No. 121
Accession #: AL445467.6
Genomic sequence: chrX: 15985515-15985779
Sequence definition: genomic match
Sequence ID: No. 122
Accession #: BM976799
Genomic sequence: chr1: 54049149-54049432
Sequence definition: genomic/EST match
Sequence ID: No. 123
Accession #: no match to index
Genomic sequence: No match BLAT
Sequence definition: No match BLAT
Sequence ID: No. 124
Accession #: NT_007933.414
Genomic sequence: chr7: 98285605-98286140
Sequence definition: Genscan prediction
Sequence ID: No. 125
Accession #: NM_020428
Genomic sequence: chr19: 10964586-10965036
Sequence definition: *Homo sapiens* CTL2 gene CTL2 mRNA
Sequence ID: No. 126
Accession #: no match to index
Genomic sequence: No match BLAT
Sequence definition: No match BLAT
Sequence ID: No. 127
Accession #: NM_006292
Genomic sequence: chr11: 19444265-19444422
Sequence definition: *Homo sapiens* tumor susceptibility gene 101 TSG101 mRNA
Sequence ID: No. 128
Accession #: NM_052932
Genomic sequence: chr11: 102306433-102306907
Sequence definition: *Homo sapiens* pro-oncosis receptor inducing membrane injury gene PORIMIN mRNA
Sequence ID: No. 129
Accession #: NM_000014
Genomic sequence: chr12: 9416444-9416720
Sequence definition: *Homo sapiens* alpha-2-macroglobulin A2M mRNA
Sequence ID: No. 130
Accession #: NM_002337
Genomic sequence: chr4: 3426547-3433294
Sequence definition: low density lipoprotein-related
Sequence ID: No. 131
Accession #: AL834445
Genomic sequence: chr20: 23304135-23304477
Sequence definition: *Homo sapiens* mRNA; cDNA DKFZp761J109

TABLE 1-continued

Sequence information of the DATAS fragments and the alternatively spliced isoforms.

Sequence ID: No. 132
Accession #: NM_004986
Genomic sequence: chr14: 49879277-49880762
Sequence definition: kinectin 1
Sequence ID: No. 133
Accession #: NM_024295
Genomic sequence: chr8: 124092754-124095061
Sequence definition: hypothetical protein MGC3067
Sequence ID: No. 134
Accession #: AC018457.14
Genomic sequence: chr3: 165236534-165236724
Sequence definition: genomic match
Sequence ID: No. 135
Accession #: NM_004753
Genomic sequence: chr1: 12208898-12258427
Sequence definition: *Homo sapiens* short-chain dehydrogenase/reductase 1 SDR1 mRNA
Sequence ID: No. 136
Accession #: NM_004753
Genomic sequence: chr1: 12221576-12258383
Sequence definition: *Homo sapiens* short-chain dehydrogenase/reductase 1 SDR1 mRNA
Sequence ID: No. 137
Accession #: NM_004753
Genomic sequence: chr1: 12221576-12258383
Sequence definition: *Homo sapiens* short-chain dehydrogenase/reductase 1 SDR1 mRNA
Sequence ID: No. 138
Accession #: NM_004753
Genomic sequence: chr1: 12221576-12258383
Sequence definition: *Homo sapiens* short-chain dehydrogenase/reductase 1 SDR1 mRNA
Sequence ID: No. 139
Accession #: NM_004753
Genomic sequence: chr1: 12221576-12258383
Sequence definition: *Homo sapiens* short-chain dehydrogenase/reductase 1 SDR1 mRNA
Sequence ID: No. 140
Accession #: D87438
Genomic sequence: chr16: 14996279-15058862
Sequence definition: Human mRNA for KIAA0251 gene partial cds
Sequence ID: No. 141
Accession #: D87438
Genomic sequence: chr16: 15018972-15027737
Sequence definition: Human mRNA for KIAA0251 gene partial cds
Sequence ID: No. 142
Accession #: AB007932
Genomic sequence: chr1: 204843635-205060532
Sequence definition: *Homo sapiens* plexin A2 long form PLXNA2 mRNA
Sequence ID: No. 143
Accession #: AB007932
Genomic sequence: chr1: 204843635-205060532
Sequence definition: *Homo sapiens* plexin A2 long form PLXNA2 mRNA
Sequence ID: No. 144
Accession #: AB007932
Genomic sequence: chr1: 204843635-205060532
Sequence definition: *Homo sapiens* plexin A2 long form PLXNA2 mRNA
Sequence ID: No. 145
Accession #: AB037745
Genomic sequence: chr1: 108833848-108851509
Sequence definition: *Homo sapiens* mRNA for KIAA1324 protein partial cds
Sequence ID: No. 146
Accession #: AB037745
Genomic sequence: chr1: 108851126-108851424
Sequence definition: *Homo sapiens* mRNA for KIAA1324 protein partial cds
Sequence ID: No. 147
Accession #: AB037745
Genomic sequence: chr1: 108851126-108851424
Sequence definition: *Homo sapiens* mRNA for KIAA1324 protein partial cds
Sequence ID: No. 148
Accession #: AB037745
Genomic sequence: chr1: 108851126-108851424
Sequence definition: *Homo sapiens* mRNA for KIAA1324

TABLE 1-continued

Sequence information of the DATAS fragments and the alternatively spliced isoforms.

protein partial cds
Sequence ID: No. 149
Accession #: AB037745
Genomic sequence: chr1: 108851126-108851424
Sequence definition: *Homo sapiens* mRNA for KIAA1324 protein partial cds
Sequence ID: No. 150
Accession #: NM_002253
Genomic sequence: chr4: 55795152-55795458
Sequence definition: *Homo sapiens* kinase insert domain receptor a type III receptor tyrosine kinase KDR mRNA
Sequence ID: No. 151
Accession #: NM_004879
Genomic sequence: chr11: 125479160-125481382
Sequence definition: *Homo sapiens* etoposide induced 2.4 mRNA EI24 mRNA
Sequence ID: No. 152
Accession #: BC041788
Genomic sequence: chr8: 144841449-144841809
Sequence definition: *Homo sapiens* Similar to RIKEN cDNA 1110025J15 gene
clone MGC: 32881 IMAGE: 4738372 mRNA complete cds
Sequence ID: No. 153
Accession #: AB033073
Genomic sequence: chr20: 46925235-46925516
Sequence definition: *Homo sapiens* mRNA for KIAA1247 protein partial cds
Sequence ID: No. 154
Accession #: NT_011520.136
Genomic sequence: chr22: 21548074-21562329
Sequence definition: Genscan prediction
Sequence ID: No. 155
Accession #: NM_005581
Genomic sequence: chr19: 49998069-49998792
Sequence definition: *Homo sapiens* Lutheran blood group Auberger b antigen included LU mRNA
Sequence ID: No. 156
Accession #: NM_004355
Genomic sequence: chr5: 149769000-149775442
Sequence definition: *Homo sapiens* CD74 antigen invariant polypeptide of major histocompatibility complex class II antigen-associated CD74 mRNA
Sequence ID: No. 157
Accession #: NM_000484
Genomic sequence: chr21: 26174980-26175131
Sequence definition: *Homo sapiens* amyloid beta A4 precursor protein protease nexin-II Alzheimer disease APP mRNA
Sequence ID: No. 158
Accession #: NM_005745
Genomic sequence: chrX: 150566783-150575554
Sequence definition: *Homo sapiens* accessory protein BAP31 BCAP31 mRNA
Sequence ID: No. 159
Accession #: NM_005570
Genomic sequence: chr18: 56780509-56781078
Sequence definition: *Homo sapiens* lectin mannose-binding 1 LMAN1 mRNA
Sequence ID: No. 160
Accession #: NT_029218.14
Genomic sequence: chr1: 19080562-19080917
Sequence definition: Genscan prediction
Sequence ID: No. 161
Accession #: NT_011387.8
Genomic sequence: chr20: 410654-410816
Sequence definition: Genscan prediction
Sequence ID: No. 162
Accession #: NM_002587
Genomic sequence: chr5: 141227996-141231527
Sequence definition: *Homo sapiens* protocadherin 1 PDCH1
Sequence ID: No. 163
Accession #: NT_035036.5
Genomic sequence: chr10: 51263955-51274232
Sequence definition: Genscan prediction
Sequence ID: No. 164
Accession #: NM_007176
Genomic sequence: chr14: 74107662-74107815
Sequence definition: *Homo sapien* Chr 14 open reading frame TABLE 1-continued Sequence information of the DATAS fragments and the alternatively spliced isoforms.

Sequence ID: No. 165
Accession #: AP000531.1
Genomic sequence: chr22: 14703272-14703359
Sequence definition: poor genomic match to repeat
Sequence ID: No. 166
Accession #: NM_020182
Genomic sequence: chr20: 56850452-56936716
Sequence definition: *Homo sapiens* transmembrane prostate androgen induced RNA TMEPAI mRNA
Sequence ID: No. 167
Accession #: NM_020182
Genomic sequence: chr20: 56850452-56936716
Sequence definition: *Homo sapiens* transmembrane prostate androgen induced RNA TMEPAI mRNA
Sequence ID: No. 168
Accession #: NM_020182
Genomic sequence: chr20: 56850452-56936716
Sequence definition: *Homo sapiens* transmembrane prostate androgen induced RNA TMEPAI mRNA
Sequence ID: No. 169
Accession #: NM_020182
Genomic sequence: chr20: 56850452-56936716
Sequence definition: *Homo sapiens* transmembrane prostate androgen induced RNA TMEPAI mRNA
Sequence ID: No. 170
Accession #: NM_020182
Genomic sequence: chr20: 56850452-56936716
Sequence definition: *Homo sapiens* transmembrane prostate androgen induced RNA TMEPAI mRNA
Sequence ID: No. 171
Accession #: NM_020182
Genomic sequence: chr20: 56850452-56936716
Sequence definition: *Homo sapiens* transmembrane prostate androgen induced RNA TMEPAI mRNA
Sequence ID: No. 172
Accession #: NM_020182
Genomic sequence: chr20: 56850452-56936716
Sequence definition: *Homo sapiens* transmembrane prostate androgen induced RNA TMEPAI mRNA
Sequence ID: No. 173
Accession #: AK092666_01
Sequence definition: Novel spliced isoform of STEAP2
Sequence ID: No. 174
Accession #: AK092666_01
Sequence definition: Protein translation of novel spliced isoform of STEAP2
Sequence ID: No. 175
Accession #: AK092666_02
Sequence definition: Novel spliced isoform of STEAP2
Sequence ID: No. 176
Accession #: AK092666_02
Sequence definition: Protein translation of novel spliced isoform of STEAP2
Sequence ID: No. 177
Accession #: AK092666_03
Sequence definition: Novel spliced isoform of STEAP2
Sequence ID: No. 178
Accession #: AK092666_03
Sequence definition: Protein translation of novel spliced isoform of STEAP2
Sequence ID: No. 179
Accession #: AK092666_04
Sequence definition: Novel spliced isoform of STEAP2
Sequence ID: No. 180
Accession #: AK092666_04
Sequence definition: Protein translation of novel spliced isoform of STEAP2
Sequence ID: No. 181
Accession #: AK092666_05
Sequence definition: Novel spliced isoform of STEAP2
Sequence ID: No. 182
Accession #: AK092666_05
Sequence definition: Novel spliced isoform of STEAP2
Sequence ID: No. 183
Accession #: AK092666_01aa
Sequence definition: Novel amino acids generated by spliced isoforms TABLE 1-continued

| Sequence information of the DATAS fragments and the alternatively spliced isoforms. |
| --- |
| AK092666_01, AK092666_03, AK092666_05<br>Sequence ID: No. 184<br>Accession #: AK092666_02aa<br>Sequence definition: Novel amino acids generated by spliced isoform AK092666_02<br>Sequence ID: No. 185<br>Accession #: AK092666_04aa<br>Sequence definition: Novel amino acids generated by spliced isoform AK092666_04 |

REFERENCES

Alcaraz et al., Cancer Res., 55:3998-4002, 1994.

Allhoff et al., World J. Urol., 7:12-16, 1989.

An et al., Proc. Amer. Assn. Canc. Res., 36:82, 1995.

An et al., Molec. Urol., 2: 305-309, 1998.

Antibodies: A Laboratory Manual, Cold Spring Harbor Laboratory, Cold Spring Harbor Press, Cold Spring Harbor, N.Y., 1988.

Babian et al., J. Urol., 156:432-437, 1996.

Badalament et al., J. Urol., 156:1375-1380, 1996.

Baichwal and Sugden, In: Gene Transfer, Kucherlapati (Ed.), Plenum Press, New York, pp 117-148, 1986.

Bangharn et al., J. Mol. Biol. 13: 238-252, 1965.

Barinaga, Science, 271: 1233, 1996.

Bedzyk et al., J. Biol. Chem., 265:18615, 1990

Bell et al., "Gynecological and Genitourinary Tumors," In: Diagnostic Immunopathology, Colvin, Bhan and McCluskey (Eds.), 2nd edition, Ch. 31, Raven Press, New York, pp 579-597, 1995.

Bellus, J Macromol. Sci. Pure Appl. Chem., A31(1):1355-1376, 1994.

Benvenisty and Neshif, Proc. Nat. Acad Sci. USA, 83:9551-9555, 1986.

Bittner et al., Methods in Enzymol, 153:516-544, 1987.

Bookstein et al., Science, 247:712-715, 1990a.

Bookstein et al., Proc. Nat'l Acad. Sci. USA, 87:7762-7767, 1990b.

Bova et al., Cancer Res., 53:3869-3873, 1993

Brawn et al., The Prostate, 28:295-299, 1996.

Campbell, In: Monoclonal Antibody Technology, Laboratory Techniques in Biochemistry and Molecular Biology, Burden and Von Knippenberg (Eds.), Vol.13:75-83, Elsevier, Amsterdam, 1984.

Capaldi et al., Biochem. Biophys. Res. Comm, 76:425, 1977.

Carter and Coffey, In: Prostate Cancer: The Second Tokyo Symposium, J. P. Karr and H. Yamanak (Eds.), Elsevier, New York, pp 19-27, 1989.

Carter and Coffey, Prostate, 16:3948, 1990.

Carter et al., Proc. Nat'l Acad Sci. USA, 87:8751-8755, 1990.

Carter et al., Proc. Nat'l Acad Sci. USA93: 749-753, 1996.

Carter et al., J. Urol., 157:2206-2209, 1997.

Cech et al., Cell, 27:487496, 1981.

Chang et al., Hepatology, 14: 124A, 1991.

Chaudhary et al., Proc. Nat'l Acad. Sci., 87:9491, 1990

Chen and Okayama, MoL Cell Biol., 7:2745-2752, 1987.

Chen et al., Clin. Chem., 41:273-282, 1995a.

Chen et al., Proc. Am. Urol. Assn, 153:267A, 1995.

Chinault and Carbon, "Overlap Hybridization Screening: Isolation and Characterization of Overlapping DNA Fragments Surrounding the LEU2 Gene on Yeast Chromosome III," Gene, 5:111-126, 1979.

Chomczynski and Sacchi, Anal. Biochem., 162:156-159, 1987.

Christensson et al., J. Urol., 150:100-105, 1993.

Coffin, In: Virology, Fields et al. (Eds.), Raven Press, New York, pp 1437-1500, 1990.

Colberre-Garapin et al., J. Mol. Biol., 150:1, 1981.

Colvin et al., Diagnostic Immunopathology, 2nd edition, Raven Press, New York, 1995.

Cooner et al., J. Urol., 143:1146-1154, 1990.

Couch et al., Am. Rev. Resp. Dis., 88:394-403, 1963.

Coupar et al., Gene, 68:1-10, 1988.

Culver et al., Science, 256:1550-1552, 1992.

Davey et al., EPO No. 329 822.

Deamer and Uster, "Liposome Preparation: Methods and Mechanisms," In: Liposomes, M. Ostro (Ed.), 1983.

Diamond et al., J. Urol., 128:729-734, 1982.

Donahue et al., J. Biol. Chem., 269:8604-8609, 1994.

Dong et al., Science, 268:884-886, 1995.

Dubensky et al., Proc. Nat. Acad. Sci. USA, 81:7529-7533, 1984.

Dumont et al., J. Immunol., 152:992-1003, 1994.

Elledge et al., Cancer Res. 54:3752-3757, 1994

European Patent Application EPO No. 320 308

Fearon et al., Science, 247:47-56, 1990.

Fechheirneret al., Proc. Natl. Acad. Sci. USA, 84:8463-8467, 1987.

Forster and Symons, Cell, 49:211-220, 1987.

Fraley et al., Proc. Natl. Acad. Sci USA, 76:3348-3352, 1979.

Friedmann, Science, 244:1275-1281, 1989.

Freifelder, In: Physical Biochemistry Applications to Biochemistry and Molecular Biology, 2nd ed., Wm. Freeman and Co., New York, N.Y., 1982.

Frohman, In: PCR Protocols: A Guide to Methods and Applications, Academic Press, New York, 1990.

Gefter et al., Somatic Cell Genet., 3:231-236, 1977.

Gerlach et al., Nature (London), 328:802-805, 1987.

Ghosh-Choudhury et al., EMBO J., 6:1733-1739, 1987.

Gingeras et al., PCT Application WO 88/10315.

Ghosh and Bachhawat, In: Liver Diseases, Targeted Diagnosis and Therapy Using Specific Receptors and Ligands, Wu et al. (Eds.), Marcel Dekker, New York, pp 87-104, 1991.

Goding, In: Monoclonal Antibodies: Principles and Practice, 2nd ed., Academic Press, Orlando, Fla., pp 60-61, 65-66, 71-74, 1986.

Gomez-Foix et al., J. Biol. Chem., 267:25129-25134, 1992.

Gopal, Mol. Cell Biol., 5:1188-1190, 1985.

Graham et al., J. Gen. Virol., 36:59-72, 1977.

Graham and van der Eb, Virology, 52:456-467, 1973.

Graham and Prevec, In: Methods in Molecular Biology: Gene Transfer and Expression Protocols 7, E. J. Murray (Ed.), Humana Press, Clifton, N.J., pp 205-225, 1991.

Gregoriadis (ed.), In: Drug Carriers in Biology and Medicine, pp 287-341, 1979.

Grunhaus and Horwitz, Sem. Virol., 3:237-252, 1992.

Harland and Weintraub, J. Cell Biol., 101:1094-1099, 1985.

Harris et al., J. Urol., 157:1740-1743, 1997.

Heng et al., Proc. Nat. Acad. Sci. USA, 89: 9509-9513, 1992.

Hermonat and Muzycska, Proc. Nat. Acad. Sci USA, 81:6466-6470, 1984.

Hersdorffer et al., DNA Cell Biol., 9:713-723, 1990.

Herz and Gerard, Proc. Natl Acad Sci. USA, 90:2812-2816, 1993.

Hess et al., J. Adv. Enzyme Reg., 7:149, 1968.

Hitzeman et al., J. Biol. Chem., 255:2073, 1980.

Holland et al., Biochemistry, 17:4900, 1978.

Horoszewicz, Kawinski and Murphy, Anticancer Res., 7:927-936, 1987.
Horwich, et al., J. Virol., 64:642-650, 1990.
Huang et al., Prostate, 23: 201-212, 1993.
Innis et al., In: PCR Protocols, Academic Press, Inc., San Diego Calif., 1990.
Inouye et al., Nucl. Acids Res., 13:3101-3109, 1985.
Isaacs et al., Cancer Res., 51:4716-4720, 1991.
Isaacs et al., Sem. Oncol., 21:1-18, 1994.
Israeli et al., Cancer Res., 54:1807-1811, 1994.
Jacobson et al., JAMA, 274:1445-1449, 1995.
Johnson et al., In: Biotechnology and Pharmacy, Pezzuto et al., (Eds.), Chapman and Hall, New York, 1993.
Jones, Genetics, 85:12, 1977.
Jones and Shenk, Cell, 13:181-188, 1978.
Joyce, Nature, 338:217-244, 1989.
Kaneda et al., Science, 243:375-378, 1989.
Kato el al., J. Biol. Chem., 266:3361-3364, 1991.
Kent, et al., Genome Res. 12:996-1006 (2002).
Kim and Cech, Proc. Natl. Acad. Sci. USA, 84:8788-8792, 1987.
Kingsman el al., Gene, 7:141, 1979.
Klein et al., Nature, 327:70-73, 1987.
Kohler and Milstein, Nature, 256:495-497, 1975.
Kohler and Milstein, Eur. J. Immunol., 6:511-519, 1976.
Kwoh et al., Proc. Nat. Acad. Sci. USA, 86:1173, 1989.
Landis et al., CA Cancer J. Clin., 48: 6-29, 1998.
Le Gal La Salle et al., Science, 259:988-990, 1993.
Levrero et al., Gene, 10 1: 195-202, 1991.
Liang and Pardee, Science, 257:967-971, 1992.
Liang and Pardee, U.S. Pat. No. 5,262,311, 1993.
Liang et al., Cancer Res., 52:6966-6968, 1992.
Lifton, Science, 272:676, 1996.
Lilja et al., Clin. Chem., 37:1618-1625, 1991.
Lithrup et al., Cancer, 74:3146-3150, 1994.
Lowy et al., Cell, 22:817, 1980.
Macoska et al., Cancer Res., 54:3824-3830, 1994.
Mann et al., Cell, 33:153-159, 1983.
Markowitz et al., J. Virol., 62:1120-1124, 1988.
Marley et al., Urology, 48(6A): 16-22, 1996.
McCormack et al., Urology, 45:729-744, 1995.
Michel and Westhof, J. Mol. Biol. 216:585-610, 1990.
Miki et al., Science, 266:66-71, 1994.
Miller et al., PCT Application, WO 89/06700.
Mok et al., Gynecol. Oncol., 52:247-252, 1994.
Morahan et al., Science 272:1811, 1996.
Mulligan et al., Proc. Nat'l Acad. Sci. USA, 78:2072, 1981.
Mulligan, Science, 260:926-932, 1993.
Murphy et al., Cancer, 78: 809-818, 1996.
Murphy et al., Prostate, 26:164-168, 1995.
Nakamura et al., In: Handbook of Experimental Immunology, (4th Ed.), Weir, E., Herzenberg, L. A.; Blackwell, C., Herzenberg, L. (Eds.), Vol. 1, Chapter 27, Blackwell Scientific Publ., Oxford, 1987.
Nicolas and Rubinstein, In: Vectors: A Survey of Molecular Cloning Vectors and Their Uses, Rodriguez and Denhardt (Eds.), Butterworth, Stoneham, p 494-513, 1988.
Nicolau and Sene, Biochim. Biophys. Acta, 721:185-190, 1982.
O'Dowd et al., J. Urol., 158:687-698, 1997.
O'Hare et al., Proc. Nat'l Acad. Sci. USA, 78:1527, 1981.
Oesterling et al., J. Urol., 154:1090-1095, 1995.
Ohara et al., Proc. Nat'l Acad. Sci. USA, 86:5673-5677, 1989.
Orozco et al., Urology, 51:186-195, 1998.
Parker et al., CA Cancer J. Clin., 65:5-27, 1996.
Partin and Oesterling, Urology, 48 (6A): 1-3, 1996.
Partin and Oesterling, J. Urol., 152:1358-1368, 1994.
Partin and Oesterling (Eds.), Urology, 48(6A) Supplement: 1-87, 1996.
Paskind et al., Virology, 67:242-248, 1975.
PCT Application No. PCT/US87/00880
Pettersson et al., Clin. Chem., 41(10):1480-1488, 1995.
Piironen et al., Clin. Chem. 42:1034-1041, 1996.
Potter et al., Proc. Nat. Acad. Sci. USA, 81:7161-7165, 1984.
Racher et al., Biotechnology Techniques, 9:169-174, 1995.
Ragot et al., Nature, 361:647-650, 1993.
Ralph and Veltri, Advanced Laboratory, 6:51-56, 1997.
Ralph et al., Proc. Natl. Acad. Sci. USA, 90(22):10710-10714, 1993.
Reinhold-Hurek and Shub, Nature, 357:173-176, 1992.
Renan, Radiother. Oncol., 19:197-218, 1990.
Ribas de Pouplana and Fothergill-Gilmore, Biochemistry, 33:7047-7055, 1994.
Rich et al., Hum. Gene Ther., 4:461-476, 1993.
Ridgeway, In: Vectors: A Survey of Molecular Cloning Vectors and Their Uses, Rodriguez R L, Denhardt D T (Eds.), Butterworth, Stoneham, pp 467492, 1988.
Rippe et al., Mol. Cell Biol., 10:689-695, 1990.
Rosenfeld et al., Science, 252:431-434, 1991.
Rosenfeld et al., Cell, 68:143-155, 1992.
Roux et al., Proc. Nat'l Acad. Sci. USA, 86:9079-9083, 1989.
Sager et al., FASEB J., 7:964-970, 1993.
Sambrook et al., (ed.), In: Molecular Cloning, Cold Spring Harbor Laboratory Press, Cold Spring Harbor, N.Y., 1989.
Santerre et al., Gene, 30: 147-156, 1984.
Sarver, et al., Science, 247:1222-1225, 1990.
Scanlon et al., Proc Natl Acad Sci USA, 88:10591-10595, 1991.
Sidransky et al., Science, 252:706-709, 1991.
Sidransky et al., Cancer Res., 52:2984-2986, 1992.
Silver et al., Clin. Cancer Res., 3:81-85, 1997.
Slamon et al., Science, 224:256-262, 1984.
Slamon et al., Science, 235:177-182, 1987.
Slamon et al., Science, 244:707-712, 1989.
Smith, U.S. Pat. No. 4,215,051.
Soh et al., J. Urol., 157:2212-2218, 1997.
Stenman et al., Cancer Res., 51:222-226, 1991.
Stinchcomb et al., Nature, 282:39, 1979.
Stratford-Perricaudet and Perricaudet, In: Human Gene Transfer, O. Cohen-Haguenauer et al., (Eds.), John Libbey Eurotext, France, pp 51-61, 1991.
Stratford-Perricaudet et al., Hum. Gene. Ther., 1:241-256, 1990.
Sun and Cohen, Gene, 137:127-132, 1993.
Szoka and Papahadjopoulos, Proc. Nat'l. Acad. Sci. USA, 75: 4194-4198, 1978.
Szybalska et al., Proc. Nat'l Acad. Sci. USA, 48:2026, 1962.
Takahashi et al., Cancer Res., 54:3574-3579, 1994.
Taparowsky et al., Nature, 300:762-764, 1982.
Temin, In: Gene Transfer, Kucherlapati R. (Ed.), Plenum Press, New York, pp 149-188:, 1986.
Tooze, In: Molecular Biology of DNA Tumor Viruses, 2nd ed., Cold Spring Harbor Laboratory, Cold Spring Harbor, N.Y., 1991.
Top et al., J. Infect. Dis., 124:155-160, 1971.
Tschemper et al., Gene, 10:1 57, 1980.
Tur-Kaspaet al., Mol. Cell Biol., 6:716-718, 1986.
U.S. patent application Ser. No. 08/692,787
U.S. Pat. No. 4,196,265
U.S. Pat. No. 4,215,051
U.S. Pat. No. 4,683,195
U.S. Pat. No. 4,683,202
U.S. Pat. No. 4,800,159

U.S. Pat. No. 4,883,750
U.S. Pat. No. 5,354,855
U.S. Pat. No. 5,359,046
Varmus et al., Cell, 25:23-36, 1981.
Veltri et al., J. Cell Biochem., 19(suppl):249-258, 1994.
Veltri et al., Urology, 48: 685-691, 1996.
Veltri et al., Sem. Urol. Oncol., 16:106-117, 1998.
Veltri et al., Urology,53:139-147, 1999.
Visakorpi et al., Am. J. Pathol., 145:1-7, 1994.
Wagner et al., Science, 260:1510-1513, 1993.
Walker et al., Proc. Nat'l Acad. Sci. USA, 89:392-396, 1992.
Watson et al., Cancer Res., 54:4598-4602, 1994.
Welsh et al., Nucl. Acids Res., 20:4965-4970, 1992.
Wigler et at, Cell, 11:223, 1977.
Wigler et al., Proc. Nat'l Acad. Sci. USA, 77:3567, 1980.
Wingo et al., CA Cancer J. Clin., 47: 239-242, 1997.
WO 90/07641, filed Dec. 21, 1990.
Wong et al., Int. J. Oncol., 3:13-17, 1993.
Wu and Wu, J. Biol. Chem., 262: 4429-4432, 1987.
Wu and Wu, Biochemistry, 27: 887-892, 1988.
Wu and Wu, Adv. Drug Delivery Rev., 12: 159-167, 1993.
Wu el al., Genomics, 4:560, 1989.
Yang et al., Proc. Natl. Acad. Sci. USA, 87:9568-9572, 1990.
Yokoda et al., Cancer Res. 52, 3402-3408, 1992.
Zlotta et al, J. Urol., 157:1315-1321, 1997.

What is claimed is:

1. An isolated nucleic acid that is expressed by human prostate cancer cells, wherein said nucleic acid comprises the sequence of SEQ ID NO: 92.

2. A diagnostic kit for detection of prostate cancer which comprises a nucleic acid according to claim 1 and a detectable label.

3. An isolated nucleic acid component comprising a detectable label and a nucleic acid sequence comprising the sequence of SEQ ID NO: 92.

4. The nucleic acid component of claim 3 wherein said detectable label is selected from the group consisting of an indicator enzyme, a radiolabel, a fluorophore and a paramagnetic particle.

5. The kit of claim 2 wherein said detectable label is selected from the group consisting of an indicator enzyme, a radiolabel, a fluorophore and a paramagnetic particle.

* * * * *